(12) United States Patent
Labéguère et al.

(10) Patent No.: US 10,829,478 B2
(45) Date of Patent: Nov. 10, 2020

(54) 5-[3-[PIPERAZIN-1-YL]-3-OXO-PROPYL]-IMIDAZOLIDINE-2,4-DIONE DERIVATIVES AS ADAMTS 4 AND 5 INHIBITORS FOR TREATING E.G. OSTEOARTHRITIS

(71) Applicant: Galapagos NV, Mechelen (BE)

(72) Inventors: Frédéric Gilbert Labéguère, Frouzins (FR); Rama Heng, Paris (FR); Frédéric André De Ceuninck, Paris (FR); Luke Jonathan Alvey, Romainville (FR); David Amantini, Romainville (FR); Franck Laurent Brebion, Romainville (FR); Pierre Marc Marie Joseph Deprez, Romainville (FR); Romain Luc Marie Gosmini, Romainville (FR); Hélène Marie Jary, Romainville (FR); Christophe Peixoto, Romainville (FR); Iuliana Ecaterina Pop-Botez, Houilles (FR); Marie Laurence Claire Varin, Romainville (FR)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 16/308,349

(22) PCT Filed: Jun. 1, 2017

(86) PCT No.: PCT/EP2017/063271
§ 371 (c)(1),
(2) Date: Dec. 7, 2018

(87) PCT Pub. No.: WO2017/211666
PCT Pub. Date: Dec. 14, 2017

(65) Prior Publication Data
US 2019/0315719 A1      Oct. 17, 2019

(30) Foreign Application Priority Data

Jun. 9, 2016 (GB) .................................. 1610055.4

(51) Int. Cl.
C07D 403/06 (2006.01)
C07D 401/14 (2006.01)
C07D 403/14 (2006.01)

(52) U.S. Cl.
CPC ......... *C07D 403/06* (2013.01); *C07D 401/14* (2013.01); *C07D 403/14* (2013.01)

(58) Field of Classification Search
CPC .. C07D 401/04; C07D 401/06; C07D 401/14; C07D 403/06
See application file for complete search history.

(56) References Cited

U.S. PATENT DOCUMENTS

| | | | |
|---|---|---|---|
| 9,926,281 B2 * | 3/2018 | Brebion | C07D 401/14 |
| 10,487,060 B2 * | 11/2019 | Brebion | C07D 405/12 |
| 2009/0137603 A1 * | 5/2009 | Nara | C07D 239/90 |
| | | | 514/252.16 |

FOREIGN PATENT DOCUMENTS

| | | | |
|---|---|---|---|
| WO | WO 2013/153189 A1 | 10/2013 | |
| WO | WO 2014/066151 A1 | 5/2014 | |
| WO | WO 2016/102347 A1 | 6/2016 | |

OTHER PUBLICATIONS

Neogi. Current Opinion in Rheumatology, 2011, 23, 185-191 (Year: 2011).*
Abbaszade, I., et al., "Cloning and Characterization of ADAMTS11, an Aggrecanase from the ADAMTS Family", J. Biol. Chem., vol. 274, No. 33, pp. 23443-23450, 1999.
Bendele, A., "Animal models of rheumatoid arthritis", J. Musculoskelet. Neuronal Interact, vol. 1, No. 4, pp. 377-385, 2001.
Botter, S.M., et al., "ADAMTS5-/- mice have less subchondral bone changes after induction of osteoarthritis through surgical instability: implications for a link between cartilage and subchondral bone changes", Osteoarthritis Cartilage, vol. 17, pp. 636-645, 2009.
Chockalingam, P.S., et al., "Elevated aggrecanase activity in a rat model of joint injury is attenuated by an aggrecanase specific inhibitor", Osteoarthritis Cartilage, vol. 19, pp. 315-323, 2011.
Clegg, D.O., et al., "Glucosamine, Chondroitin Sulfate, and the Two in Combination for Painful Knee Osteoarthritis", N. Engl. J. Med. vol. 354, No. 8, pp. 795-808, Feb. 23, 2006.

(Continued)

Primary Examiner — Noble E Jarrell
(74) Attorney, Agent, or Firm — Arent Fox LLP

(57) ABSTRACT

The present invention discloses compounds according to Formula I:

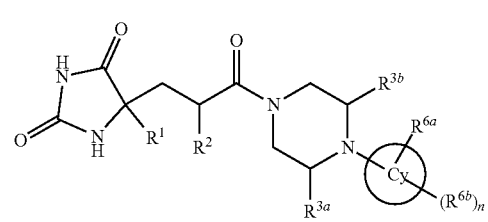

Wherein $R^1$, $R^2$, $R^{3a}$, $R^{3b}$, $R^{6a}$, $R^{6b}$, the subscript n and Cy are as defined herein.

The present invention relates to compounds inhibiting ADAMTS, methods for their production, pharmaceutical compositions comprising the same, and methods of treatment using the same, for the prophylaxis and/or treatment of inflammatory diseases, and/or diseases involving degradation of cartilage and/or disruption of cartilage homeostasis by administering the compound of the invention.

37 Claims, No Drawings
Specification includes a Sequence Listing.

(56) References Cited

OTHER PUBLICATIONS

Dufour, A., et al., "Missing the target: matrix metalloproteinase antitargets in inflammation and cancer", Trends Pharmacol. Sci., vol. 34, No. 4, pp. 233-242, Apr. 2013.
Durocher, Y., et al., "High-level and high-throughput recombinant protein production by transient transfection of suspension-growing human 293-EBNA1 cells", Nucleic Acids Res. vol. 30, No. 2, e9, pp. 1-9, 2002.
Georgiadis, D., et al., "Specific targeting of metzincin family members with small-molecule inhibitors: Progress toward a multifarious challenge", Bioorg. Med. Chem., vol. 16, pp. 8781-8794, 2008.
Glasson, S.S., et al., "Deletion of active ADAMTS5 prevents cartilage degradation in a murine model of osteoarthritis", Nature vol. 434, pp. 644-648, Mar. 31, 2005.
International Search Report as cited in PCT/EP2017/063271, dated Sep. 7, 2017.
Janusz, M.J., "Induction of osteoarthritis in the rat by surgical tear of the meniscus: Inhibition of joint damage by a matrix metalloproteinase inhibitor", Osteoarthritis Cartilage, vol. 10, pp. 785-791, 2002.
Jorgenson, E., "A genome-wide association study identifies four novel susceptibility loci underlying inguinal hernia", Nat. Commun., vol. 6, pp. 1-9, 2015.
Kato, I., et al., "Total Synthesis of Mappicine Ketone (Nothapodytine B) by Means of Sulfur-Directed 5-exo-Selective Aryl Radical Cyclization onto Enamides", J. Org. Chem., vol. 68, pp. 7983-7989, 2003.
Larsson, S., et al., "An ARGS-aggrecan assay for analysis in blood and synovial fluid", Osteoarthritis Cartilage, vol. 22, pp. 242-249, 2015.
Little, C.B., et al., "Blocking aggrecanase cleavage in the aggrecan interglobular domain abrogates cartilage erosion and promotes cartilage repair", J. Clin. Invest., vol. 117, No. 6 pp. 1627-1636, Jun. 2007.
Loignon, M., et al., "Stable high volumetric production of glycosylated human recombinant IFNalpha2b in HEK293 cells", BMC Biotechnol., vol. 8, p. 65, 2008.
Malfait, A.M., "ADAMTS-5 deficient mice do not develop mechanical allodynia associated with osteoarthritis following medial meniscal destabilization", Osteoarthritis Cartilage, vol. 18, pp. 572-580, 2010.
Mobasheri, A., "The Future of Osteoarthritis Therapeutics: Targeted Pharmacological Therapy", Curr. Rheumatol. Rep., vol. 15, p. 364, 2013.
Pond, M.J., et al., "Experimentally-induced Osteoarthritis in the Dog", Ann. Rheum. Dis., vol. 32, pp. 387-388, 1973.
Pritzker, K.P.H., et al., "Osteoarthritis cartilage histopathology: grading and staging", Osteoarthritis Cartilage, vol. 14, pp. 13-29, 2006.
Shi, C., et al., "Purification and Characterization of a Recombinant G-Protein-Coupled Receptor, *Saccharomyces cerevisiae* Ste2p, Transiently Expressed in HEK293 EBNA1 Cells", Biochemistry (Mosc.), vol. 44, pp. 15705-15714, 2005.
Shin, Y.-J., et al., "Substrate-specific gene expression profiles in different kidney cell types are associated with Fabry disease", Mol. Med. Rep., vol. 12, pp. 5049-5057, 2015.
Shiomi, T., et al., "Matrix metalloproteinases, a disintegrin and metalloproteinases, and a disintegrin and metalloproteinases with thrombospondin motifs in non-neoplastic diseases", Pathol. Int., vol. 60, No. 7, pp. 477-496, 2010.
Stanton, H., et al., "ADAMTS5 is the major aggrecanase in mouse cartilage in vivo and in vitro", Nature, vol. 434, pp. 648-652, 2005.
Stanton, H., et al., "Investigating ADAMTS-mediated aggrecanolysis in mouse cartilage", Nat. Protoc., vol. 6, pp. 388-404, 2011.
Tortorella, M.D., et al., "Will the real aggrecanase(s) step up: evaluating the criteria that define aggrecanase activity in osteoarthritis", Curr. Pharm. Biotechnol., vol. 9, pp. 16-23, 2008.
Wieland, H.A., et al., "Osteoarthritis—an untreatable disease?", Nat. Rev. Drug Discov., vol. 4, pp. 331-344, 2005.
Durham et al., "A Highly Selective Hydantoin Inhibitor of Aggrecanase 1 and Aggrecanase 2 with a Low Projected Human Dose," Journal of Medicinal Chemistry, (2017), vol. 60, pp. 5933-5939.

\* cited by examiner

5-[3-[PIPERAZIN-1-YL]-3-OXO-PROPYL]-IMIDAZOLIDINE-2,4-DIONE DERIVATIVES AS ADAMTS 4 AND 5 INHIBITORS FOR TREATING E.G. OSTEOARTHRITIS

CROSS-REFERENCE TO RELATED APPLICATIONS

This application is the 35 U.S.C. 371 National Phase Application of PCT Application No. PCT/EP2017/063271, filed Jun. 1, 2017, which claims priority to GB Application No. 1610055.4, filed Jun. 9, 2016, the disclosure of which is hereby incorporated by reference in its entirety.

FIELD OF THE INVENTION

The present invention relates to hydantoin compounds, and their use in the prophylaxis and/or treatment of inflammatory diseases, and/or diseases involving degradation of cartilage and/or disruption of cartilage homeostasis. In a particular aspect, the present compounds are ADAMTS inhibitors, particularly ADAMTS-5 and/or ADAMTS-6. The present invention also provides methods for the production of a compound of the invention, pharmaceutical compositions comprising a compound of the invention, methods for the prophylaxis and/or treatment of inflammatory diseases, and/or diseases involving degradation of cartilage and/or disruption of cartilage homeostasis by administering a compound of the invention.

BACKGROUND OF THE INVENTION

Cartilage is an avascular tissue of which chondrocytes are the main cellular component. One of the functional roles of cartilage in the joint is to allow bones to articulate on each other smoothly. Loss of articular cartilage, therefore, causes the bones to rub against each other leading to pain and loss of mobility, and is the hallmark of various diseases, among which rheumatoid arthritis and osteoarthritis are the most prominent.

The chondrocytes in normal articular cartilage occupy approximately 5% of the tissue volume, while the extracellular matrix makes up the remaining 95% of the tissue. The chondrocytes secrete the components of the matrix, mainly proteoglycans (including aggrecan) and collagens, which in turn supply the chondrocytes with an environment suitable for their survival under mechanical stress. Collagen type II, together with collagen type IX, is arranged in solid fibril-like structures, and provides cartilage with high mechanical strength properties, whereas aggrecan and other proteoglycans can absorb water and provide the resilient and shock-absorbing properties of the cartilage.

Under physiological conditions, cartilage homeostasis is maintained by a balance between the production (anabolism) and degradation (catabolism) of aggrecan and collagen. However, in OA and other joint disorders, this balance shifts toward catabolism. Loss of aggrecan occurs early in the onset of cartilage destruction, initially at the joint surface then spreading more deeply at more advanced stages (Pond and Nuki, 1973).

Osteoarthritis (also referred to as OA, or wear-and-tear arthritis) is the most common form of arthritis and is characterized by loss of articular cartilage, often associated with the subchondral bone re-modelling and pain. The disease mainly affects hands, spine and weight-bearing joints such as knees, and hips. During the disease process, the cartilage progressively deteriorates, which can be graded. At more advanced stages, the deeper layers of cartilage are affected, leading to calcification and exposure of the subchondral bone (Wieland et al., 2005).

The clinical manifestations of the development of the osteoarthritis condition include: increased volume of the joint, pain, crepitation and functional disability that lead to pain and reduced mobility of the joints. When disease further develops, pain at rest emerges. If the condition persists without correction and/or therapy, the joint is destroyed leading to disability.

Osteoarthritis is difficult to treat. At present, no cure is available and treatment focuses on relieving pain and preventing the affected joint from becoming deformed. Common treatments are currently limited to steroidal and non-steroidal anti-inflammatory drugs (NSAIDS), which provide symptomatic relief for pain and inflammation but do not arrest or slow down the progression of the disease (Mobasheri, 2013).

Therapeutic methods for the correction of the articular cartilage lesions that appear during the osteoarthritic disease have been developed, but so far none of them have been able to slow down the disease progression or to promote the regeneration of articular cartilage in situ and in vivo.

Although some dietary supplements as chondroitin and glucosamine sulfate have been advocated as safe and effective options for the treatment of osteoarthritis, a clinical trial revealed that both treatments did not reduce pain associated to osteoarthritis (Clegg et al., 2006).

In severe cases, joint replacement may be necessary. This is especially true for hips and knees. If a joint is extremely painful and cannot be replaced, it may be fused. This procedure stops the pain, but results in the permanent loss of joint function, making walking and bending difficult.

Another possible treatment is the transplantation of cultured autologous chondrocytes. Here chondral cellular material is taken from the patient, sent to a laboratory where it is expanded. The material is then implanted in the damaged tissues to cover the tissue's defects.

Yet another treatment includes the intra-articular instillation of Hylan G-F 20 (Synvisc, Hyalgan, Artz etc.), a substance that improves temporarily the rheology of the synovial fluid, producing an almost immediate sensation of free movement and a marked reduction of pain.

Other methods include application of tendinous, periosteal, facial, muscular or perichondral grafts; implantation of fibrin or cultured chondrocytes; implantation of synthetic matrices, such as collagen, carbon fiber; and administration of electromagnetic fields. All of these have reported minimal and incomplete effects, resulting in a poor quality tissue that can neither support the weighted load nor allow the restoration of an articular function with normal movement.

The ADAMTS family of secreted zinc metalloproteinases includes nineteen members that are known to bind and degrade extra cartilage matrix (ECM) components (Shiomi et al., 2010). Several members of the ADAMTS family have been found to cleave aggrecan, the major proteoglycan component of cartilage: ADAMTS-1, -4, -5, -8, -9, -15, -16 and -18. Since the expression and/or aggrecanase degrading activity of ADAMTS-1, -8, -9, -15, -16 and -18 are quite low, ADAMTS-4 (aggrecanase-1) and ADAMTS-5 (aggrecanase-2) are believed to be the two major functional aggrecanases (Tortorella and Malfait, 2008).

Although the role of ADAMTS-6 remains unclear, it has been recently associated with inguinal hernia (Jorgenson et al., 2015), vertebral disc degeneration diseases (Gruber et al., 2010), and Fabry disease (Shin et al., 2015).

ADAMTS-5 was identified in 1999 (Abbaszade et al., 1999). In 2005, two independent groups identified ADAMTS-5 as the principal aggrecanase in mouse cartilage (Glasson et al., 2005; Stanton et al., 2005). Proteolysis of aggrecan by ADAMTS-5 occurs at different sites: however cleavage at the Glu373-Ala374 bond (aggrecan IGD) is likely more important in the pathogenesis of osteoarthritis and inflammatory arthritis since a loss of integrity at this bond results in the loss of an entire aggrecan molecule, which is highly detrimental to cartilage integrity and function (Little et al., 2007).

Studies in genetically engineered mouse models (GeMMs) have demonstrated that ADAMTS-5 ablation protects against cartilage damage and aggrecan loss after osteoarthritis induction through surgical instability of the medial meniscus (DMM) (Glasson et al., 2005). Moreover in the DMM model ADAMTS-5 knock-out mice showed reduced subchondral bone changes (Botter et al., 2009) and did not develop osteoarthritis-associated mechanical allodynia (Malfait et al., 2010). Besides preclinical evidence, clinical evidence also indicates the importance of and interest in ADAMTS-5 as a target for osteoarthritis. Recently, studies with an antibody targeting ADAMTS-5 (Chiusaroli et al., 2013) have been reported. ELISA's have been developed allowing the measurement of aggrecanase-derived cartilage neo-epitope levels in the synovial fluid as well as blood from rodents to human. This method revealed increased levels of ADAMTS-5 derived neo-epitope levels in the joints of rats in which cartilage degradation was induced by meniscal tear as well as in joints of osteoarthritis patients, thereby providing further translational evidence for the importance of this protease in the development of osteoarthritis (Chockalingam et al., 2011; Larsson et al., 2014).

These findings provide strong evidence for a central role of ADAMTS-5 in osteoarthritis pathology as a key target and an ADAMTS-5 inhibitor capable to reach the joint cartilage at sufficient levels is expected to exert a protective effect on cartilage in osteoarthritic patients.

Matrix metalloproteinases (MMPs) constitute another family of 23 zinc metalloproteinases with many structural elements in common with ADAMTS family members (Georgiadis and Yiotakis, 2008). Clinical studies on broad spectrum MMP inhibitors in oncology revealed that inhibition of particular MMPs was associated with poorer prognosis and undesirable side effects. In particular, MMP8 and MMP12 have been categorized as antitargets based on in vivo animal studies (Dufour and Overall, 2013). Therefore, there is a need for selective ADAMTS, and in particular ADAMTS-5 inhibitors without affecting the activity of structurally related MMPs, and more particularly MMP-8 and -12.

Therefore the identification of novel inhibitors of ADAMTS, in particular ADAMTS-5, could provide desirable tools for the prophylaxis and/or treatment of diseases involving cartilage degradation, in particular osteoarthritis, and/or rheumatoid arthritis.

It is therefore an object of the present invention to provide compounds and their use in the prophylaxis and/or treatment of inflammatory diseases, and/or diseases involving degradation of cartilage and/or disruption of cartilage homeostasis. In particular the compounds of the present invention are inhibitors of ADAMTS, and more particularly ADAMTS-5 and/or ADAMTS-6.

SUMMARY OF THE INVENTION

The present invention is based on the identification of novel hydantoin compounds that may be useful for the prophylaxis and/or treatment of inflammatory diseases, and/or diseases involving degradation of cartilage and/or disruption of cartilage homeostasis. In a particular aspect, the present compounds are ADAMTS inhibitors, particularly ADAMTS-5 and/or ADAMTS-6. The present invention also provides methods for the production of these compounds, pharmaceutical compositions comprising these compounds and methods for treating inflammatory diseases, and/or diseases involving degradation of cartilage and/or disruption of cartilage homeostasis by administering the compounds of the invention.

Accordingly, in a first aspect of the invention, the compounds of the invention are provided having a Formula (I):

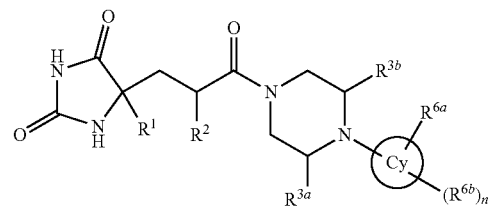

wherein
$R^1$ is:
  H,
  $C_{1-4}$ alkyl optionally substituted with one or more independently selected $R^4$ groups,
  $C_{3-7}$ monocyclic cycloalkyl optionally substituted with one or more independently selected $R^4$ groups,
  4-7 membered monocyclic heterocycloalkyl comprising 1 to 2 heteroatoms independently selected from N, O, and S, optionally substituted with one or more independently selected $C_{1-4}$ alkyl, —C(=O)$C_{1-4}$ alkyl, or —C(=O)O$C_{1-4}$ alkyl,
  phenyl optionally substituted with one or more independently selected $R^5$ groups,
  phenyl fused to a 5-6 membered monocyclic heterocycloalkyl comprising 1, 2 or 3 heteroatoms independently selected from N, O, and S, which heterocycloalkyl is optionally substituted with one or more =O,
  5-6 membered monocyclic heteroaryl comprising 1 or 2 heteroatoms independently selected from N, O, and S, optionally substituted with one or more independently selected $R^5$ groups;
$R^2$ is independently selected from:
  H,
  OH,
  $C_{1-4}$ alkoxy, and
  $C_{1-4}$ alkyl optionally substituted with one
    OH,
    —CN,
    $C_{1-4}$ alkoxy optionally substituted with one phenyl, and
    5-6 membered monocyclic heteroaryl comprising 1 or 2 heteroatoms independently selected from N, O, and S, optionally substituted with one or more independently selected $C_{1-4}$ alkyl;
each $R^{3a}$, and $R^{3b}$ is independently selected from H, and $C_{1-4}$ alkyl optionally substituted with one or more halo;
Cy is
  6-10 membered monocyclic or fused bicyclic aryl,
  5-10 membered monocyclic or fused bicyclic heteroaryl comprising 1, 2 or 3 heteroatoms independently selected from N, O, and S;

$R^4$ is
  halo,
  OH,
  —CN,
  $C_{1-4}$ alkyl,
  $C_{1-4}$ alkoxy optionally substituted with one $C_{1-4}$ alkoxy, or phenyl,
  $C_{1-4}$ thioalkoxy,
  4-7-membered monocyclic heterocycloalkyl comprising one or more heteroatoms independently selected from N, S, and O, optionally substituted with one or more halo, or —C(=O)O$C_{1-4}$ alkyl,
  phenyl,
  —S(=O)$_2C_{1-4}$ alkyl
  —C(=O)O$R^{7a}$
  —C(=O)N$R^{7b}R^{7c}$
  —NHC(=O)O$R^{7d}$
  —NHC(=O)$R^{7e}$
  —N$R^{8a}R^{8b}$;
each $R^5$ is
  halo,
  OH,
  —CN,
  $C_{1-4}$ alkyl optionally substituted with one or more independently selected halo, —N$R^{9a}R^{9b}$, or —C(=O)N$R^{9c}R^{9d}$,
  $C_{1-4}$ alkoxy optionally substituted with —N$R^{9e}R^{9f}$, or —S(=O)$_2C_{1-4}$ alkyl;
each $R^{6a}$ is
  $C_{2-4}$ alkyl optionally substituted with one or more halo,
  $C_{1-4}$ alkoxy optionally substituted with one or more halo,
the subscript n is 0, 1, 2 or 3
each $R^{6b}$ is independently selected from
  halo,
  —CN,
  —NO$_2$,
  —$C_{1-4}$ alkyl,
  —$C_{1-4}$ alkoxy
  5-10 membered monocyclic or fused bicyclic heteroaryl comprising 1, 2 or 3 heteroatoms independently selected from N, O, and S, optionally substituted with one or more independently selected halo, $C_{1-4}$ alkyl, or $C_{1-4}$ alkoxy, and
  —N$R^{9g}R^{9h}$;
each $R^{7a}$, $R^{7b}$, $R^{7c}$, $R^{7d}$, or $R^{7e}$ is H, or $C_{1-4}$ alkyl optionally substituted with OH or $C_{1-4}$ alkoxy;
each $R^{8a}$, or $R^{8b}$ is independently selected from H, and $C_{1-4}$ alkyl optionally substituted with OH, $C_{1-4}$ alkoxy, or phenyl;
each $R^{9a}$, $R^{9b}$, $R^{9c}$, $R^{9d}$, $R^{9e}$, $R^{9f}$, $R^{9g}$, $R^{9h}$ is independently selected from H, and $C_{1-4}$ alkyl;
or a pharmaceutically acceptable salt, or a solvate, or a pharmaceutically acceptable salt of a solvate thereof; or a biologically active metabolite thereof;
provided that when $R^1$, $R^2$, $R^{3a}$ and $R^{3b}$ are H, Cy is phenyl and $R^{6a}$ is —OCH$_3$, then the subscript n is not 0.

In a particular aspect, the compounds of the invention may exhibit selectivity towards the ADAMTS protease family, in particular towards the ADAMTS-5 and/or ADAMTS-6. In a further particular aspect, the compounds of the invention may show low activity on MMP family members, in particular MMP8 and/or MMP12. Such selectivity may result in improved drug safety and/or reduce off-target associated risks.

In a further aspect, the present invention provides pharmaceutical compositions comprising a compound of the invention, and a pharmaceutical carrier, excipient or diluent. In a particular aspect, the pharmaceutical composition may additionally comprise further therapeutically active ingredients suitable for use in combination with the compounds of the invention. In a more particular aspect, the further therapeutically active ingredient is an agent for the prophylaxis and/or treatment of inflammatory diseases, and/or diseases involving degradation of cartilage and/or disruption of cartilage homeostasis.

Moreover, the compounds of the invention, useful in the pharmaceutical compositions and treatment methods disclosed herein, are pharmaceutically acceptable as prepared and used.

In a further aspect of the invention, this invention provides a method of treating a mammal, in particular humans, afflicted with a condition selected from among those listed herein, and particularly inflammatory diseases, and/or diseases involving degradation of cartilage and/or disruption of cartilage homeostasis, which method comprises administering an effective amount of the pharmaceutical composition or compounds of the invention as described herein.

The present invention also provides pharmaceutical compositions comprising a compound of the invention, and a suitable pharmaceutical carrier, excipient or diluent for use in medicine. In a particular aspect, the pharmaceutical composition is for use in the prophylaxis and/or treatment of inflammatory diseases, and/or diseases involving degradation of cartilage and/or disruption of cartilage homeostasis.

In a particular aspect, the compounds of the invention are provided for use in the prophylaxis and/or treatment of osteoarthritis.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

It will be appreciated that compounds of the invention may be metabolized to yield biologically active metabolites.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Alkyl' means straight or branched aliphatic hydrocarbon having the specified number of carbon atoms. Particular alkyl groups have 1 to 6 carbon atoms or 1 to 4 carbon atoms. Branched means that one or more alkyl groups such as methyl, ethyl or propyl is attached to a linear alkyl chain. Particular alkyl groups are methyl (—CH$_3$), ethyl (—CH$_2$—CH$_3$), n-propyl (—CH$_2$—CH$_2$—CH$_3$), isopropyl (—CH(CH$_3$)$_2$), n-butyl (—CH$_2$—CH$_2$—CH$_2$—CH$_3$), tert-butyl (—CH$_2$—C(CH$_3$)$_3$), sec-butyl (—CH$_2$—CH(CH$_3$)$_2$), n-pentyl (—CH$_2$—CH$_2$—CH$_2$—CH$_2$—CH$_3$), n-hexyl (—CH$_2$—CH$_2$—CH$_2$—CH$_2$—CH$_2$—CH$_3$), and 1,2-dimethylbutyl (—CHCH$_3$)—C(CH$_3$)H$_2$—CH$_2$—CH$_3$). Particular alkyl groups have between 1 and 4 carbon atoms.

'Alkenyl' refers to monovalent olefinically (unsaturated) hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$) and the like.

'Alkylene' refers to divalent alkene radical groups having the number of carbon atoms specified, in particular having 1 to 6 carbon atoms and more particularly 1 to 4 carbon atoms which can be straight-chained or branched. This term is exemplified by groups such as methylene (—CH$_2$—), ethylene (—CH$_2$—CH$_2$—), or —CH(CH$_3$)— and the like.

'Alkynylene' refers to divalent alkyne radical groups having the number of carbon atoms and the number of triple bonds specified, in particular 2 to 6 carbon atoms and more particularly 2 to 4 carbon atoms which can be straight-chained or branched. This term is exemplified by groups such as —C≡C—, —CH$_2$—C≡C—, and —C(CH$_3$)H—C≡CH—.

'Alkoxy' refers to the group O-alkyl, where the alkyl group has the number of carbon atoms specified. In particular the term refers to the group —O—C$_{1-6}$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Amino' refers to the radical —NH$_2$.

'Aryl' refers to a monovalent aromatic hydrocarbon group derived by the removal of one hydrogen atom from a single carbon atom of a parent aromatic ring system. In particular aryl refers to an aromatic ring structure, monocyclic or fused polycyclic, with the number of ring atoms specified. Specifically, the term includes groups that include from 6 to 10 ring members. Particular aryl groups include phenyl, and naphthyl.

'Cycloalkyl' refers to a non-aromatic hydrocarbyl ring structure, monocyclic, fused polycyclic, bridged polycyclic, or spirocyclic, with the number of ring atoms specified. A cycloalkyl may have from 3 to 12 carbon atoms, in particular from 3 to 10, and more particularly from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 4, and particularly from 1 to 3 heteroatoms, more typically 1 or 2 heteroatoms, for example a single heteroatom.

'Heteroaryl' means an aromatic ring structure, monocyclic or fused polycyclic, that includes one or more heteroatoms independently selected from O, N and S and the number of ring atoms specified. In particular, the aromatic ring structure may have from 5 to 9 ring members. The heteroaryl group can be, for example, a five membered or six membered monocyclic ring or a fused bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered monocyclic heteroaryl groups include but are not limited to pyrrolyl, furanyl, thiophenyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered monocyclic heteroaryl groups include but are not limited to pyridinyl, pyrazinyl, pyridazinyl, pyrimidinyl and triazinyl.

Particular examples of bicyclic heteroaryl groups containing a five membered ring fused to another five-membered ring include but are not limited to imidazothiazolyl and imidazoimidazolyl.

Particular examples of bicyclic heteroaryl groups containing a six membered ring fused to a five membered ring include but are not limited to benzofuranyl, benzothiophenyl, benzoimidazolyl, benzoxazolyl, isobenzoxazolyl, benzisoxazolyl, benzothiazolyl, benzoisothiazolyl, isobenzofuranyl, indolyl, isoindolyl, indolizinyl, purinyl (e.g. adenine, guanine), indazolyl, pyrazolopyrimidinyl, triazolopyrimidinyl, and pyrazolopyridinyl groups.

Particular examples of bicyclic heteroaryl groups containing two fused six membered rings include but are not limited to quinolinyl, isoquinolinyl, pyridopyridinyl, quinoxalinyl, quinazolinyl, cinnolinyl, phthalazinyl, naphthyridinyl, and pteridinyl groups. Particular heteroaryl groups are those derived from thiophenyl, pyrrolyl, benzothiophenyl, benzofuranyl, indolyl, pyridinyl, quinolinyl, imidazolyl, oxazolyl and pyrazinyl.

Examples of representative heteroaryls include the following:

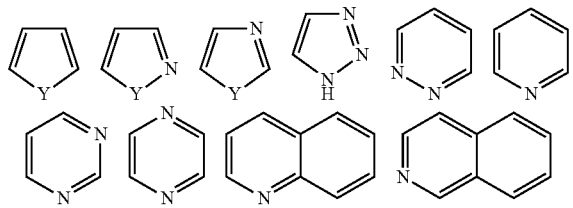

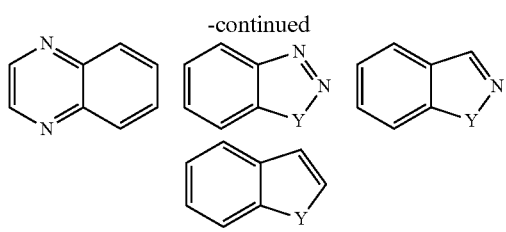

wherein each Y is selected from >C=O, NH, O and S.

'Heterocycloalkyl' means a non-aromatic fully saturated ring structure, monocyclic, fused polycyclic, spirocyclic, or bridged polycyclic, that includes one or more heteroatoms independently selected from O, N and S and the number of ring atoms specified. The heterocycloalkyl ring structure may have from 4 to 12 ring members, in particular from 4 to 10 ring members and more particularly from 4 to 7 ring members. Each ring may contain up to four heteroatoms typically selected from nitrogen, sulphur and oxygen. Typically the heterocycloalkyl ring will contain up to 4 heteroatoms, more typically up to 3 heteroatoms, more usually up to 2, for example a single heteroatom. Examples of heterocyclic rings include, but are not limited to azetidinyl, oxetanyl, thietanyl, pyrrolidinyl (e.g. 1-pyrrolidinyl, 2-pyrrolidinyl and 3-pyrrolidinyl), tetrahydrofuranyl (e.g. 1-tetrahydrofuranyl, 2-tetrahydrofuranyl and 3-tetrahydrofuranyl), tetrahydrothiophenyl (e.g. 1-tetrahydrothiophenyl, 2-tetrahydrothiophenyl and 3-tetrahydrothiophenyl), piperidinyl (e.g. 1-piperidinyl, 2-piperidinyl, 3-piperidinyl and 4-piperidinyl), tetrahydropyranyl (e.g. 4-tetrahydropyranyl), tetrahydrothiopyranyl (e.g. 4-tetrahydrothiopyranyl), morpholinyl, thiomorpholinyl, dioxanyl, or piperazinyl.

As used herein, the term 'heterocycloalkenyl' means a 'heterocycloalkyl', which comprises at least one double bond. Particular examples of heterocycloalkenyl groups are shown in the following illustrative examples:

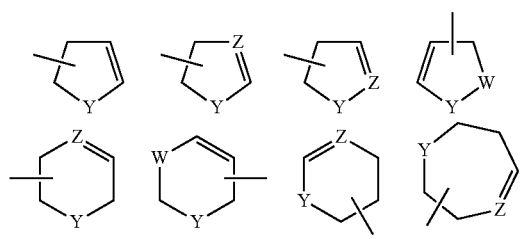

wherein each W is selected from $CH_2$, NH, O and S; each Y is selected from NH, O, C(=O), $SO_2$, and S; and each Z is selected from N or CH.

Particular examples of monocyclic rings are shown in the following illustrative examples:

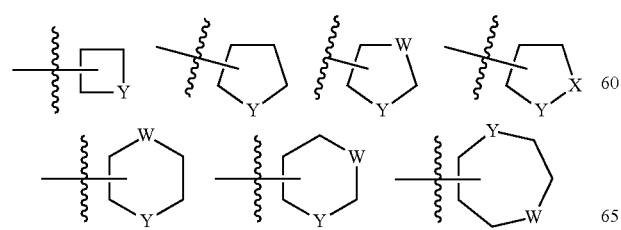

wherein each W and Y is independently selected from —$CH_2$—, —NH—, —O— and —S—.

Particular examples of fused bicyclic rings are shown in the following illustrative examples:

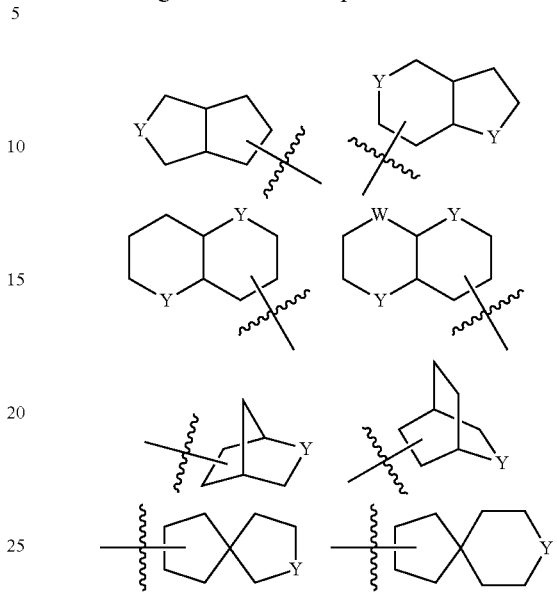

wherein each W and Y is independently selected from —$CH_2$—, —NH—, —O— and —S—.

Particular examples of bridged bicyclic rings are shown in the following illustrative examples:

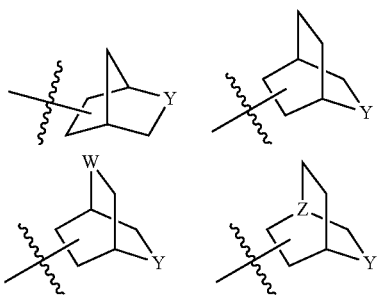

wherein each W and Y is independently selected from —$CH_2$—, —NH—, —O— and —S— and each Z is selected from N and CH.

Particular examples of spirocyclic rings are shown in the following illustrative examples:

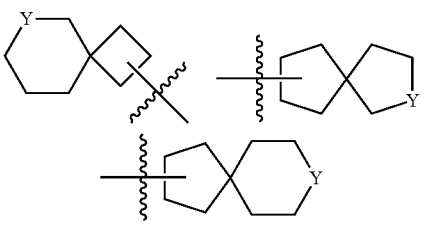

wherein each Y is selected from —$CH_2$—, —NH—, —O— and —S—.

'Hydroxyl' refers to the radical —OH.
'Oxo' refers to the radical =O.

'Substituted' refers to a group in which one or more hydrogen atoms are each independently replaced with the same or different substituent(s).

'Sulfo' or 'sulfonic acid' refers to a radical such as —SO$_3$H.

'Thiol' refers to the group —SH.

As used herein, term 'substituted with one or more' refers to one to four substituents. In one embodiment it refers to one to three substituents. In further embodiments it refers to one or two substituents. In a yet further embodiment it refers to one substituent.

'Thioalkoxy' refers to the group —S-alkyl where the alkyl group has the number of carbon atoms specified. In particular the term refers to the group —S—C$_{1-6}$ alkyl. Particular thioalkoxy groups are thiomethoxy, thioethoxy, n-thiopropoxy, isothiopropoxy, n-thiobutoxy, tert-thiobutoxy, sec-thiobutoxy, n-thiopentoxy, n-thiohexoxy, and 1,2-dimethyl-thiobutoxy. Particular thioalkoxy groups are lower thioalkoxy, i.e. with between 1 and 6 carbon atoms. Further particular alkoxy groups have between 1 and 4 carbon atoms.

One having ordinary skill in the art of organic synthesis will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. The term 'pharmaceutically acceptable cation' refers to an acceptable cationic counterion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, EtOH, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The "effective amount" can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically, (e.g. stabilization of a physical parameter), or both. In a further embodiment, "treating" or "treatment" relates to slowing the progression of the disease.

As used herein the term 'inflammatory diseases' refers to the group of conditions including rheumatoid arthritis, osteoarthritis, juvenile idiopathic arthritis, psoriasis, psoriatic arthritis, allergic airway disease (e.g. asthma, rhinitis), chronic obstructive pulmonary disease (COPD), inflammatory bowel diseases (e.g. Crohn's disease, ulcerative colitis), endotoxin-driven disease states (e.g. complications after bypass surgery or chronic endotoxin states contributing to e.g. chronic cardiac failure), and related diseases involving cartilage, such as that of the joints. Particularly the term refers to rheumatoid arthritis, osteoarthritis, allergic airway disease (e.g. asthma), chronic obstructive pulmonary disease (COPD) and inflammatory bowel diseases. More particularly the term refers to rheumatoid arthritis, and osteoarthritis (OA). Most particularly the term refers to osteoarthritis (OA).

As used herein the term 'allergic disease(s)' refers to the group of conditions characterized by a hypersensitivity disorder of the immune system including, allergic airway disease (e.g. asthma, rhinitis), sinusitis, eczema and hives, as well as food allergies or allergies to insect venom.

As used herein the term 'asthma' as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate the cause.

As used herein the term 'diseases involving degradation of cartilage and/or disruption of cartilage homeostasis' includes conditions such as osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the term refers to osteoarthritis (OA).

'Compound(s) of the invention', and equivalent expressions, are meant to embrace compounds of the Formula(e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-8}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism [1]. Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_{1-8}$ alkyl, $C_{2-8}$ alkenyl, $C_{6-10}$ optionally substituted aryl, and ($C_{6-10}$ aryl)-($C_{1-4}$ alkyl) esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2H$ or D), carbon-13 ($^{13}C$), nitro ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible.

An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e. as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of 71 electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

The Invention

The present invention is based on the identification of novel hydantoin compounds that may be useful for the prophylaxis and/or treatment of inflammatory diseases, and/or diseases involving degradation of cartilage and/or disruption of cartilage homeostasis. In a particular aspect, the present compounds are ADAMTS inhibitors, particularly ADAMTS-5 and/or ADAMTS-6.

The present invention also provides methods for the production of these compounds, pharmaceutical compositions comprising these compounds and methods for treating inflammatory diseases, and/or diseases involving degradation of cartilage and/or disruption of cartilage homeostasis by administering the compounds of the invention.

Accordingly, in a first aspect of the invention, the compounds of the invention are provided having a Formula (I):

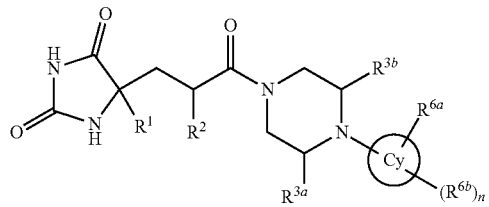

I $R^1$ is:
H,
$C_{1-4}$ alkyl optionally substituted with one or more independently selected $R^4$ groups,
$C_{3-7}$ monocyclic cycloalkyl optionally substituted with one or more independently selected $R^4$ groups,
4-7 membered monocyclic heterocycloalkyl comprising 1 to 2 heteroatoms independently selected from N, O, and S, optionally substituted with one or more independently selected $C_{1-4}$ alkyl, —C(=O)$C_{1-4}$ alkyl, or —C(=O)O$C_{1-4}$ alkyl,
phenyl optionally substituted with one or more independently selected $R^5$ groups,
phenyl fused to a 5-6 membered monocyclic heterocycloalkyl comprising 1, 2 or 3 heteroatoms independently selected from N, O, and S, which heterocycloalkyl is optionally substituted with one or more =O,
5-6 membered monocyclic heteroaryl comprising 1 or 2 heteroatoms independently selected from N, O, and S, optionally substituted with one or more independently selected $R^5$ groups;

$R^2$ is independently selected from:
H,
OH,
$C_{1-4}$ alkoxy, and
$C_{1-4}$ alkyl optionally substituted with one
OH,
—CN,
$C_{1-4}$ alkoxy optionally substituted with one phenyl, and 5-6 membered monocyclic heteroaryl comprising 1 or 2 heteroatoms independently selected from N, O, and S, optionally substituted with one or more independently selected $C_{1-4}$ alkyl;
each $R^{3a}$, and $R^{3b}$ is independently selected from H, and $C_{1-4}$ alkyl optionally substituted with one or more halo;
Cy is
6-10 membered monocyclic or fused bicyclic aryl,
5-10 membered monocyclic or fused bicyclic heteroaryl comprising 1, 2 or 3 heteroatoms independently selected from N, O, and S;
$R^4$ is
halo,
OH,
—CN,
$C_{1-4}$ alkyl,
$C_{1-4}$ alkoxy optionally substituted with one $C_{1-4}$ alkoxy, or phenyl,
$C_{1-4}$ thioalkoxy,
4-7-membered monocyclic heterocycloalkyl comprising one or more heteroatoms independently selected from N, S, and O, optionally substituted with one or more halo, or —C(=O)O$C_{1-4}$ alkyl,
phenyl,
—S(=O)$_2$$C_{1-4}$ alkyl
—C(=O)O$R^{7a}$
—C(=O)N$R^{7b}R^{7c}$
—NHC(=O)O$R^{7d}$
—NHC(=O)$R^{7e}$
—N$R^{8a}R^{8b}$;
each $R^5$ is
halo,
OH,
—CN,
$C_{1-4}$ alkyl optionally substituted with one or more independently selected halo, —N$R^{9a}R^{9b}$, or —C(=O)N$R^{9c}R^{9d}$,
$C_{1-4}$ alkoxy optionally substituted with —N$R^{9e}R^{9f}$, or —S(=O)$_2$$C_{1-4}$ alkyl;
each $R^{6a}$ is
$C_{2-4}$ alkyl optionally substituted with one or more halo,
$C_{1-4}$ alkoxy optionally substituted with one or more halo,
the subscript n is 0, 1, 2 or 3
each $R^{6b}$ is independently selected from:
halo,
—CN,
—NO$_2$,
—$C_{1-4}$ alkyl,
—$C_{1-4}$ alkoxy
5-10 membered monocyclic or fused bicyclic heteroaryl comprising 1, 2 or 3 heteroatoms independently selected from N, O, and S, optionally substituted with one or more independently selected halo, $C_{1-4}$ alkyl, or $C_{1-4}$ alkoxy, and
—N$R^{9g}R^{9h}$;
each $R^{7a}$, $R^{7b}$, $R^{7c}$, $R^{7d}$, or $R^{7e}$, is H, or $C_{1-4}$ alkyl optionally substituted with OH or $C_{1-4}$ alkoxy;
each $R^{8a}$, or $R^{8b}$ is independently selected from H, and $C_{1-4}$ alkyl optionally substituted with OH, $C_{1-4}$ alkoxy, or phenyl;
each $R^{9a}$, $R^{9b}$, $R^{9c}$, $R^{9d}$, $R^{9e}$, $R^{9f}$, $R^{9g}$, $R^{9h}$ is independently selected from H, and $C_{1-4}$ alkyl;
or a pharmaceutically acceptable salt, or a solvate, or a pharmaceutically acceptable salt of a solvate thereof; or a biologically active metabolite thereof;
provided that when $R^1$, $R^2$, $R^{3a}$ and $R^{3b}$ are H, Cy is phenyl and $R^{6a}$ is —OCH$_3$, then the subscript n is not 0.

In one embodiment, a compound of the invention is according to Formula II:

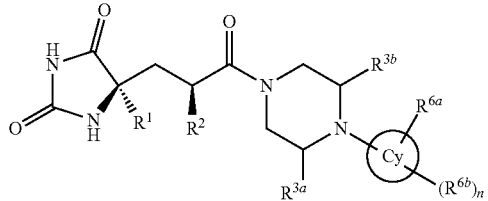

II wherein $R^1$, $R^2$, $R^{3a}$, $R^{3b}$, $R^{6a}$, $R^{6b}$, the subscript n and Cy are as defined above.

In one embodiment, a compound of the invention is according to Formula I or II, wherein $R^1$ is H.

In another embodiment, a compound of the invention is according to Formula I or II, wherein $R^1$ is $C_{1-4}$ alkyl. In a particular embodiment, $R^1$ is Me, Et, Pr, iPr, or tBu. In a more particular embodiment, $R^1$ is Me, or Et. In a particular embodiment, $R^1$ is Me.

In another embodiment, a compound of the invention is according to Formula I or II, wherein $R^1$ is $C_{1-4}$ alkyl substituted with one or more independently selected $R^4$ groups. In another embodiment, $R^1$ is Me, or Et, each of which is substituted with one or more independently selected $R^4$ groups. In a particular embodiment, $R^1$ is $C_{1-4}$ alkyl substituted with one, two or three independently selected $R^4$ groups. In another particular embodiment, $R^1$ is Me, or Et, each of which is substituted with one, two or three independently selected $R^4$ groups. In a more particular embodiment, $R^1$ is $C_{1-4}$ alkyl substituted with one $R^4$ group. In another more particular embodiment, $R^1$ is Me, or Et, each of which is substituted with one $R^4$ group. In a most particular embodiment, $R^1$ is —$CH_2$—$R_4$.

In one embodiment, a compound of the invention is according to Formula I or II, wherein $R^1$ is $C_{3-7}$ monocyclic cycloalkyl. In a particular embodiment, $R^1$ is cyclopropyl, cyclobutyl, cyclopentyl, or cyclohexyl. In a more particular embodiment, $R^1$ is cyclopropyl.

In another embodiment, a compound of the invention is according to Formula I or II, wherein $R^1$ is $C_{3-7}$ monocyclic cycloalkyl substituted with one or more independently selected $R^4$ groups. In another embodiment, $R^1$ is cyclopropyl, cyclobutyl, cyclopentyl, or cyclohexyl, each of which is substituted with one or more independently selected $R^4$ groups. In a particular embodiment, $R^1$ is $C_{3-7}$ monocyclic cycloalkyl substituted with one, two or three independently selected $R^4$ groups. In another particular embodiment, $R^1$ is cyclopropyl, cyclobutyl, cyclopentyl, or cyclohexyl, each of which is substituted with one, two or three independently selected $R^4$ groups. In a more particular embodiment, $R^1$ is $C_{3-7}$ monocyclic cycloalkyl substituted with one $R^4$ group. In another more particular embodiment, $R^1$ is cyclopropyl, cyclobutyl, cyclopentyl, or cyclohexyl, each of which is substituted with one $R^4$ group.

In one embodiment, a compound of the invention is according to Formula I or II, wherein $R^4$ is halo, OH, and CN. In a more particular embodiment, each $R^4$ is independently selected from F, Cl, OH, and CN.

In one embodiment, a compound of the invention is according to Formula I or II, wherein $R^4$ is $C_{1-4}$ alkyl. In a particular embodiment, $R^4$ is —$CH_3$, —$CH_2CH_3$, or —$CH(CH_3)_2$. In a more particular embodiment, $R^4$ is —$CH_3$.

In one embodiment, a compound of the invention is according to Formula I or II, wherein $R^4$ is $C_{1-4}$ alkoxy. In a particular embodiment, $R^4$ is OMe, OEt, or OiPr. In a more particular embodiment, $R^4$ is OMe.

In one embodiment, a compound of the invention is according to Formula I or II, wherein $R^4$ is $C_{1-4}$ alkoxy substituted with one $C_{1-4}$ alkoxy, or phenyl. In a particular embodiment, $R^4$ is OMe, OEt, or OiPr, each of which is substituted with one $C_{1-4}$ alkoxy, or phenyl. In a more particular embodiment, $R^4$ is $C_{1-4}$ alkoxy substituted with one OMe, OEt, or phenyl. In another more particular embodiment, $R^4$ is OMe, OEt, or OiPr, each of which is substituted with one OMe, OEt, or phenyl. In a most particular embodiment, $R^4$ is —$OCH_2$—$CH_2$—$OCH_3$, —$OCH_2$-Ph.

In one embodiment, a compound of the invention is according to Formula I or II, wherein $R^4$ is $C_{1-4}$ thioalkoxy. In a particular embodiment, $R^4$ is —$SCH_3$, or —$SCH_2CH_3$. In a more particular embodiment, $R^4$ is —$SCH_3$.

In one embodiment, a compound of the invention is according to Formula I or II, wherein $R^4$ is 4-7-membered monocyclic heterocycloalkyl comprising one or more heteroatoms independently selected from N, S, and O. In a particular embodiment, $R^4$ is azetidinyl, pyrrolidinyl, piperidinyl, piperazinyl, morpholinyl, tetrahydrofuranyl, tetrahydropyranyl, or dioxanyl. In a more particular embodiment, $R^4$ is azetidinyl, pyrrolidinyl, piperidinyl, or morpholinyl.

In one embodiment, a compound of the invention is according to Formula I or II, wherein $R^4$ is 4-7-membered monocyclic heterocycloalkyl comprising one or more heteroatoms independently selected from N, S, and O, substituted with one or more halo, —C(=O)O$C_{1-4}$ alkyl. In a particular embodiment, $R^4$ is 4-7-membered monocyclic heterocycloalkyl comprising one or more heteroatoms independently selected from N, S, and O, substituted with one, two or three independently selected F, Cl, —C(=O)OCH$_3$, —C(=O)OCH$_2$CH$_3$, or —C(=O)OC(CH$_3$)$_3$. In another particular embodiment, $R^4$ is azetidinyl, pyrrolidinyl, piperidinyl, piperazinyl, morpholinyl, tetrahydrofuranyl, tetrahydropyranyl, or dioxanyl, each of which is substituted with one, two or three independently selected F, Cl, —C(=O)OCH$_3$, —C(=O)OCH$_2$CH$_3$, or —C(=O)OC(CH$_3$)$_3$. In a more particular embodiment, $R^4$ is 4-7-membered monocyclic heterocycloalkyl comprising one or more heteroatoms independently selected from N, S, and O, substituted with one F, Cl, —C(=O)OCH$_3$, —C(=O)OCH$_2$CH$_3$, or —C(=O)OC(CH$_3$)$_3$. In another particular embodiment, $R^4$ is azetidinyl, pyrrolidinyl, piperidinyl, piperazinyl, morpholinyl, tetrahydrofuranyl, tetrahydropyranyl, or dioxanyl, each of which is substituted with one F, Cl, —C(=O)OCH$_3$, —C(=O)OCH$_2$CH$_3$, or —C(=O)OC(CH$_3$)$_3$. In a most particular embodiment, $R^4$ is azetidinyl, pyrrolidinyl, piperidinyl, or morpholinyl, each of which is substituted with one, two or three independently selected F, Cl. In another most particular embodiment, $R^4$ is azetidinyl, pyrrolidinyl, piperidinyl, or morpholinyl, each of which is substituted with one —C(=O)OCH$_3$, —C(=O)OCH$_2$CH$_3$, or —C(=O)OC(CH$_3$)$_3$.

In one embodiment, a compound of the invention is according to Formula I or II, wherein $R^4$ is phenyl.

In one embodiment, a compound of the invention is according to Formula I or II, wherein $R^4$ is —S(=O)$_2$C$_{1-4}$ alkyl. In a particular embodiment, $R^4$ is —S(=O)$_2$CH$_3$, or —S(=O)$_2$CH$_2$CH$_3$.

In one embodiment, a compound of the invention is according to Formula I or II, wherein $R^4$ is —C(=O)OR$^{7a}$, and R$^{7a}$ is as previously described. In a particular embodiment, $R^{7a}$ is H. In another particular embodiment, $R^{7a}$ is $C_{1-4}$ alkyl. In yet another particular embodiment, $R^{7a}$ is $C_{1-4}$ alkyl substituted with one OH, $C_{1-4}$ alkoxy. In a more particular embodiment, $R^{7a}$ is Me, Et, iPr or tBu. In another more particular embodiment, $R^{7a}$ is Me, Et, iPr or tBu, each of which is substituted with one OH, $C_{1-4}$ alkoxy. In yet another more particular embodiment, $R^{7a}$ is Me, Et, iPr or tBu, each of which is substituted with one OH, —$OCH_3$. In a most particular embodiment, $R^4$ is —C(=O)$OCH_3$, —C(=O)$OCH_2CH_3$, or —C(=O)OC($CH_3$)$_3$.

In one embodiment, a compound of the invention is according to Formula I or II, wherein $R^4$ is —C(=O)$NR^{7b}R^{7c}$, and each $R^{7b}$ or $R^{7c}$ is as previously described. In a particular embodiment, $R^{7b}$ and $R^{7c}$ are H. In another particular embodiment, one of $R^{7b}$ or $R^{7c}$ is H, and the other is $C_{1-4}$ alkyl. In yet another particular embodiment, one of $R^{7b}$ or $R^{7c}$ is H, and the other is $C_{1-4}$ alkyl substituted with one OH, $C_{1-4}$ alkoxy. In a further particular embodiment, $R^{7b}$ and $R^{7c}$ are $C_{1-4}$ alkyl. In a more particular embodiment, one of $R^{7b}$ or $R^{7c}$ is H, and the other is Me, Et, iPr or tBu. In another more particular embodiment, one of $R^{7b}$ or $R^{7c}$ is H, and the other is Me, Et, iPr or tBu, each of which is substituted with one OH, $C_{1-4}$ alkoxy. In yet another more particular embodiment, one of $R^{7b}$ or $R^{7c}$ is H, and the other is Me, Et, iPr or tBu, each of which is substituted with one OH, —$OCH_3$. In a most particular embodiment, $R^4$ is —C(=O)$NHCH_3$, —C(=O)N($CH_3$)$_2$, —C(=O)$NHCH_2CH_3$, —C(=O)$NHCH_2CH_2$—OH or —C(=O)$NHCH_2CH_2$—$OCH_3$.

In one embodiment, a compound of the invention is according to Formula I or II, wherein $R^4$ is —NHC(=O)$OR^{7d}$, and $R^{7d}$ is as previously described. In a particular embodiment, $R^{7d}$ is H. In another particular embodiment, $R^{7d}$ is $C_{1-4}$ alkyl. In yet another particular embodiment, $R^{7d}$ is $C_{1-4}$ alkyl substituted with one OH, $C_{1-4}$ alkoxy. In a more particular embodiment, $R^{7d}$ is Me, Et, iPr or tBu. In another more particular embodiment, $R^{7d}$ is Me, Et, iPr or tBu, each of which is substituted with one OH, $C_{1-4}$ alkoxy. In yet another more particular embodiment, $R^{7d}$ is Me, Et, iPr or tBu, each of which is substituted with one OH, —$OCH_3$. In a most particular embodiment, $R^4$ is —NHC(=O)$OCH_3$, —NHC(=O)$OCH_2CH_3$, or —NHC(=O)OC($CH_3$)$_3$.

In one embodiment, a compound of the invention is according to Formula I or II, wherein $R^4$ is —NHC(=O)$R^{7e}$, and $R^{7e}$ is as previously described. In a particular embodiment, $R^{7e}$ is H. In another particular embodiment, $R^{7e}$ is $C_{1-4}$ alkyl. In yet another particular embodiment, $R^{7e}$ is $C_{1-4}$ alkyl substituted with one OH, $C_{1-4}$ alkoxy. In a more particular embodiment, $R^{7e}$ is Me, Et, iPr or tBu. In another more particular embodiment, $R^{7e}$ is Me, Et, iPr or tBu, each of which is substituted with one OH, $C_{1-4}$ alkoxy. In yet another more particular embodiment, $R^{7e}$ is Me, Et, iPr or tBu, each of which is substituted with one OH, —$OCH_3$. In a most particular embodiment, $R^4$ is —NHC(=O)$CH_3$, —NHC(=O)$CH_2CH_3$, or —NHC(=O)C($CH_3$)$_3$.

In one embodiment, a compound of the invention is according to Formula I or II, wherein $R^4$ is —$NR^{8a}R^{8b}$, and each $R^{8a}$ or $R^{8b}$ is as previously described. In a particular embodiment, $R^{8a}$ and $R^{8b}$ are H. In another embodiment, one of $R^{8a}$ or $R^{8b}$ is H, and the other is $C_{1-4}$ alkyl. In yet another particular embodiment, one of $R^{8a}$ or $R^{8b}$ is H, and the other is $C_{1-4}$ alkyl substituted with one OH, $C_{1-4}$ alkoxy, or phenyl. In a further particular embodiment, $R^{8a}$ and $R^{8b}$ are $C_{1-4}$ alkyl. In a more particular embodiment, one of $R^{8a}$ or $R^{8b}$ is H, and the other is Me, Et, iPr or tBu. In another more particular embodiment, one of $R^{8a}$ or $R^{8b}$ is H, and the other is Me, Et, iPr or tBu, each of which is substituted with one OH, $C_{1-4}$ alkoxy, or phenyl. In yet another more particular embodiment, one of $R^{8a}$ or $R^{8b}$ is H, and the other is Me, Et, iPr or tBu, each of which is substituted with one OH, —$OCH_3$, or phenyl. In a most particular embodiment, $R^4$ is —$NH_2$, —$NHCH_3$, —N($CH_3$)$_2$, —$NHCH_2$Phenyl, or —$NHCH_2CH_2$—$OCH_3$.

In another embodiment, a compound of the invention is according to Formula I or II, wherein $R^1$ is 4-7 membered monocyclic heterocycloalkyl comprising 1 to 2 heteroatoms independently selected from N, O, and S. In a particular embodiment, $R^1$ is azetidinyl, pyrrolidinyl, piperidinyl, piperazinyl, morpholinyl, tetrahydrofuranyl, tetrahydropyranyl, or dioxanyl. In a more particular embodiment, $R^1$ is azetidinyl.

In one embodiment, a compound of the invention is according to Formula I or II, wherein $R^1$ is 4-7 membered monocyclic heterocycloalkyl comprising 1 to 2 heteroatoms independently selected from N, O, and S, substituted with one or more independently selected $C_{1-4}$ alkyl, —C(=O)$C_{1-4}$ alkyl, or —C(=O)O$C_{1-4}$ alkyl. In another embodiment, $R^1$ is azetidinyl, pyrrolidinyl, piperidinyl, piperazinyl, morpholinyl, tetrahydrofuranyl, tetrahydropyranyl, or dioxanyl, each of which is substituted with one or more independently selected $C_{1-4}$ alkyl, —C(=O)$C_{1-4}$ alkyl, or —C(=O)O$C_{1-4}$ alkyl. In a particular embodiment, $R^1$ is 4-7 membered monocyclic heterocycloalkyl comprising 1 to 2 heteroatoms independently selected from N, O, and S, substituted with one $C_{1-4}$ alkyl, —C(=O)$C_{1-4}$ alkyl, or —C(=O)O$C_{1-4}$ alkyl. In another particular embodiment, $R^1$ is azetidinyl, pyrrolidinyl, piperidinyl, piperazinyl, morpholinyl, tetrahydrofuranyl, tetrahydropyranyl, or dioxanyl, each of which is substituted with one $C_{1-4}$ alkyl, —C(=O)$C_{1-4}$ alkyl, or —C(=O)O$C_{1-4}$ alkyl. In a more particular embodiment, $R^1$ is 4-7 membered monocyclic heterocycloalkyl comprising 1 to 2 heteroatoms independently selected from N, O, and S, substituted with one or more independently selected —$CH_3$, —C(=O)$CH_3$, or —C(=O)OC($CH_3$)$_3$. In another more particular embodiment, $R^1$ is azetidinyl, pyrrolidinyl, piperidinyl, piperazinyl, morpholinyl, tetrahydrofuranyl, tetrahydropyranyl, or dioxanyl, each of which is substituted with one or more independently selected —$CH_3$, —C(=O)$CH_3$, —C(=O)$OCH_3$, or —C(=O)OC($CH_3$)$_3$. In yet another more particular embodiment, $R^1$ is azetidinyl, pyrrolidinyl, piperidinyl, piperazinyl, morpholinyl, tetrahydrofuranyl, tetrahydropyranyl, or dioxanyl, each of which is substituted with one —C(=O)$CH_3$, —C(=O)$OCH_3$, or —C(=O)OC($CH_3$)$_3$.

In one embodiment, a compound of the invention is according to Formula I or II, wherein $R^1$ is phenyl.

In another embodiment, a compound of the invention is according to Formula I or II, wherein $R^1$ is phenyl substituted with one or more independently selected $R^5$ groups. In a particular embodiment, $R^1$ is phenyl substituted with one, two, or three independently selected $R^5$ groups. In another particular embodiment, $R^1$ is phenyl substituted with one $R^5$ group.

In one embodiment, a compound of the invention is according to Formula I or II, wherein $R^1$ is 5-6 membered monocyclic heteroaryl comprising 1 or 2 heteroatoms independently selected from N, O, and S. In a particular embodiment, $R^1$ is imidazolyl, pyrazolyl, thiazolyl, oxazolyl, pyridinyl, pyrimidinyl or pyrazinyl. In a more particular embodiment, $R^1$ is pyridinyl.

In another embodiment, a compound of the invention is according to Formula I or II, wherein $R^1$ is 5-6 membered monocyclic heteroaryl comprising 1, 2 or 3 heteroatoms independently selected from N, O, and S substituted with one or more independently selected R⁵ groups. In another embodiment R¹ is imidazolyl, pyrazolyl, thiazolyl, oxazolyl, pyridinyl, pyrimidinyl or pyrazinyl, each of which is substituted with one or more independently selected R⁵ groups. In a particular embodiment, R¹ is 5-6 membered monocyclic heteroaryl comprising 1, 2 or 3 heteroatoms independently selected from N, O, and S substituted with one, two, or three independently selected R⁵ groups. In another particular embodiment, R¹ is imidazolyl, pyrazolyl, thiazolyl, oxazolyl, pyridinyl, pyrimidinyl or pyrazinyl, each of which is substituted with one, two, or three independently selected R⁵ groups. In a more particular embodiment, R¹ is 5-6 membered monocyclic heteroaryl comprising 1, 2 or 3 heteroatoms independently selected from N, O, and S substituted with one R⁵ group. In another more particular embodiment, R¹ is imidazolyl, pyrazolyl, thiazolyl, oxazolyl, pyridinyl, pyrimidinyl or pyrazinyl, each of which is substituted with one R⁵ group.

In one embodiment, a compound of the invention is according to Formula I or II, wherein R⁵ is halo, OH, or CN. In a particular embodiment, R⁵ is F, Cl, OH, or CN.

In one embodiment, a compound of the invention is according to Formula I or II, wherein R⁵ is $C_{1-4}$ alkyl. In a particular embodiment, R⁵ is Me, Et, or iPr.

In another embodiment, a compound of the invention is according to Formula I or II, wherein R⁵ is $C_{1-4}$ alkyl substituted with one or more independently selected halo, —NR⁹ᵃR⁹ᵇ, —C(=O)NR⁹ᶜR⁹ᵈ, wherein R⁹ᵃ, R⁹ᵇ, R⁹ᶜ, or R⁹ᵈ is as previously described. In another embodiment, R⁵ is Me, or Et, each of which is substituted with one or more independently selected halo, —NR⁹ᵃR⁹ᵇ, —C(=O)NR⁹ᶜR⁹ᵈ. In a particular embodiment, R⁵ is $C_{1-4}$ alkyl substituted with one, two or three independently selected halo, —NR⁹ᵃR⁹ᵇ, or —C(=O)NR⁹ᶜR⁹ᵈ. In another particular embodiment, R⁵ is Me, or Et, each of which is substituted with one, two, or three independently selected halo, —NR⁹ᵃR⁹ᵇ, or —C(=O)NR⁹ᶜR⁹ᵈ. In a more particular embodiment, R⁵ is $C_{1-4}$ alkyl substituted with one halo, —NR⁹ᵃR⁹ᵇ, or —C(=O)NR⁹ᶜR⁹ᵈ. In another more particular embodiment, R⁵ is Me, or Et, each of which is substituted with one halo, —NR⁹ᵃR⁹ᵇ, or —C(=O)NR⁹ᶜR⁹ᵈ. In one embodiment, each R⁹ᵃ, R⁹ᵇ, R⁹ᶜ, or R⁹ᵈ is independently selected from H, Me, and Et. In a most particular embodiment, R⁵ is —CF₃, —CH₂NH₂, —CH₂NHMe, —CH₂NMe₂, —CH₂C(=O)NH₂, —CH₂C(=O)NHMe, or —CH₂C(=O)NMe₂.

In one embodiment, a compound of the invention is according to Formula I or II, wherein R⁵ is $C_{1-4}$ alkoxy. In a particular embodiment, R⁵ is —OMe, —OEt, or -OiPr.

In another embodiment, a compound of the invention is according to Formula I or II, wherein R⁵ is $C_{1-4}$ alkoxy substituted with one —NR⁹ᵉR⁹ᶠ, wherein R⁹ᵉ are R⁹ᶠ as previously described. In another embodiment, R⁵ is —OEt, substituted with one —NR⁹ᵉR⁹ᶠ. In one embodiment, each R⁹ᵉ, and R⁹ᶠ, is independently selected from H, Me, and Et. In a most particular embodiment, R⁵ is —OCH₂CH₂NH₂, —OCH₂CH₂NHMe, or —OCH₂CH₂NMe₂.

In another embodiment, a compound of the invention is according to Formula I or II, wherein R⁵ is —S(=O)₂$C_{1-4}$ alkyl. In a particular embodiment, R⁵ is —S(=O)₂CH₃.

In one embodiment, a compound of the invention is according to Formula IIIa or IIIb:

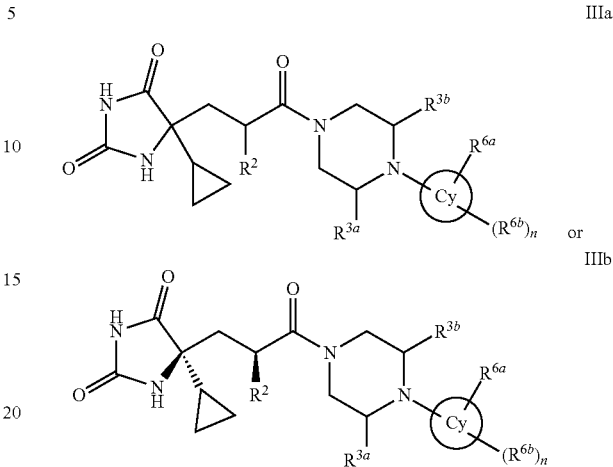

wherein R², R³ᵃ, R³ᵇ, R⁶ᵃ, R⁶ᵇ, the subscript n and Cy are as defined above.

In one embodiment, a compound of the invention is according to Formula IIIc or IIId:

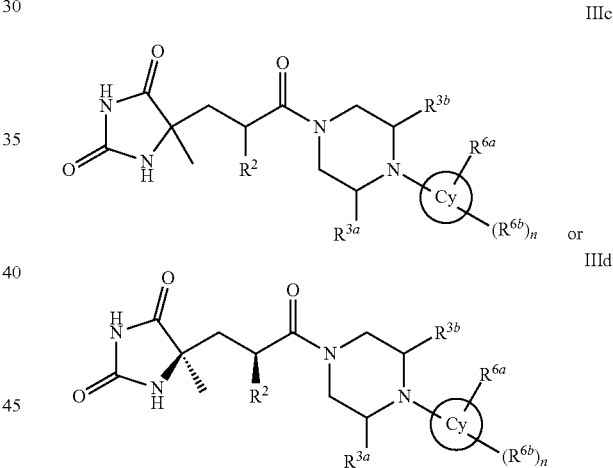

wherein R², R³ᵃ, R³ᵇ, R⁶ᵃ, R⁶ᵇ, the subscript n and Cy are as defined above.

In one embodiment, a compound of the invention is according to any one of Formulae I-IIId, wherein R² is H.

In one embodiment, a compound of the invention is according to any one of Formulae I-IIId, wherein R² is —OH.

In one embodiment, a compound of the invention is according to any one of Formulae I-IIId, wherein R² is $C_{1-4}$ alkoxy. In a particular embodiment, R² is —OMe, —OEt, or -OiPr. In a more particular embodiment, R² is —OMe.

In one embodiment, a compound of the invention is according to any one of Formulae I-IIId, wherein R² is $C_{1-4}$ alkyl. In a particular embodiment, R² is Me, Et, or iPr. In a more particular embodiment, R² is Me, or Et.

In one embodiment, a compound of the invention is according to any one of Formulae I-IIId, wherein R² is $C_{1-4}$ alkyl substituted with one OH, or CN. In a particular embodiment, $R^2$ is Me, or Et, each of which is substituted with one OH, or CN. In a more particular embodiment, $R^2$ is —$CH_2$—OH, or —$CH_2$—CN.

In one embodiment, a compound of the invention is according to any one of Formulae I-IIId, wherein $R^2$ is $C_{1-4}$ alkyl substituted with one $C_{1-4}$ alkoxy optionally substituted with one phenyl. In another embodiment, $R^2$ is Me, or Et, each of which is substituted with one $C_{1-4}$ alkoxy optionally substituted with one phenyl. In a particular embodiment, $R^2$ is $C_{1-4}$ alkyl substituted with one —OMe, —OEt, each of which is optionally substituted with one phenyl. In another particular embodiment, $R^2$ is Me, or Et, each of which is substituted with one —OMe, —OEt, each of which is optionally substituted with one phenyl. In a more particular embodiment, $R^2$ is —$CH_2OCH_3$, —$CH_2OCH_2CH_3$, —$CH_2OCH_2CH_2OCH_3$, or —$CH_2OCH_2Phenyl$.

In one embodiment, a compound of the invention is according to any one of Formulae I-IIId, wherein $R^2$ is $C_{1-4}$ alkyl substituted with one 5-6 membered monocyclic heteroaryl comprising 1 or 2 heteroatoms independently selected from N, O, and S, optionally substituted with one or more independently selected $C_{1-4}$ alkyl. In another embodiment, $R^2$ is Me, or Et, each of which is substituted with one 5-6 membered monocyclic heteroaryl comprising 1 or 2 heteroatoms independently selected from N, O, and S, optionally substituted with one or more independently selected $C_{1-4}$ alkyl. In a particular embodiment, $R^2$ is $C_{1-4}$ alkyl substituted with one imidazolyl, pyrrazolyl, oxazolyl, each of which is optionally substituted with one or more independently selected $C_{1-4}$ alkyl. In another particular embodiment, $R^2$ is Me or Et, each of which is substituted with one imidazolyl, pyrrazolyl, oxazolyl, each of which is optionally substituted with one or more independently selected $C_{1-4}$ alkyl. In a more particular embodiment, $R^2$ is $C_{1-4}$ alkyl substituted with one imidazolyl, pyrrazolyl, oxazolyl, each of which is optionally substituted with one or more independently selected Me, or Et. In another embodiment, $R^2$ is Me, or Et, each of which is substituted with one imidazolyl, pyrrazolyl, oxazolyl, each of which is optionally substituted with one or more independently selected Me, or Et.

In one embodiment, a compound of the invention is according to Formula IVa or IVb:

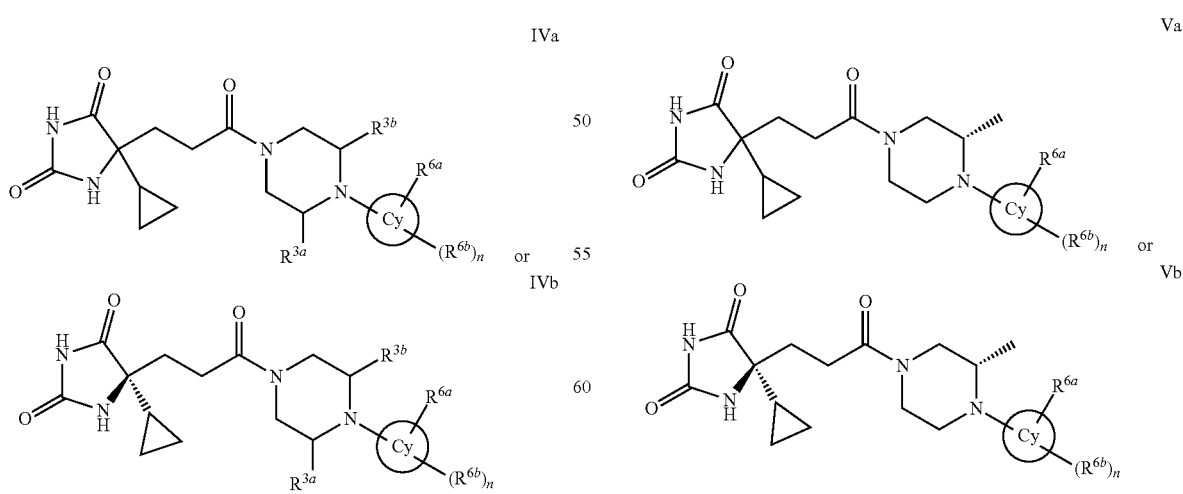

wherein $R^{3a}$, $R^{3b}$, $R^{6a}$, $R^{6b}$, the subscript n and Cy are as defined above.

In one embodiment, a compound of the invention is according to Formula IVc or IVd:

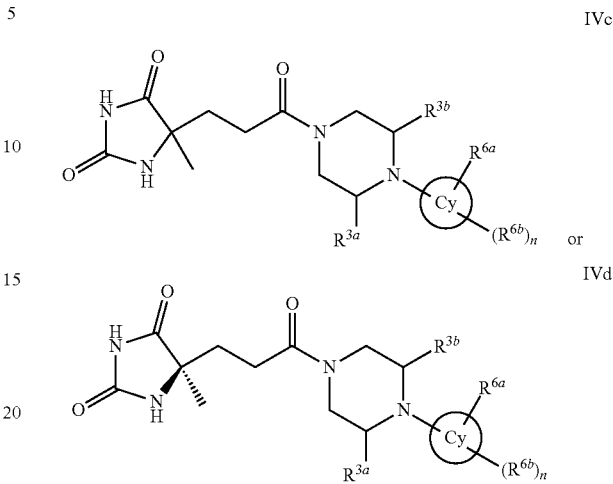

wherein $R^{3a}$, $R^{3b}$, $R^{6a}$, $R^{6b}$, the subscript n and Cy are as defined above.

In one embodiment, a compound of the invention is according to any one of Formulae I-IVd, wherein $R^{3a}$, and $R^{3b}$ are both H. In another embodiment, one of $R^{3a}$ and $R^{3b}$ is H, and the other is $C_{1-4}$ alkyl optionally substituted with one or more halo. In a particular embodiment, one of $R^{3a}$ and $R^{3b}$ is H, and the other is Me or Et optionally substituted with one or more halo. In another particular embodiment, one of $R^{3a}$ and $R^{3b}$ is H, and the other is Me or Et. In a more particular embodiment, one of $R^{3a}$ and $R^{3b}$ is H, and the other is Me, Et or $CF_3$. In a most particular embodiment, one of $R^{3a}$ and $R^{3b}$ is H, and the other is Me. In another most particular embodiment, one of $R^{3a}$ and $R^{3b}$ is H, and the other is $CF_3$. In another most particular embodiment, $R^{3a}$ and $R^{3b}$ are both Me.

In one embodiment, a compound of the invention is according to Formula Va or Vb:

wherein $R^{6a}$, $R^{6b}$, the subscript n and Cy are as defined above.

In one embodiment, a compound of the invention is according to Formula Vc or Vd:

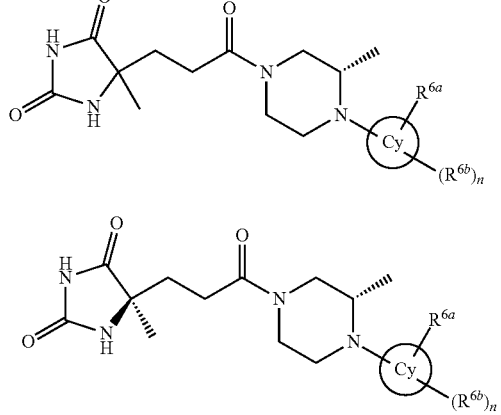

wherein $R^{6a}$, $R^{6b}$, the subscript n and Cy are as defined above.

In one embodiment, a compound of the invention is according to any one of Formulae I-Vd, wherein Cy is 6-10 membered monocyclic or fused bicyclic aryl. In a particular embodiment, Cy is phenyl, or naphthyl. In a more particular embodiment, Cy is phenyl.

In one embodiment, a compound of the invention is according to any one of Formulae I-Vd, wherein Cy is 5-10 membered monocyclic or fused bicyclic heteroaryl comprising 1, 2 or 3 heteroatoms independently selected from N, O, and S. In a particular embodiment, Cy is pyrazolyl, oxazolyl, oxadiazolyl, thiazolyl, pyridinyl, pyrazinyl, pyridazinyl, pyrimidinyl, indolyl, indazolyl, pyrrolopyridinyl, or benzofuranyl. In a more particular embodiment, Cy is pyridinyl.

In one embodiment, a compound of the invention is according to Formula VIa, or VIb:

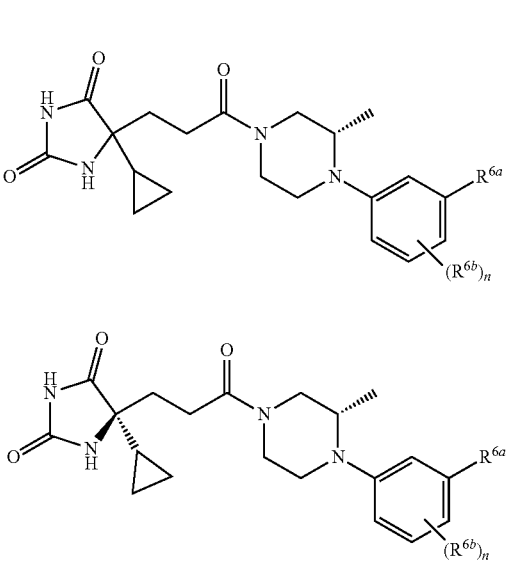

wherein $R^{6a}$, $R^{6b}$, and the subscript n are as defined above.

In one embodiment, a compound of the invention is according to Formula VIc or VId:

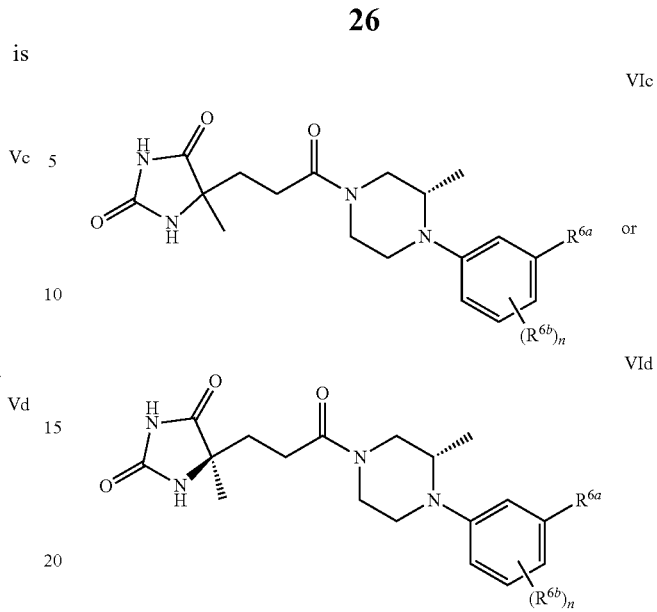

wherein $R^{6a}$, $R^{6b}$, and the subscript n are as defined above.

In one embodiment, a compound of the invention is according to any one of Formulae I-VId, wherein $R^{6a}$ is $C_{2-4}$ alkyl optionally substituted with one or more halo. In a particular embodiment, $R^{6a}$ is —$CH_2CH_3$, or —$CH(CH_3)_2$, each of which is optionally substituted with one or more halo. In another particular embodiment, $R^{6a}$ is $C_{2-4}$ alkyl optionally substituted with one or more F. In a more particular embodiment, $R^{6a}$ is —$CH_2CH_3$, or —$CH(CH_3)_2$, each of which is optionally substituted with one or more F. In a most particular embodiment, $R^{6a}$ is —$CH_2CH_3$, or —$CH(CH_3)_2$. In a further most particular embodiment, $R^{6a}$ is —$CH_2CH_3$.

In one embodiment, a compound of the invention is according to any one of Formulae I-VId, wherein $R^{6a}$ is $C_{1-4}$ alkoxy optionally substituted with one or more halo. In a particular embodiment, $R^{6a}$ is —$OCH_3$, —$OCH_2CH_3$, each of which is optionally substituted with one or more halo. In another particular embodiment, $R^{6a}$ is $C_{1-4}$ alkoxy optionally substituted with one or more F. In a more particular embodiment, $R^{6a}$ is —$OCH_3$, —$OCH_2CH_3$, each of which is optionally substituted with one or more F. In a most particular embodiment, $R^{6a}$ is —$OCH_3$, —$OCH_2CH_3$, or —$OCF_3$. In a further most particular embodiment, $R^{6a}$ is —$OCH_3$.

In one embodiment, a compound of the invention is according to any one of Formulae I-VId, wherein the subscript n is 0.

In one embodiment, a compound of the invention is according to any one of Formulae I-VId, wherein the subscript n is 1, 2, or 3. In a particular embodiment, the subscript n in 1 or 2.

In one embodiment, a compound of the invention is according to any one of Formulae I-VId, wherein $R^{6b}$ is halo, —CN, —$NO_2$, $C_{1-4}$ alkyl, or $C_{1-4}$ alkoxy. In a particular embodiment, $R^{6b}$ is halo, $C_{1-4}$ alkyl, or $C_{1-4}$ alkoxy. In a more particular embodiment, $R^{6b}$ is F, Cl, —$CH_3$, —$CH_2CH_3$, —$OCH_3$, or —$OCH_2CH_3$. In a most particular embodiment, $R^{6b}$ is F, Cl, —$CH_3$, or —$OCH_3$.

In one embodiment, a compound of the invention is according to any one of Formulae I-VIb, wherein $R^{6b}$ is 5-10 membered monocyclic or fused bicyclic heteroaryl comprising 1, 2 or 3 heteroatoms independently selected from N, O, and S, optionally substituted with one or more independently selected halo, $C_{1-4}$ alkyl, $C_{1-4}$ alkoxy. In another embodiment, $R^{6b}$ is pyrrazolyl, oxazolyl, oxadiazolyl, thiazolyl, pyridinyl, pyrazinyl, pyridazinyl, or pyrimidinyl, each of which is optionally substituted with one or more independently selected halo, $C_{1-4}$ alkyl, $C_{1-4}$ alkoxy. In a particular embodiment, $R^{6b}$ is 5-10 membered monocyclic or fused bicyclic heteroaryl comprising 1, 2 or 3 heteroatoms independently selected from N, O, and S, optionally substituted with one, two, or three independently selected halo, $C_{1-4}$ alkyl, or $C_{1-4}$ alkoxy. In another particular embodiment, $R^{6b}$ is pyrrazolyl, oxazolyl, oxadiazolyl, thiazolyl, pyridinyl, pyrazinyl, pyridazinyl, or pyrimidinyl, each of which is optionally substituted with one, two, or three independently selected halo, $C_{1-4}$ alkyl, or $C_{1-4}$ alkoxy. In a more particular embodiment, $R^{6b}$ is 5-10 membered monocyclic or fused bicyclic heteroaryl comprising 1, 2 or 3 heteroatoms independently selected from N, O, and S, optionally substituted with one halo, $C_{1-4}$ alkyl, $C_{1-4}$ alkoxy. In another more particular embodiment, $R^{6b}$ is pyrrazolyl, oxazolyl, oxadiazolyl, thiazolyl, pyridinyl, pyrazinyl, pyridazinyl, or pyrimidinyl, each of which is optionally substituted with one halo, $C_{1-4}$ alkyl, or $C_{1-4}$ alkoxy. In a most particular embodiment, $R^{6b}$ is 5-10 membered monocyclic or fused bicyclic heteroaryl comprising 1, 2 or 3 heteroatoms independently selected from N, O, and S, optionally substituted with one, two, or three independently selected F, Cl, Me, Et, —OMe, or —OEt. In another more particular embodiment, $R^{6b}$ is pyrrazolyl, oxazolyl, oxadiazolyl, thiazolyl, pyridinyl, pyrazinyl, pyridazinyl, or pyrimidinyl, each of which is optionally substituted with one, two, or three independently selected F, Cl, Me, Et, —OMe, or —OEt.

In one embodiment, a compound of the invention is according to any one of Formulae I-VIb, wherein $R^{6b}$ is $-NR^{9g}R^{9h}$, wherein $R^{9g}$ and $R^{9h}$ are as previously described. In a particular embodiment, $R^{9g}$ and $R^{9h}$ are both H. In another particular embodiment, $R^{9g}$ and $R^{9h}$ are both $C_{1-4}$ alkyl. In yet another particular embodiment, one of $R^{9g}$ and $R^{9h}$ is H, and the other is $C_{1-4}$ alkyl. In a more particular embodiment, $R^{6b}$ is —NH$_2$, —NHMe, or —NMe$_2$.

In one embodiment, a compound of the invention is according to Formula VIIa, or VIIb:

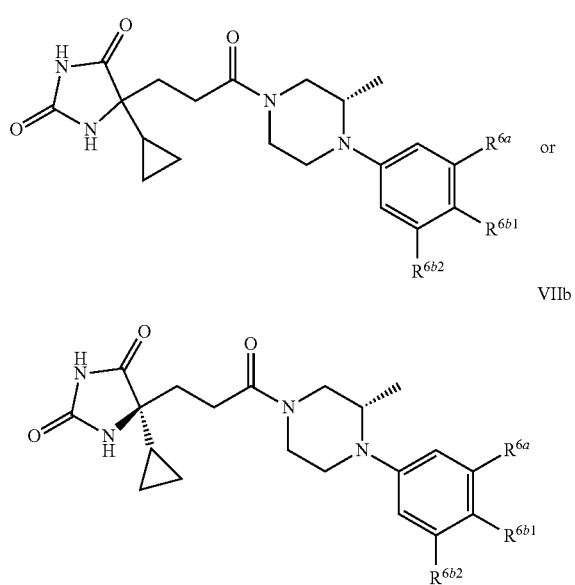

wherein $R^{6a}$, $R^{6b}$, and the subscript n are as defined above.

In one embodiment, a compound of the invention is according to Formula VIIc or VIId:

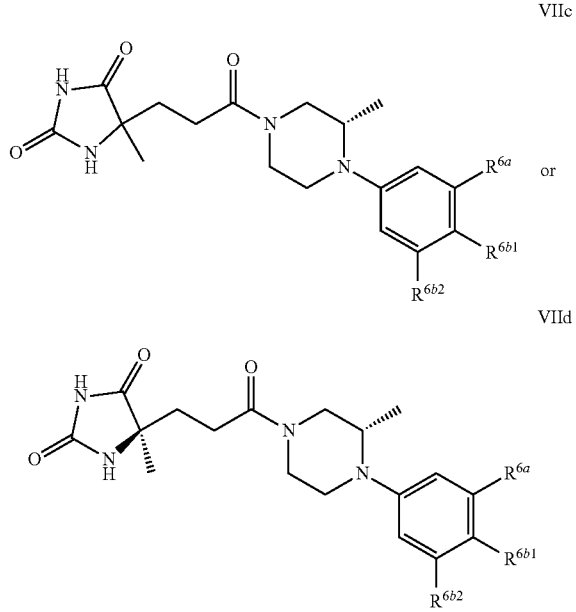

wherein $R^{6a}$ is as defined above, and each $R^{6b1}$ and $R^{6b2}$ is independently selected from H, halo, —CN, —NO$_2$, $C_{1-4}$ alkyl, and $C_{1-4}$ alkoxy.

In one embodiment, a compound of the invention is according to Formula VIIa, VIIb, VIIc or VIId wherein $R^{6a}$ is $C_{1-4}$ alkoxy optionally substituted with one or more halo. In a particular embodiment, $R^{6a}$ is —OCH$_3$, —OCH$_2$CH$_3$, each of which is optionally substituted with one or more halo. In another particular embodiment, $R^{6a}$ is $C_{1-4}$ alkoxy optionally substituted with one or more F. In a more particular embodiment, $R^{6a}$ is —OCH$_3$, —OCH$_2$CH$_3$, each of which is optionally substituted with one or more F. In a most particular embodiment, $R^{6a}$ is —OCH$_3$, —OCH$_2$CH$_3$, or —OCF$_3$. In a further most particular embodiment, $R^{6a}$ is —OCH$_3$.

In another particular embodiment, a compound of the invention is according to Formula VIIa, VIIb, VIIc or VIId, wherein each $R^{6b1}$ and $R^{6b2}$ is independently selected from H, halo, —CN, —NO$_2$, $C_{1-4}$ alkyl, and $C_{1-4}$ alkoxy. In a particular embodiment, each $R^{6b1}$ and $R^{6b2}$ is independently selected from H, F, Cl, —CN, —NO$_2$, —CH$_3$, —CH$_2$CH$_3$, —OCH$_3$, or —OCH$_2$CH$_3$. In a more particular embodiment, each $R^{6b1}$ and $R^{6b2}$ is independently selected from H, F, Cl, —CH$_3$, or —OCH$_3$.

In one embodiment, a compound of the invention is selected from:
5-[3-[4-(3-methoxyphenyl)piperazin-1-yl]-3-oxo-propyl]-5-methyl-imidazolidine-2,4-dione,
5-cyclopropyl-5-[3-[4-(3-methoxyphenyl)piperazin-1-yl]-3-oxo-propyl]imidazolidine-2,4-dione,
5-methyl-5-[3-oxo-3-[4-[4-(trifluoromethoxy)phenyl]piperazin-1-yl]propyl]imidazolidine-2,4-dione,
5-methyl-5-[3-oxo-3-[4-[2-(trifluoromethoxy)phenyl]piperazin-1-yl]propyl]imidazolidine-2,4-dione,
5-[3-[4-(4-methoxyphenyl)piperazin-1-yl]-3-oxo-propyl]-5-methyl-imidazolidine-2,4-dione, 5-[3-[4-(3-methoxyphenyl)piperazin-1-yl]-3-oxo-propyl]-5-(3-pyridyl)imidazolidine-2,4-dione,
5-[3-[4-(2-methoxyphenyl)piperazin-1-yl]-3-oxo-propyl]-5-methyl-imidazolidine-2,4-dione,
5-[3-[4-(3-methoxyphenyl)piperazin-1-yl]-3-oxo-propyl]-5-(2-pyridyl)imidazolidine-2,4-dione,
5-[3-[4-(4-fluoro-3-methoxy-phenyl)piperazin-1-yl]-3-oxo-propyl]-5-methyl-imidazolidine-2,4-dione,
5-[3-[4-(4-chloro-3-methoxy-phenyl)piperazin-1-yl]-3-oxo-propyl]-5-methyl-imidazolidine-2,4-dione,
5-[3-[4-(3,5-dimethoxyphenyl)piperazin-1-yl]-3-oxo-propyl]-5-methyl-imidazolidine-2,4-dione,
5-[3-[4-(3-fluoro-5-methoxy-phenyl)piperazin-1-yl]-3-oxo-propyl]-5-methyl-imidazolidine-2,4-dione,
5-[3-[4-(3-chloro-5-methoxy-phenyl)piperazin-1-yl]-3-oxo-propyl]-5-methyl-imidazolidine-2,4-dione,
5-[3-[4-(3,4-difluoro-5-methoxy-phenyl)piperazin-1-yl]-3-oxo-propyl]-5-methyl-imidazolidine-2,4-dione,
5-cyclopropyl-5-[3-[4-(3-fluoro-5-methoxy-phenyl)piperazin-1-yl]-3-oxo-propyl]imidazolidine-2,4-dione,
5-[3-[4-(3-ethoxyphenyl)piperazin-11-yl]-3-oxo-propyl]-5-methyl-imidazolidine-2,4-dione,
5-cyclopropyl-5-[3-[4-(4-fluoro-3-methoxy-phenyl)piperazin-1-yl]-3-oxo-propyl]imidazolidine-2,4-dione,
5-cyclopropyl-5-[3-[4-(3,4-difluoro-5-methoxy-phenyl)piperazin-1-yl]-3-oxo-propyl]imidazolidine-2,4-dione,
(R)-5-[3-[4-(3-fluoro-5-methoxy-phenyl)piperazin-1-yl]-3-oxo-propyl]-5-methyl-imidazolidine-2,4-dione
(R)-5-[3-[4-(3,4-difluoro-5-methoxy-phenyl)piperazin-1-yl]-3-oxo-propyl]-5-methyl-imidazolidine-2,4-dione
5-cyclopropyl-5-[3-[(3S)-4-(3,4-difluoro-5-methoxy-phenyl)-3-methyl-piperazin-1-yl]-3-oxo-propyl]imidazolidine-2,4-dione,
5-[3-[(3 S)-4-(3,4-difluoro-5-methoxy-phenyl)-3-methyl-piperazin-1-yl]-3-oxo-propyl]-5-methyl-imidazolidine-2,4-dione,
5-[3-[4-(3-fluoro-5-methoxy-phenyl)piperazin-1-yl]-3-oxo-propyl]-5-(3-pyridyl)imidazolidine-2,4-dione,
5-[3-[(3S)-4-(4-chloro-3-methoxy-phenyl)-3-methyl-piperazin-1-yl]-3-oxo-propyl]-5-methyl-imidazolidine-2,4-dione,
5-[3-[(3 S)-4-(3,5-dimethoxyphenyl)-3-methyl-piperazin-1-yl]-3-oxo-propyl]-5-methyl-imidazolidine-2,4-dione,
(5 S)-5-cyclopropyl-5-[(2S)-3-[4-(3-fluoro-5-methoxy-phenyl)piperazin-1-yl]-2-methyl-3-oxo-propyl]imidazolidine-2,4-dione,
(5R)-5-[(2S)-3-[4-(3-fluoro-5-methoxy-phenyl)piperazin-1-yl]-2-methyl-3-oxo-propyl]-5-methyl-imidazolidine-2,4-dione,
5-[3-[4-(3,4-difluoro-5-methoxy-phenyl)piperazin-1-yl]-3-oxo-propyl]-5-(3-pyridyl)imidazolidine-2,4-dione,
5-cyclopropyl-5-[(2S)-3-[(3S)-4-(3,4-difluoro-5-methoxy-phenyl)-3-methyl-piperazin-1-yl]-2-methyl-3-oxo-propyl]imidazolidine-2,4-dione,
5-[3-[(3 S)-4-(4-chloro-3,5-dimethoxy-phenyl)-3-methyl-piperazin-1-yl]-3-oxo-propyl]-5-methyl-imidazolidine-2,4-dione,
5-[3-[4-(4-chloro-3,5-dimethoxy-phenyl)piperazin-1-yl]-3-oxo-propyl]-5-methyl-imidazolidine-2,4-dione,
5-[3-[4-(5-methoxy-2-methyl-phenyl)piperazin-1-yl]-3-oxo-propyl]-5-methyl-imidazolidine-2,4-dione,
5-[3-[4-(3-methoxy-2-methyl-phenyl)piperazin-1-yl]-3-oxo-propyl]-5-methyl-imidazolidine-2,4-dione,
5-[3-[4-(4-chloro-5-methoxy-2-methyl-phenyl)piperazin-1-yl]-3-oxo-propyl]-5-methyl-imidazolidine-2,4-dione,
5-[3-[(3S)-4-(5-methoxy-2-methyl-phenyl)-3-methyl-piperazin-1-yl]-3-oxo-propyl]-5-methyl-imidazolidine-2,4-dione,
5-[3-[(3 S)-4-(4-chloro-5-methoxy-2-methyl-phenyl)-3-methyl-piperazin-1-yl]-3-oxo-propyl]-5-methyl-imidazolidine-2,4-dione,
(5S)-5-cyclopropyl-5-[3-[(3 S)-4-(3,4-difluoro-5-methoxy-phenyl)-3-methyl-piperazin-1-yl]-3-oxo-propyl]imidazolidine-2,4-dione,
5-[3-[4-(4-chloro-3-fluoro-5-methoxy-phenyl)piperazin-1-yl]-3-oxo-propyl]-5-methyl-imidazolidine-2,4-dione,
5-[3-[(3S)-4-(4-chloro-3-fluoro-5-methoxy-phenyl)-3-methyl-piperazin-1-yl]-3-oxo-propyl]-5-methyl-imidazolidine-2,4-dione,
5-[3-[4-(4-chloro-3,5-dimethoxy-phenyl)piperazin-1-yl]-2-methyl-3-oxo-propyl]-5-methyl-imidazolidine-2,4-dione,
5-[3-[4-(4-chloro-3-methoxy-phenyl)-3-methyl-piperazin-1-yl]-2-methyl-3-oxo-propyl]-5-methyl-imidazolidine-2,4-dione,
5-[3-[(3S)-4-(3,4-difluoro-5-methoxy-phenyl)-3-methyl-piperazin-1-yl]-2-methyl-3-oxo-propyl]-5-methyl-imidazolidine-2,4-dione,
5-[3-[4-(3,4-difluoro-5-methoxy-phenyl)piperazin-1-yl]-2-methyl-3-oxo-propyl]-5-methyl-imidazolidine-2,4-dione,
5-[3-[(3S)-4-(4-chloro-3,5-dimethoxy-phenyl)-3-methyl-piperazin-1-yl]-2-methyl-3-oxo-propyl]-5-methyl-imidazolidine-2,4-dione,
5-[3-[(3S)-4-(4-chloro-5-methoxy-2-methyl-phenyl)-3-methyl-piperazin-1-yl]-2-methyl-3-oxo-propyl]-5-methyl-imidazolidine-2,4-dione,
5-[3-[(3S)-4-(3,4-difluoro-5-methoxy-phenyl)-3-methyl-piperazin-1-yl]-2-methyl-3-oxo-propyl]-5-(methoxymethyl)imidazolidine-2,4-dione,
5-[3-[(3S)-4-(4-chloro-3-methoxy-phenyl)-3-methyl-piperazin-1-yl]-2-methyl-3-oxo-propyl]-5-(methoxymethyl)imidazolidine-2,4-dione,
5-[3-[4-(3,4-dichloro-5-methoxy-phenyl)piperazin-1-yl]-3-oxo-propyl]-5-methyl-imidazolidine-2,4-dione,
5-[3-[(3 S)-4-(3,4-difluoro-5-methoxy-phenyl)-3-methyl-piperazin-1-yl]-2-methyl-3-oxo-propyl]-5-(2-pyridyl)imidazolidine-2,4-dione,
5-[3-[4-(3-chloro-4-fluoro-5-methoxy-phenyl)piperazin-1-yl]-3-oxo-propyl]-5-methyl-imidazolidine-2,4-dione,
5-[3-[4-(3,4-difluoro-5-methoxy-phenyl)piperazin-1-yl]-2-methyl-3-oxo-propyl]imidazolidine-2,4-dione,
5-[3-[4-(3,4-difluoro-5-methoxy-phenyl)piperazin-1-yl]-2-methyl-3-oxo-propyl]-5-[(3,3-difluoropyrrolidin-1-yl)methyl]imidazolidine-2,4-dione,
5-[3-[(3 S)-4-(3-chloro-4-fluoro-5-methoxy-phenyl)-3-methyl-piperazin-11-yl]-3-oxo-propyl]-5-methyl-imidazolidine-2,4-dione,
(5 S)-5-[(2S)-3-[4-(3,4-difluoro-5-methoxy-phenyl)piperazin-1-yl]-2-methyl-3-oxo-propyl]-5-(2-pyridyl)imidazolidine-2,4-dione,
(5R)-5-[3-[(3 S)-4-(4-chloro-3-methoxy-phenyl)-3-methyl-piperazin-1-yl]-3-oxo-propyl]-5-methyl-imidazolidine-2,4-dione,
(5R)-5-[(2R)-3-[4-(3,4-difluoro-5-methoxy-phenyl)piperazin-1-yl]-2-(hydroxymethyl)-3-oxo-propyl]-5-methyl-imidazolidine-2,4-dione,
(5R)-5-[(2S)-3-[4-(3,4-difluoro-5-methoxy-phenyl)piperazin-1-yl]-2-methyl-3-oxo-propyl]-5-ethyl-imidazolidine-2,4-dione,
5-[3-[4-(4-chloro-2-methoxy-5-methyl-phenyl)piperazin-1-yl]-3-oxo-propyl]-5-methyl-imidazolidine-2,4-dione, (5 S)-5-[(2S)-3-[4-(3,4-difluoro-5-methoxy-phenyl)piperazin-1-yl]-2-methyl-3-oxo-propyl]-5-(methoxymethyl)imidazolidine-2,4-dione,
5-cyclopropyl-5-[3-[(3S)-4-(5-methoxy-3-pyridyl)-3-methyl-piperazin-1-yl]-3-oxo-propyl]imidazolidine-2,4-dione,
5-[3-[(3S)-4-(3,4-difluoro-5-methoxy-phenyl)-3-methyl-piperazin-1-yl]-3-oxo-propyl]-5-(6-methyl-2-pyridyl)imidazolidine-2,4-dione,
(5S)-5-[3-[(3S)-4-(3-chloro-4-fluoro-5-methoxy-phenyl)-3-methyl-piperazin-1-yl]-3-oxo-propyl]-5-cyclopropyl-imidazolidine-2,4-dione,
(5R)-5-[3-[(3 S)-4-(3-chloro-4-fluoro-5-methoxy-phenyl)-3-methyl-piperazin-1-yl]-3-oxo-propyl]-5-methyl-imidazolidine-2,4-dione,
5-cyclopropyl-5-[3-[(3 S)-4-(5-methoxy-3-pyridyl)-3-methyl-piperazin-1-yl]-2-methyl-3-oxo-propyl]imidazolidine-2,4-dione,
(5S)-5-[3-[(3S)-4-(4-chloro-3-fluoro-5-methoxy-phenyl)-3-methyl-piperazin-1-yl]-3-oxo-propyl]-5-cyclopropyl-imidazolidine-2,4-dione,
(5R)-5-[3-[(3S)-4-(4-fluoro-5-methoxy-2-methyl-phenyl)-3-methyl-piperazin-1-yl]-3-oxo-propyl]-5-methyl-imidazolidine-2,4-dione,
(5R)-5-[3-[4-(4-fluoro-5-methoxy-2-methyl-phenyl)piperazin-1-yl]-3-oxo-propyl]-5-methyl-imidazolidine-2,4-dione,
(5R)-5-[3-[4-(3-chloro-2-methoxy-phenyl)piperazin-1-yl]-3-oxo-propyl]-5-methyl-imidazolidine-2,4-dione,
(5R)-5-[3-[(3 S)-4-(3-chloro-2-methoxy-phenyl)-3-methyl-piperazin-1-yl]-3-oxo-propyl]-5-methyl-imidazolidine-2,4-dione,
(5R)-5-[3-[4-(3-ethylphenyl)piperazin-1-yl]-3-oxo-propyl]-5-methyl-imidazolidine-2,4-dione,
(5R)-5-[3-[4-(4-chloro-3-ethyl-phenyl)piperazin-1-yl]-3-oxo-propyl]-5-methyl-imidazolidine-2,4-dione,
(5R)-5-[3-[4-(3,5-diethylphenyl)piperazin-1-yl]-3-oxo-propyl]-5-methyl-imidazolidine-2,4-dione,
(5R)-5-[3-[4-(4-chloro-2-methoxy-phenyl)piperazin-1-yl]-3-oxo-propyl]-5-methyl-imidazolidine-2,4-dione,
(5R)-5-[3-[4-(4-fluoro-3,5-dimethoxy-phenyl)piperazin-1-yl]-3-oxo-propyl]-5-methyl-imidazolidine-2,4-dione,
(5R)-5-[3-[(3 S)-4-(4-chloro-3-ethyl-phenyl)-3-methyl-piperazin-1-yl]-3-oxo-propyl]-5-methyl-imidazolidine-2,4-dione,
(5R)-5-[3-[(3 S)-4-(4-chloro-2-methoxy-phenyl)-3-methyl-piperazin-1-yl]-3-oxo-propyl]-5-methyl-imidazolidine-2,4-dione,
(5R)-5-[3-[4-(5-chloro-2-methoxy-phenyl)piperazin-1-yl]-3-oxo-propyl]-5-methyl-imidazolidine-2,4-dione,
(5R)-5-[3-[4-(4-fluoro-2-methoxy-phenyl)piperazin-1-yl]-3-oxo-propyl]-5-methyl-imidazolidine-2,4-dione,
(5R)-5-[3-[4-(4-chloro-3-ethoxy-5-methoxy-phenyl)piperazin-1-yl]-3-oxo-propyl]-5-methyl-imidazolidine-2,4-dione,
(5R)-5-[3-[(3 S)-4-(4-chloro-3-ethoxy-5-methoxy-phenyl)-3-methyl-piperazin-1-yl]-3-oxo-propyl]-5-methyl-imidazolidine-2,4-dione,
(5R)-5-[3-[(3 S)-4-(4-fluoro-2-methoxy-phenyl)-3-methyl-piperazin-1-yl]-3-oxo-propyl]-5-methyl-imidazolidine-2,4-dione,
(5R)-5-[3-[4-(3-fluoro-2-methoxy-phenyl)piperazin-1-yl]-3-oxo-propyl]-5-methyl-imidazolidine-2,4-dione,
(5R)-5-[3-[4-(5-fluoro-2-methoxy-phenyl)piperazin-1-yl]-3-oxo-propyl]-5-methyl-imidazolidine-2,4-dione,
(5R)-5-[3-[(3 S)-4-(3-fluoro-2-methoxy-phenyl)-3-methyl-piperazin-1-yl]-3-oxo-propyl]-5-methyl-imidazolidine-2,4-dione,
(5R)-5-[3-[(3 S)-4-(4-chloro-3-isopropyl-phenyl)-3-methyl-piperazin-1-yl]-3-oxo-propyl]-5-methyl-imidazolidine-2,4-dione,
(5R)-5-[3-[(3S)-4-[4-chloro-3-(trifluoromethoxy)phenyl]-3-methyl-piperazin-1-yl]-3-oxo-propyl]-5-methyl-imidazolidine-2,4-dione,
(5R)-5-[3-[4-(4-chloro-3-isopropyl-phenyl)piperazin-1-yl]-3-oxo-propyl]-5-methyl-imidazolidine-2,4-dione,
(5R)-5-[3-[4-[4-chloro-3-(trifluoromethoxy)phenyl]piperazin-1-yl]-3-oxo-propyl]-5-methyl-imidazolidine-2,4-dione,
(5R)-5-[3-[(3 S)-4-(4-fluoro-3,5-dimethoxy-phenyl)-3-methyl-piperazin-1-yl]-3-oxo-propyl]-5-methyl-imidazolidine-2,4-dione,
(5R)-5-[3-[(3 S)-4-(3,4-dichloro-5-methoxy-phenyl)-3-methyl-piperazin-1-yl]-3-oxo-propyl]-5-methyl-imidazolidine-2,4-dione,
(5R)-5-[3-[(3 S)-4-(5-chloro-2-methoxy-phenyl)-3-methyl-piperazin-1-yl]-3-oxo-propyl]-5-methyl-imidazolidine-2,4-dione,
(5R)-5-[3-[(3 S)-4-(4,5-dichloro-2-methoxy-phenyl)-3-methyl-piperazin-1-yl]-3-oxo-propyl]-5-methyl-imidazolidine-2,4-dione,
(5R)-5-[3-[(3 S)-4-(4-fluoro-3-methoxy-phenyl)-3-methyl-piperazin-1-yl]-3-oxo-propyl]-5-methyl-imidazolidine-2,4-dione,
(5R)-5-[3-[4-(4,5-dichloro-2-methoxy-phenyl)piperazin-1-yl]-3-oxo-propyl]-5-methyl-imidazolidine-2,4-dione,
(5R)-5-[3-[(3S)-4-(4-chloro-2-methoxy-5-methyl-phenyl)-3-methyl-piperazin-1-yl]-3-oxo-propyl]-5-methyl-imidazolidine-2,4-dione,
(5R)-5-[3-[(3 S)-4-(3-chloro-5-methoxy-phenyl)-3-methyl-piperazin-1-yl]-3-oxo-propyl]-5-methyl-imidazolidine-2,4-dione,
(5R)-5-[3-[4-(4-chloro-2,5-dimethoxy-phenyl)piperazin-1-yl]-3-oxo-propyl]-5-methyl-imidazolidine-2,4-dione,
2-[4-[3-[(3 S)-4-(4-chloro-3-ethyl-phenyl)-3-methyl-piperazin-1-yl]-3-oxo-propyl]-2,5-dioxo-imidazolidin-4-yl]acetic acid,
(5R)-5-[3-[(3S)-4-[4-chloro-3-(dimethylamino)-5-methoxy-phenyl]-3-methyl-piperazin-1-yl]-3-oxo-propyl]-5-methyl-imidazolidine-2,4-dione,
5-[3-[(3 S)-4-(4-chloro-3-ethyl-phenyl)-3-methyl-piperazin-1-yl]-3-oxo-propyl]-5-(6-methyl-2-pyridyl)imidazolidine-2,4-dione,
5-[3-[(3 S)-4-[4-chloro-3-(trifluoromethoxy)phenyl]-3-methyl-piperazin-1-yl]-3-oxo-propyl]-5-(6-methyl-2-pyridyl)imidazolidine-2,4-dione,
(5R)-5-[3-[4-(4-chloro-5-ethyl-2-methoxy-phenyl)piperazin-1-yl]-3-oxo-propyl]-5-methyl-imidazolidine-2,4-dione,
(5R)-5-[3-[(3 S)-4-(4-chloro-5-ethyl-2-methoxy-phenyl)-3-methyl-piperazin-1-yl]-3-oxo-propyl]-5-methyl-imidazolidine-2,4-dione,
(5R)-5-[3-[(3 S)-4-(4-chloro-2,5-dimethoxy-phenyl)-3-methyl-piperazin-1-yl]-3-oxo-propyl]-5-methyl-imidazolidine-2,4-dione,
(5R)-5-[3-[(3S)-4-(4-chloro-3-methoxy-5-methyl-phenyl)-3-methyl-piperazin-1-yl]-3-oxo-propyl]-5-methyl-imidazolidine-2,4-dione,
(5R)-5-[3-[(3 S)-4-(4-chloro-3-ethyl-5-methoxy-phenyl)-3-methyl-piperazin-1-yl]-3-oxo-propyl]-5-methyl-imidazolidine-2,4-dione, (5R)-5-[3-[(3 S)-4-(4-chloro-3-methoxy-phenyl)-3-ethyl-piperazin-1-yl]-3-oxo-propyl]-5-methyl-imidazolidine-2,4-dione, (5R)-5-[3-[(3S)-4-[5-methoxy-2-(trifluoromethoxy)phenyl]-3-methyl-piperazin-1-yl]-3-oxo-propyl]-5-methyl-imidazolidine-2,4-dione, (5R)-5-[3-[(3S)-4-(4-chloro-3-methoxy-phenyl)-3-isopropyl-piperazin-1-yl]-3-oxo-propyl]-5-methyl-imidazolidine-2,4-dione, (5R)-5-[3-[(3 S)-4-(4-chloro-3,5-dimethoxyphenyl)-3-methyl-piperazin-1-yl]-3-oxo-propyl]-5-methyl-imidazolidine-2,4-dione, (5R)-5-[3-[(3 S)-4-(4-chloro-3-ethoxy-phenyl)-3-methyl-piperazin-1-yl]-3-oxo-propyl]-5-methyl-imidazolidine-2,4-dione, (5R)-5-[3-[4-(4-chloro-3-methoxy-5-methyl-phenyl)piperazin-1-yl]-3-oxo-propyl]-5-methyl-imidazolidine-2,4-dione, (5R)-5-[3-[(3 S)-4-(4,5-difluoro-2-methoxy-phenyl)-3-methyl-piperazin-1-yl]-3-oxo-propyl]-5-methyl-imidazolidine-2,4-dione, tert-butyl 3-[4-[3-[(3S)-4-(4-chloro-3-ethyl-phenyl)-3-methyl-piperazin-1-yl]-3-oxo-propyl]-2,5-dioxo-imidazolidin-4-yl]propanoate, (5R)-5-[3-[4-(4-chloro-3-ethyl-5-methoxy-phenyl)piperazin-1-yl]-3-oxo-propyl]-5-methyl-imidazolidine-2,4-dione, 3-[4-[3-[(3 S)-4-(4-chloro-3-ethyl-phenyl)-3-methyl-piperazin-1-yl]-3-oxo-propyl]-2,5-dioxo-imidazolidin-4-yl]propanoic acid, 5-[3-[(3S)-4-(4-chloro-3-ethyl-5-methoxy-phenyl)-3-methyl-piperazin-1-yl]-2-methyl-3-oxo-propyl]-5-(methoxymethyl)imidazolidine-2,4-dione, (5R)-5-[3-[4-(4-chloro-3-methoxy-phenyl)-3-(trifluoromethyl)piperazin-1-yl]-3-oxo-propyl]-5-methyl-imidazolidine-2,4-dione, (5R)-5-[3-[(3 S)-4-(4-chloro-3-fluoro-5-methoxy-phenyl)-3-methyl-piperazin-1-yl]-3-oxo-propyl]-5-methyl-imidazolidine-2,4-dione, 5-[3-[(3S)-4-(4-chloro-3-fluoro-5-methoxy-phenyl)-3-methyl-piperazin-1-yl]-2-methyl-3-oxo-propyl]-5-methyl-imidazolidine-2,4-dione, 5-[3-[(3S)-4-(4-chloro-3-fluoro-5-methoxy-phenyl)-3-methyl-piperazin-1-yl]-2-methyl-3-oxo-propyl]-5-(methoxymethyl)imidazolidine-2,4-dione, (5R)-5-[(2S)-3-[4-(4-chloro-3-fluoro-5-methoxy-phenyl)piperazin-1-yl]-2-methyl-3-oxo-propyl]-5-methyl-imidazolidine-2,4-dione, (5 S)-5-[(2S)-3-[4-(4-chloro-3-fluoro-5-methoxy-phenyl)piperazin-1-yl]-2-methyl-3-oxo-propyl]-5-(methoxymethyl)imidazolidine-2,4-dione, 5-[3-[(3S)-4-(4-chloro-3-ethyl-phenyl)-3-methyl-piperazin-1-yl]-2-methyl-3-oxo-propyl]-5-(methoxymethyl)imidazolidine-2,4-dione, 5-[3-[(3S)-4-(4-chloro-3-methoxy-5-methyl-phenyl)-3-methyl-piperazin-1-yl]-2-methyl-3-oxo-propyl]-5-methyl-imidazolidine-2,4-dione, 5-[3-[(3S)-4-(4-chloro-3-methoxy-5-methyl-phenyl)-3-methyl-piperazin-1-yl]-2-methyl-3-oxo-propyl]-5-(methoxymethyl)imidazolidine-2,4-dione, (5R)-5-[3-[(3R)-4-(3,4-difluoro-5-methoxy-phenyl)-3-methyl-piperazin-1-yl]-3-oxo-propyl]imidazolidine-2,4-dione, (5R)-5-[3-[4-(3,4-difluoro-5-methoxy-phenyl)piperazin-1-yl]-3-oxo-propyl]imidazolidine-2,4-dione, (5R)-5-[3-[(3S)-4-(3,4-difluoro-5-methoxy-phenyl)-3-methyl-piperazin-1-yl]-3-oxo-propyl]imidazolidine-2,4-dione, 5-cyclopropyl-5-[3-[4-(3-fluoro-5-methoxy-phenyl)piperazin-1-yl]-2-methyl-3-oxo-propyl]imidazolidine-2,4-dione, 5-[3-[4-(3-fluoro-5-methoxy-phenyl)piperazin-1-yl]-2-methyl-3-oxo-propyl]-5-methyl-imidazolidine-2,4-dione, (5R)-5-[3-[(3 S)-4-(3,5-dimethoxyphenyl)-3-methyl-piperazin-1-yl]-3-oxo-propyl]imidazolidine-2,4-dione, (5R)-5-[3-[(3 S)-4-(4-chloro-3-methoxy-phenyl)-3-methyl-piperazin-1-yl]-3-oxo-propyl]imidazolidine-2,4-dione, 5-cyclopropyl-5-[3-[(3S)-4-(3,4-difluoro-5-methoxy-phenyl)-3-methyl-piperazin-1-yl]-2-methyl-3-oxo-propyl]imidazolidine-2,4-dione, (5R)-5-[3-[4-(4-chloro-3,5-dimethoxy-phenyl)piperazin-1-yl]-3-oxo-propyl]imidazolidine-2,4-dione, (5R)-5-[3-[4-(5-methoxy-2-methyl-phenyl)piperazin-1-yl]-3-oxo-propyl]imidazolidine-2,4-dione, (5R)-5-[3-[4-(3-methoxy-2-methyl-phenyl)piperazin-1-yl]-3-oxo-propyl]imidazolidine-2,4-dione, (5R)-5-[3-[4-(4-chloro-5-methoxy-2-methyl-phenyl)piperazin-1-yl]-3-oxo-propyl]imidazolidine-2,4-dione, (5R)-5-[3-[(3 S)-4-(4-chloro-3,5-dimethoxy-phenyl)-3-methyl-piperazin-1-yl]-3-oxo-propyl]imidazolidine-2,4-dione, (5R)-5-[3-[(3 S)-4-(5-methoxy-2-methyl-phenyl)-3-methyl-piperazin-1-yl]-3-oxo-propyl]imidazolidine-2,4-dione, (5R)-5-[3-[(3 S)-4-(3-methoxy-2-methyl-phenyl)-3-methyl-piperazin-1-yl]-3-oxo-propyl]imidazolidine-2,4-dione, (5R)-5-[3-[(3S)-4-(4-chloro-5-methoxy-2-methyl-phenyl)-3-methyl-piperazin-1-yl]-3-oxo-propyl]imidazolidine-2,4-dione, (5R)-5-[3-[4-(4-chloro-3-fluoro-5-methoxy-phenyl)piperazin-1-yl]-3-oxo-propyl]imidazolidine-2,4-dione, (5R)-5-[3-[(3 S)-4-(4-chloro-3-fluoro-5-methoxy-phenyl)-3-methyl-piperazin-1-yl]-3-oxo-propyl]imidazolidine-2,4-dione, (5R)-5-[3-[4-(3,4-dichloro-5-methoxy-phenyl)piperazin-1-yl]-3-oxo-propyl]imidazolidine-2,4-dione, (5 S)-5-[3-[(3 S)-4-(4-chloro-3-methoxy-phenyl)-3-methyl-piperazin-1-yl]-3-oxo-propyl]-5-methyl-imidazolidine-2,4-dione, (5R)-5-[3-[4-(3-chloro-4-fluoro-5-methoxy-phenyl)piperazin-1-yl]-3-oxo-propyl]imidazolidine-2,4-dione, (5R)-5-[3-[(3 S)-4-(3-chloro-4-fluoro-5-methoxy-phenyl)-3-methyl-piperazin-1-yl]-3-oxo-propyl]imidazolidine-2,4-dione, (5R)-5-[3-[4-(4-chloro-3-ethoxy-5-methoxy-phenyl)piperazin-1-yl]-3-oxo-propyl]imidazolidine-2,4-dione, (5R)-5-[3-[(3 S)-4-(4-chloro-3-ethoxy-5-methoxy-phenyl)-3-methyl-piperazin-1-yl]-3-oxo-propyl]imidazolidine-2,4-dione, and (5R)-5-[3-[4-(4-fluoro-3,5-dimethoxy-phenyl)piperazin-1-yl]-3-oxo-propyl]imidazolidine-2,4-dione, In one embodiment, the compound is not (5R)-5-[3-[(3S)-4-(4-chloro-3-methoxy-5-methyl-phenyl)-3-methyl-piperazin-1-yl]-3-oxo-propyl]-5-methyl-imidazolidine-2,4-dione.

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (Bundgaard, 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Particularly useful are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base.

Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17$^{th}$ edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2—Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3—Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4—Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5—Injection

A compound of the invention according to Formula I may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of A compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of inflammatory diseases, and/or diseases involving degradation of cartilage and/or disruption of cartilage homeostasis.

In another embodiment, the present invention provides compounds of the invention, or pharmaceutical compositions comprising a compound of the invention for use in the manufacture of a medicament for use in the prophylaxis and/or treatment of inflammatory diseases, and/or diseases involving degradation of cartilage and/or disruption of cartilage homeostasis.

In one embodiment, the present invention provides pharmaceutical compositions comprising a compound of the invention, and another therapeutic agent. In a particular embodiment, the other therapeutic agent is an agent for the prophylaxis and/or treatment of inflammatory diseases, and/ or diseases involving degradation of cartilage and/or disruption of cartilage homeostasis.

In additional method of treatment aspects, this invention provides methods of prophylaxis and/or treatment of inflammatory diseases, and/or diseases involving degradation of cartilage and/or disruption of cartilage homeostasis, which methods comprise the administration of an effective amount of a compound of the invention or one or more of the pharmaceutical compositions herein described for the treatment or prophylaxis of said condition.

In additional method of treatment aspects, this invention provides methods of prophylaxis and/or treatment of a mammal afflicted with inflammatory diseases, and/or diseases involving degradation of cartilage and/or disruption of cartilage homeostasis, which methods comprise the administration of an effective amount of a compound of the invention or one or more of the pharmaceutical compositions herein described for the treatment or prophylaxis of said condition.

In one embodiment, the present invention provides compounds of the invention or pharmaceutical compositions comprising a compound of the invention, for use in the prophylaxis and/or treatment of inflammatory diseases. In a particular embodiment, the inflammatory disease is selected from rheumatoid arthritis, and osteoarthritis. More particularly, the inflammatory disease is osteoarthritis.

In another embodiment, the present invention provides compounds of the invention, or pharmaceutical compositions comprising a compound of the invention for use in the manufacture of a medicament for use in the prophylaxis and/or treatment of inflammatory diseases. In a particular embodiment, the inflammatory disease is selected from rheumatoid arthritis, and osteoarthritis. More particularly, the inflammatory disease is osteoarthritis.

In additional method of treatment aspects, this invention provides methods of prophylaxis and/or treatment of a mammal afflicted with inflammatory diseases, which methods comprise the administration of an effective amount of a compound of the invention or one or more of the pharmaceutical compositions herein described for the treatment or prophylaxis of said condition. In a particular embodiment, the inflammatory disease is selected from rheumatoid arthritis, and osteoarthritis. More particularly, the inflammatory disease is osteoarthritis.

In one embodiment, the present invention provides compounds of the invention or pharmaceutical compositions comprising a compound of the invention, for use in the prophylaxis and/or treatment of diseases involving degradation of cartilage and/or disruption of cartilage homeostasis. In a particular embodiment, the diseases involving degradation of cartilage and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the diseases involving degradation of cartilage and/or disruption of cartilage homeostasis is osteoarthritis (OA).

In another embodiment, the present invention provides compounds of the invention, or pharmaceutical compositions comprising a compound of the invention for use in the manufacture of a medicament for use in the prophylaxis and/or treatment of diseases involving degradation of cartilage and/or disruption of cartilage homeostasis. In a particular embodiment, the diseases involving degradation of cartilage and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly, the diseases involving degradation of cartilage and/or disruption of cartilage homeostasis is osteoarthritis (OA).

In additional method of treatment aspects, this invention provides methods of prophylaxis and/or treatment of a mammal afflicted with diseases involving degradation of cartilage and/or disruption of cartilage homeostasis, which methods comprise the administration of an effective amount of a compound of the invention or one or more of the pharmaceutical compositions herein described for the treatment or prophylaxis of said condition. In a particular embodiment, the diseases involving degradation of cartilage and/or disruption of cartilage homeostasis is selected from osteoarthritis, psoriatic arthritis, juvenile rheumatoid arthritis, gouty arthritis, septic or infectious arthritis, reactive arthritis, reflex sympathetic dystrophy, algodystrophy, achondroplasia, Paget's disease, Tietze syndrome or costal chondritis, fibromyalgia, osteochondritis, neurogenic or neuropathic arthritis, arthropathy, sarcoidosis, amylosis, hydarthrosis, periodical disease, rheumatoid spondylitis, endemic forms of arthritis like osteoarthritis deformans endemica, Mseleni disease and Handigodu disease; degeneration resulting from fibromyalgia, systemic lupus erythematosus, scleroderma and ankylosing spondylitis. More particularly the diseases involving degradation of cartilage and/or disruption of cartilage homeostasis is osteoarthritis (OA).

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 1 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 1000 mg of a compound of the invention, with particular doses each providing from about 10 to about 500 mg and especially about 30 to about 250 mg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compound of the inventions that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment and/or prophylaxis of a disease involving inflammation, particular agents include, but are not limited to, immunoregulatory agents e.g. azathioprine, corticosteroids (e.g. prednisolone or dexamethasone), cyclophosphamide, cyclosporin A, tacrolimus, mycophenolate, mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prophylaxis of arthritis (e.g. rheumatoid arthritis), particular agents include but are not limited to analgesics, non-steroidal anti-inflammatory drugs (NSAIDS), steroids, synthetic DMARDS (for example but without limitation methotrexate, leflunomide, sulfasalazine, Auranofin, sodium aurothiomalate, penicillamine, chloroquine, hydroxychloroquine, azathioprine, tofacitinib, baricitinib, fostamatinib, and cyclosporin), and biological DMARDS (for example but without limitation infliximab, etanercept, adalimumab, rituximab, and abatacept).

In one embodiment, a compound of the invention is co-administered with another therapeutic agent for the treatment and/or prophylaxis of SLE, particular agents include but are not limited to: human monoclonal antibodies (belimumab (Benlysta)), Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid, immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, a compound of the invention is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort™), fluocinonide, vitamin D3 analogues (for example, calcipotriol), argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive™, Enbrel™, Humira™, Remicade™, Raptiva™ and ustekinumab (a IL-12 and IL-23 blocker). Additionally, a compound of the invention may be administered in combination with other therapies including, but not limited to phototherapy, or photochemotherapy (e.g. psoralen and ultraviolet A phototherapy (PUVA)).

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

Chemical Synthetic Procedures

General

The compound of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art [2].

The following methods are presented with details as to the preparation of a compound of the invention as defined hereinabove and the comparative examples. A compound of the invention may be prepared from known or commercially available starting materials and reagents by one skilled in the art of organic synthesis.

All reagents are of commercial grade and are used as received without further purification, unless otherwise stated. Commercially available anhydrous solvents are used for reactions conducted under inert atmosphere. Reagent grade solvents are used in all other cases, unless otherwise specified. Column chromatography is performed on silica gel 60 (35-70 µm). Thin layer chromatography is carried out using pre-coated silica gel 60F-254 plates (thickness 0.25 mm). $^1$H NMR spectra are recorded on a 400 MHz Avance Bruker spectrometer or a 300 MHz DPX Bruker spectrometer. Chemical shifts (δ) for $^1$H NMR spectra are reported in parts per million (ppm) relative to tetramethylsilane (δ 0.00) or the appropriate residual solvent peak, i.e. $CHCl_3$ (δ 7.27), as internal reference. Multiplicities are given as singlet (s), doublet (d), triplet (t), quartet (q), quintuplet (quin), multiplet (m) and broad (br). Electrospray MS spectra are obtained on a Waters platform LC/MS spectrometer or with Waters Acquity UPLC with Waters Acquity PDA detector and SQD mass spectrometer. Columns used: UPLC BEH C18 1.7 µm 2.1×5 mm VanGuard Pre-column with Acquity UPLC BEH C18 1.7 µm 2.1×30 mm Column or Acquity UPLC BEH C18 1.7 µm 2.1×50 mm Column. All the methods are using MeCN/$H_2O$ gradients. MeCN and $H_2O$ contain either 0.1% Formic Acid or 0.05% $NH_3$. Preparative LCMS: column used, Waters XBridge Prep C18 5 µm ODB 30 mm ID×100 mm L (preparative column) and Waters XBridge C18 5 µm 4.6 mm ID×100 mm L (analytical column). All the methods are using MeCN/$H_2O$ gradients. MeCN and $H_2O$ contain either 0.1% Formic Acid or 0.1% Diethylamine. Chiral HPLC analysis are obtained from a Waters 2690 Alliance HPLC system. Microwave heating is performed with a Biotage Initiator. Optical rotation was determined on a Dr. Kernchen Propol digital automatic polarimeter.

TABLE I

List of abbreviations used in the experimental section:

| Abbreviation | Definition |
|---|---|
| µL | microliter |
| APMA | 4-aminophenylmercuric acetate |
| AUC | Area Under the Curve |
| BAL | Broncho-alveolar lavage |
| BALF | Broncho-alveolar lavage fluid |
| BINAP | 2,2'-Bis(diphenylphosphino)-1,1'-binaphthalene |
| br. d | Broad doublet |
| Boc | tert-Butyloxy-carbonyl |
| br. s | Broad singlet |
| BSA | Bovine serum albumine |
| br. t | Broad triplet |
| Cat. | Catalytic amount |
| cDNA | copy deoxyribonucleic acid |
| Cpd | Compound |
| d | doublet |
| DavePhos | 2-Dicyclohexylphosphino-2'-(N,N-dimethylamino)biphenyl |
| DCM | Dichloromethane |
| DEAD | diethyl azodicarboxylate |
| DIPE | Diisopropylether |

TABLE I-continued

List of abbreviations used in the experimental section:

| Abbreviation | Definition |
| --- | --- |
| DIPEA | N,N-diisopropylethylamine |
| DMA | Dimethylacetamide |
| DMAP | 4-Dimethylaminopyridine |
| DME | Dimethoxyethane |
| DMF | N,N-dimethylformamide |
| DMPU | 1,3-Dimethyl-3,4,5,6-tetrahydro-2(1H)-pyrimidinone |
| DMSO | Dimethylsulfoxide |
| dppf | 1,1'-Bis(diphenylphosphino)ferrocene |
| EDC | 1-ethyl-3-(3-dimethylaminopropyl)carbodiimide) |
| EDC•HCl | N-(3-Dimethylaminopropyl)-N'-ethylcarbodiimide hydrochloride |
| eq. | Equivalent |
| $Et_2O$ | Diethyl ether |
| EtOAc | Ethyl acetate |
| EtOH | Ethanol |
| FBS | Fetal bovine serum |
| FITC | Fluorescein Isothiocyanate |
| g | gram |
| h | hour |
| HATU | O-(7-azabenzotriazol-1-yl)-N,N,N',N'-tetramethyluronium hexafluorophosphate |
| HOBt | Hydroxybenzotriazole |
| HPLC | High pressure liquid chromatography |
| HRP | horseradish peroxydase |
| Int | Intermediate |
| JohnPhos | (2-Biphenyl)di-tert-butylphosphine |
| kg | kilogram |
| L | liter |
| LCMS | Liquid Chromatography-Mass Spectrometry |
| LDA | Lithium diisopropylamide |
| LiHMMDS | Lithium bis(trimethylsilyl)amide |
| m | multiplet |
| m-CPBA | 3-Chloroperbenzoic acid |
| MeCN | Acetonitrile |
| MEK | Methyl ethyl ketone |
| MeOH | Methanol |
| mg | milligram |
| min | minute |
| mL | millilitre |
| mmol | millimoles |
| MMP | Matrix Metallo Proteinase |
| Ms'd | Mass measured by LC-MS |
| Mtd | Method |
| MW | Molecular weight |
| N.A. | Not available |
| nBuOH | n-Butanol |
| Nva | Norvaline |
| NMR | Nuclear Magnetic Resonance |
| PBF | phosphate buffered formalin |
| PBS | Phosphate buffered saline |
| PCR | Polymerase chain reaction |
| $Pd(PPh_3)_4$ | Tetrakis(triphenylphosphine)palladium(0) |
| Pd/C | Palladium on Carbon 10% |
| $Pd_2(dba)_3$ | Tris(dibenzylideneacetone)dipalladium(0) |
| $PdCl_2$dppf | [1,1'-Bis(diphenylphosphino)ferrocene]dichloropalladium(II) |
| $PdCl_2[P(o-Tol)_3]_2$ | Dichlorobis(tri-o-tolylphosphine)palladium(II) |
| $Pd(OAc)_2$ | Palladium(II) acetate |
| PEG | Polyethylene glycol |
| PEPPSI™-IPr | [1,3-Bis(2,6-Diisopropylphenyl)imidazol-2-ylidene](3-chloropyridyl)palladium(II) dichloride |
| ppm | part-per-million |
| q | quadruplet |
| QrtPCR | quantitative real-time PCR |
| QTL | quantitative trait loci |
| r.t. | room temperature |
| RNA | Ribonucleic acid |
| Rt | retention time |
| RuPhos | 2-Dicyclohexylphosphino-2',6'-diisopropoxybiphenyl |
| s | singlet |
| sept | septuplet |
| SFC | Supercritical fluid chromatography |
| SM | Starting Material |
| Ster | Stereochemistry |
| t | triplet |
| TBAF | Tetra-n-butylammonium fluoride |
| t-BuOH | Tert-butanol |
| TBDPSCl | Tert-butyldiphenylsilyl chloride |
| TBSCl | Tert-butyldimethylsilyl chloride |
| TEA | Triethylamine |
| TFA | Trifluoroacetic acid |
| THF | Tetrahydrofuran |
| XantPhos | 4,5-Bis(diphenylphosphino)-9,9-dimethylxanthene |
| XPhos | 2-Dicyclohexylphosphino-2',4',6'-triisopropylbiphenyl |
| Bn | benzyl |
| BOP; | (Benzotriazol-1-yloxy)tris(dimethylamino)phosphonium hexafluorophosphate |
| $(COCl)_2$; | Oxalyl chhloride |
| $Et_3N$ | Triethyl amine |
| iPrOH; | isopropanol |
| NaOtBu; | Sodium terbutoxide |
| quin | quintuplet |
| MS | Mass spectrometry |
| NBS | N-Bromosuccinimide |
| $Pd(OH)_2$/C | Charcoal supported palladium hydroxide |
| $PBu_3$ | Tri-butyl phosphine |
| PDA; | Photodiode Array |
| tBu | Tert-Butyl |
| tBuLi | Tert-Butyl lithium |
| UPLC | Ultra Performance Liquid Chromatography |
| UPLC/MS | Ultra Performance Liquid Chromatography coupled mass spectrometry |

Example 1. Synthetic Preparation of the Compounds of the Invention

1.1. General Synthetic Methods
1.1.1.1. Synthetic Methods Overview
B: Preparation of Ketoester

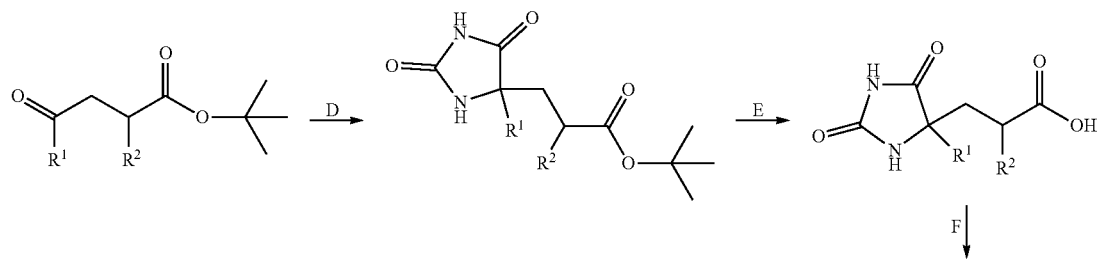

C: Preparation of Ketoamide NH

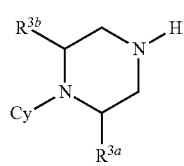

A: Preparation of Arylpiperidine
General methods A: Preparation of arylpiperazine
 Method A1: Buchwald reaction with NBoc-piperazine
 Method A2: HCl NBoc deprotection
 Method A3: HCl NBoc deprotection+basic workup
 Method A4: HCl NBoc deprotection+aqueous workup
 Method A5: Buchwald reaction with NH-piperazine
General methods B: Preparation of ketoester
 Method B1: from Meldrum's acid
 Method B2: esterification
 Method B3: Stetter reaction
 Method B4: via epoxide opening
General method C: preparation of ketoamide
 Method C1: preparation of acrylamide
 Method C2: Stetter reaction
 Method C3: via furan oxidation
General method D: Bucherer Bergs reaction
General method E: Method for preparation of hydantoin propionic acids
General method F: Amide bond formation
 Method F1: EDC/HOBt
 Method F2: HATU
 Method F3: BOP
General method G: Functionalization of final compound
 Method G1: O-debenzylation 1.1.1.2. General Methods A: Preparation of Arylpiperazine 1.1.1.2.1 Method A1: Buchwald Reaction with NBoc-Piperazine

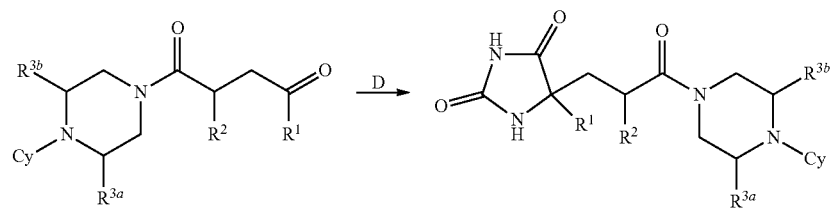

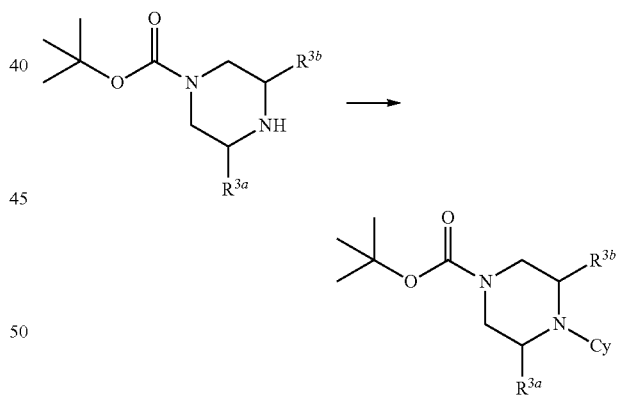

A flask is charged with N-Boc protected piperazine (1 eq.), bromoderivative (0.5-2 eq.), BINAP (0.042-0.12 eq.), NaOtBu (0.7-1.4 eq.) and toluene. The reaction mixture is degassed with $N_2$ and $Pd_2(dba)_3$ (0.021-0.06 eq.) is added. Reaction mixture is heated at 90-110° C. for 2 h-20 h. The reaction mixture is quenched by addition of water or saturated $NaHCO_3$ solution, extracted with DCM or EtOAc. The combined organic layers are washed with water and brine, dried (over anhydrous $Na_2SO_4$ or $MgSO_4$), filtered and concentrated in vacuo to afford the expected arylpiperazine (used as such or purified by flash chromatography on silica gel).

Illustrative Synthesis of ((S)-4-(4-Chloro-3-methoxy-5-methyl-phenyl)-3-methyl-piperazine-1-carboxylic Acid Tert-Butyl Ester

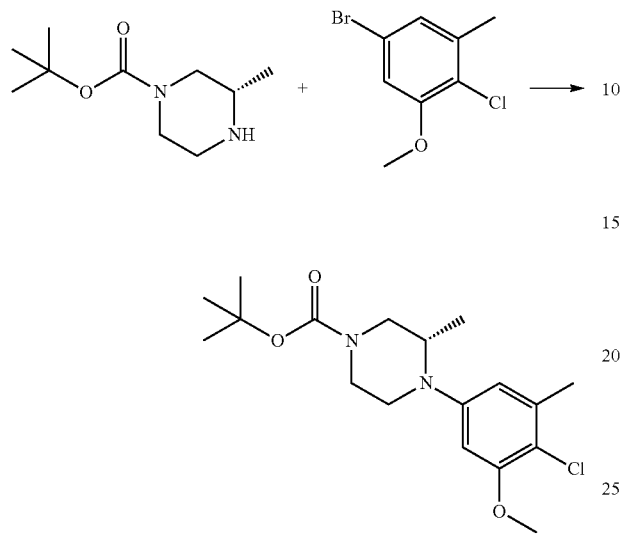

A flask is charged with (S)-3-methyl-piperazine-1-carboxylic acid tert-butyl ester (161 mg, 0.800 mmol, 1.2 eq.), 5-Bromo-2-chloro-1-methoxy-3-methyl-benzene (162 mg, 0.690 mmol, 1.0 eq.), BINAP (44 mg, 0.073 mmol, 0.1 eq.), NaOtBu (90 mg, 0.940 mmol, 1.4 eq.) and toluene (1.5 mL). The reaction mixture is degassed with $N_2$ and $Pd_2(dba)_3$ (31 mg, 0.034 mmol, 0.05 eq.) is added. Reaction mixture is heated at 95° C. for 2 h, quenched with water, extracted with DCM. The combined organic layers are washed with water and brine, dried over anhydrous $Na_2SO_4$, filtered and concentrated in vacuo to give crude compound. Crude is used as such. LCMS: MW (calcd): 320; m/z MW (obsd): 321 (M+H).

1.1.1.2.2 Method A2 (HCl)

A flask is charged with N-tert-butoxycarbonyl derivative (1 eq.), HCl 4N in dioxane (10 to 40 eq.) is added. The reaction mixture is stirred at r.t. for 1 h to 2 days. If a precipitate is formed, it is filtered and washed with $Et_2O$ or $CH_3CN$, otherwise, the reaction mixture is concentrated in vacuo. Both work up afford the expected arylpiperazine as hydrochloride salt.

Illustrative Synthesis of Int 068

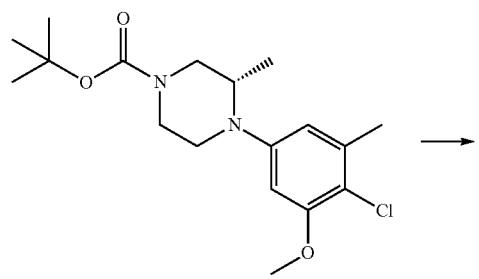

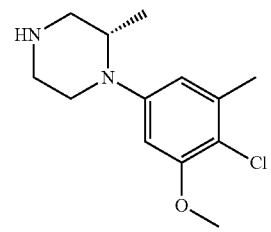

A flask is charged with N-tert-butoxycarbonyl derivative (crude, 0.67 mmol, 1 eq.), HCl 4N in dioxane (4 mL) is added. The reaction mixture is stirred at r.t. overnight and concentrated in vacuo. The residue is triturated in $Et_2O$, filtered and dried in vacuo to afford the expected product as hydrochloride salt. LCMS: MW (calcd): 255; m/z MW (obsd): 255 (M+H).

1.1.1.2.3 Method A3 (HCl+Basic Work Up)

To a solution of N-tert-butoxycarbonyl derivative (1 eq.) in acetonitrile or DCM is added HCl 4N in dioxane (10 to 40 eq.). The reaction mixture is stirred at r.t. for 1 h to 2 days, concentrated in vacuo and the residue is taken up in water and EtOAc or DCM. The aqueous layer is separated and basified (with either NaOH 1N solution or with a saturated $Na_2CO_3$ or $NaHCO_3$ solution) and extracted with EtOAc or DCM. The combined organic layers are dried over anhydrous $Na_2SO_4$ (or $MgSO_4$), filtered and concentrated in vacuo to afford the expected arylpiperazine.

Illustrative Synthesis of Int 046

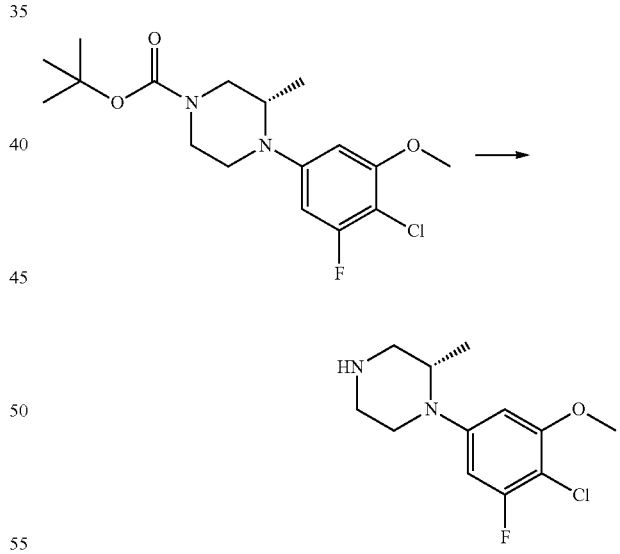

N-tert-butoxycarbonyl derivative (crude, 0.680 mmol, 1 eq.) in a solution of HCl 4N in dioxane (25 mL) is stirred at r.t. overnight, concentrated in vacuo and the residue is taken up in HCl 1N and DCM. The aqueous layer is separated and basified with NaOH 1N solution or with a saturated $Na_2CO_3$ solution and extracted with DCM. The combined organic layers are dried over anhydrous $Na_2SO_4$ (or $MgSO_4$), filtered and concentrated in vacuo to afford the expected product. LCMS: MW (calcd): 259; m/z MW (obsd): 259-261 (M+H).

1.1.1.2.3.1. Method A4 (Aqueous HCl)
Illustrative Synthesis of Int 074

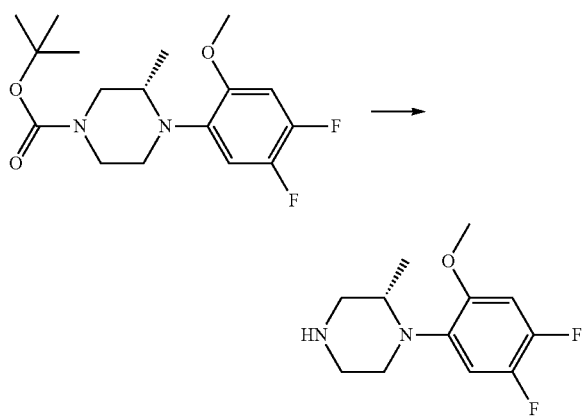

A flask is charged with N-tert-butoxycarbonyl derivative (154 mg, 0.45 mmol, 1.0 eq.) and concentrated aqueous HCl (37%, 7.5 mL, 90.0 mmol, 200 eq.). The reaction mixture is stirred for 16 h at r.t. then for 1 h at 80° C. Water (100 mL) is added and the mixture is extracted with EtOAc. The aqueous phase is made basic by the addition of NaOH (3.8 g, 94.5 mmol, 210 eq.) and extracted with DCM. The organic phase is collected, washed with brine, dried over anhydrous MgSO$_4$, filtered and concentrated in vacuo to afford the expected product. LCMS: MW (calcd): 220; m/z MW (obsd): 221 (M+H).

1.1.1.2.4 Method A5: Buchwald Reaction with NH-Piperazine

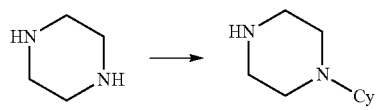

A flask is charged with bromoaryl derivative (1 eq.), piperazine (4-6 eq.), BINAP (0.06-0.22 eq.), NaOtBu (1.4-2.5 eq.) and toluene. The reaction mixture is degassed with N$_2$ and Pd$_2$(dba)$_3$ (0.03-0.11 eq.) is added. Reaction mixture is heated at 100-110° C. for 2 h-20 h. The reaction mixture is extracted with HCl 1N solution. The aqueous layer is basified with NaOH 2N solution and extracted with EtOAc or DCM. The combined organic layers are washed with water and brine, dried (over anhydrous Na$_2$SO$_4$ or MgSO$_4$), filtered and concentrated in vacuo to afford the expected arylpiperazine used without further purification.

Illustrative Synthesis of Int 045

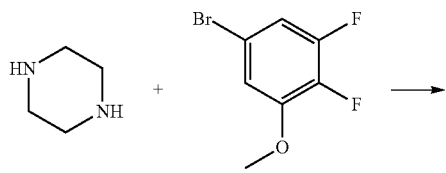

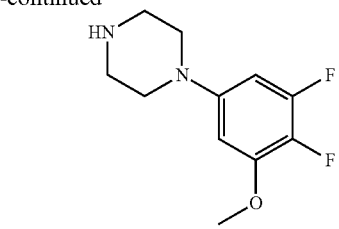

A flask is charged with 5-Bromo-1,2-difluoro-3-methoxybenzene (400 mg, 1.79 mmol, 1 eq.), piperazine (927 mg, 10.76 mmol, 6 eq.), BINAP (134 mg, 0.215 mmol, 0.12 eq.), NaOtBu (241 mg, 2.511 mmol, 1.4 eq.) and toluene (3 mL). The reaction mixture is degassed with N$_2$ and Pd$_2$(dba)$_3$ (99 mg, 0.108 mmol, 0.06 eq.) is added. Reaction mixture is heated at 100° C. overnight. The reaction mixture is extracted with HCl 1N solution. The aqueous layer is basified with NaOH 2N solution and extracted with DCM. The combined organic layers are washed with water and brine, dried over anhydrous MgSO$_4$, filtered and concentrated in vacuo to afford the expected product. LCMS: MW (calcd): 228. MW (obsd): 229 (M+H).

1.1.1.3. General Methods B: Preparation of Ketoester
1.1.1.3.1 Method B1: from Meldrum's Acid

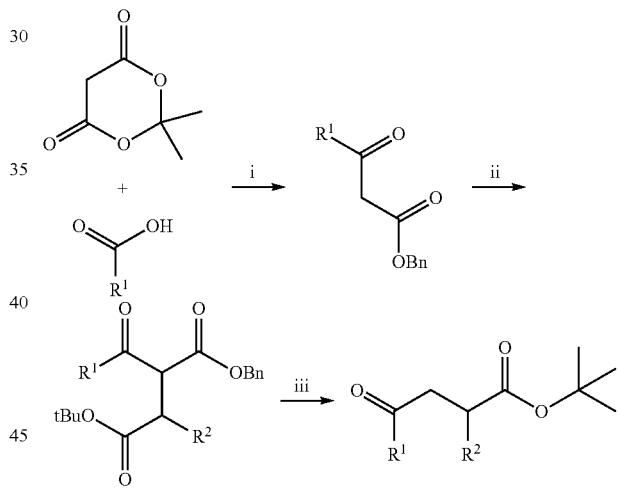

Step i)

To a solution of the carboxylic acid (1 eq.) in DCM at 0° C. under N$_2$ atmosphere is added portionwise DMAP (1.5 eq.) then 2,2-Dimethyl-[1,3]dioxane-4,6-dione (1.1 eq.) then EDC.HCl (1.2 eq.). After 10 min at 0° C., the reaction mixture is warmed to r.t. and stirred for 4 h. The reaction mixture is quenched with a solution of KHSO$_4$ 5%. The aqueous phase is extracted with DCM, the combined organic layers are washed with a solution of KHSO$_4$ 5%, water and brine, dried over anhydrous Na$_2$SO$_4$, filtered and concentrated in vacuo. This residue is taken up in anhydrous toluene and benzyl alcohol (1.1 eq.) is added. The reaction mixture is stirred at 120° C. for 16 h to 20 h, concentrated in vacuo and purified by flash chromatography on silica gel to afford the expected β-ketoester.

Step ii)

To a solution of the β-ketoester (1 eq.) in MEK are added K$_2$CO$_3$ (2 eq.), NaI (0.1 eq.) and bromoderivative (1 eq.). The reaction mixture is stirred at 90° C. for 6 h to 16 h and cooled to r.t. Water is added, reaction mixture acidified to pH 8 and extracted with EtOAc. The combined organic layers are washed with water and brine, dried over anhydrous Na$_2$SO$_4$, filtered and concentrated in vacuo. The residue is purified by flash chromatography on silica gel to afford the expected γ-ketoester.

Step iii)

To a solution of the γ-ketoester (1 eq.) in MeOH are added Pd(OH)$_2$/C (0.01 eq.), and cyclohexene (50 eq.). The reaction mixture is stirred at 70° C. for 19 h. The reaction mixture is filtered on celpure P65 and the filtrate is concentrated in vacuo. The residue is purified by flash chromatography on silica gel to afford the expected γ-ketoester.

Illustrative Synthesis of Int 029

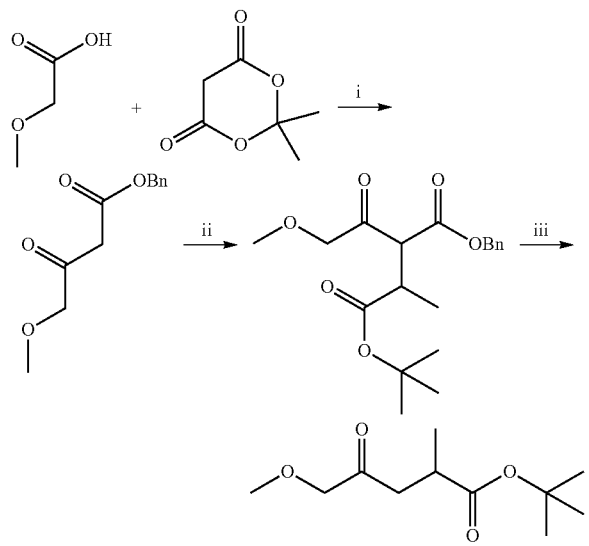

Step i)

To a solution of methoxy-acetic acid (5.11 mL, 0.067 mol, 1 eq.) in DCM (160 mL) at 0° C. under N$_2$ atmosphere is added portionwise DMAP (12.21 g, 0.100 mol, 1.5 eq.) then 2,2-Dimethyl-[1,3]dioxane-4,6-dione (10.56 g, 0.073 mol, 1.1 eq.) then EDC.HCl (15.32 g, 0.080 mol, 1.2 eq.). After 10 min at 0° C., the reaction mixture is warmed to r.t. and stirred for 4 h. The reaction mixture is quenched with a solution of KHSO$_4$ 5%. The aqueous phase is extracted with DCM, the combined organic layers are washed with a solution of KHSO$_4$ 5%, water and brine, dried over anhydrous Na$_2$SO$_4$, filtered and concentrated in vacuo. This residue is taken up in anhydrous toluene (220 mL) and benzyl alcohol (7.59 mL, 0.073 mol, 1.1 eq.) is added. The reaction mixture is stirred at 120° C. for 16 h, concentrated in vacuo and purified by flash chromatography on silica gel (eluting with DCM 100%) to afford the expected 3-ketoester. LCMS: MW (calcd): 222; m/z MW (obsd): 245.3 (M+Na)

Step ii)

To a solution of the β-ketoester (8.96 g, 0.040 mol, 1 eq.) in MEK (120 mL) are added K$_2$CO$_3$ (11.14 g, 0.081 mol, 2 eq.), NaI (0.6 g, 0.004 mol, 0.1 eq.) and 2-Bromo-propionic acid tert-butyl ester (6.69 mL, 0.040 mol, 1 eq.). The reaction mixture is stirred at 90° C. for 6 h and cooled to r.t. Water is added, reaction mixture is acidified to pH 8 and extracted with EtOAc. The combined organic layers are washed with water and brine, dried over anhydrous Na$_2$SO$_4$, filtered and concentrated in vacuo. The residue is purified by flash chromatography on silica gel (eluting with Heptane/EtOAc 100/0 to 50/50) to afford the expected γ-ketoester. LCMS: MW (calcd): 350; m/z MW (obsd): 373.4 (M+Na)

Step iii)

To a solution of the γ-ketoester (6.42 g, 0.018 mol, 1 eq.) in MeOH are added Pd(OH)$_2$/C (0.642 g, 0.002 mol, 0.01 eq.), and cyclohexene (93 mL, 0.916 mol, 50 eq.). The reaction mixture is stirred at 70° C. for 19 h. The reaction mixture is filtered on celpure P65, washed with MeOH and the filtrate is concentrated in vacuo. The residue is purified by flash chromatography on silica gel (eluting with Heptane/EtOAc 100/0 to 70/30) to afford the expected product. LCMS: MW (calcd): 216; m/z MW (obsd): 239.3 (M+Na).

1.1.1.3.2 Method B2: Esterification

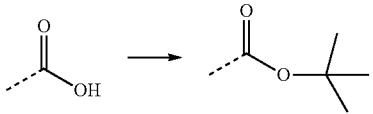

A glass pressure flask is charged with the carboxylic acid (1 eq.), DCM and concentrated H$_2$SO$_4$ (0.1 eq.). It is capped and weighted as such. It is then cooled to −45° C., the flask is opened and isobutene is bubbled through the cold reaction mixture for approximately 5 min. The flask is capped and weighted. The process is repeated until the expected weigh of isobutene is obtained (5 eq.). The reaction mixture is stirred at r.t. for 4 days, then the flask is cooled to −45° C. prior to opening. A saturated NaHCO$_3$ solution is added portionwise, and the vigorous stirring kept for 30 min. The organic layer is separated; the aqueous layer is extracted with DCM. The combined organic layers are washed with brine, dried over anhydrous MgSO$_4$ and concentrated in vacuo (with a minimum vacuum of 50 mbar) to afford the expected γ-ketoester.

Illustrative Synthesis of Int 042

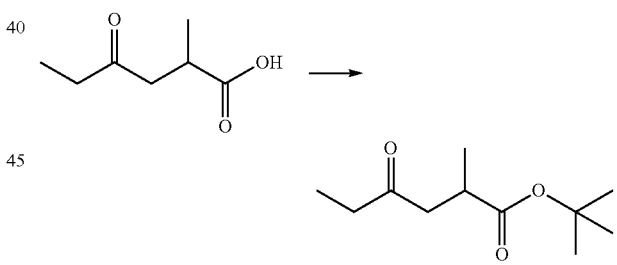

A glass pressure flask is charged with 2-Methyl-4-oxo-hexanoic acid (Kato et al., 2003) (7.3 g, 50.6 mmol, 1 eq.), DCM (40 mL) and concentrated H$_2$SO$_4$ (270 µL, 5.06 mmol, 0.1 eq.). The flask is capped and weighted as such. It is then cooled to −45° C., the flask is opened and isobutene is bubbled through the cold reaction mixture for approximately 5 min. The flask is capped and weighted (11 g of isobutene is condensed). The process is repeated until the expected weigh of isobutene is obtained (14.2 g, 253.2 mmol, 5 eq.). The reaction mixture is stirred at r.t. for 4 days, then the flask is cooled to −45° C. prior to opening. A saturated NaHCO$_3$ solution is added portionwise, and the vigorous stirring kept for 30 min. The organic layer is separated; the aqueous layer is extracted with DCM. The combined organic layers are washed with brine, dried over anhydrous MgSO$_4$ and concentrated in vacuo (with a minimum vacuum of 50 mbar) to afford the expected product.

1.1.1.3.3 Method B3: Stetter Reaction

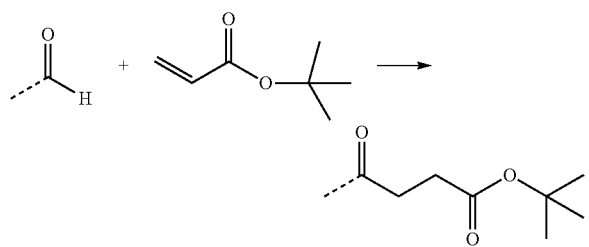

A vial is charged with aldehyde (1 eq.), tert-butyl ester acrylate (1 eq.), PBu₃ (1 eq.) and dry THF. The vial is capped and heated at 70° C. for 2 h to 16 h. The reaction mixture is partitioned between EtOAc and water. The combined organic layers are washed with brine, dried over anhydrous MgSO₄, filtered and concentrated in vacuo to afford the expected γ-ketoester after purification by flash chromatography on silica gel.

Illustrative Synthesis of Int 014

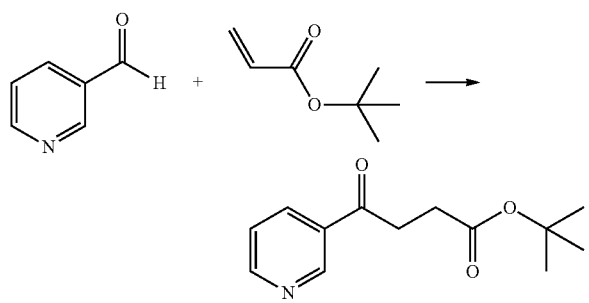

To a solution of Pyridine-3-carbaldehyde (16 mL, 170.29 mmol, 1.0 eq.) in THF (300 mL) is added PBu₃ (42.537 mL, 170.29 mmol, 1.0 eq.) and the reaction mixture is heated at 50° C. for 5 min. tert-butyl ester acrylate (24.803 mL, 170.29 mmol, 1 eq.) is added and the reaction mixture is stirred at 80° C. for 3 h. This process (heating 3 h and addition of tert-butyl ester acrylate) is repeated until no evolution is observed by TLC (EtOAc) and UPLC/MS. The reaction mixture is concentrated in vacuo and the residue is purified by flash chromatography on silica gel (eluting with Heptane/EtOAc 100/0 to 0/100) to afford the expected product. LCMS: MW (calcd): 235; m/z MW (obsd): 236 (M+H).

1.1.1.3.4 Method B4: Via Epoxide Opening

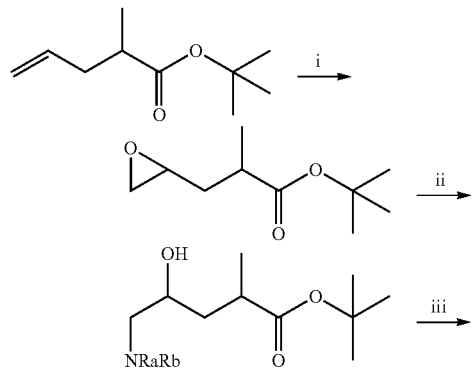

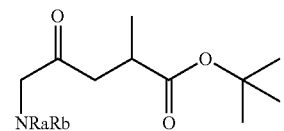

Step i)

To a solution of alkene (1 eq.) in DCM at 0° C., is added m-CPBA (1.5 eq.) and the reaction mixture is stirred at r.t. overnight. The white precipitate is filtered and washed with DCM. The filtrate is washed with a saturated NaHCO₃ solution, brine, dried over anhydrous MgSO₄ and concentrated in vacuo. The residue is purified by flash chromatography on silica gel to afford the expected epoxide.

Step ii)

A sealed tube is charged with the epoxide (1 eq.), EtOH and secondary amine (1.5 eq.). After heating at reflux for 3 h30, the reaction mixture is concentrated in vacuo. The residue is taken up in DCM, washed with a saturated NH₄Cl solution, dried over anhydrous MgSO₄, filtered and concentrated in vacuo to afford the expected aminoalcohol used in next step without further purification.

Step iii)

A two necked flask, under N₂ atmosphere, is charged with dry DCM and (COCl)₂ (1.1 eq.). The reaction mixture is cooled to −70° C., a solution of DMSO (2.4 eq.) in dry DCM is added dropwise and the reaction mixture is stirred at −70° C./−60° C. for 45 min. A solution of the aminoalcohol (1 eq.) in dry DCM is added dropwise and the reaction mixture is stirred for 1 h at −60° C. Et₃N (5 eq.) is added dropwise. Reaction mixture stirred at −40° C. for 30 min then warmed to r.t. and stirred overnight. Water is added, the organic layer is separated and washed with brine, dried over anhydrous MgSO₄ and concentrated in vacuo. The residue is purified by flash chromatography on silica gel to afford the expected γ-ketoester.

Illustrative Synthesis of Int 021

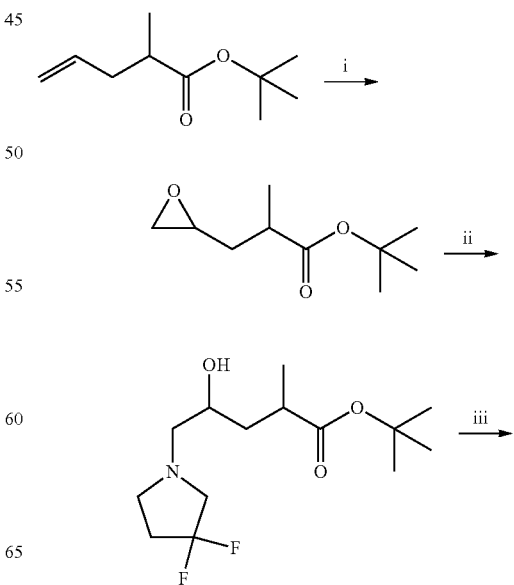

-continued

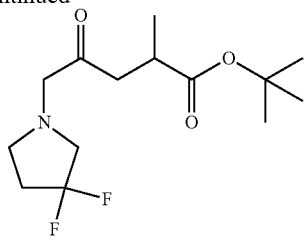

Step i)

To a solution of Int 022 (2 g, 11.8 mmol, 1 eq.) in DCM (20 mL) at 0° C., is added m-CPBA (3.05 g, 17.7 mmol, 1.5 eq.) and the reaction mixture is stirred at r.t. overnight. The white precipitate is filtered and washed with DCM. The filtrate is washed with a saturated NaHCO$_3$ solution, brine, dried over anhydrous MgSO$_4$ and concentrated in vacuo. The residue is purified by flash chromatography on silica gel (eluting with Heptane/EtOAc 100/0 to 80/20) to afford the expected epoxide.

Step ii)

A sealed tube is charged with the epoxide (0.9 g, 4.84 mmol, 1 eq.), EtOH (15 mL) and 3,3-difluoropyrrolidine hydrochloride (0.903 g, 6.29 mmol, 1.3 eq.). After heating at reflux for 4 h30, the reaction mixture is concentrated in vacuo. The residue is taken up in DCM, washed with a saturated NH$_4$Cl solution, dried over anhydrous MgSO$_4$, filtered and concentrated in vacuo. The residue is purified by flash chromatography on silica gel (eluting with DCM/acetone 100/0 to 90/10) to afford the expected product.

Step iii)

A two necked flask, under N$_2$ atmosphere, is charged with dry DCM (5 mL) and (COCl)$_2$ (0.153 mL, 1.81 mmol, 1.1 eq.). The reaction mixture is cooled to −70° C., a solution of DMSO (0.281 mL, 3.96 mmol, 2.4 eq.) in dry DCM (0.5 mL) is added dropwise and the reaction mixture is stirred at −70° C./−60° C. for 45 min. A solution of the aminoalcohol (0.450 g, 1.65 mmol, 1 eq.) in dry DCM (2 mL) is added dropwise and the reaction mixture is stirred for 1 h at −60° C. Et$_3$N (1.19 mL, 8.24 mmol, 5 eq.) is added dropwise. Reaction mixture stirred at −40° C. for 30 min then warmed to r.t. and stirred overnight. Water is added, the organic layer is separated and washed with brine, dried over anhydrous MgSO$_4$ and concentrated in vacuo. The residue is purified by flash chromatography on silica gel (eluting with DCM/acetone 90/10) to afford the expected product.

1.1.1.4. General Method C: Preparation of Ketoamide 1.1.1.4.1 Method C1: Preparation of Acrylamide

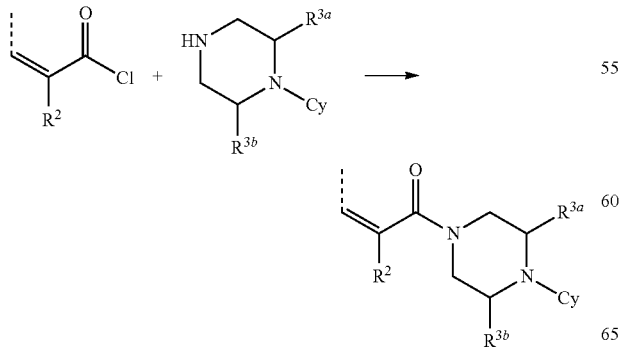

To a solution of piperazine (1 eq.) and Et$_3$N (1.5 eq.) in DCM at 0° C. is added dropwise the acryloyl chloride derivative (1.5 eq.). Reaction mixture is stirred at 0° C. for 1 h and allowed to reach r.t. Water and DCM are added, the organic layer is separated. The aqueous layer is extracted with DCM, the combined organic layers are washed with brine and dried over anhydrous Na$_2$SO$_4$, filtered and concentrated in vacuo to afford the expected acrylamide after purification by flash chromatography on silica gel.

Illustrative Synthesis of Int 001

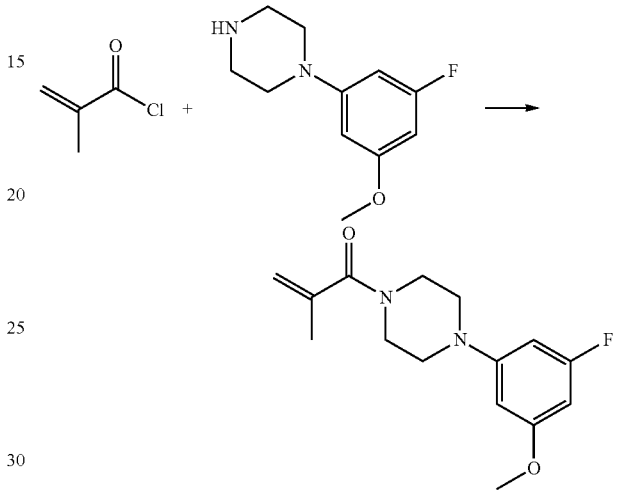

To a solution of 1-(3-Fluoro-5-methoxy-phenyl)-piperazine (2.06 g, 9.8 mmol, 1 eq.) and Et$_3$N (1.5 mL, 14.7 mmol, 1.5 eq.) in DCM at 0° C. is added dropwise 2-Methylacryloyl chloride (2.05 mL, 14.7 mmol, 1.5 eq.). Reaction mixture is stirred at 0° C. for 1 h and allowed to reach r.t. Water and DCM are added, the organic layer is separated. The aqueous layer is extracted with DCM, the combined organic layers are washed with brine and dried over anhydrous Na$_2$SO$_4$, filtered and concentrated in vacuo. The residue is purified by flash chromatography on silica gel (eluting with DCM/MeOH 100/0 to 90/10) to afford the expected product. LCMS: MW (calcd): 278; m/z MW (obsd): 279 (M+H).

1.1.1.4.2 Method C2: Stetter Reaction

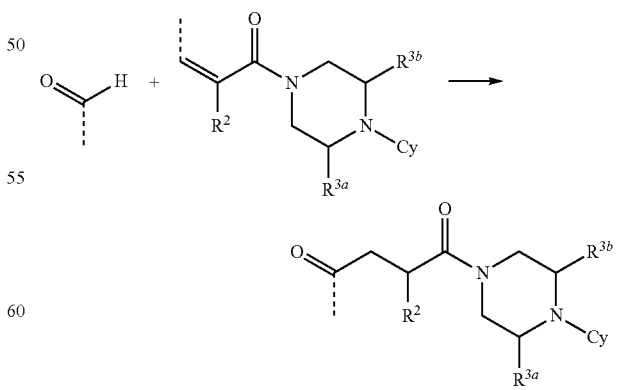

A vial is charged with bis(1,5-cyclooctadiene)rhodium(I) tetrafluoroborate (0.10 eq.), 1,4-bis(diphenylphosphino)butane (0.10 eq.), dry DCM and sealed with a septum. The flask is evacuated and refilled with H₂ (3 times) and the reaction mixture is stirred under an atmosphere of H₂. After 3 h, volatiles are removed under a nitrogen stream. The residue is combined with acrylamide (1 eq.), aldehyde (1.5 equiv.) and 1,2-dichloroethane in a vial under a N₂ atmosphere. The vial is sealed with a cap and heated at 100° C. After 16 h, the mixture is concentrated in vacuo and purified by flash chromatography on silica gel to afford the expected γ-ketoamide.

Illustrative Synthesis of Int 007

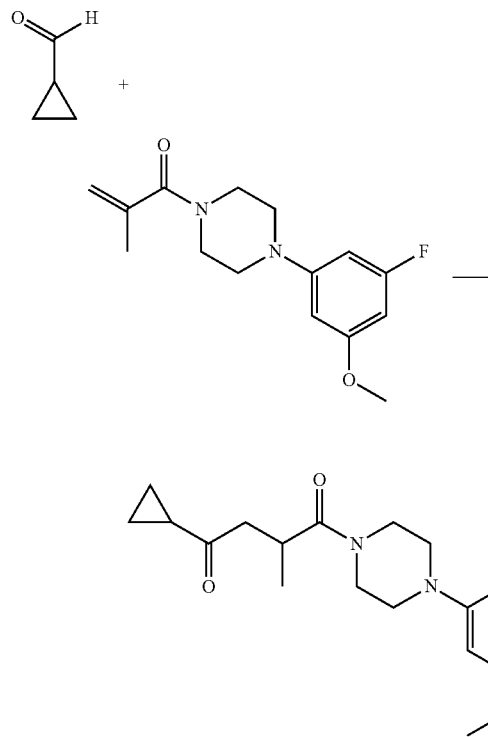

A vial is charged with bis(1,5-cyclooctadiene)rhodium(I) tetrafluoroborate (0.054 g, 0.132 mmol, 0.10 eq.), 1,4-bis(diphenylphosphino)butane (0.056 g, 0.132 mmol, 0.10 eq.), dry DCM (2 mL) and sealed with a septum. The flask is evacuated and refilled with H₂ (3 times) and the reaction mixture is stirred under an atmosphere of H₂. After 3 h, volatiles are removed under a nitrogen stream. The residue is combined with Int 001 (0.397 g, 1.328 mmol, 1 eq.), cyclopropane carboxaldehyde (0.406 g, 2.00 mmol, 1.5 equiv.) and 1,2-dichloroethane (2 mL) in a vial under a N2 atmosphere. The vial is sealed with a cap and heated at 100° C. After 2 days, the mixture is concentrated in vacuo. The residue is purified by flash chromatography on silica gel (eluting with Heptane/EtOAc 100/0 to 0/100, then DCM/MeOH 90/10) to afford Int 007. LCMS: MW (calcd): 348; m/z MW (obsd): 349 (M+H).

1.1.1.4.3 Method C3: Via Furan Oxidation

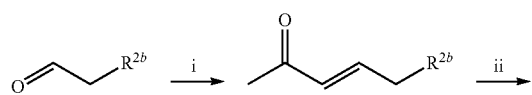

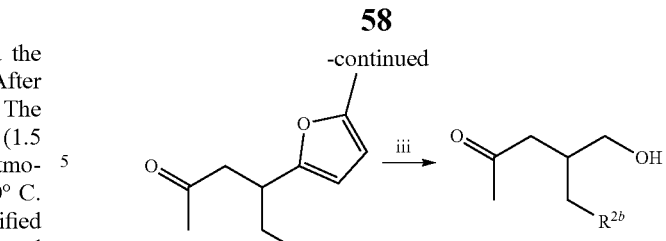

Step i)
To a solution of phosphonate (1.1 eq.) in EtOH is added K₂CO₃ (1.2 eq.). The reaction mixture is stirred at r.t. for 2 h prior to addition of the aldehyde (1 eq.). The reaction mixture is stirred at r.t. (1 h to 3 h), diluted with EtOAc and filtered on celpure P65. The filtrate is concentrated in vacuo. The residue is taken up in EtOAc and washed with a saturated NH₄Cl solution, a saturated NaHCO₃ solution, brine and dried over anhydrous MgSO₄, filtered, concentrated in vacuo and purified by flash chromatography on silica gel to afford the expected α,β-unsaturated ketone.

Step ii)
To a solution of the α,β-unsaturated ketone (1 eq.) in dry MeOH are added PdCl₂ (0.1 eq.) and 2-methylfuran (2 eq.). The reaction mixture is stirred at r.t. for 3 h to 24 h, diluted with EtOAc and filtered on celpure P65. The filtrate is concentrated in vacuo and purified by flash chromatography on silica gel to afford the expected ketone.

Step iii)
To a solution of ketone (1 eq.) in Heptane/EtOAc/water (1/3/4) is added NaIO₄ (7 eq.). The reaction mixture is stirred for 10 min then RuCl₃.3H₂O (0.02 eq.) is added. The reaction mixture is stirred for 30 min to 1 h30, filtered on celpure P65, washed with MeCN and the filtrate is concentrated in vacuo. The residue is purified by flash chromatography on silica gel to afford the expected γ-ketoacid.

Illustrative Synthesis of Int 018

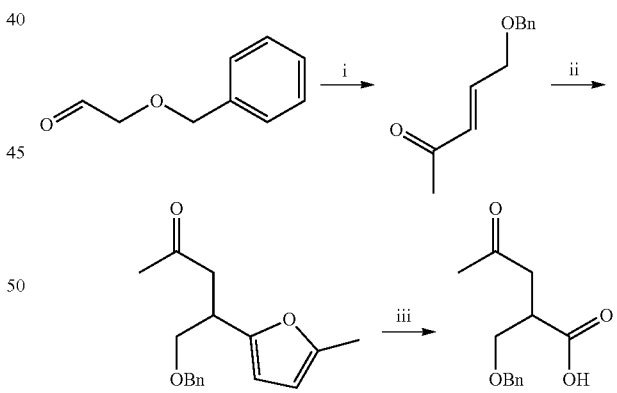

Step i)
To a solution of dimethyl acetylmethylphosphonate (14.22 g, 73.24 mmol, 1.1 eq.) in EtOH (150 mL) is added K₂CO₃ (11 g, 79.90 mmol, 1.2 eq.). The reaction mixture is stirred at r.t. for 2 h prior to addition of benzyloxy-acetaldehyde (10 g, 66.59 mmol, 1 eq.). The reaction mixture is stirred at r.t. for 3 h, diluted with EtOAc and filtered on celpure P65. The filtrate is concentrated in vacuo. The residue is taken up in EtOAc and washed with a saturated NH₄Cl solution, a saturated NaHCO₃ solution, brine and dried over anhydrous MgSO₄, filtered, concentrated in vacuo and purified by flash chromatography on silica gel (eluting with Heptane/EtOAc 100/0 to 80/20) to afford the expected α,β-unsaturated ketone.

Step ii)

To a solution of the α,β-unsaturated ketone (8.7 g, 45.73 mmol, 1 eq.) in dry MeOH (183 mL) are added PdCl$_2$ (0.811 g, 0.457 mmol, 0.1 eq.) and 2-methylfuran (8.25 mL, 91.46 mmol, 2 eq.). The reaction mixture is stirred at r.t. for 3 h, diluted with EtOAc and filtered on celpure P65. The filtrate is concentrated in vacuo and purified by flash chromatography on silica gel eluting with Heptane/EtOAc 100/0 to 85/15) to afford the expected ketone.

Step iii)

To a solution of ketone (1 g, 3.67 mmol, 1 eq.) in Heptane/EtOAc/water (6 mL/18 mL/24 mL) is added NaIO$_4$ (5.48 g, 25.69 mmol, 7 eq.). The reaction mixture is stirred for 10 min then RuCl$_3$.3H$_2$O (0.019 g, 0.073 mmol, 0.02 eq.) is added. The reaction mixture is stirred for 1 h15, filtered on celpure P65, washed with MeCN and the filtrate is concentrated in vacuo. The residue is purified by flash chromatography on silica gel (eluting with DCM/MeOH 98/2 to 95/5) to afford the expected product (stored at 4° C.).

1.1.1.5. General Method D: Bucherer Bergs Reaction

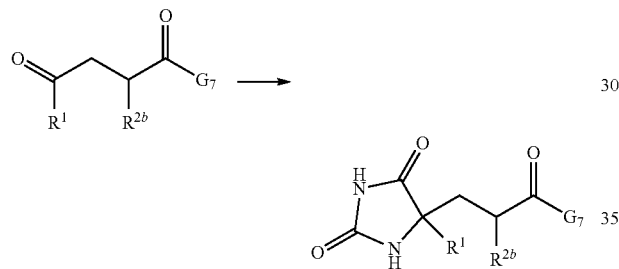

G$_7$=O-Alk$_1$, Alk$_2$-N-Alk$_3$

A pressure reactor or an open round bottom flask equipped with a condenser is charged with a solution of (NH$_4$)$_2$CO$_3$ or (NH$_4$)HCO$_3$ (8-12 eq.) in water. KCN (2 to 4 eq.) is added portionwise then a solution of γ-ketoester or γ-ketoamide (1 eq.) in EtOH is added. The vessel is sealed and heated at 60-90° C. for 1 h to 2 days. The reaction mixture is cooled to r.t., combined with water and extracted with AcOEt or CHCl$_3$/nBuOH 10%. The combined organic layers are washed with water and brine, dried (over anhydrous Na$_2$SO$_4$ or MgSO$_4$), filtered and concentrated in vacuo. The residue is either recrystallized or purified by flash chromatography on silica gel to afford the expected hydantoin derivative.

Illustrative Synthesis of (R)-5-Methyl-5-((S)-2-methyl-3-oxo-butyl)-imidazolidine-2,4-dione+(S)-5-Methyl-5-((R)-2-methyl-3-oxo-butyl)-imidazolidine-2,4-dione

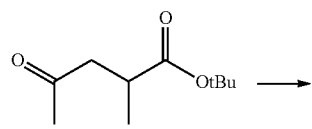

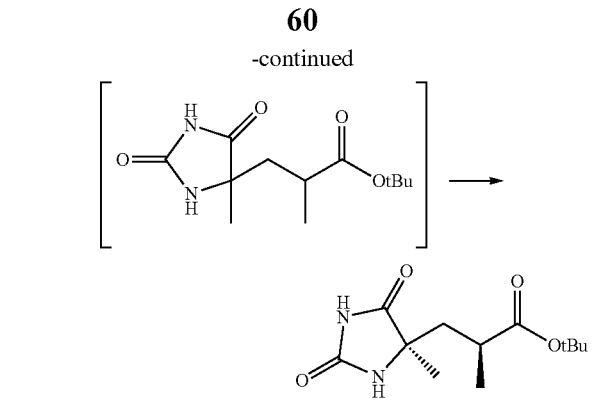

A pressure reactor is charged with a solution of (NH$_4$)$_2$CO$_3$ (79.4 g, 0.826 mol, 8 eq.) in water (400 mL). KCN (20 g, 0.307 mol, 3 eq.) is added portionwise then a solution of γ-ketoester (19.15 g, 0.103 mol, 1 eq.) in EtOH (400 mL) is added. The vessel is sealed and heated at 90° C. overnight. The reaction mixture is cooled to r.t., combined with water and extracted with CHCl$_3$/nBuOH 10%. The combined organic layers are washed with brine, dried over anhydrous MgSO$_4$, filtered, concentrated in vacuo.

The above reaction is performed twice and the two crude residues are gathered for recrystallization. A flask is charged with the two crude residues, EtOH (250 mL) is added and the reaction mixture is heated at reflux. Upon complete dissolution, the reaction mixture is allowed to cool to r.t. for 2 days, it is filtered and the crystalline solid is combined with EtOH (200 mL), heated to reflux, cooled to r.t. overnight and filtered to afford the expected hydantoin as a trans-Me racemic mixture (LCMS: >99% de, MW (calcd): 256; m/z MW (obsd): 257 (M+H)).

Illustrative Synthesis of Cpd 02

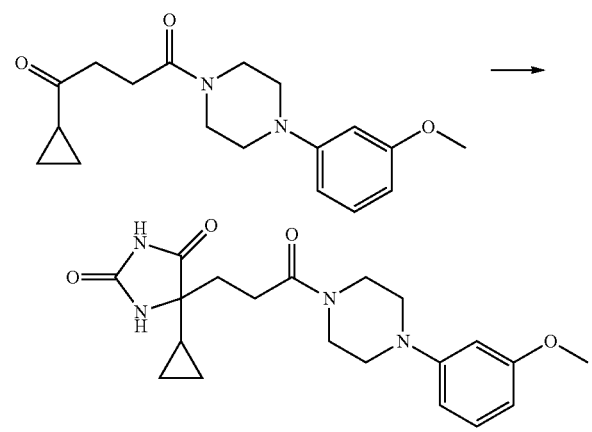

A pressure reactor is charged with (NH$_4$)$_2$CO$_3$ (0.645 g, 6.71 mmol, 10 eq.), KCN (0.175 g, 2.69 mmol, 4 eq.), Int 003 (0.248 g, 0.671 mmol, 1 eq.), EtOH (4 mL) and water (2 mL). The vessel is sealed and heated at 60° C. for 40 h. The reaction mixture is cooled to r.t., combined with water and extracted with DCM. The combined organic layers are washed with brine, dried over anhydrous MgSO$_4$, filtered, concentrated in vacuo. Purification by flash chromatography on silica gel (eluting with DCM/iPrOH 20/1). (LCMS: MW (calcd): 386; m/z MW (obsd): 387 (M+H)).

1.1.1.6. General Method E: Method for Preparation of Hydantoin Propionic Acids

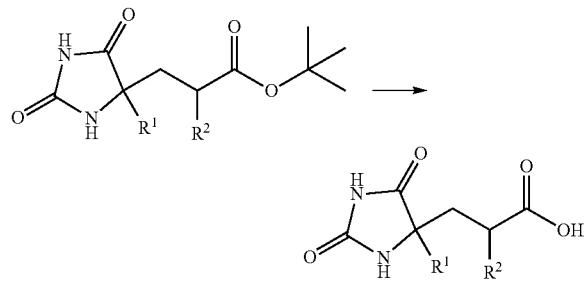

A flask is charged with tert-butyl ester (1 eq.) and HCl 4N in dioxane (5 to 40 eq.). In some cases, an additional solvent such as DCM, dioxane or water is added to increase solubility. The reaction mixture is stirred at r.t. for 1 h to 4 days until complete conversion. The reaction mixture is either concentrated in vacuo or filtered and washed with Et$_2$O to afford the expected carboxylic acid.

Illustrative Synthesis of Int 040

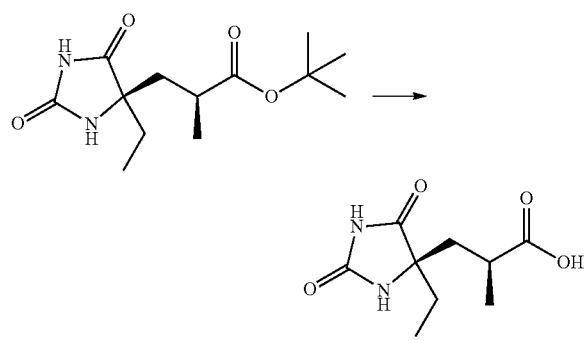 [SMILES: CC[C@]1(C[C@H](C)C(=O)OC(C)(C)C)NC(=O)NC1=O ; CC[C@]1(C[C@H](C)C(=O)O)NC(=O)NC1=O]

A flask is charged with Int 041 (3.6 g, 13.32 mmol, 1 eq.) and HCl 4N in dioxane (33.3 mL, 133 mmol, 10 eq.). The reaction mixture is stirred at r.t. for 2 days and concentrated in vacuo to afford the expected product.

1.1.1.7. General Method F: Amide Bond Formation

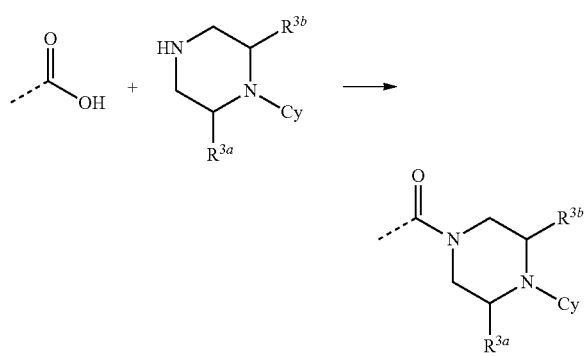

1.1.1.7.1 Method F1: EDC/HOBt

A solution of acid (1 eq.), Et$_3$N (3 to 4 eq.), HOBt (0.1 to 1.1 eq.) in DMF (or DCM) is stirred at r.t. EDC.HCl (1 to 1.2 eq.) is added, then amine (0.95 to 2 eq.) is added and the reaction mixture is stirred at r.t. for 5 h to 2 days. The reaction mixture is partitioned between DCM (or EtOAC) and water, extracted with DCM (or EtOAc). The combined organic layers are washed with water and brine, dried over anhydrous Na$_2$SO$_4$ (or MgSO$_4$), filtered, concentrated in vacuo and purified by flash chromatography on silica gel or preparative LCMS to afford the expected amide.

Illustrative Synthesis of Cpd 06

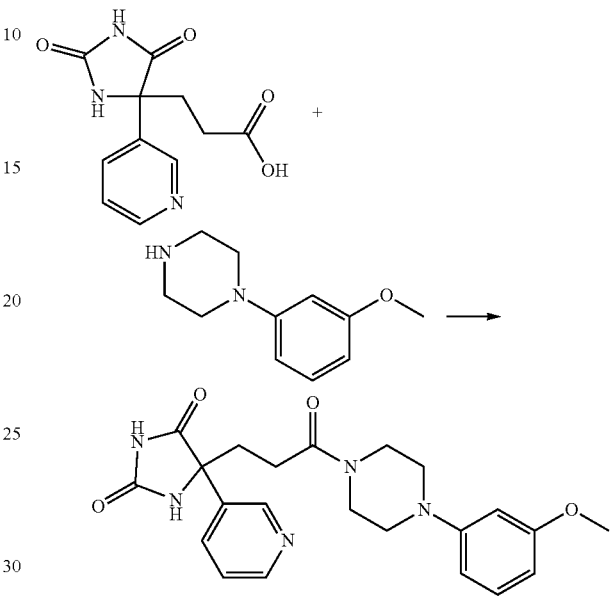

A solution of 3-(2,5-Dioxo-4-pyridin-3-yl-imidazolidin-4-yl)-propionic acid (100 mg, 0.40 mmol, 1 eq.), Et$_3$N (168 μL, 1.20 mmol, 3 eq.), HOBt (57 mg, 0.42 mmol, 1.05 eq.) in DMF (1 mL) is stirred at r.t. EDC.HCl (81 mg, 0.42 mmol, 1.05 eq.) is added, then 1-(3-Methoxy-phenyl)-piperazine (116 mg, 0.60 mmol, 1.5 eq.) is added and the reaction mixture is stirred at r.t. overnight. The reaction mixture is partitioned between DCM and water, extracted with DCM. The combined organic layers are washed with water and brine, dried over anhydrous MgSO$_4$, filtered, concentrated in vacuo and purified by preparative LCMS to afford the expected product. LCMS: MW (calcd): 423; m/z MW (obsd): 424 (M+H).

1.1.1.7.2 Method F2: HATU

A flask is charged with acid (1 eq.), amine (0.85 to 1.1 eq.), HATU (0.85 to 1.1 eq.) and DMF (or THF). DIPEA (2 to 6 eq.) is added and the reaction mixture is stirred at r.t. for 5 h to 2 days. The reaction mixture is partitioned between EtOAc and water, extracted with EtOAc. The combined organic layers are washed with water and brine, dried (over anhydrous Na$_2$SO$_4$, MgSO$_4$, or hydrophobic column), filtered, concentrated in vacuo and purified by flash chromatography on silica gel or preparative LCMS to afford the expected amide.

Illustrative Synthesis of Cpd 105

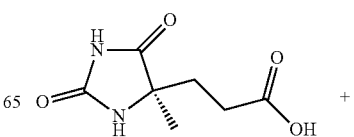

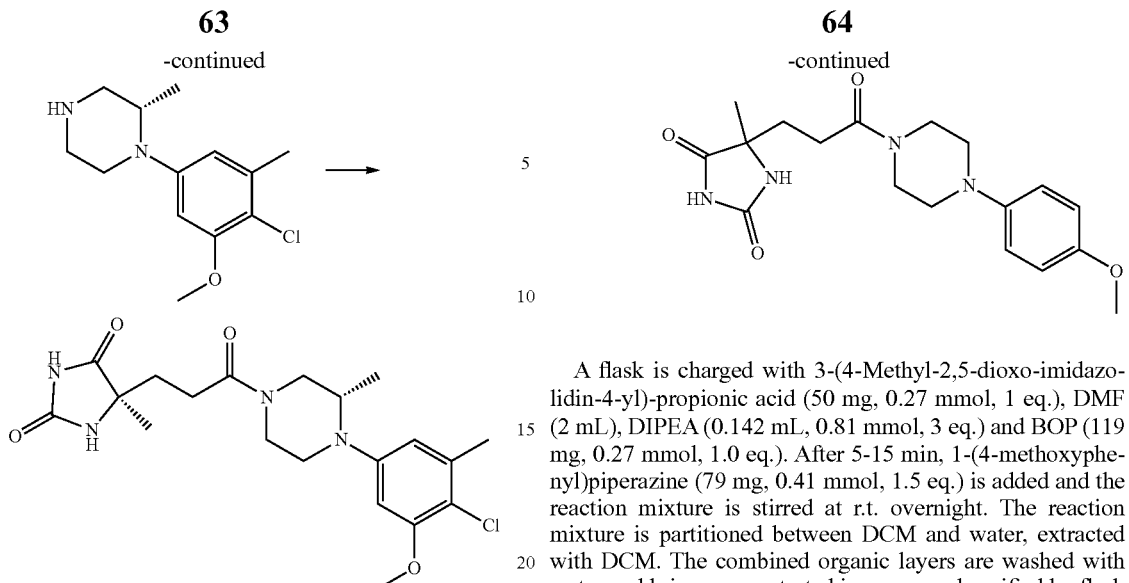

A flask is charged with Int 043 (70 mg, 0.35 mmol, 1.1 eq.), Int 068 (95 mg, 0.32 mmol, 1 eq.), HATU (127 mg, 0.34 mmol, 1.05 eq) and DMF (3 mL). DIPEA (167 µL, 0.96 mmol, 3 eq.) is added and the reaction mixture is stirred at r.t. overnight. The reaction mixture is partitioned between EtOAc and water, extracted with EtOAc. The combined organic layers are washed with water and brine, dried over hydrophobic column, filtered, concentrated in vacuo and purified by flash chromatography on silica gel (eluting with DCM/MeOH 100/0 to 96/4) to afford the expected product. LCMS: MW (calcd): 517; m/z MW (obsd): 423-425 (M+H).

1.1.1.7.3 Method F3: BOP

A flask is charged with acid (1 eq.), DMF (or DCM), DIPEA or Et$_3$N (2 to 6 eq.) and BOP (0.77 to 1.1 eq.). After 5-15 min, amine (0.77 to 1.5 eq.) is added and the reaction mixture is stirred at r.t. for 5 h to 2 days. The reaction mixture is partitioned between EtOAc (or DCM) and water, extracted with EtOAc (or DCM). The combined organic layers are washed with water and brine, dried (over anhydrous Na$_2$SO$_4$, MgSO$_4$, or hydrophobic column), filtered, concentrated in vacuo and purified by flash chromatography on silica gel or preparative LCMS to afford the expected amide.

Illustrative Synthesis of Cpd005

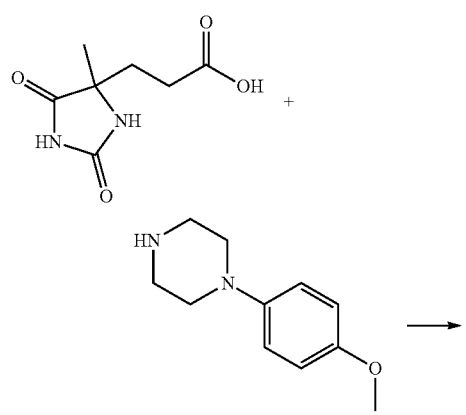

A flask is charged with 3-(4-Methyl-2,5-dioxo-imidazolidin-4-yl)-propionic acid (50 mg, 0.27 mmol, 1 eq.), DMF (2 mL), DIPEA (0.142 mL, 0.81 mmol, 3 eq.) and BOP (119 mg, 0.27 mmol, 1.0 eq.). After 5-15 min, 1-(4-methoxyphenyl)piperazine (79 mg, 0.41 mmol, 1.5 eq.) is added and the reaction mixture is stirred at r.t. overnight. The reaction mixture is partitioned between DCM and water, extracted with DCM. The combined organic layers are washed with water and brine, concentrated in vacuo and purified by flash chromatography on silica gel (eluting with DCM/EtOAc 90/10) afford the expected product. LCMS: MW (calcd): 360; m/z MW (obsd): 361 (M+H).

1.1.1.8. General Method G: Functionalization of Final Compound 1.1.1.8.1 Method G1: O-Debenzylation

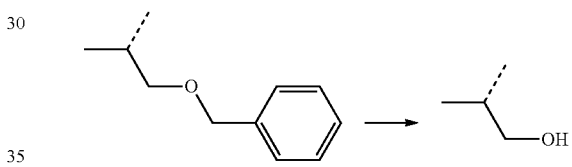

To a solution of benzyloxy derivative (1 eq.) in dry THF or MeOH under argon atmosphere is added Pd(OH)$_2$/C (50% w/w). The reaction mixture is stirred under H$_2$ atmosphere at r.t. for 5 h to 2 days then filtered on celpure P65. The filtrate is concentrated in vacuo and purified by flash chromatography on silica gel to afford the expected alcohol.

Illustrative Synthesis of Cpd 56

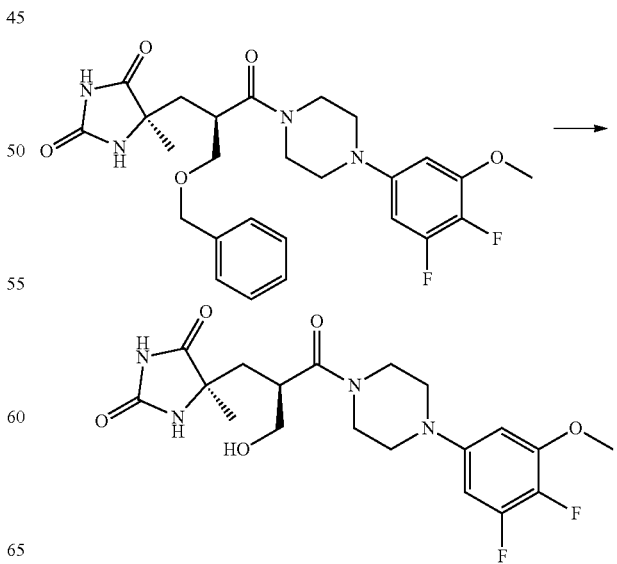

To a solution of Int 005 (105 mg, 0.20 mmol, 1 eq.) in dry THF (10 mL) under argon atmosphere is added Pd(OH)$_2$/C (50 mg, 50% w/w). The reaction mixture is stirred under H$_2$ atmosphere at r.t. for 5 h then filtered on celpure P65. The filtrate is concentrated in vacuo and purified by flash chromatography on silica gel (eluting with DCM/MeOH 100/0 to 90/10) to afford the expected product. LCMS: MW (calcd): 426; m/z MW (obsd): 427 (M+H).

1.2. Preparation of the Compounds of the Invention.
1.2.1. Cpd 98

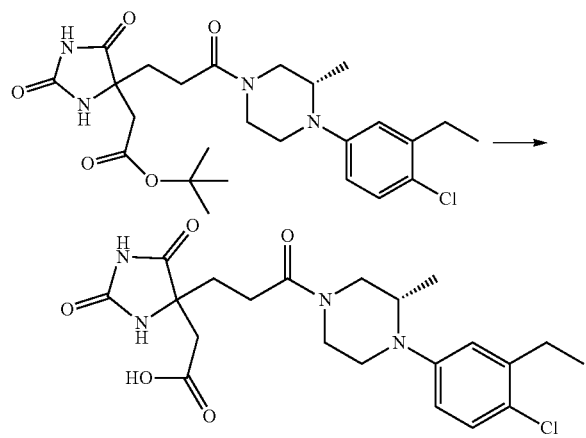

A flask is charged with Int 009 (28 mg, 0.06 mmol, 1.0 eq.) and a solution of HCl in dioxane (4N) (1 mL) is added, and stirring is kept at room temperature for 3 h. Reaction mixture is diluted with water, solution of NaHCO$_3$ is added and extracted with DCM. Organic layers are combined and evaporated under reduced pressure to obtain crude product which is purified by flash chromatography on silica gel (DCM/MeOH 100/0 to 92/8) to afford the expected carboxylic acid. LCMS: MW (calcd): 450; m/z MW (obsd): 451-453 (M+H).

1.2.2. Cpd 116

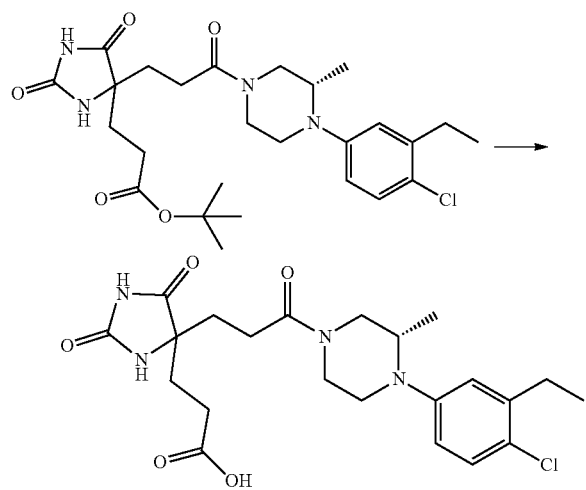

A flask is charged with Cpd 114 (68 mg, 0.013 mmol, 1.0 eq.) and a solution of HCl in dioxane (4.0M, 10 mL, 40 mmol, 300 eq.). The flask is capped with an oil bubbler and slowly flushed with a stream of N$_2$. After 64 h, volatiles are removed via rotary evaporation, and the residue is dissolved in a solution of HCl in dioxane (4.0M, 10 mL, 40 mmol, 300 eq.). The reaction mixture is allowed to stir at r.t. for 40 h. Volatiles are removed via rotary evaporation. The residue is dissolved in DMSO and purified by preparative LC-MS to afford the expected product. LCMS: MW (calcd): 464; m/z MW (obsd): 465 (M+H).

1.2.3. Int 002

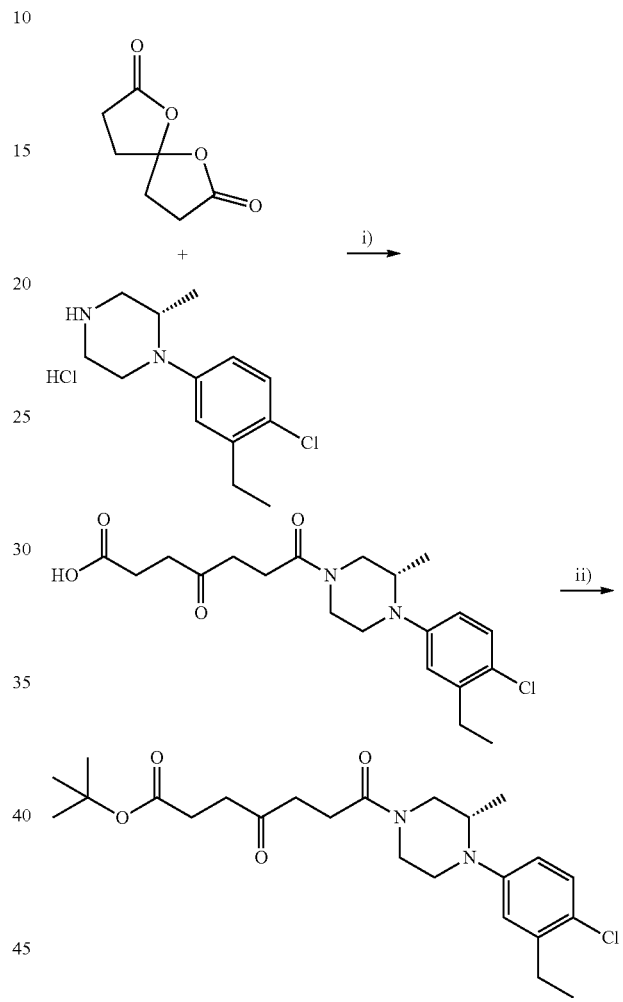

Step i)
A vial is charged with 1,6-dioxaspiro[4.4]nonane-2,7-dione (47.4 mg, 0.30 mmol, 1 eq), Int 062 (79 mg, 0.29 mmol, 0.95 eq), dry dioxane (2 mL), and triethyl amine (0.2 mL, 1.4 mmol, 4.7 eq). After 16 h, the mixture is combined with DCM (100 mL) and aqueous H$_3$PO$_4$/NaH$_2$PO$_4$ (1M, 100 mL) in a separatory funnel and agitated. The organic phase is collected, washed with brine (100 mL), and dried over MgSO$_4$. After filtration, volatiles are removed via rotary evaporation to give the expected product which is used in the following synthetic step without further purification.

Step ii)
A pressure vessel is charged with the acid synthesized in step i) (0.92 mol) and DCM (10 mL), and cooled in a NaCl/ice bath (−20° C.). Isobutene (3.06 g, 54.5 mmol, 59 eq) is condensed into the cold solution, and concentrated H$_2$SO$_4$ (0.1 mL, 1.8 mmol, 2.0 eq) is added. The vessel is hermetically sealed, and then the cold bath is removed. After 16 h, the vessel is cooled in a NaCl/ice bath (−20° C.), and opened. Et₃N (1.0 mL, 7.2 mmol, 7.8 eq) is added, and the cold bath is removed. Once all volatiles had evaporated, the mixture is combined with H₂O (100 mL) and DCM (100 mL) in a separatory funnel, and agitated. The organic phase is collected, washed with brine (100 mL) and dried over MgSO₄. After filtration, volatiles are removed from the filtrate via rotary evaporation. The residue is purified by flash chromatography on silica gel (EtOAc/DCM 1:4), to afford the expected compound Int 002.

1.2.4. Int 010

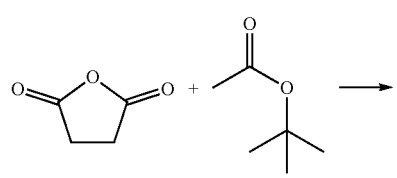

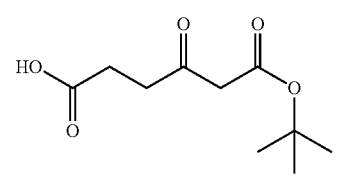

A solution of n-Butyl lithium (1.6M in hexane) (25 mL, 40 mmol, 2.0 eq) is added at 0° C. to a stirred solution of 1,1,1,3,3,3-hexamethyldisilazane (8.5 mL, 41 mmol, 2.04 eq) in anhydrous THF (17 mL). After cooling to −78° C., tertbutyl acetate (5.44 mL, 40 mmol, 2.0 eq) is added within 20 min to the solution and stirring is continued for 45 min. The resulting o-lithio acetic ester solution is added dropwise over 30 min to a solution of succinic anhydride (2 g, 20 mmol, 1.0 eq) in THF (24 mL). The resulting mixture is stirred for 3 h in a methanol/dry ice bath while the temperature is allowed to increase to −20° C.

The reaction mixture is warmed up to room temperature, then concentrated HCl (4 mL) and water (25 mL) are added. The organic solvent is evaporated, and the resulting aqueous solution is adjusted to pH=2, and extraction with ethyl acetate followed. Organic layers are combined, dried over Na₂SO₄, filtered, and concentrated under reduced pressure to give the expected product (used in the next step without further purification).

1.2.5. Int 017

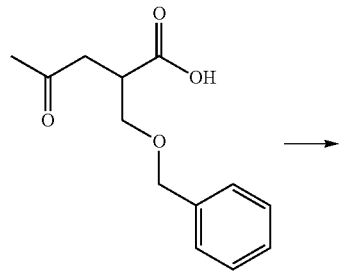

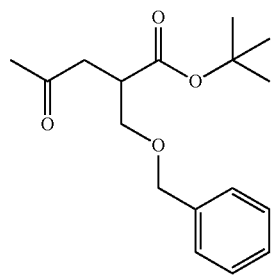

To a solution of Int 018 (530 mg, 2.24 mmol, 1 eq.) in toluene (7 mL) is added N,N-dimethylformamide di-tert-butyl acetal (2.69 mL, 11.2 mmol, 5 eq.). Reaction mixture is heated at 100° C. in a sealed tube for 4.5 h, quenched by addition of a saturated NaHCO₃ solution at 0° C., extracted with EtOAc. The combined organic layers are washed with saturated NaHCO₃ solution, brine, dried over anhydrous Na₂SO₄, filtered, concentrated in vacuo and purified by flash chromatography on silica gel (Heptane/EtOAc 100/0 to 60/40) to afford the expected product. LCMS: MW (calcd): 292; m/z MW (obsd): 315 (M+Na)

1.2.6. Int 025

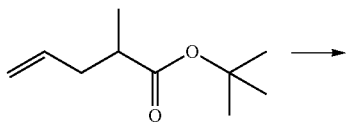

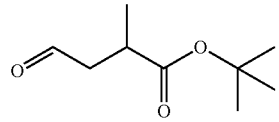

A three neck flask is charged with a solution of alkene Int 022 (6.3 g, 37 mmol, 1 eq.) and suddan III (cat.) in DCM and cooled at −78° C. O₃ is bubbled trough the reaction mixture until the color became deep blue. The reaction mixture is purged with N₂ for 30 min, Me₂S is added and the reaction mixture is allowed to warm to r.t. overnight. The reaction mixture is washed with water and brine, dried over anhydrous MgSO₄, filtered and concentrated in vacuo. Purification by flash chromatography on silica gel (Heptane/EtOAc 100/0 to 80/20) affords the expected product.

1.2.7. Int 026

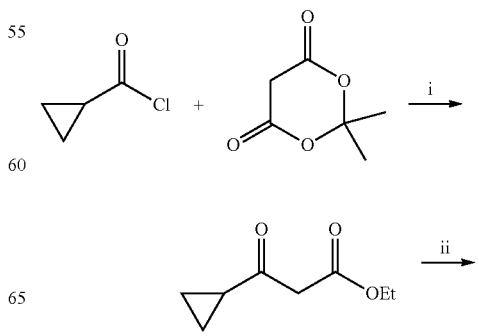

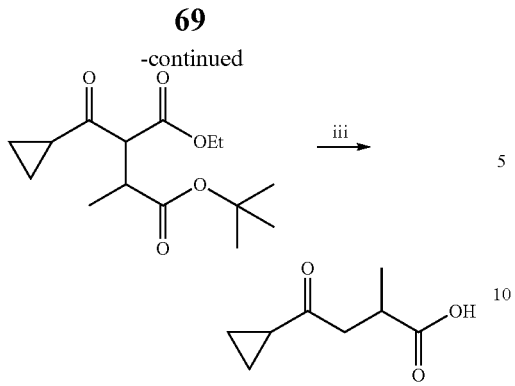

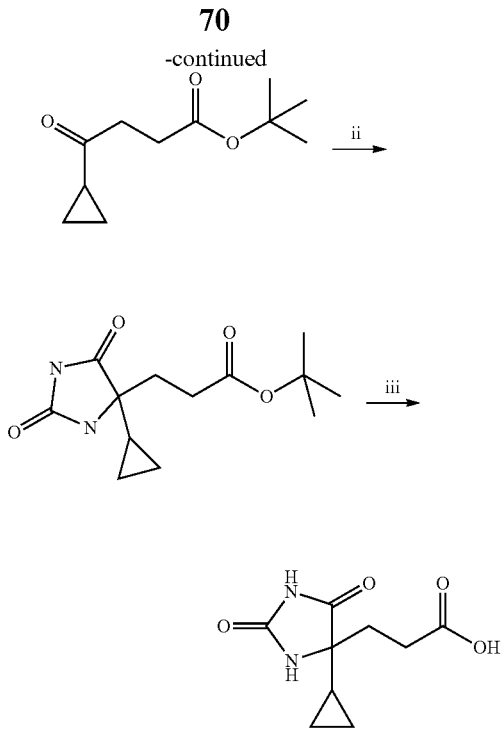

Step i)

To a solution of Meldrum's acid (2,2-dimethyl-[1,3]dioxane-4,6-dione, 50.10 g, 0.347 mol, 1 eq.) in DCM (500 mL) and pyridine (90 mL, 1.11 mol, 3.2 eq.) at 0° C., cyclopropanecarbonyl chloride (35 mL, 0.386 mol, 1.1 eq.) is added dropwise. After 2 h, the cold bath is removed and the reaction mixture is stirred at r.t. overnight and combined with a solution of HCl 2N. The organic layer is collected, washed with brine, dried over anhydrous MgSO$_4$, filtered over activated charcoal and concentrated in vacuo. This residue is taken up in ethanol (300 mL) and stirred at reflux overnight, concentrated in vacuo and purified by flash chromatography on silica gel (Heptane/EtOAc 80/20) to afford the expected β-ketoester. LCMS: MW (calcd): 156; m/z MW (obsd): 157 (M+H); 179 (M+Na)

Step ii)

To a solution of the β-ketoester (16.09 g, 0.103 mol, 1 eq.) in MEK (200 mL) are added K$_2$CO$_3$ (28.56 g, 0.207 mol, 2 eq.), NaI (1.65 g, 0.011 mol, 0.1 eq.) and 2-Bromo-propionic acid tert-butyl ester (18 mL, 0.108 mol, 1.04 eq.). The reaction mixture is heated at reflux for 40 h and cooled to r.t. Water is added, reaction mixture acidified to pH 8 and extracted with EtOAc. The combined organic layers are washed with water and brine, dried over anhydrous MgSO$_4$, filtered and concentrated in vacuo to afford the expected γ-ketoester used as such in next step. LCMS: MW (calcd): 284; m/z MW (obsd): 307 (M+Na)

Step iii)

To a solution of the γ-ketoester (29.2 g, 0.103 mol, 1 eq.) in EtOH (100 mL) is added a solution of NaOH (12.6 g, 0.315 mol, 3 eq.) in water (100 mL). The reaction mixture is heated at reflux for 16 h, cooled to r.t., diluted with water (500 mL) and cooled in an ice bath. To this is added dropwise H$_3$PO$_4$ (85%, 4 mL, 0.059 mol) and conc. HCl (24 mL, 0.288 mol), the ice bath is removed and reaction mixture is stirred at r.t. for 30 min. The reaction mixture is cooled in an ice bath and a solution of NaOH (17 g, 0.425 mol) in water (50 mL) is added to adjust the pH to 8. The solution is combined with DCM, the aqueous layer is collected, cooled in an ice bath and the pH adjusted to pH=2 with conc. HCl. The solution is saturated with NaCl and extracted with DCM. The combined organic layers are dried over anhydrous MgSO$_4$, filtered, concentrated in vacuo to afford the expected product. LCMS: MW (calcd): 156; m/z MW (obsd): 157 (M+H); 179 (M+Na).

1.2.8. Int 033

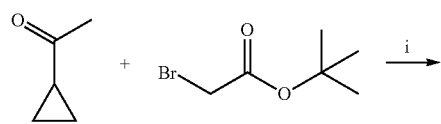

Step i)

A solution of LDA (3.0 L, 5.98 mol, 1.17 eq.) in THF (2.5 L) is cooled to −78° C. A solution of 1-cyclopropylethanone (460 g, 5.11 mol, 1 eq.) in THF (0.5 L) is added dropwise, then warmed to 20° C. and stirred for 30 min. The reaction mixture is cooled to −78° C. and tert-butyl bromoacetate (997 g, 5.11 mol, 1 eq.) in THF (0.5 L) is added slowly. The reaction is stirred at 0° C. overnight, quenched with saturated NH$_4$Cl aq. (3.3 L), extracted with EtOAc (0.5 L×3), washed with water (0.5 L×2), saturated NH$_4$Cl aq. (1 L), and brine (1 L), dried over anhydrous Na$_2$SO$_4$. Purification by distillation under reduced pressure (5 mbar, 95° C.) affords the expected γ-ketoester.

Step ii)

A mixture of γ-ketoester 4-Cyclopropyl-4-oxo-butyric acid tert-butyl ester (120 g, 605 mmol, 1 eq.), (NH$_4$)$_2$CO$_3$ (494 g, 5.15 mol, 8.5 eq.), NaCN (60 g, 1.45 mol, 2.4 eq.), H$_2$O (600 mL) and ethanol (600 mL) is heated at 60° C. for 18 h in the sealed reactor. The reaction mixture is poured in a mixture of EtOAc (900 mL) and water (900 mL), and the aqueous layer is additionally extracted with EtOAc (3×600 mL). The organic layer is concentrated until only about 100 mL EtOAc left, and added 500 mL petroleum ether dropwise to afford the expected hydantoin derivative.

Step iii)

A flask is charged with a solution of hydantoin (200 g, 746 mmol, 1.0 eq.) in dioxane (100 mL) and is cooled in an ice bath, HCl 4N in dioxane (1 L) is added slowly. The reaction mixture is stirred at r.t. for 4 h and concentrated in vacuo. The resulting solid is suspended in 240 mL of acetonitrile, then stirred at reflux for 1 h, and allowed to cool down to r.t. under stirring. The resulting solid is separated by filtration, washed twice with acetonitrile (2×30 mL), and finally dried under vacuum at 45° C. to afford the expected carboxylic acid. LC/MS: MW (calcd): 212; m/z MW (obsd): 211 (M−H).

1.2.9. Int 034

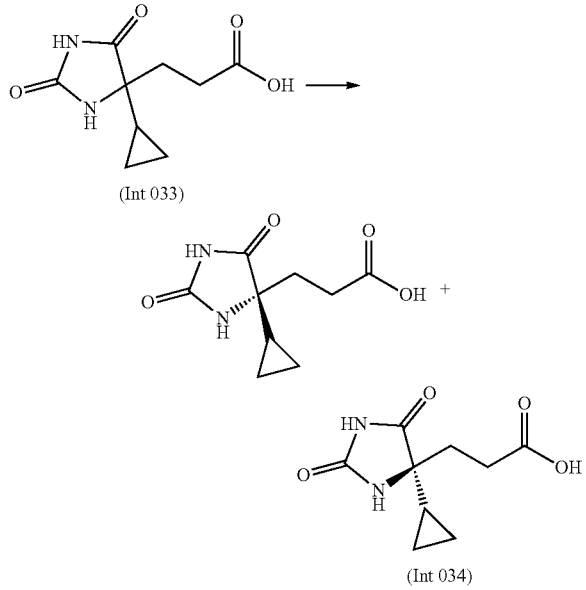

The racemic hydantoin propionic acid is separated by SFC to afford a fast eluting isomer ((R)-enantiomer) and a slow eluting isomer ((S)-enantiomer).

The purification is done in 2 stages.

Conditions of the first separation: preparative SFC, Column: ChiralPak AD-10 μm, 300×50 mm I.D., Mobile phase: A for CO₂ and B for Ethanol, Gradient: B 45%, Flow rate: 200 mL/min, Back pressure: 100 bar, Column temperature: 38° C., Wavelength: 220 nm, Cycletime: ~10.0 min. The compound is dissolved in methanol to ~120 mg/mL, and loaded on the column (16 mL per injection). After separation, the fractions are dried off via rotary evaporator to get the desired isomers.

Conditions of the second separation: Prep HPLC, Column: C18, 250×50 mm I.D., Mobile phase: A for H₂O and B for Acetonitrile, Gradient: B 5%-20% in 15 min linearly, Flow rate: 80 mL/min, Wavelength: 220 nm. The compound is dissolved in methanol (~100 mg/mL) and loaded on the column (10 mL per injection). After separation, the fraction is concentrated via rotary evaporator and the remaining aqueous layer is lyophilized.

1.2.10. Int 043 and 138

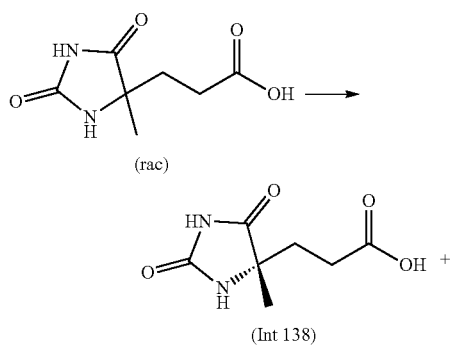

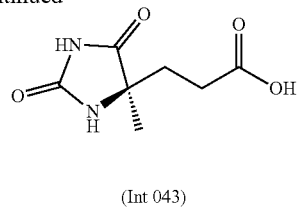

The racemic 3-(4-Methyl-2,5-dioxo-imidazolidin-4-yl) propionic acid (805 g) is separated by SFC to afford 384 g of the faster eluting isomer and 388 g of the slower eluting isomer. Conditions of the separation: Instrument: Thar350 preparative SFC, Column: ChiralPak AD-10 μm, 300×50 mm I.D., Mobile phase: A for CO₂ and B for IPA (0.1% TFA), Gradient: B 25%, Flow rate: 220 mL/min, Back pressure: 100 bar, Column temperature: 38° C., Wavelength: 210 nm, Cycletime: ~3.8 min, Sample preparation: Compound is dissolved in methanol to ~80 mg/mL, Injection: 1.0 mL per injection, Work up: After separation, the fractions are dried off via rotary evaporator at bath temperature 40° C. to get the desired isomers.

1.2.11. Int 117

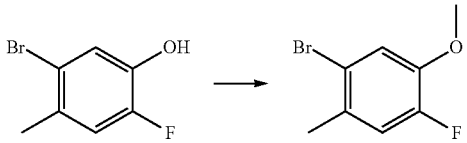

5-Bromo-2-fluoro-4-methyl-phenol (1.50 g, 7.3 mmol, 1.0 eq.), potassium carbonate (3.03 g, 22.0 mmol, 3.0 eq.) and methyl iodide (1.37 mL, 22.0 mmol, 3.0 eq.) are dissolved in acetonitrile (12 mL) and submitted to microwave irradiation for 20 min at 100° C. The reaction mixture is evaporated under reduced pressure, dissolved in water and extracted with DCM. The combined organic layers are dried over anhydrous Na₂SO₄, filtered and concentrated in vacuo to afford the expected product.

1.2.12. Int 118

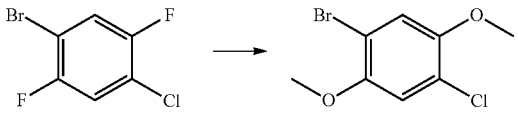

1-Bromo-4-chloro-2,5-difluoro-benzene (1.0 g, 4.4 mmol, 1.0 eq.) is dissolved in MeOH (10 mL) and a solution of sodium methoxide in MeOH (25% wt, 1.90 mL, 8.8 mmol, 2.0 eq.) is added. The reaction mixture is submitted to microwave irradiation for 50 min at 120° C. The reaction mixture is diluted with water and extracted with DCM. The combined organic layers are dried over anhydrous Na₂SO₄, filtered and concentrated in vacuo. Crystallization upon standing and filtration afford the expected product.

1.2.13. Int 119

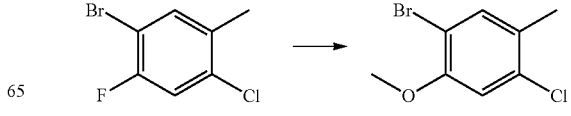

1-Bromo-4-chloro-2-fluoro-5-methyl-benzene (1.0 g, 4.5 mmol, 1.0 eq.) is dissolved in MeOH (10 mL) and a solution of sodium methoxide in MeOH (25% wt, 1.9 mL, 9.0 mmol, 2.0 eq.) is added. The reaction mixture is submitted to microwave irradiation for 50 min at 120° C. The reaction mixture is diluted with water and extracted with DCM. The combined organic layers are dried over anhydrous $Na_2SO_4$, filtered and concentrated in vacuo. Crystallization upon standing and filtration afford the expected product.

1.2.14. Int 120

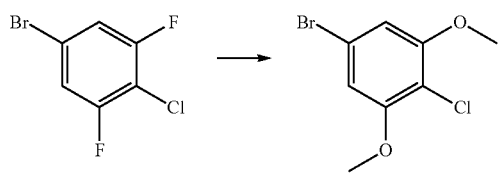

A solution of 1-bromo-4-chloro-3,5-difluorobenzene (100 mg, 0.44 mmol, 1.0 eq.) and sodium methylate (59 mg, 1.1 mmol, 2.5 eq.) in DMA (0.6 mL) is heated at 100° C. for 3 h. Sodium methoxide (12 mg, 0.22 mmol, 0.5 eq.) is added and the mixture is heated at 100° C. for 1 h, then cooled to r.t. Water (6 mL) is added and the solid is collected by filtration and dried under suction to give the expected product.

1.2.15. Int 121

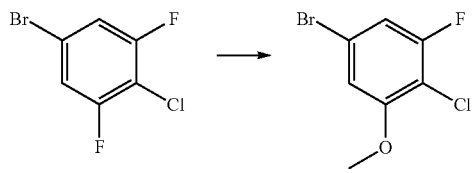

A solution of 1-bromo-4-chloro-3,5-difluorobenzene (300 mg, 1.3 mmol, 1.0 eq.) and sodium methoxide (105 mg, 2.6 mmol, 2.0 eq.) in MeOH (5.2 mL) is heated at 70° C. for 18 h. The methanol is evaporated under vacuo, and the residue is partitioned between water and DCM. The aqueous layer is extracted with DCM. The combined organic layers are washed with brine, dried over anhydrous $Na_2SO_4$, filtered and concentrated in vacuo to afford the expected product which is used as such in the next step.

1.2.16. Int 122

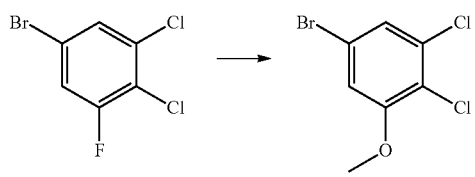

1-bromo-3,4-dichloro-5-fluorobenzene (365 mg, 1.5 mmol, 1.0 eq.) is heated in a 0.5M solution of sodium methoxide in methanol (6.0 mL, 3.0 mmol, 2.0 eq.) at 70° C. for 4 h, then at 85° C. for 18 h. The reaction mixture is cooled in an ice water bath. The solid is filtered and dried under suction to afford the expected product.

1.2.17. Int 123

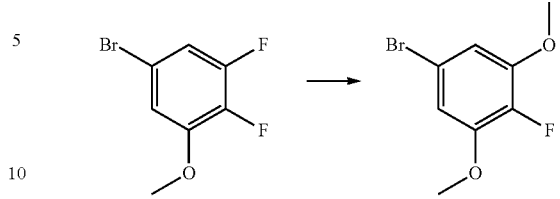

A solution of 1-bromo-3,4-difluoro-5-methoxy-benzene (1.11 g, 5.0 mmol, 1.0 eq.) and sodium methoxide (405 mg, 7.5 mmol, 1.5 eq.) in DMA (5 mL) is heated at 100° C. for 1 h. The reaction mixture is then poured into 60 mL of water and ice, stirred and the resulting solid is filtered and dried under suction to afford the expected product.

1.2.18. Int 124

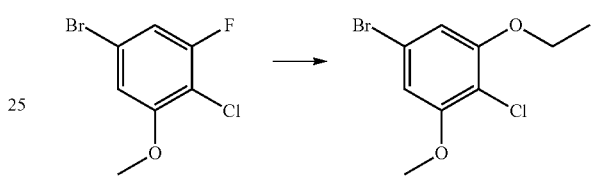

A solution of 1-bromo-4-chloro-3-fluoro-5-methoxy-benzene (542 mg, 2.3 mmol, 1.0 eq.) and sodium ethoxide (308 mg, 4.6 mmol, 2.0 eq.) in DMA (2.3 mL) is heated at 110° C. for 1.5 h. The reaction mixture is then poured into 100 mL of water. The aqueous layer is extracted 3 times with EtOAc. The combined organic phases are washed successively with water and brine, dried over anhydrous $Na_2SO_4$, filtered and concentrated in vacuo to afford the expected product which is used as such in the next step.

1.2.19. Int 125

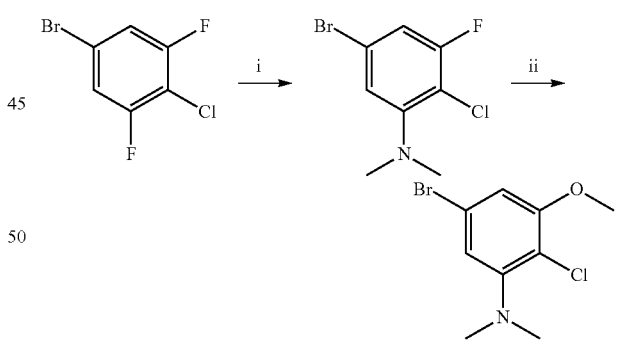

Step i)

1-bromo-4-chloro-3,5-difluorobenzene (682 mg, 3.0 mmol, 1.0 eq.), dimethylamine hydrochloride (734 mg, 9.0 mmol, 3.0 eq.) and DIPEA (2.1 mL, 12.0 mmol, 4.0 eq.) are heated in DMA (2.1 mL) in a sealed microwave vial at 125° C. for 18 h. The reaction mixture is then poured into water and brine. The aqueous layer is extracted 3 times with EtOAc. The combined organic phases are washed successively with water and brine, dried over anhydrous $Na_2SO_4$, filtered and concentrated in vacuo to afford the expected product. LCMS: MW (calcd): 251; m/z MW (obsd): 252-254 (M+H).

Step ii)

A solution of (5-bromo-2-chloro-3-fluoro-phenyl)-dimethyl-amine (599 mg, 2.4 mmol, 1.0 eq.) and sodium methoxide (259 mg, 4.8 mmol, 2.0 eq.) in DMA (2.4 mL) is heated at 110° C. for 2 h. The reaction mixture is then poured into 1000 mL of water and ice, stirred and extracted 3 times with EtOAc. The combined organic phases are washed successively with water and brine, dried over anhydrous $Na_2SO_4$, filtered and concentrated in vacuo to afford the expected product. LCMS: MW (calcd): 263; m/z MW (obsd): 264-266 (M+H).

1.2.20. Int 126

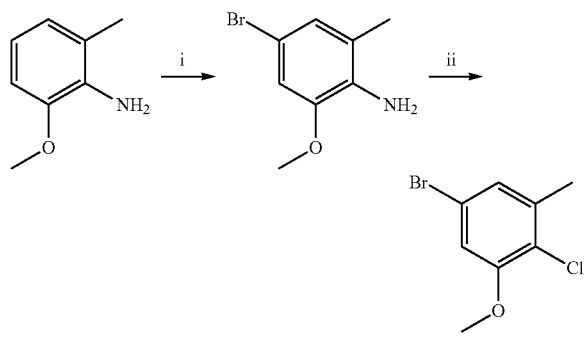

Step i)

To a solution of 2-methoxy-6-methylaniline (13.47 g, 98.3 mmol, 1.0 eq.) in DCM (1.3 L) and MeOH (520 mL) is added benzyltrimethylammonium tribromide (38.3 g, 98.3 mmol, 1.0 eq.) and calcium carbonate (39.3 g, 393.2 mmol, 4.0 eq.). The reaction mixture is stirred at r.t. for 1 h. The solid is filtered and washed with DCM. The filtrate is washed twice with water. The combined aqueous layers are extracted twice with $Et_2O$. The combined organic phases are dried over anhydrous $Na_2SO_4$, filtered, concentrated in vacuo to afford the expected product. LCMS: MW (calcd): 215; m/z MW (obsd): 216-218 (M+H).

Step ii)

To 4-bromo-2-methoxy-6-methyl-aniline (20.85 g, 96.5 mmol, 1.0 eq.) in a 6N aqueous HCl solution (54 mL, 326 mmol, 3.4 eq.) at 0° C. is added slowly, under vigorous stirring, a 0° C.-cooled solution of sodium nitrite (6.49 g, 94 mmol, 1.0 eq.) in water (27 mL). The resulting mixture is added quickly to a 0° C.-cooled solution of CuCl (46.1 g, 465.5 mmol, 4.8 eq.) in concentrated HCl (41 mL), and the flask is rinsed with 75 mL of water. The reaction mixture is stirred at 0° C. for 30 min, then at reflux for 18 h. The reaction mixture is cooled back to r.t., diluted with water and brine and extracted 3 times with DCM. The combined organic phases are washed successively with water and brine, dried over anhydrous $Na_2SO_4$, filtered, concentrated in vacuo. The residue is stirred in 300 mL of heptane at 100° C. for 15 min, hot filtered through Whatman glass microfibers filter and washed with heptane. The filtrate is concentrated under reduced pressure and the residue is purified by flash chromatography on silica gel to afford the expected product.

1.2.21. Int 127

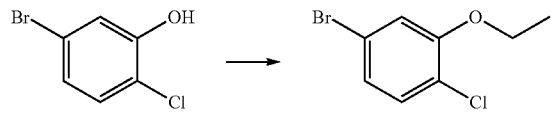

A mixture of 5-bromo-2-chlorophenol (300 mg, 1.5 mmol, 1.0 eq.), ethyl iodide (233 µL, 2.9 mmol, 2.0 eq.) and potassium carbonate (400 mg, 2.9 mmol, 2.0 eq.) in acetone (3 mL) is heated at 55° C. in a sealed vial for 18 h. Water is added and the reaction mixture is extracted twice with EtOAc. The combined organic phases are washed with water, dried over anhydrous $Na_2SO_4$, filtered and concentrated in vacuo to afford the expected product.

1.2.22. Int 128

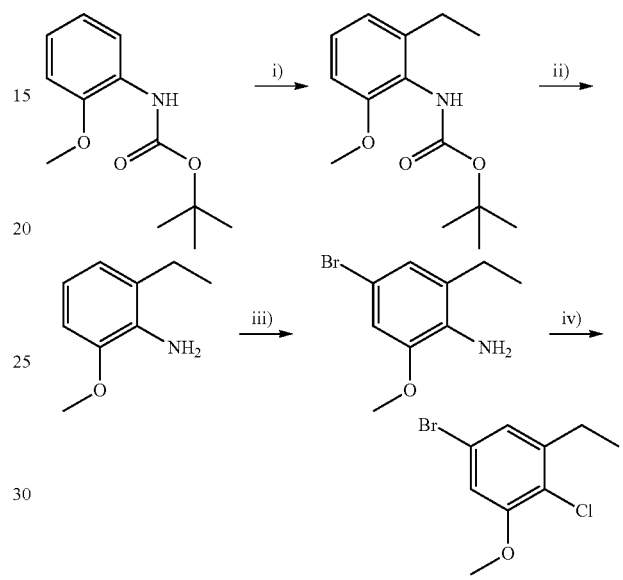

Step i)

N-boc-2-methoxy aniline (2.0 g, 9.0 mmol, 1.0 eq) is stirred in dry $Et_2O$ at −78° C. t-BuLi in pentane (1.6 M, 17 mL, 27 mmol, 3.0 eq) is then added dropwise at −78° C. Once addition is complete, the mixture is stirred at −78° C. for 10 min, then 20 min at 0° C. The mixture is then cooled back to −78° C., and a solution of iodoethane (1.4 mL, 18.0 mmol, 2.0 eq) in dry $Et_2O$ is then added dropwise, and stirring is kept at −78° C. After a few min, the dry ice/acetone bath is removed, and the mixture is warm up to room temperature, and left at rt. overnight. The mixture is then carefully quenched with water. Brine is added, and the aqueous layer is extracted with $Et_2O$ (three times). The combined organic layers are dried over $Na_2SO_4$, and concentrated under reduced pressure and the residue is purified by flash chromatography (Heptane/AcOEt 100/0 to 85/15), to afford the expected compound. LCMS: MW (calcd): 251; m/z MW (obsd): 252 (M+H).

Step ii)

N-boc-substituted aniline (945 mg, 3.76 mmol, 1.0 eq) is stirred in dioxane (5 mL), and HCl (4N in dioxane) is added. The mixture is stirred at rt; for 1 h30, and water and EtOAc are added. NaOH (2M) is added to the aqueous layer until a pH higher than 10 is reached and is then extracted with DCM (3 times). The combined organic layers are washed with water, brine, dried over $Na_2SO_4$, filtered, and concentrated under reduced pressure to afford the expected deprotected aniline.

Step iii) and Step iv)

Identical procedures from Int 126 Step i) and step ii) were applied for step iii) and step iv), to afford Int 128.

1.2.23. Int 129

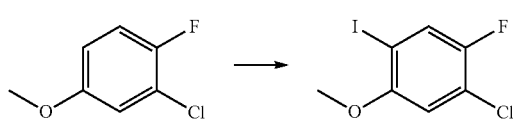

A mixture of 3-chloro-4-fluoroanisole (2.52 g, 15.7 mmol, 1.0 eq.), silver trifluoroacetate (8.53 g, 38.6 mmol, 2.5 eq.), iodine (7.94 g, 31.3 mmol, 2.0 eq.) and chloroform (100 mL) is stirred at r.t. for 16 h. The reaction mixture is filtered through a silica plug on a fritted funnel and rinsed with chloroform. The filtrate is washed successively with an aqueous solution of $Na_2S_2O_3$, water and brine, dried over $MgSO_4$, filtered and concentrated in vacuo. The residue is purified by flash chromatography on silica gel to afford the expected product.

1.2.24. Int 130

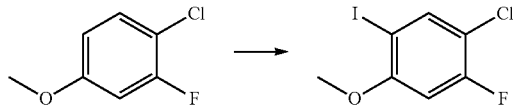

A mixture of 4-chloro-3-fluoroanisole (2.52 g, 15.7 mmol, 1.0 eq.), silver trifluoroacetate (8.57 g, 38.8 mmol, 2.5 eq.), iodine (7.95 g, 31.3 mmol, 2.0 eq.) and chloroform (100 mL) is stirred at r.t. for 16 h. The reaction mixture is filtered through a silica plug on a fritted funnel and rinsed with chloroform. The filtrate is washed successively with an aqueous solution of $Na_2S_2O_3$, water and brine, dried over $MgSO_4$, filtered and concentrated in vacuo. The residue is purified by flash chromatography on silica gel to afford the expected product.

1.2.25. Int 131

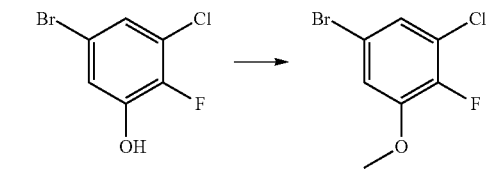

5-Bromo-3-chloro-2-fluorophenol (113 mg, 0.5 mmol, 1.0 eq.) is dissolved in MeCN (1 mL) in a microwave vial. Iodomethane (94 μL, 1.5 mmol, 3.0 eq.) and potassium carbonate (138 mg, 1.0 mmol, 2.0 eq.) are successively added. The vial is submitted to microwave irradiation at 100° C. for 10 min. The mixture is filtered and the salts are washed with EtOAc. The filtrate is then partitioned between water and EtOAc. The organic phase is dried over $Na_2SO_4$, filtered and concentrated in vacuo to afford the expected product, which is used as such in the next step.

1.2.26. Int 132

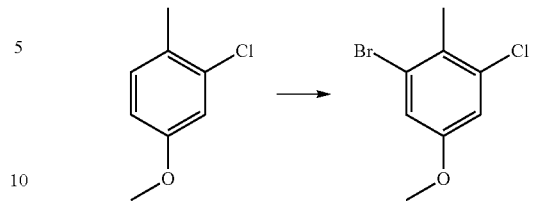

To 2-chloro-4-methoxytoluene (344 μL, 2.5 mmol, 1.0 eq.) in MeCN (1.5 mL) at 0° C. is added NBS (500 mg, 3.0 mmol, 1.2 eq.) in 2 portions (2nd half after 30 min stirring). The reaction mixture is allowed to stir at r.t. for 18 h. The solvent is removed in vacuo, and the residue is dissolved in DCM and washed with brine, dried over anhydrous $Na_2SO_4$, filtered and concentrated in vacuo to afford the expected product as a mixture, which is used as such in the next step.

1.2.27. Int 133

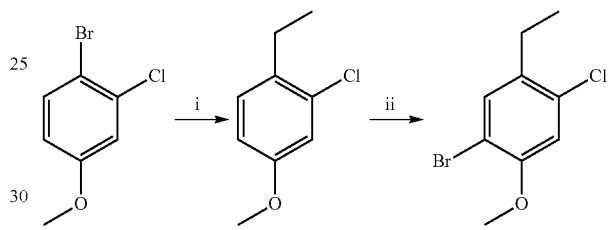

Step i)

To a solution of 1-bromo-2-chloro-4-methoxybenzene (2.0 g, 9.0 mmol, 1.0 eq.) in dioxane (180 mL) are added a diethylzinc solution in THF (18 mL, 1M, 18.0 mmol, 2.0 eq.) and [1,1'-bis(diphenylphosphino)ferrocene]dichloropalladium (II) (330 mg, 0.45 mmol, 0.05 eq.). The resulting solution is bubbled through with argon and stirred at reflux for 18 h. The reaction mixture is cooled to r.t., diluted with water (100 mL) and extracted 3 times with DCM. The combined organic phases are dried over anhydrous $Na_2SO_4$, filtered, concentrated in vacuo and purified by flash chromatography on silica gel to afford the expected product.

Step ii)

To 2-chloro-1-ethyl-4-methoxybenzene (1.36 g, 8.0 mmol, 1.0 eq.) in polyethyleneglycol (8 mL) cooled at 0° C. is added NBS (1.49 g, 8.4 mmol, 1.05 eq.) portionwise. The reaction mixture is allowed to warm to r.t. and is stirred for 18 h. The reaction mixture is diluted with water (20 mL) and extracted 3 times with DCM. The combined organic phases are dried over anhydrous $Na_2SO_4$, filtered, concentrated in vacuo and purified by flash chromatography on silica gel to afford the expected product.

1.2.28. Int 134

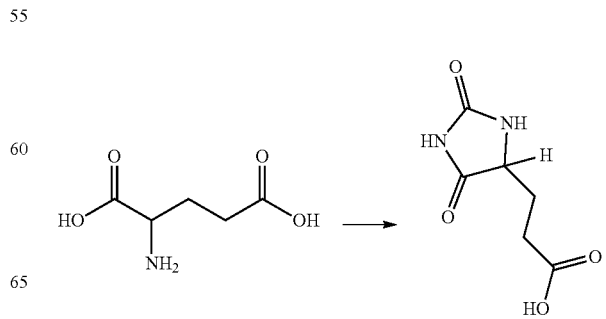

Int 134 is prepared from 2-Amino-pentanedioic acid using same experimental procedure as for preparation of Int 136
1.2.29. Int 136

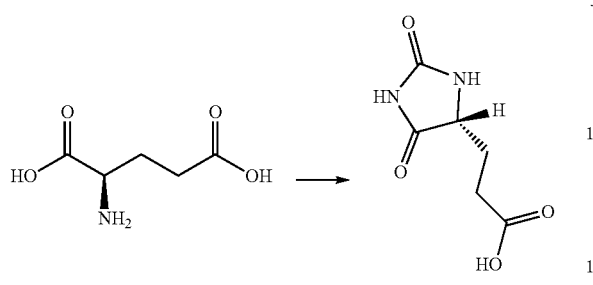

A round bottomed flask (1 L) is charged with (R)-2-Amino-pentanedioic acid, H₂O and heated at 80° C. After 6 h, the flask is allowed to cool to room temperature. Aqueous HCl (6 N, 200 mL, 1.2 mol) is slowly added. The flask was then heated at 60° C. After 1 h, the flask is allowed to cool to room temperature. After 24 h, volatiles are removed via rotary evaporation. The resulting solid is stirred in 360 mL of boiling dioxane. The suspension is then filtered out while the solvent is still hot, and the filtrate is let at room temperature over the weekend. Evaporation of the filtrate gives a white crude product (15.7 g). The crude is recrystallized from 140 mL of boiling water to give the expected compound.

1.2.30. Int 139

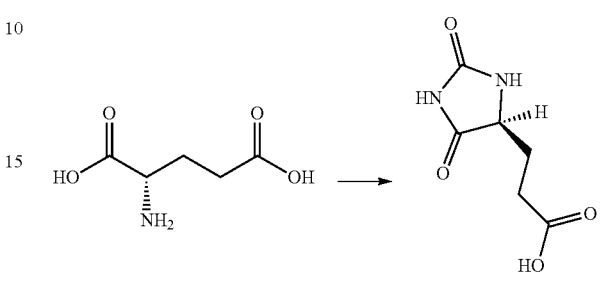

Int 139 is prepared from (S)-2-Amino-pentanedioic acid using same experimental procedure as for preparation of Int 136.

TABLE II

Illustrative intermediate for the synthesis of illustrative compounds of the invention

| Int | Chemistry | Name | Mtd | SM | MW | Ms'd |
|---|---|---|---|---|---|---|
| 001 | | 1-[4-(3-fluoro-5-methoxy-phenyl)piperazin-1-yl]-2-methyl-prop-2-en-1-one | C1 | 2-Methyl-acryloyl chloride + Int 048 | 278 | 279 |
| 002 | | tert-butyl 7-[(3S)-4-(4-chloro-3-ethyl-phenyl)-3-methyl-piperazin-1-yl]-4,7-dioxo-heptanoate | See above | 1,6-dioxaspiro[4.4]nonane-2,7-dione + Int 062 | 451 | 451-453 |

TABLE II-continued

| No. | Structure | Name | Method | Starting materials | MW | M+H |
|---|---|---|---|---|---|---|
| 003 | 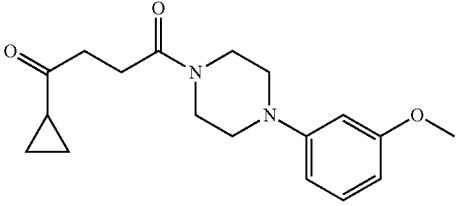 [SMILES: COc1cccc(N2CCN(C(=O)CCC(=O)C3CC3)CC2)c1] | 1-cyclopropyl-4-[4-(3-methoxyphenyl)piperazin-1-yl]butane-1,4-dione | F3 | 4-Cyclopropyl-4-oxo-butyric acid + 1-(3-Methoxy-phenyl)-piperazine | 316 | N.A. |
| 004 | 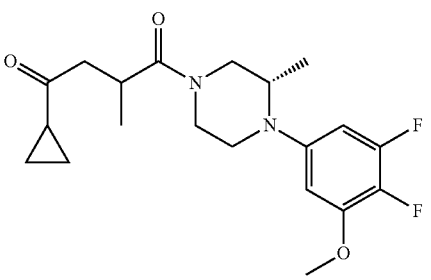 [SMILES: COc1cc(N2CCN(C(=O)C(C)CC(=O)C3CC3)C[C@@H]2C)cc(F)c1F] | 4-cyclopropyl-1-[(3S)-4-(3,4-difluoro-5-methoxy-phenyl)-3-methyl-piperazin-1-yl]-2-methyl-butane-1,4-dione | F3 | Int 026 + Int 047 | 380 | 381 |
| 005 | 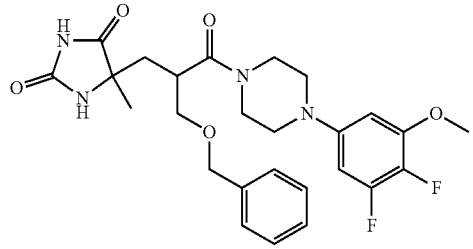 Trans | 5-[2-(benzyloxymethyl)-3-[4-(3,4-difluoro-5-methoxy-phenyl)piperazin-1-yl]-3-oxo-propyl]-5-methyl-imidazolidine-2,4-dione | F2 | Int 015 + Int 045 | 517 | N.A. |
| 006 | 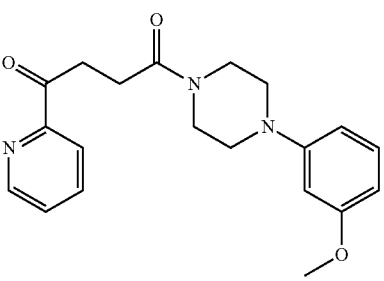 [SMILES: COc1cccc(N2CCN(C(=O)CCC(=O)c3ccccn3)CC2)c1] | 1-[4-(3-methoxyphenyl)piperazin-1-yl]-4-(2-pyridyl)butane-1,4-dione | F1 | 4-Oxo-4-pyridin-2-yl-butyric acid + 1-(3-Methoxy-phenyl)-piperazine | 353 | 354 |
| 007 | 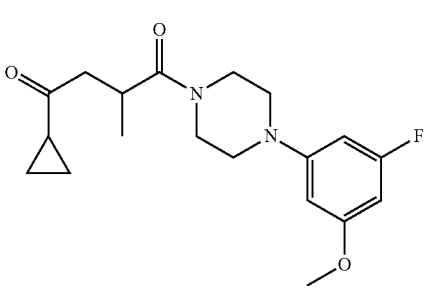 [SMILES: COc1cc(F)cc(N2CCN(C(=O)C(C)CC(=O)C3CC3)CC2)c1] | 4-cyclopropyl-1-[4-(3-fluoro-5-methoxy-phenyl)piperazin-1-yl]-2-methyl-butane-1,4-dione | C2 | Int 001 + cyclopropane carboxaldehyde | 348 | 349 |

TABLE II-continued

| | | | | | | |
|---|---|---|---|---|---|---|
| 008 | | 1-[4-(3-fluoro-5-methoxy-phenyl)piperazin-1-yl]-2-methyl-pentane-1,4-dione | C2 | Int 001 + acetaldehyde | 322 | 323 |
| 009 | | tert-butyl 2-[4-[3-[(3S)-4-(4-chloro-3-ethyl-phenyl)-3-methyl-piperazin-1-yl]-3-oxo-propyl]-2,5-dioxo-imidazolidin-4-yl] acetate | D | Int 011 | 507 | 507-509 |
| 010 | | 6-tert-butoxy-4,6-dioxo-hexanoic acid | See above | Succinic anhydride + tertbutyl acetate | 216 | N.A. |
| 011 | | tert-butyl 6-[(3S)-4-(4-chloro-3-ethyl-phenyl)-3-methyl-piperazin-1-yl]-3,6-dioxo-hexanoate | F2 | Int 010 + Int 062 | 437 | 437-439 |
| 012 | | 3-[2,5-dioxo-4-(3-pyridyl)imidazolidin-4-yl]propanoic acid | E | Int 013 | 249 | N.A. |

TABLE II-continued

| | Structure | Name | Method | Starting material | MW | MS |
|---|---|---|---|---|---|---|
| 013 | 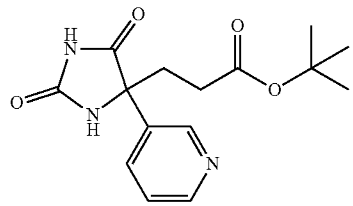 [SMILES: CC(C)(C)OC(=O)CCC1(c2cccnc2)NC(=O)NC1=O] | tert-butyl 3-[2,5-dioxo-4-(3-pyridyl)imidazolidin-4-yl]propanoate | D | Int 014 | 305 | 306 |
| 014 | 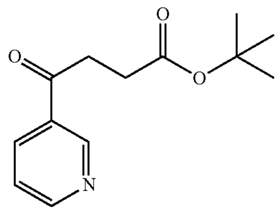 [SMILES: CC(C)(C)OC(=O)CCC(=O)c1cccnc1] | tert-butyl 4-oxo-4-(3-pyridyl)butanoate | B3 | Pyridine-3-carbaldehyde + Acrylic acid tert-butyl ester | 235 | 236 |
| 015 | Trans | 2-(benzyloxymethyl)-3-(4-methyl-2,5-dioxo-imidazolidin-4-yl)propanoic acid | E | Int 016 | 306 | 307 |
| 016 | Trans | tert-butyl 2-(benzyloxymethyl)-3-(4-methyl-2,5-dioxo-imidazolidin-4-yl)propanoate | D | Int 017 | 362 | N.A. |
| 017 | 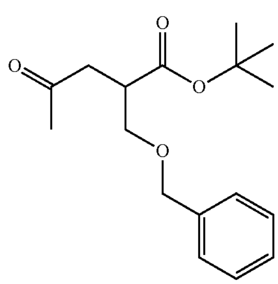 [SMILES: CC(=O)CC(COCc1ccccc1)C(=O)OC(C)(C)C] | tert-butyl 2-(benzyloxymethyl)-4-oxo-pentanoate | See above | Int 018 | 292 | 315 (M + Na) |
| 018 | 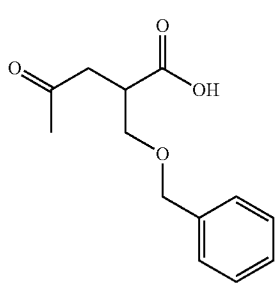 [SMILES: CC(=O)CC(COCc1ccccc1)C(=O)O] | 2-(benzyloxymethyl)-4-oxo-pentanoic acid | C3 | benzyloxy-acetaldehyde | 236 | N.A. |

TABLE II-continued

| | | | | | | |
|---|---|---|---|---|---|---|
| 019 | 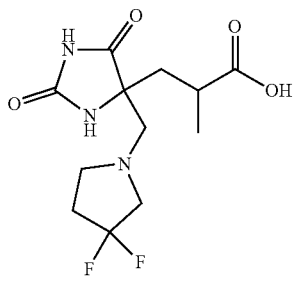 Trans | 3-[4-[(3,3-difluoropyrrolidin-1-yl)methyl]-2,5-dioxo-imidazolidin-4-yl]-2-methyl-propanoic acid | E | Int 020 | 305 | N.A. |
| 020 | 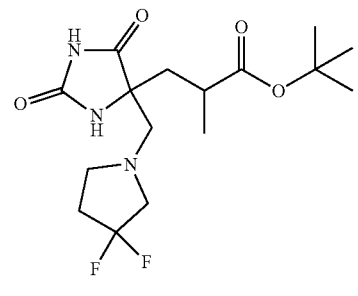 Trans | tert-butyl 3-[4-[(3,3-difluoro pyrrolidin-1-yl)methyl]-2,5-dioxo-imida-zolidin-4-yl]-2-methyl-propanoate | D | Int 021 | 361 | N.A. |
| 021 | 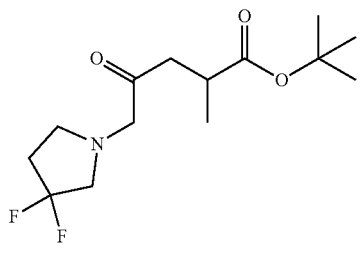 [SMILES: CC(CC(=O)CN1CCC(F)(F)C1)C(=O)OC(C)(C)C] | tert-butyl 5-(3,3-difluoropyrrolidin-1-yl)-2-methyl-4-oxo-pentanoate | B4 | Int 022 + 2,2-Difluoro-pyrrolidine hydrochloride | 291 | 292 |
| 022 | 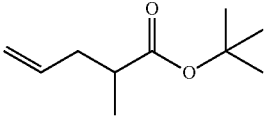 | tert-butyl 2-methylpent-4-enoate | B2 | 2-Methyl-pent-4-enoic acid | 170 | N.A. |
| 023 | 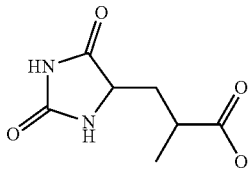 | 3-(2,5-dioxoimidazolidin-4-yl)-2-methyl-propanoic acid | E | Int 024 | 186 | N.A. |
| 024 | 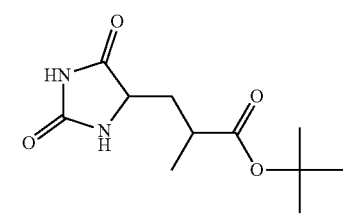 [SMILES: CC(CC1NC(=O)NC1=O)C(=O)OC(C)(C)C] | tert-butyl 3-(2,5-dioxoimidazolidin-4-yl)-2-methyl-propanoate | D | Int 025 | 242 | N.A. |
| 025 | 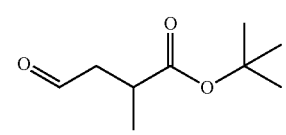 | tert-butyl 2-methyl-4-oxo-butanoate | See above | Int 022 | 172 | N.A. |

TABLE II-continued

| # | Structure | Name | Method | Starting materials | MW | MS |
|---|---|---|---|---|---|---|
| 026 | 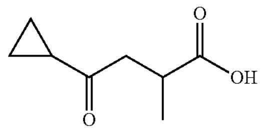 | 4-cyclopropyl-2-methyl-4-oxo-butanoic acid | See above | cyclopropane carbonyl chloride + 2,2-Dimethyl-[1,3]dioxane-4,6-dione | 156 | 155 (M − H) |
| 027 | Trans | 3-[4-(methoxymethyl)-2,5-dioxo-imidazolidin-4-yl]-2-methyl-propanoic acid | E | Int 028 | 230 | 231 |
| 028 | Trans | tert-butyl 3-[4-(methoxymethyl)-2,5-dioxo-imidazolidin-4-yl]-2-methyl-propanoate | D | Int 029 | 286 | 309 (M + Na) |
| 029 | 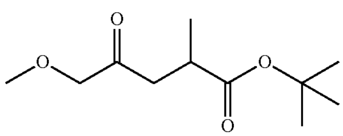 | tert-butyl 5-methoxy-2-methyl-4-oxo-pentanoate | B1 | Methoxy-acetic acid + 2,2-Dimethyl-[1,3]dioxane-4,6-dione | 216 | 239 (M + Na) |
| 030 | Trans | 3-[2,5-dioxo-4-(2-pyridyl)imidazoli-din-4-yl]-2-methyl-propanoic acid | E | Int 031 | 263 | 264 |
| 031 | Trans | tert-butyl 3-[2,5-dioxo-4-(2-pyridyl)imidazoli-din-4-yl]-2-methyl-propanoate | D | Int 032 | 319 | 320 |
| 032 | 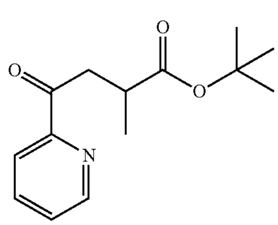 [SMILES: CC(CC(=O)c1ccccn1)C(=O)OC(C)(C)C] | tert-butyl 2-methyl-4-oxo-4-(2-pyridyl)butanoate | B1 (step ii + iii) | 3-Oxo-3-pyridin-2-yl-propionic acid benzyl ester + Bromo-acetic acid tert-butyl ester | 249 | 272 (M + Na) |

TABLE II-continued

| # | Structure | Name | Method | Starting Material | MW | MS |
|---|---|---|---|---|---|---|
| 033 | 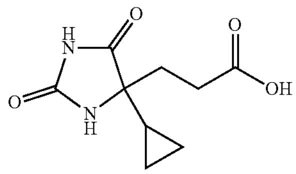 [SMILES: O=C(O)CCC1(C2CC2)NC(=O)NC1=O] | 3-(4-cyclopropyl-2,5-dioxo-imidazolidin-4-yl)propanoic acid | See above | 1-cyclopropyl-ethanone + tert-butyl bromoacetate | 212 | 211 (M − H) |
| 034 | 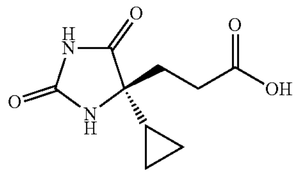 [SMILES: O=C(O)CC[C@@]1(C2CC2)NC(=O)NC1=O] | 3-((S)-4-Cyclopropyl-2,5-dioxo-imidazolidin-4-yl)-propionic acid | See above | Int 033 | 212 | N.A. |
| 035 | (Trans) | 3-(4-cyclopropyl-2,5-dioxo-imidazolidin-4-yl)-2-methyl-propanoic acid | B2 + D + E | Int 026 | 226 | 225 (M − H) |
| 036 | (Trans) | 2-methyl-3-(4-methyl-2,5-dioxo-imidazolidin-4-yl)propanoic acid | E | Int 140 | 200 | 201 |
| 037 | 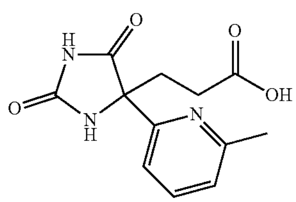 [SMILES: Cc1cccc(C2(CCC(=O)O)NC(=O)NC2=O)n1] | 3-[4-(6-methyl-2-pyridyl)-2,5-dioxo-imidazolidin-4-yl]propanoic acid | E | Int 038 | 263 | 264 |
| 038 | 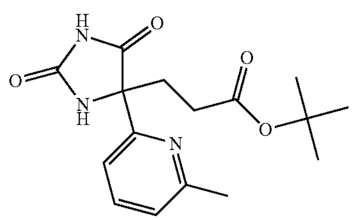 [SMILES: Cc1cccc(C2(CCC(=O)OC(C)(C)C)NC(=O)NC2=O)n1] | tert-butyl 3-[4-(6-methyl-2-pyridyl)-2,5-dioxo-imidazolidin-4-yl]propanoate | D | Int 039 | 319 | 320 |
| 039 | 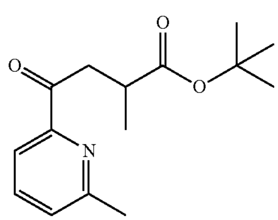 [SMILES: Cc1cccc(C(=O)CC(C)C(=O)OC(C)(C)C)n1] | tert-butyl 4-(6-methyl-2-pyridyl)-4-oxo-butanoate | B3 | 6-Methyl-pyridine-2-carbaldehyde + Acrylic acid tert-butyl ester | 249 | 250 |
| 040 | (Trans) | 3-(4-ethyl-2,5-dioxo-imidazolidin-4-yl)-2-methyl-propanoic acid | E | Int 041 | 214 | 215 |

TABLE II-continued

| | | | | | | | |
|---|---|---|---|---|---|---|---|
| 041 | 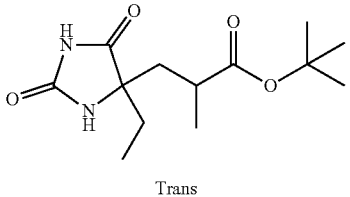 [SMILES: CCC1(CC(C)C(=O)OC(C)(C)C)NC(=O)NC1=O] Trans | | tert-butyl 3-(4-ethyl-2,5-dioxo-imidazolidin-4-yl)-2-methyl-propanoate | D | Int 042 | 270 | 271 |
| 042 | 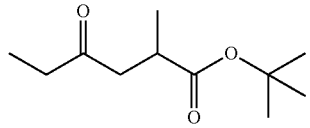 | | tert-butyl 2-methyl-4-oxo-hexanoate | B2 | 2-Methyl-4-oxo-hexanoic acid (J. Org. Chem. 2003, 68, 7983-7989 | 200 | N.A. |
| 043 | 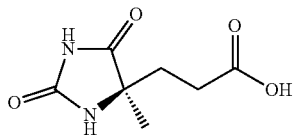 | | 3-[(4R)-4-methyl-2,5-dioxo-imidazolidin-4-yl]propanoic acid | See above | 3-(4-Methyl-2,5-dioxo-imidazolidin-4-yl)propionic acid | 186 | 373 (2M + H) |
| 044 | 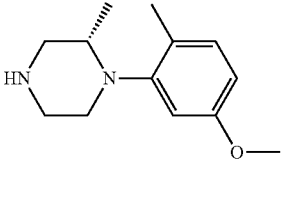 [SMILES: COc1ccc(C)c(N2CCNC[C@@H]2C)c1] | | (2S)-1-(5-methoxy-2-methyl-phenyl)-2-methyl-piperazine | A1 + A2 | (S)-3-Methyl-piperazine-1-carboxylic acid tert-butyl ester + 1-bromo-2-methyl-5-methoxy benzene | 220 | 221 |
| 045 | 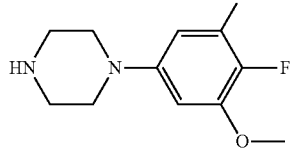 | | 1-(3,4-difluoro-5-methoxy-phenyl)piperazine | A5 | Piperazine + 5-Bromo-1,2-difluoro-3-methoxy-benzene | 228 | N.A. |
| 046 | 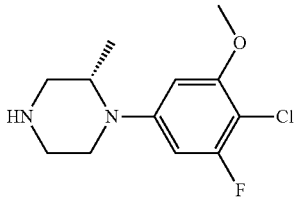 | | (2S)-1-(4-chloro-3-fluoro-5-methoxy-phenyl)-2-methyl-piperazine | A1 + A3 | (S)-3-Methyl-piperazine-1-carboxylic acid tert-butyl ester + 5-Bromo-2-chloro-1-fluoro-3-methoxy-benzene | 259 | 259-261 |
| 047 | 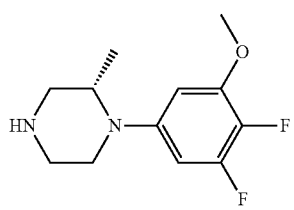 | | (2S)-1-(3,4-difluoro-5-methoxy-phenyl)-2-methyl-piperazine | A1 + A2 | (S)-3-Methyl-piperazine-1-carboxylic acid tert-butyl ester + 5-Bromo-1,2-difluoro-3-methoxy-benzene | 242 | 243 |
| 048 | 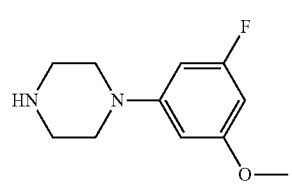 | | 1-(3-fluoro-5-methoxy-phenyl)piperazine | A5 | Piperazine + 1-Bromo-3-fluoro-5-methoxy-benzene | 210 | 211 |

TABLE II-continued

| | | | | | | |
|---|---|---|---|---|---|---|
| 049 | | (2S)-1-(5-methoxy-3-pyridyl)-2-methyl-piperazine | A1 + A3 | (S)-3-Methyl-piperazine-1-carboxylic acid tert-butyl ester + 3-Bromo-5-methoxy-pyridine | 207 | N.A. |
| 050 | | (2S)-1-(4-chloro-3-methoxy-phenyl)-2-methyl-piperazine | A1 + A2 | (S)-3-Methyl-piperazine-1-carboxylic acid tert-butyl ester + 4-Bromo-1-chloro-2-methoxy-benzene | 241 | 241 |
| 051 | | 1-(4-chloro-2,5-dimethoxy-phenyl)piperazine | A1 + A3 | Piperazine-1-carboxylic acid tert-butyl ester + Int 118 | 257 | 257-259 |
| 052 | | (2S)-1-(3-chloro-4-fluoro-5-methoxy-phenyl)-2-methyl-piperazine | A1 + A2 | (S)-3-Methyl-piperazine-1-carboxylic acid tert-butyl ester + Int 131 | 259 | 259 |
| 053 | | 1-[2-(trifluoromethoxy)phenyl]piperazine | A5 | Piperazine + 2-bromo trifluoro-methoxy benzene | 246 | 247 |
| 054 | | 1-[4-(trifluoromethoxy)phenyl]piperazine | A5 | piperazine + 1-Bromo-4-trifluoro-methoxy-benzene | 246 | 247 |
| 055 | | 1-(3,5-dimethoxyphenyl)piperazine | A5 | Piperazine + 1-Bromo-3,5-dimethoxy-benzene | 222 | 223 |
| 056 | | 1-(3-chloro-5-methoxy-phenyl)piperazine | A1 + A2 | Piperazine-1-carboxylic acid tert-butyl ester + 1-Bromo-3-chloro-5-methoxy-benzene | 227 | 227-229 |

TABLE II-continued

| | | | | | | |
|---|---|---|---|---|---|---|
| 057 | 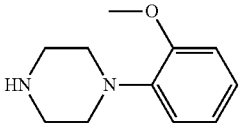 | 1-(2-methoxyphenyl)piperazine | A5 | Piperazine + 1-Bromo-3-methoxy-benzene | 192 | 193 |
| 058 | 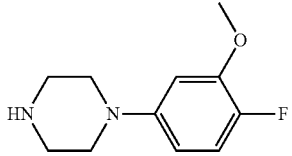 | 1-(4-fluoro-3-methoxy-phenyl)piperazine | A5 | Piperazine + 4-Bromo-1-fluoro-2-methoxy-benzene | 210 | 211 |
| 059 | 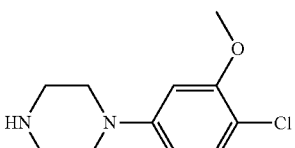 | 1-(4-chloro-3-methoxy-phenyl)piperazine | A5 | Piperazine + 4-Bromo-1-chloro-2-methoxy-benzene | 227 | 227-229 |
| 060 | 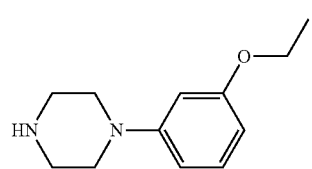 | 1-(3-ethoxyphenyl)piperazine | A5 | Piperazine + 1-Bromo-3-ethoxy-benzene | 206 | 207 |
| 061 | 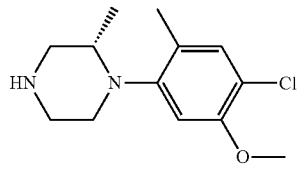 [SMILES: COc1cc(N2CCNC[C@@H]2C)c(C)cc1Cl] | (2S)-1-(4-chloro-5-methoxy-2-methyl-phenyl)-2-methyl-piperazine | A1 + A2 | (S)-3-Methyl-piperazine-1-carboxylic acid tert-butyl ester + 1-bromo-2-methyl-4-chloro-5-methoxy benzene | 255 | N.A. |
| 062 | 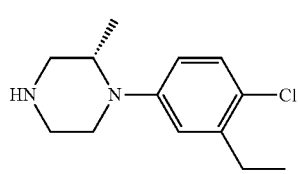 [SMILES: CCc1cc(N2CCNC[C@@H]2C)ccc1Cl] | (2S)-1-(4-chloro-3-ethyl-phenyl)-2-methyl-piperazine | A1 + A2 | (S)-3-Methyl-piperazine-1-carboxylic acid tert-butyl ester + 1-bromo-3-ethyl-4-chloro benzene | 239 | 239 |
| 063 | 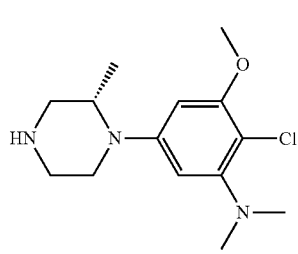 [SMILES: COc1cc(N2CCNC[C@@H]2C)cc(N(C)C)c1Cl] | 2-chloro-3-methoxy-N,N-dimethyl-5-[(2S)-2-methylpiperazin-1-yl]aniline | A1 + A2 | (S)-3-Methyl-piperazine-1-carboxylic acid tert-butyl ester + Int 125 | 284 | 284 |
| 064 | 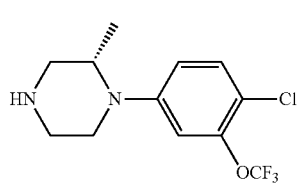 [SMILES: C[C@H]1CNCCN1c1ccc(Cl)c(OC(F)(F)F)c1] | (2S)-1-[4-chloro-3-(trifluoromethoxy)phenyl]-2-methyl-piperazine | A1 + A2 | (S)-3-Methyl-piperazine-1-carboxylic acid tert-butyl ester + 1-bromo-3-trifluoro-methoxy-4-chlorobenzene | 295 | 295 |

TABLE II-continued

| | | | | | | |
|---|---|---|---|---|---|---|
| 065 | | 1-(4-chloro-5-ethyl-2-methoxy-phenyl)piperazine | A1 + A2 | Piperazine-1-carboxylic acid tert-butyl ester + Int 133 | 255 | 255 |
| 066 | | (2S)-1-(4-chloro-5-ethyl-2-methoxy-phenyl)-2-methyl-piperazine | A1 + A2 | (S)-3-Methyl-piperazine-1-carboxylic acid tert-butyl ester + Int 133 | 269 | 269 |
| 067 | | (2S)-1-(4-chloro-2,5-dimethoxy-phenyl)-2-methyl-piperazine | A1 + A3 | (S)-3-Methyl-piperazine-1-carboxylic acid tert-butyl ester + Int 118 | 271 | 271-273 |
| 068 | | (2S)-1-(4-chloro-3-methoxy-5-methyl-phenyl)-2-methyl-piperazine | A1 + A2 | (S)-3-Methyl-piperazine-1-carboxylic acid tert-butyl ester + Int 126 | 255 | 255 |
| 069 | | (2S)-1-(4-chloro-3-methoxy-phenyl)-2-ethyl-piperazine | A1 + A2 | (S)-3-Ethyl-piperazine-1-carboxylic acid tert-butyl ester + 4-bromo-1-chloro-2-methoxy benzene | 255 | 255 |
| 070 | | (2S)-1-[5-methoxy-2-(trifluoromethoxy)phenyl]-2-methyl-piperazine | A1 + A3 | (S)-3-Methyl-piperazine-1-carboxylic acid tert-butyl ester + 2-Bromo-1-trifluoro-methoxy-4-methoxy-benzene | 290 | 291-293 |
| 071 | | (2S)-1-(4-chloro-3-methoxy-phenyl)-2-isopropyl-piperazine | A1 + A3 | (S)-3-Isopropyl-piperazine-1-carboxylic acid tert-butyl ester + 5-bromo-2-chloro anisole | 269 | 269-271 |

TABLE II-continued

| | | | | | | |
|---|---|---|---|---|---|---|
| 072 | | (2S)-1-(4-chloro-3-ethoxy-phenyl)-2-methyl-piperazine | A1 + A2 | (S)-3-Methyl-piperazine-1-carboxylic acid tert-butyl ester + Int 127 | 255 | 255 |
| 073 | | 1-(4-chloro-3-methoxy-5-methyl-phenyl)piperazine | A5 | Piperazine + Int 126 | 241 | 241 |
| 074 | | (2S)-1-(4,5-difluoro-2-methoxy-phenyl)-2-methyl-piperazine | A1 + A4 | (S)-3-Methyl-piperazine-1-carboxylic acid tert-butyl ester + 2-bromo-4,5-difluoroanisole | 242 | 243 |
| 075 | | 1-(4-chloro-3-ethyl-5-methoxy-phenyl)piperazine | A5 | Piperazine + Int 128 | 255 | 255 |
| 076 | | (2S)-1-(4-chloro-3-ethyl-5-methoxy-phenyl)-2-methyl-piperazine | A1 + A3 | (S)-3-Methyl-piperazine-1-carboxylic acid tert-butyl ester + Int 128 | 269 | 269 |
| 077 | | 1-(4-chloro-3-methoxy-phenyl)-2-(trifluoromethyl)piperazine | A1 + A1 + A2 | Trifluoro-methyl-piperazine + 2-chloro-5-bromo anisole | 295 | 295 |
| 078 | | 1-(4-chloro-3-fluoro-5-methoxy-phenyl)piperazine | A5 | Piperazine + Int 121 | 245 | 245 |
| 079 | | (2S)-1-(4-chloro-3,5-dimethoxy-phenyl)-2-methyl-piperazine | A1 + A2 A1 + A3 | (S)-3-Methyl-piperazine-1-carboxylic acid tert-butyl ester + Int 120 | 271 | 271 |

TABLE II-continued

| | | | | | | |
|---|---|---|---|---|---|---|
| 080 | | (2S)-1-(3,5-dimethoxyphenyl)-2-methyl-piperazine | A1 + A2 | (S)-3-Methyl-piperazine-1-carboxylic acid tert-butyl ester + 1-bromo-3,5-dimethoxy-benzene | 236 | 237 |
| 081 | | 1-(3,4-dichloro-5-methoxy-phenyl)piperazine | A5 | Piperazine + Int 122 | 261 | 261 |
| 082 | | 1-(3-chloro-4-fluoro-5-methoxy-phenyl)piperazine | A1 + A2 | Piperazine-1-carboxylic acid tert-butyl ester + Int 131 | 245 | N.A. |
| 083 | | 1-(4-chloro-2-methoxy-5-methyl-phenyl)piperazine | A1 + A2 | Piperazine-1-carboxylic acid tert-butyl ester + Int 119 | 241 | N.A. |
| 084 | | 1-(4-chloro-3,5-dimethoxy-phenyl)piperazine | A5 | Piperazine + Int 120 | 257 | 257-259 |
| 085 | | (2S)-1-(4-fluoro-5-methoxy-2-methyl-phenyl)-2-methyl-piperazine | A1 + A3 | (S)-3-Methyl-piperazine-1-carboxylic acid tert-butyl ester + Int 117 | 238 | 239 |
| 086 | | 1-(4-fluoro-5-methoxy-2-methyl-phenyl)piperazine | A1 + A3 | Piperazine-1-carboxylic acid tert-butyl ester + Int 117 | 224 | 225 |
| 087 | | 1-(3-chloro-2-methoxy-phenyl)piperazine | A1 + A2 | Piperazine-1-carboxylic acid tert-butyl ester + 2-bromo-6-chloro anisole | 227 | 227-229 |

TABLE II-continued

| | | | | | | |
|---|---|---|---|---|---|---|
| 088 | | (2S)-1-(3-chloro-2-methoxy-phenyl)-2-methyl-piperazine | A1 + A2 | (S)-3-Methyl-piperazine-1-carboxylic acid tert-butyl ester + 2-bromo-6-chloro anisole | 241 | 241-243 |
| 089 | | 1-(5-methoxy-2-methyl-phenyl)piperazine | A5 | Piperazine + 1-bromo-2-methyl-5-methoxy benzene | 206 | 207 |
| 090 | | 1-(3-ethylphenyl)piperazine | A5 | Piperazine + 1-bromo-3-ethyl benzene | 190 | 191 |
| 091 | | 1-(4-chloro-3-ethyl-phenyl)piperazine | A5 | Piperazine + 1-bromo-3-ethyl-4-chloro benzene | 225 | 225 |
| 092 | | 1-(3,5-diethylphenyl)piperazine | A5 | Piperazine + 1-bromo-3,5-diethyl benzene | 218 | 219 |
| 093 | | 1-(4-chloro-2-methoxy-phenyl)piperazine | A1 + A3 | Piperazine-1-carboxylic acid tert-butyl ester + 2-bromo-5-chloro anisole | 227 | 227-229 |
| 094 | | 1-(4-fluoro-3,5-dimethoxy-phenyl)piperazine | A1 + A3 | Piperazine-1-carboxylic acid tert-butyl ester + Int 123 | 240 | 241 |
| 095 | | (2S)-1-(4-chloro-2-methoxy-phenyl)-2-methyl-piperazine | A1 + A2 | (S)-3-Methyl-piperazine-1-carboxylic acid tert-butyl ester + 2-bromo-5-chloro anisole | 241 | 241-243 |

TABLE II-continued

| | | | | | | |
|---|---|---|---|---|---|---|
| 096 | | 1-(5-chloro-2-methoxy-phenyl)piperazine | A1 + A2 | Piperazine-1-carboxylic acid tert-butyl ester + 2-bromo-4-chloro anisole | 227 | 227-229 |
| 097 | | 1-(4-fluoro-2-methoxy-phenyl)piperazine | A1 + A2 | Piperazine-1-carboxylic acid tert-butyl ester + 2-bromo-5-fluoro anisole | 210 | 211 |
| 098 | | 1-(4-chloro-3-ethoxy-5-methoxy-phenyl)piperazine | A5 | Piperazine + Int 124 | 271 | 271 |
| 099 | | 1-(3-methoxy-2-methyl-phenyl)piperazine | A5 | Piperazine + 1-bromo-2-methyl-3-methoxy benzene | 206 | 207 |
| 100 | | (2S)-1-(4-chloro-3-ethoxy-5-methoxy-phenyl)-2-methyl-piperazine | A1 + A2 | (S)-3-Methyl-piperazine-1-carboxylic acid tert-butyl ester + Int 124 | 285 | 285 |
| 101 | | (2S)-1-(4-fluoro-2-methoxy-phenyl)-2-methyl-piperazine | A1 + A2 | (S)-3-Methyl-piperazine-1-carboxylic acid tert-butyl ester + 2-bromo-5-fluoro anisole | 224 | N.A. |
| 102 | | 1-(3-fluoro-2-methoxy-phenyl)piperazine | A1 + A2 | Piperazine-1-carboxylic acid tert-butyl ester + 2-bromo-6-fluoro anisole | 210 | 211 |
| 103 | | 1-(5-fluoro-2-methoxy-phenyl)piperazine | A1 + A2 | Piperazine-1-carboxylic acid tert-butyl ester + 2-bromo-4-fluoro anisole | 210 | 211 |

TABLE II-continued

| # | Structure | Name | Method | Starting materials | MW calc | MW found |
|---|---|---|---|---|---|---|
| 104 | 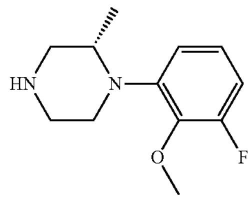 [SMILES: COc1c(F)cccc1N1CCNC[C@@H]1C] | (2S)-1-(3-fluoro-2-methoxy-phenyl)-2-methyl-piperazine | A1 + A2 | (S)-3-Methyl-piperazine-1-carboxylic acid tert-butyl ester + 2-bromo-6-fluoro anisole | 224 | 225 |
| 105 | 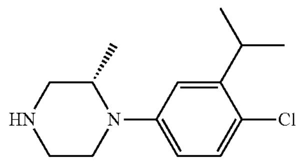 [SMILES: CC(C)c1cc(N2CCNC[C@@H]2C)ccc1Cl] | (2S)-1-(4-chloro-3-isopropyl-phenyl)-2-methyl-piperazine | A1 + A2 | (S)-3-Methyl-piperazine-1-carboxylic acid tert-butyl ester + 1-bromo-3-isopropyl-4-chlorobenzene | 253 | 253 |
| 106 | 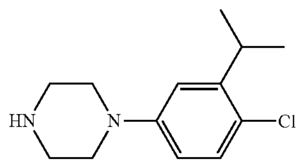 [SMILES: CC(C)c1cc(N2CCNCC2)ccc1Cl] | 1-(4-chloro-3-isopropyl-phenyl)piperazine | A5 | Piperazine + 1-bromo-3-isopropyl-4-chlorobenzene | 239 | 239 |
| 107 | 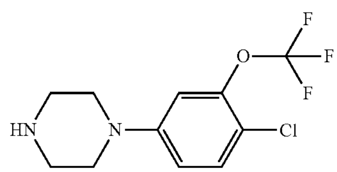 [SMILES: FC(F)(F)Oc1cc(N2CCNCC2)ccc1Cl] | 1-[4-chloro-3-(trifluoromethoxy)phenyl]piperazine | A5 | Piperazine + 1-bromo-3-trifluoro-methoxy-4-chlorobenzene | 281 | 281 |
| 108 | 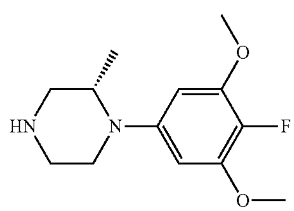 [SMILES: COc1cc(N2CCNC[C@@H]2C)cc(OC)c1F] | (2S)-1-(4-fluoro-3,5-dimethoxy-phenyl)-2-methyl-piperazine | A1 + A3 | (S)-3-Methyl-piperazine-1-carboxylic acid tert-butyl ester + Int 123 | 254 | 255 |
| 109 | 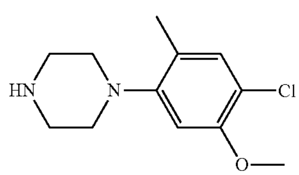 [SMILES: COc1cc(N2CCNCC2)c(C)cc1Cl] | 1-(4-chloro-5-methoxy-2-methyl-phenyl)piperazine | A5 | Piperazine + 1-bromo-2-methyl-4-chloro-5-methoxy benzene | 241 | 241 |
| 110 | 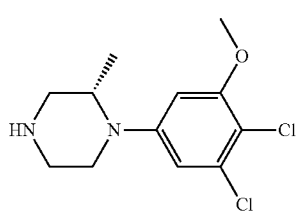 [SMILES: COc1cc(N2CCNC[C@@H]2C)cc(Cl)c1Cl] | (2S)-1-(3,4-dichloro-5-methoxy-phenyl)-2-methyl-piperazine | A1 + A3 | (S)-3-Methyl-piperazine-1-carboxylic acid tert-butyl ester + Int 122 | 275 | 275-277-279 |
| 111 | 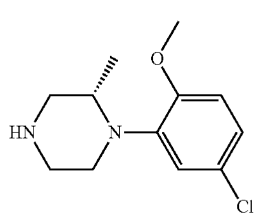 [SMILES: COc1ccc(Cl)cc1N1CCNC[C@@H]1C] | (2S)-1-(5-chloro-2-methoxy-phenyl)-2-methyl-piperazine | A1 + A3 | (S)-3-Methyl-piperazine-1-carboxylic acid tert-butyl ester + 2-bromo-4-chloro anisole | 241 | 241-243 |

TABLE II-continued

| | | | | | | |
|---|---|---|---|---|---|---|
| 112 | 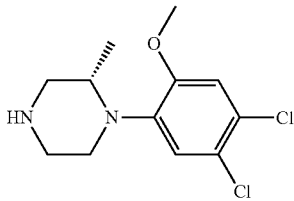 [SMILES: COc1cc(Cl)c(Cl)cc1N1CCNC[C@@H]1C] | (2S)-1-(4,5-dichloro-2-methoxy-phenyl)-2-methyl-piperazine | A1 + A3 | (S)-3-Methyl-piperazine-1-carboxylic acid tert-butyl ester + 2-bromo-4,5-dichloro anisole | 275 | 275-277-279 |
| 113 | 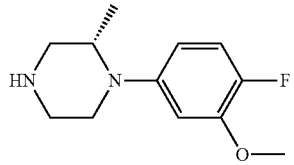 [SMILES: COc1cc(N2CCNC[C@@H]2C)ccc1F] | (2S)-1-(4-fluoro-3-methoxy-phenyl)-2-methyl-piperazine | A1 + A3 | (S)-3-Methyl-piperazine-1-carboxylic acid tert-butyl ester + 5-bromo-2-fluoro anisole | 224 | 225 |
| 114 | 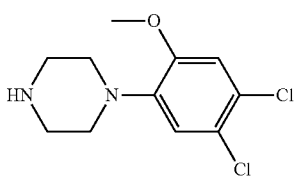 [SMILES: COc1cc(Cl)c(Cl)cc1N1CCNCC1] | 1-(4,5-dichloro-2-methoxy-phenyl)piperazine | A1 + A2 | Piperazine-1-carboxylic acid tert-butyl ester + 2-bromo-4,5-dichloro anisole | 261 | 261-263-265 |
| 115 | 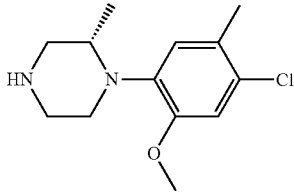 [SMILES: COc1cc(Cl)c(C)cc1N1CCNC[C@@H]1C] | (2S)-1-(4-chloro-2-methoxy-5-methyl-phenyl)-2-methyl-piperazine | A1 + A3 | (S)-3-Methyl-piperazine-1-carboxylic acid tert-butyl ester + Int 119 | 255 | 255-257 |
| 116 | 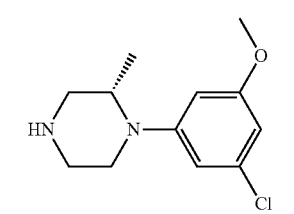 [SMILES: COc1cc(Cl)cc(N2CCNC[C@@H]2C)c1] | (2S)-1-(3-chloro-5-methoxy-phenyl)-2-methyl-piperazine | A1 + A2 | (S)-3-Methyl-piperazine-1-carboxylic acid tert-butyl ester + 3-bromo-5-chloro anisole | 241 | 241 |
| 117 | 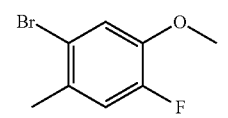 | 1-bromo-4-fluoro-5-methoxy-2-methyl-benzene | See above | 5-Bromo-2-fluoro-4-methyl-phenol | 219 | N.A. |
| 118 | 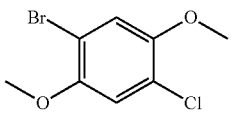 | 1-bromo-4-chloro-2,5-dimethoxy-benzene | See above | 1-Bromo-4-chloro-2,5-difluoro-benzene | 252 | N.A. |
| 119 | 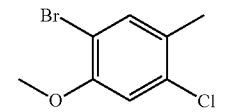 | 1-bromo-4-chloro-2-methoxy-5-methyl-benzene | See above | 1-Bromo-4-chloro-2-fluoro-5-methyl-benzene | 236 | N.A. |
| 120 | 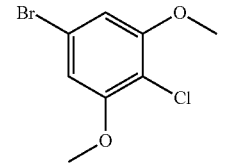 | 5-bromo-2-chloro-1,3-dimethoxy-benzene | See above | 1-bromo-4-chloro-3,5-difluoro-benzene | 252 | N.A. |

TABLE II-continued

| | | | | | | |
|---|---|---|---|---|---|---|
| 121 | (structure) | 5-bromo-2-chloro-1-fluoro-3-methoxy-benzene | See above | 1-bromo-4-chloro-3,5-difluoro-benzene | 239 | N.A. |
| 122 | (structure) | 5-bromo-1,2-dichloro-3-methoxy-benzene | See above | 1-bromo-3,4-dichloro-5-fluorobenzene | 256 | N.A. |
| 123 | (structure) | 5-bromo-2-fluoro-1,3-dimethoxy-benzene | See above | 1-bromo-3,4-difluoro-5-methoxy-benzene | 235 | N.A. |
| 124 | (structure) | 5-bromo-2-chloro-1-ethoxy-3-methoxy-benzene | See above | Int 121 | 266 | N.A. |
| 125 | (structure) | 5-bromo-2-chloro-3-methoxy-N,N-dimethyl-aniline | See above | 1-bromo-4-chloro-3,5-difluoro-benzene | 265 | 264-266 |
| 126 | (structure) | 5-bromo-2-chloro-1-methoxy-3-methyl-benzene | See above | 2-methoxy-6-methylaniline | 236 | N.A. |
| 127 | (structure) | 4-bromo-1-chloro-2-ethoxy-benzene | See above | 5-bromo-2-chlorophenol | 236 | N.A. |
| 128 | (structure) | 5-bromo-2-chloro-1-ethyl-3-methoxy-benzene | See above | N-boc-2-methoxy aniline + iodoethane | 250 | N.A. |
| 129 | (structure) | 1-chloro-2-fluoro-4-iodo-5-methoxy-benzene | See above | 3-chloro-4-fluoroanisole | 286 | N.A. |
| 130 | (structure) | 1-chloro-2-fluoro-5-iodo-4-methoxy-benzene | See above | 4-chloro-3-fluoroanisole | 286 | N.A. |

TABLE II-continued

| # | Structure | Name | Method | Starting Materials | MW | MS |
|---|---|---|---|---|---|---|
| 131 | 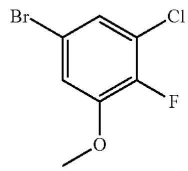 | 5-bromo-1-chloro-2-fluoro-3-methoxy-benzene | See above | 5-Bromo-3-chloro-2-fluorophenol | 239 | N.A. |
| 132 | 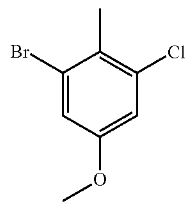 | 1-bromo-3-chloro-5-methoxy-2-methyl-benzene | See above | 2-chloro-4-methoxy-toluene | 236 | N.A. |
| 133 | 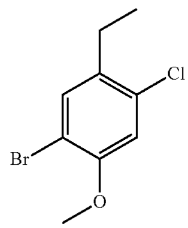 | 1-bromo-4-chloro-5-ethyl-2-methoxy-benzene | See above | 1-bromo-2-chloro-4-methoxy-benzene | 250 | N.A. |
| 134 | 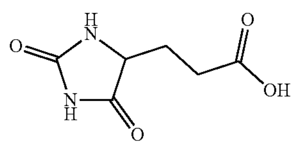 [SMILES: O=C(O)CCC1NC(=O)NC1=O] | 3-(2,5-Dioxo-imidazolidin-4-yl)-propionic acid | See above | DL-Glutamic acid monohydrate | 172 | 172 |
| 135 | 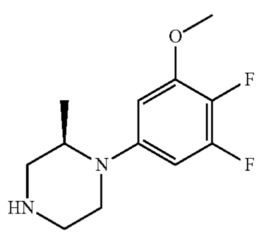 [SMILES: COc1cc(N2CCNC[C@H]2C)cc(F)c1F] | (R)-1-(3,4-Difluoro-5-methoxy-phenyl)-2-methyl-piperazine | A1 + A2 | (R)-3-Methyl-piperazine-1-carboxylic acid tert-butyl ester + 5-Bromo-1,2-difluoro-3-methoxy-benzene | 242 | 242 |
| 136 | 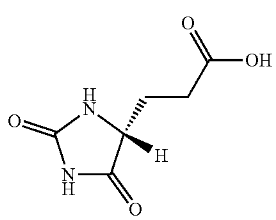 [SMILES: O=C(O)CC[C@H]1NC(=O)NC1=O] | 3-((R)-2,5-Dioxo-imidazolidin-4-yl)-propionic acid | See above | (R)-2-Amino-pentanedioic acid | 172 | 172 |
| 137 | 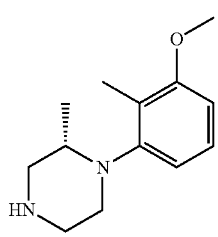 [SMILES: COc1cccc(N2CCNC[C@@H]2C)c1C] | (S)-1-(3-Methoxy-2-methyl-phenyl)-2-methyl-piperazine | A1 + A2 | (S)-3-Methyl-piperazine-1-carboxylic acid tert-butyl ester + 1-Bromo-3-methoxy-2-methyl-benzene | 220 | 220 |
| 138 | 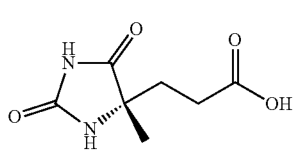 | 3-[(4S)-4-methyl-2,5-dioxo-imidazolidin-4-yl]propanoic acid | See above | 3-(4-Methyl-2,5-dioxo-imidazolidin-4-yl)propionic acid | 186 | 373 (2M + H) |

TABLE II-continued

| | | | | | | |
|---|---|---|---|---|---|---|
| 139 | (structure) | 3-((S)-2,5-Dioxo-imidazolidin-4-yl)-propionic acid | See above | (S)-2-Amino-pentanedioic acid | 172 | 172 |
| 140 | (structure) | 2-Methyl-3-(4-methyl-2,5-dioxo-imidazolidin-4-yl)-propionic acid tert-butyl ester | B1 step ii + step iii + D | 3-Oxo-butyric acid benzyl ester | 186 | N.A. |

TABLE III

Illustrative compounds of the invention

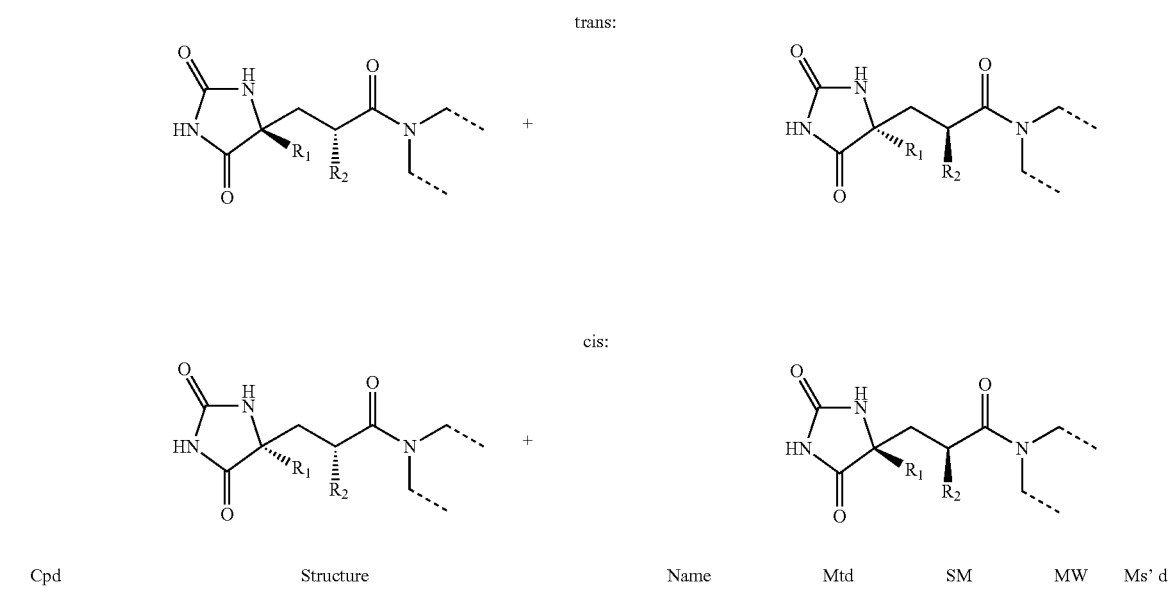

trans:

cis:

| Cpd | Structure | Name | Mtd | SM | MW | Ms' d |
|---|---|---|---|---|---|---|
| 1 | (structure) | 5-[3-[4-(3-methoxyphenyl)piperazin-1-yl]-3-oxo-propyl]-5-methyl-imidazolidine-2,4-dione | F1 | 3-(4-Methyl-2,5-dioxo-imidazolidin-4-yl)propionic acid + 1-(3-Methoxyphenyl)-piperazine | 360 | 361 |

TABLE III-continued

| | | | | | | |
|---|---|---|---|---|---|---|
| 2 | 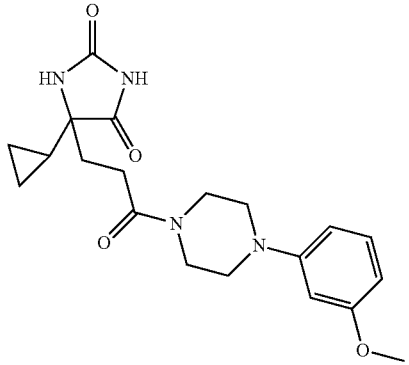 [SMILES: COc1cccc(N2CCN(C(=O)CCC3(C4CC4)NC(=O)NC3=O)CC2)c1] | 5-cyclopropyl-5-[3-[4-(3-methoxyphenyl)piperazin-1-yl]-3-oxo-propyl]imidazolidine-2,4-dione | D | Int 003 | 386 | 387 |
| 3 | 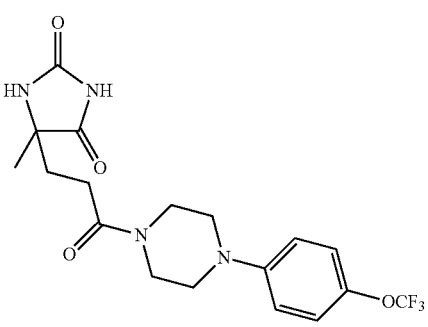 [SMILES: CC1(CCC(=O)N2CCN(c3ccc(OC(F)(F)F)cc3)CC2)NC(=O)NC1=O] | 5-methyl-5-[3-oxo-3-[4-[4-(trifluoromethoxy)phenyl]piperazin-1-yl]propyl]imidazolidine-2,4-dione | F3 | 3-(4-Methyl-2,5-dioxo-imidazolidin-4-yl)propionic acid + Int 054 | 414 | 415 |
| 4 | 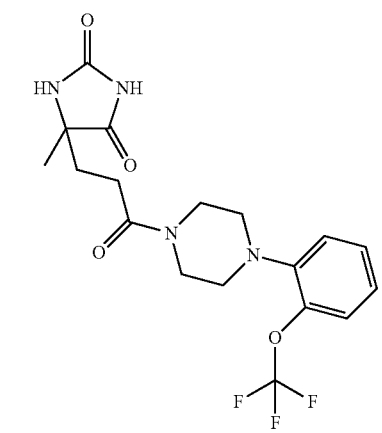 [SMILES: CC1(CCC(=O)N2CCN(c3ccccc3OC(F)(F)F)CC2)NC(=O)NC1=O] | 5-methyl-5-[3-oxo-3-[4-[2-(trifluoromethoxy)phenyl]piperazin-1-yl]propyl]imidazolidine-2,4-dione | F3 | 3-(4-Methyl-2,5-dioxo-imidazolidin-4-yl)propionic acid + Int 053 | 414 | 415 |
| 5 | 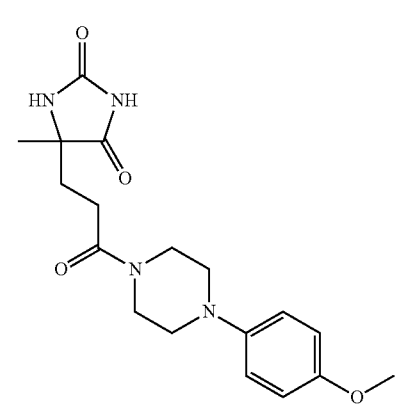 | 5-[3-[4-(4-methoxyphenyl)piperazin-1-yl]-3-oxo-propyl]-5-methyl-imidazolidine-2,4-dione | F3 | 3-(4-Methyl-2,5-dioxo-imidazolidin-4-yl)propionic acid + 1-(4-Methoxy-phenyl)pipoerazine | 360 | 361 |

TABLE III-continued
| | | | | | | |
|---|---|---|---|---|---|---|
| 6 | 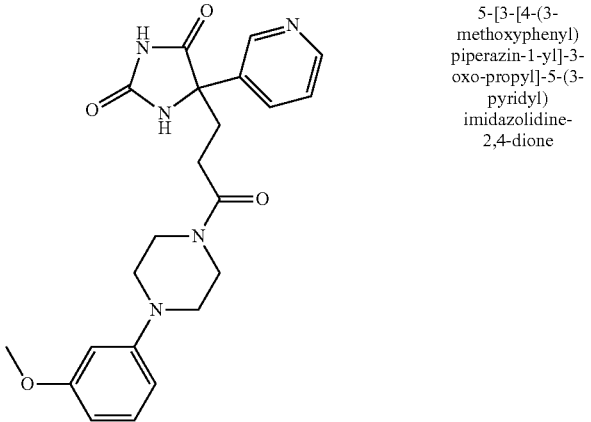 | 5-[3-[4-(3-methoxyphenyl)piperazin-1-yl]-3-oxo-propyl]-5-(3-pyridyl)imidazolidine-2,4-dione | F1 | Int 012 + 1-(3-Methoxy-phenyl)-piperazine | 423 | 424 |
| 7 | 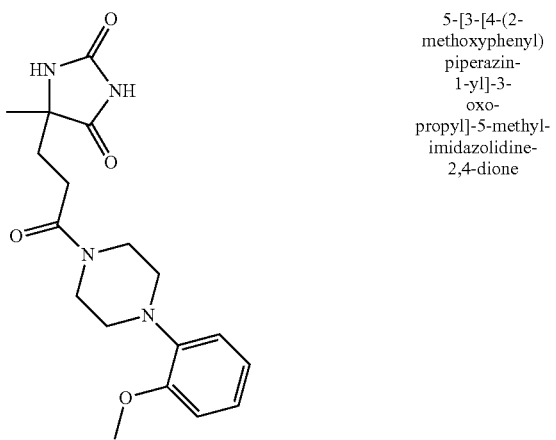 | 5-[3-[4-(2-methoxyphenyl)piperazin-1-yl]-3-oxo-propyl]-5-methyl-imidazolidine-2,4-dione | F1 | 3-(4-Methyl-2,5-dioxo-imidazolidin-4-yl)propionic acid + Int 057 | 360 | 361 |
| 8 | 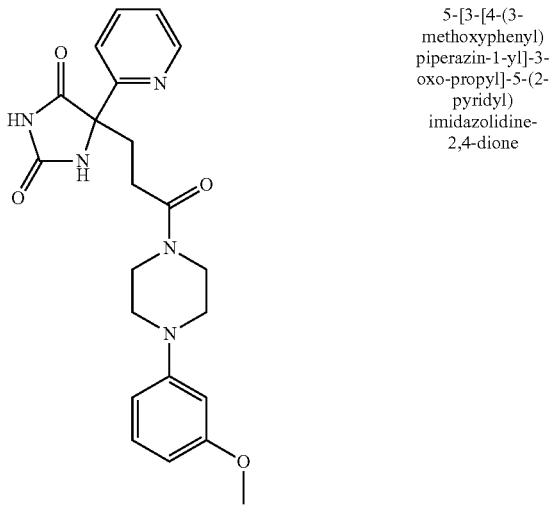 | 5-[3-[4-(3-methoxyphenyl)piperazin-1-yl]-3-oxo-propyl]-5-(2-pyridyl)imidazolidine-2,4-dione | D | Int 006 | 423 | 424 |

TABLE III-continued

| | | | | | | | |
|---|---|---|---|---|---|---|---|
| 9 | 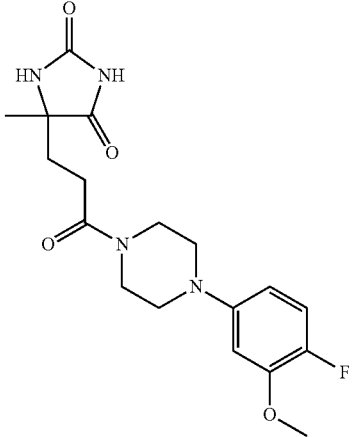 [SMILES: COc1cc(N2CCN(C(=O)CCC3(C)NC(=O)NC3=O)CC2)ccc1F] | | 5-[3-[4-(4-fluoro-3-methoxy-phenyl)piperazin-1-yl]-3-oxo-propyl]-5-methyl-imidazolidine-2,4-dione | F1 | 3-(4-Methyl-2,5-dioxo-imidazolidin-4-yl)propionic acid + Int 058 | 378 | 379 |
| 10 | 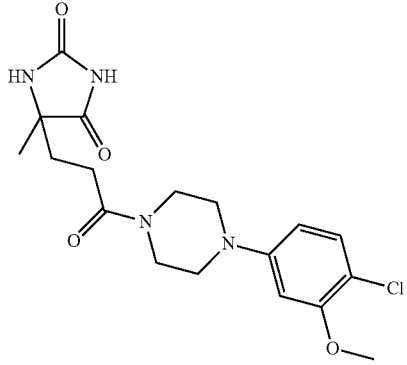 [SMILES: COc1cc(N2CCN(C(=O)CCC3(C)NC(=O)NC3=O)CC2)ccc1Cl] | | 5-[3-[4-(4-chloro-3-methoxy-phenyl)piperazin-1-yl]-3-oxo-propyl]-5-methyl-imidazolidine-2,4-dione | F1 | 3-(4-Methyl-2,5-dioxo-imidazolidin-4-yl)propionic acid + Int 059 | 395 | 395-397 |
| 11 | 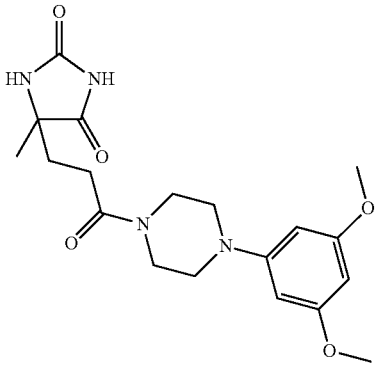 | | 5-[3-[4-(3,5-dimethoxyphenyl)piperazin-1-yl]-3-oxo-propyl]-5-methyl-imidazolidine-2,4-dione | F3 | 3-(4-Methyl-2,5-dioxo-imidazolidin-4-yl)propionic acid + Int 055 | 390 | 391 |
| 12 | 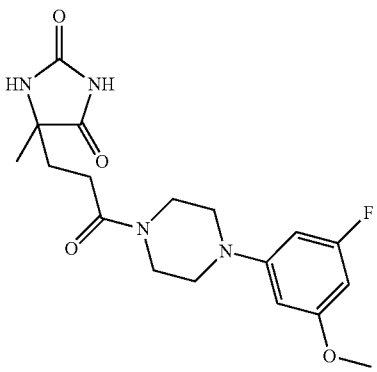 | | 5-[3-[4-(3-fluoro-5-methoxy-phenyl)piperazin-1-yl]-3-oxo-propyl]-5-methyl-imidazolidine-2,4-dione | F3 | 3-(4-Methyl-2,5-dioxo-imidazolidin-4-yl)propionic acid + Int 048 | 378 | 379 |

TABLE III-continued

| | | | | | | | |
|---|---|---|---|---|---|---|---|
| 13 | 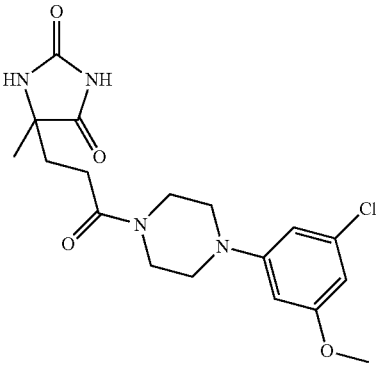 | 5-[3-[4-(3-chloro-5-methoxy-phenyl)piperazin-1-yl]-3-oxo-propyl]-5-methyl-imidazolidine-2,4-dione | F3 | 3-(4-Methyl-2,5-dioxo-imidazolidin-4-yl)propionic acid + Int 056 | 395 | 395 |
| 14 | 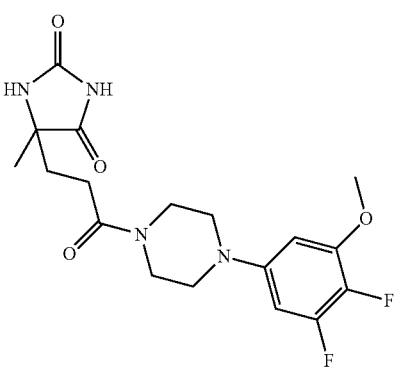 [SMILES: COc1cc(N2CCN(C(=O)CCC3(C)NC(=O)NC3=O)CC2)cc(F)c1F] | 5-[3-[4-(3,4-difluoro-5-methoxy-phenyl)piperazin-1-yl]-3-oxo-propyl]-5-methyl-imidazolidine-2,4-dione | F1 | 3-(4-Methyl-2,5-dioxo-imidazolidin-4-yl)propionic acid + Int 045 | 396 | 397 |
| 15 | 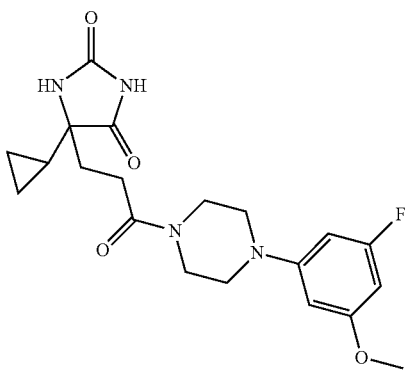 [SMILES: COc1cc(F)cc(N2CCN(C(=O)CCC3(C4CC4)NC(=O)NC3=O)CC2)c1] | 5-cyclopropyl-5-[3-[4-(3-fluoro-5-methoxy-phenyl)piperazin-1-yl]-3-oxo-propyl]imidazolidine-2,4-dione | F1 | Int 033 + Int 048 | 404 | 405 |
| 16 | 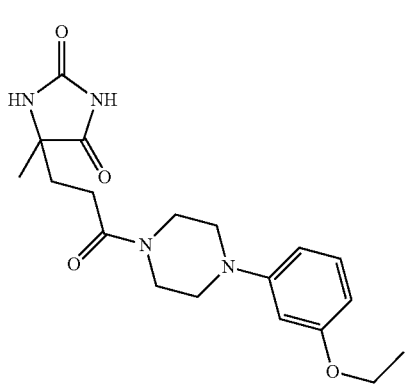 [SMILES: CCOc1cccc(N2CCN(C(=O)CCC3(C)NC(=O)NC3=O)CC2)c1] | 5-[3-[4-(3-ethoxyphenyl)piperazin-1-yl]-3-oxo-propyl]-5-methyl-imidazolidine-2,4-dione | F1 | 3-(4-Methyl-2,5-dioxo-imidazolidin-4-yl)propionic acid + Int 060 | 374 | 375 |

TABLE III-continued

| | | | | | | | |
|---|---|---|---|---|---|---|---|
| 17 | | 5-cyclopropyl-5-[3-[4-(4-fluoro-3-methoxy-phenyl)piperazin-1-yl]-3-oxo-propyl]imidazolidine-2,4-dione | F1 | Int 033 + Int 058 | 404 | 405 |
| 18 | | 5-cyclopropyl-5-[3-[4-(3,4-difluoro-5-methoxy-phenyl)piperazin-1-yl]-3-oxo-propyl]imidazolidine-2,4-dione | F1 | Int 033 + Int 045 | 422 | 423 |
| 19 | | (R)-5-[3-[4-(3-fluoro-5-methoxy-phenyl)piperazin-1-yl]-3-oxo-propyl]-5-methyl-imidazolidine-2,4-dione | F3 | Int 043 + Int 048 | 378 | 379 |
| 20 | | (R)-5-[3-[4-(3,4-difluoro-5-methoxy-phenyl)piperazin-1-yl]-3-oxo-propyl]-5-methyl-imidazolidine-2,4-dione | F3 | Int 043 + Int 045 | 396 | 397 |

TABLE III-continued
| | | | | | | |
|---|---|---|---|---|---|---|
| 21 | 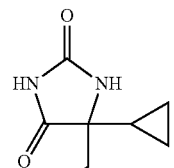 | 5-cyclopropyl-5-[3-[(3S)-4-(3,4-difluoro-5-methoxy-phenyl)-3-methyl-piperazin-1-yl]-3-oxo-propyl]imidazolidine-2,4-dione | F1 | Int 033 + Int 047 | 436 | 437 |
| 22 | 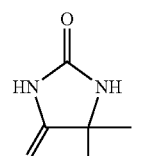 | 5-[3-[(3S)-4-(3,4-difluoro-5-methoxy-phenyl)-3-methyl-piperazin-1-yl]-3-oxo-propyl]-5-methyl-imidazolidine-2,4-dione | F1 | 3-(4-Methyl-2,5-dioxo-imidazolidin-4-yl)propionic acid + Int 047 | 410 | 411 |
| 23 | 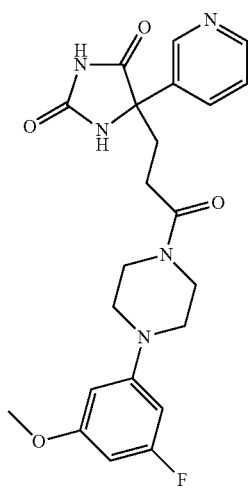 [SMILES: COc1cc(F)cc(N2CCN(C(=O)CCC3(c4cccnc4)NC(=O)NC3=O)CC2)c1] | 5-[3-[4-(3-fluoro-5-methoxy-phenyl)piperazin-1-yl]-3-oxo-propyl]-5-(3-pyridyl)imidazolidine-2,4-dione | F1 | Int 012 + Int 048 | 441 | 442 |

TABLE III-continued

| | | | | | | | |
|---|---|---|---|---|---|---|---|
| 24 | 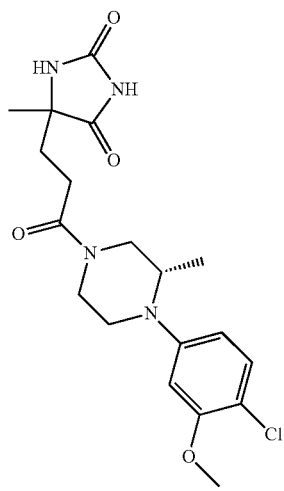 [SMILES: COc1cc(N2CCN(C(=O)CCC3(C)NC(=O)NC3=O)C[C@@H]2C)ccc1Cl] | | 5-[3-[(3S)-4-(4-chloro-3-methoxy-phenyl)-3-methyl-piperazin-1-yl]-3-oxo-propyl]-5-methyl-imidazolidine-2,4-dione | F2 | 3-(4-Methyl-2,5-dioxo-imidazolidin-4-yl)propionic acid + Int 050 | 409 | 409-411 |
| 25 | 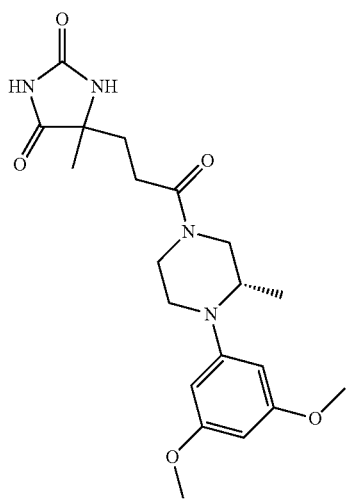 [SMILES: COc1cc(OC)cc(N2CCN(C(=O)CCC3(C)NC(=O)NC3=O)C[C@@H]2C)c1] | | 5-[3-[(3S)-4-(3,5-dimethoxy-phenyl)-3-methyl-piperazin-1-yl]-3-oxo-propyl]-5-methyl-imidazolidine-2,4-dione | F2 | 3-(4-Methyl-2,5-dioxo-imidazolidin-4-yl)propionic acid + Int 080 | 405 | 405 |
| 26 | 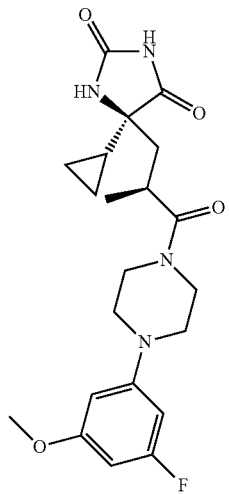 [SMILES: COc1cc(F)cc(N2CCN(C(=O)[C@@H](C)C[C@@]3(C4CC4)NC(=O)NC3=O)CC2)c1] | | (5S)-5-cyclopropyl-5-[(2S)-3-[4-(3-fluoro-5-methoxy-phenyl)piperazin-1-yl]-2-methyl-3-oxo-propyl]imidazolidine-2,4-dione | D | Int 007 | 418 | 419 |

| | | | | | | |
|---|---|---|---|---|---|---|
| 27 | 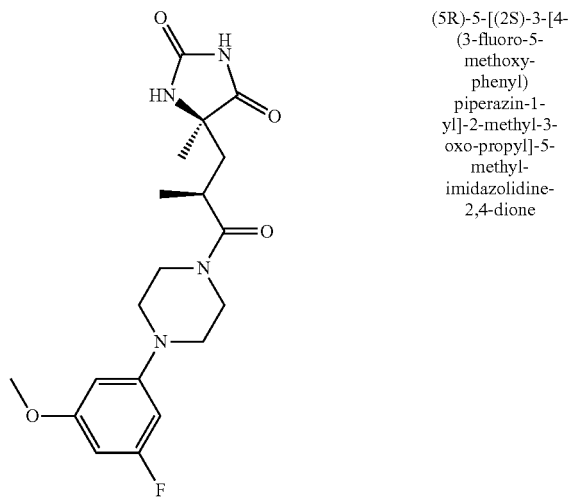 | (5R)-5-[(2S)-3-[4-(3-fluoro-5-methoxy-phenyl)piperazin-1-yl]-2-methyl-3-oxo-propyl]-5-methyl-imidazolidine-2,4-dione | D | Int 008 | 392 | 393 |
| 28 | 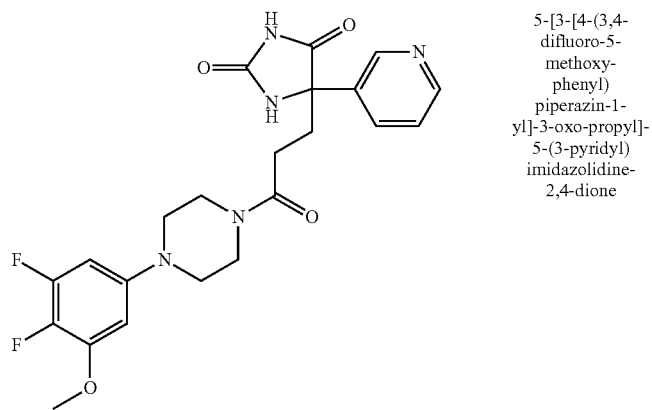 | 5-[3-[4-(3,4-difluoro-5-methoxy-phenyl)piperazin-1-yl]-3-oxo-propyl]-5-(3-pyridyl)imidazolidine-2,4-dione | F1 | Int 045 + Int 012 | 459 | 460 |
| 29 | 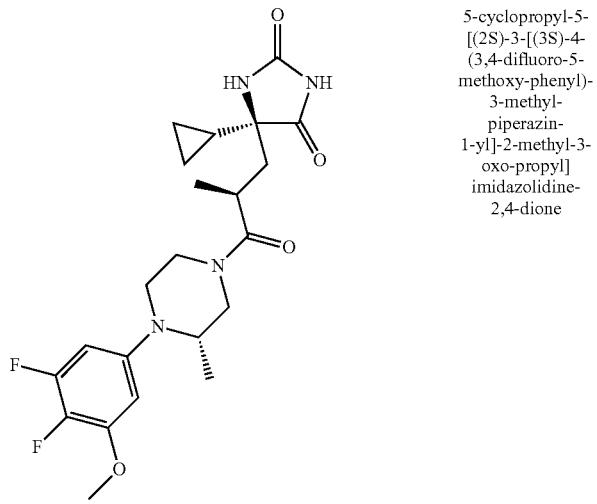 Trans | 5-cyclopropyl-5-[(2S)-3-[(3S)-4-(3,4-difluoro-5-methoxy-phenyl)-3-methyl-piperazin-1-yl]-2-methyl-3-oxo-propyl]imidazolidine-2,4-dione | D | Int 004 | 450 | 451 |

TABLE III-continued

| | | | | | | | |
|---|---|---|---|---|---|---|---|
| 30 | 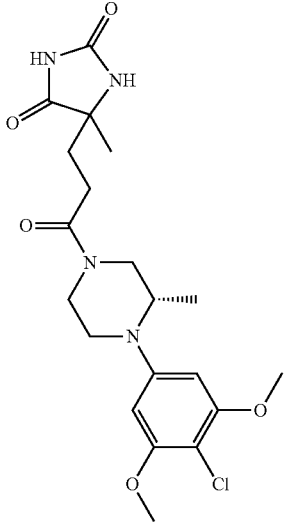 [SMILES: COc1cc(N2CCN(C(=O)CCC3(C)NC(=O)NC3=O)C[C@@H]2C)cc(OC)c1Cl] | 5-[3-[(3S)-4-(4-chloro-3,5-dimethoxy-phenyl)-3-methyl-piperazin-1-yl]-3-oxo-propyl]-5-methyl-imidazolidine-2,4-dione | F2 | 3-(4-Methyl-2,5-dioxo-imidazolidin-4-yl)propionic acid + Int 079 | 439 | 439-441 |
| 31 | 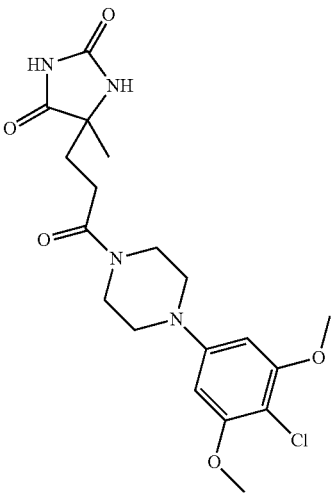 [SMILES: COc1cc(N2CCN(C(=O)CCC3(C)NC(=O)NC3=O)CC2)cc(OC)c1Cl] | 5-[3-[4-(4-chloro-3,5-dimethoxy-phenyl)piperazin-1-yl]-3-oxo-propyl]-5-methyl-imidazolidine-2,4-dione | F2 | 3-(4-Methyl-2,5-dioxo-imidazolidin-4-yl)propionic acid + Int 084 | 425 | 425-427 |
| 32 | 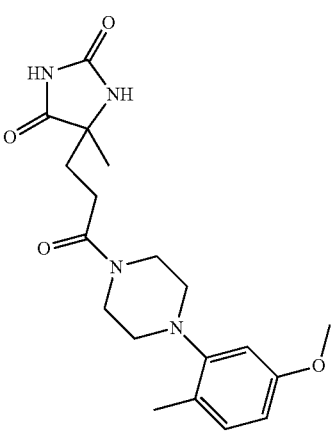 [SMILES: COc1ccc(C)c(N2CCN(C(=O)CCC3(C)NC(=O)NC3=O)CC2)c1] | 5-[3-[4-(5-methoxy-2-methyl-phenyl)piperazin-1-yl]-3-oxo-propyl]-5-methyl-imidazolidine-2,4-dione | F2 | 3-(4-Methyl-2,5-dioxo-imidazolidin-4-yl)propionic acid + Int 089 | 374 | 375 |

TABLE III-continued

| | | | | | | | |
|---|---|---|---|---|---|---|---|
| 33 | 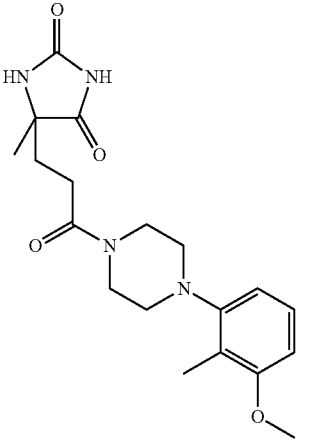 | | 5-[3-[4-(3-methoxy-2-methyl-phenyl)piperazin-1-yl]-3-oxo-propyl]-5-methyl-imidazolidine-2,4-dione | F2 | 3-(4-Methyl-2,5-dioxo-imidazolidin-4-yl)propionic acid + Int 099 | 374 | 375 |
| 34 | 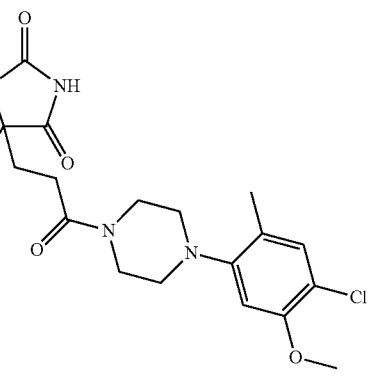 | | 5-[3-[4-(4-chloro-5-methoxy-2-methyl-phenyl)piperazin-1-yl]-3-oxo-propyl]-5-methyl-imidazolidine-2,4-dione | F2 | 3-(4-Methyl-2,5-dioxo-imidazolidin-4-yl)propionic acid + Int 109 | 409 | 409-411 |
| 35 | 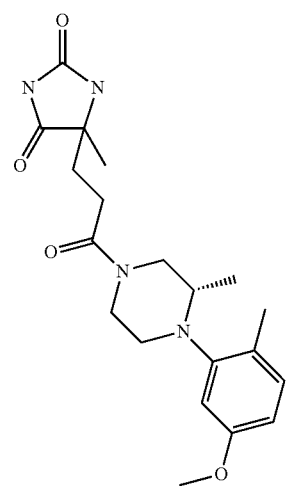 [SMILES: COc1ccc(C)c(N2CCN(C(=O)CCC3(C)NC(=O)NC3=O)C[C@@H]2C)c1] | | 5-[3-[(3S)-4-(5-methoxy-2-methyl-phenyl)-3-methyl-piperazin-1-yl]-3-oxo-propyl]-5-methyl-imidazolidine-2,4-dione | F2 | 3-(4-Methyl-2,5-dioxo-imidazolidin-4-yl)propionic acid + Int 044 | 388 | 389 |

TABLE III-continued

| 36 | 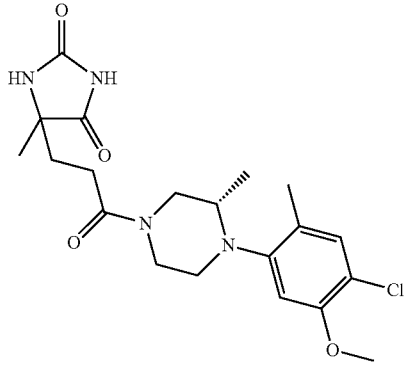 [SMILES: COc1cc(N2CCN(C(=O)CCC3(C)NC(=O)NC3=O)C[C@@H]2C)c(C)cc1Cl] | 5-[3-[(3S)-4-(4-chloro-5-methoxy-2-methyl-phenyl)-3-methyl-piperazin-1-yl]-3-oxo-propyl]-5-methyl-imidazolidine-2,4-dione | F2 | 3-(4-Methyl-2,5-dioxo-imidazolidin-4-yl)propionic acid + Int 061 | 423 | 423-425 |
| --- | --- | --- | --- | --- | --- | --- |
| 37 | 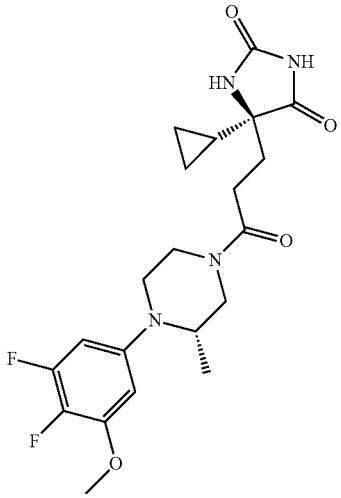 [SMILES: COc1cc(N2CCN(C(=O)CC[C@@]3(C4CC4)NC(=O)NC3=O)C[C@@H]2C)cc(F)c1F] | (5S)-5-cyclopropyl-5-[3-[(3S)-4-(3,4-difluoro-5-methoxy-phenyl)-3-methyl-piperazin-1-yl]-3-oxo-propyl]imidazolidine-2,4-dione | F2 | Int 034 + Int 047 | 436 | 437 |
| 38 | 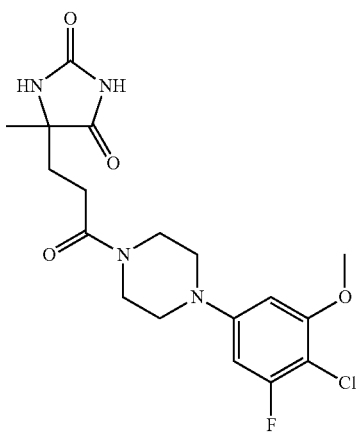 | 5-[3-[4-(4-chloro-3-fluoro-5-methoxy-phenyl)piperazin-1-yl]-3-oxo-propyl]-5-methyl-imidazolidine-2,4-dione | F2 | 3-(4-Methyl-2,5-dioxo-imidazolidin-4-yl)propionic acid + Int 078 | 413 | 413-415 |

TABLE III-continued

| 39 | 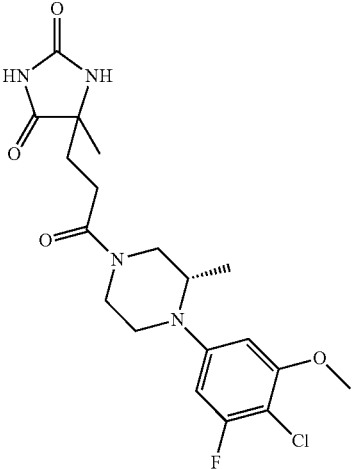 [SMILES: COc1cc(N2CCN(C(=O)CCC3(C)NC(=O)NC3=O)C[C@@H]2C)cc(F)c1Cl] | 5-[3-[(3S)-4-(4-chloro-3-fluoro-5-methoxy-phenyl)-3-methyl-piperazin-1-yl]-3-oxo-propyl]-5-methyl-imidazolidine-2,4-dione | F2 | 3-(4-Methyl-2,5-dioxo-imidazolidin-4-yl)propionic acid + Int 046 | 427 | 427-429 |
|---|---|---|---|---|---|---|
| 40 | 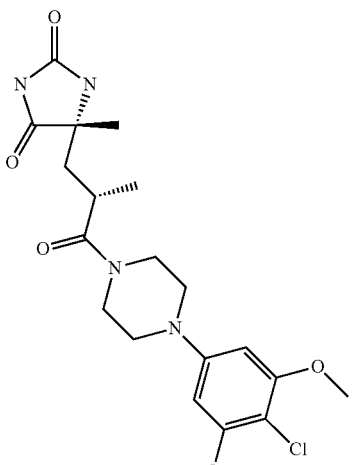<br>Trans | 5-[3-[4-(4-chloro-3,5-dimethoxy-phenyl)piperazin-1-yl]-2-methyl-3-oxo-propyl]-5-methyl-imidazolidine-2,4-dione | F1 | Int 036 + Int 084 | 439 | 439-441 |
| 41 | 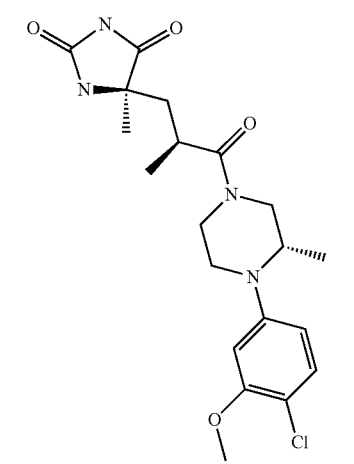<br>Trans | 5-[3-[4-(4-chloro-3-methoxy-phenyl)-3-methyl-piperazin-1-yl]-2-methyl-3-oxo-propyl]-5-methyl-imidazolidine-2,4-dione | F2 | Int 036 + Int 050 | 423 | 423-425 |

US 10,829,478 B2
TABLE III-continued
| | | | | | | | |
|---|---|---|---|---|---|---|---|
| 42 | 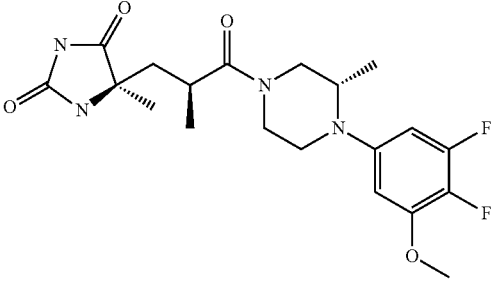<br>Trans | | 5-[3-[(3S)-4-(3,4-difluoro-5-methoxy-phenyl)-3-methyl-piperazin-1-yl]-2-methyl-3-oxo-propyl]-5-methyl-imidazolidine-2,4-dione | F2 | Int 036 + Int 047 | 424 | 425 |
| 43 | 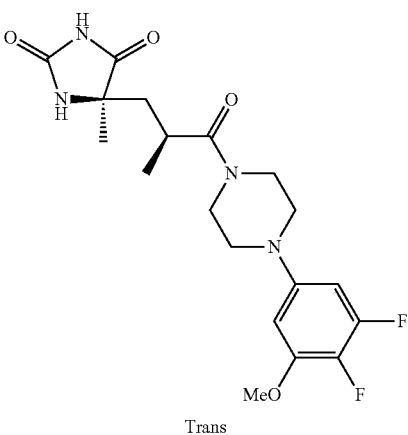 [SMILES: COc1cc(N2CCN(C(=O)[C@@H](C)C[C@@]3(C)NC(=O)NC3=O)CC2)cc(F)c1F]<br>Trans | | 5-[3-[4-(3,4-difluoro-5-methoxy-phenyl)piperazin-1-yl]-2-methyl-3-oxo-propyl]-5-methyl-imidazolidine-2,4-dione | F2 | Int 036 + Int 045 | 410 | 411 |
| 44 | 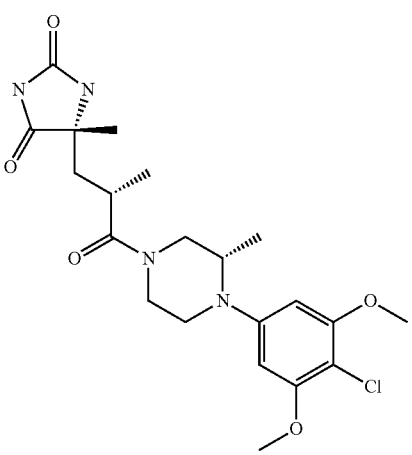<br>Trans | | 5-[3-[(3S)-4-(4-chloro-3,5-dimethoxy-phenyl)-3-methyl-piperazin-1-yl]-2-methyl-3-oxo-propyl]-5-methyl-imidazolidine-2,4-dione | F2 | Int 036 + Int 079 | 453 | 453-455 |

TABLE III-continued

| | | | | | | | |
|---|---|---|---|---|---|---|---|
| 45 | 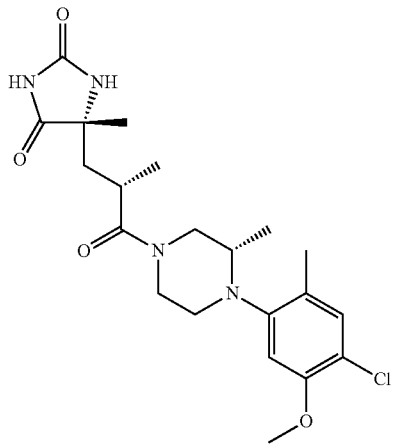<br>Trans | | 5-[3-[(3S)-4-(4-chloro-5-methoxy-2-methyl-phenyl)-3-methyl-piperazin-1-yl]-2-methyl-3-oxo-propyl]-5-methyl-imidazolidine-2,4-dione | F2 | Int 036 + Int 061 | 437 | 437-439 |
| 46 | 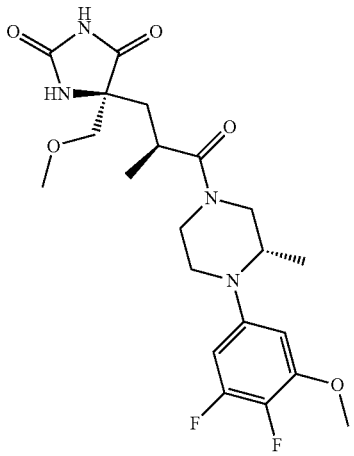<br>Trans | | 5-[3-[(3S)-4-(3,4-difluoro-5-methoxy-phenyl)-3-methyl-piperazin-1-yl]-2-methyl-3-oxo-propyl]-5-(methoxymethyl)imidazolidine-2,4-dione | F2 | Int 027 + Int 047 | 454 | 455 |
| 47 | 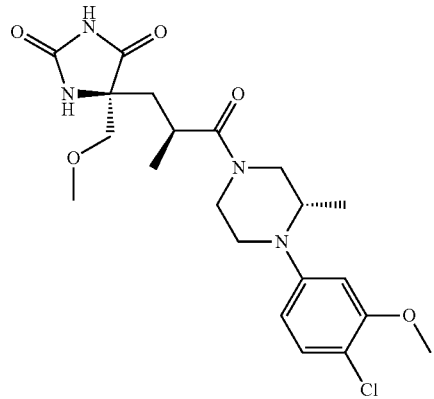<br>Trans | | 5-[3-[(3S)-4-(4-chloro-3-methoxy-phenyl)-3-methyl-piperazin-1-yl]-2-methyl-3-oxo-propyl]-5-(methoxymethyl)imidazolidine-2,4-dione | F2 | Int 027 + Int 050 | 453 | 453-455 |

TABLE III-continued

| | | | | | | |
|---|---|---|---|---|---|---|
| 48 | 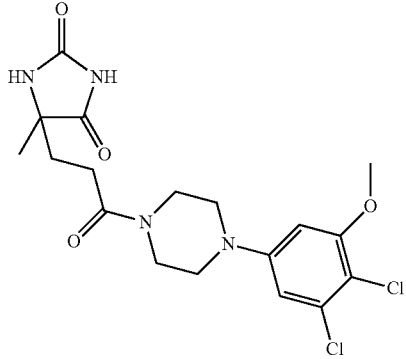 [SMILES: COc1cc(N2CCN(C(=O)CCC3(C)NC(=O)NC3=O)CC2)cc(Cl)c1Cl] | 5-[3-[4-(3,4-dichloro-5-methoxy-phenyl)piperazin-1-yl]-3-oxo-propyl]-5-methyl-imidazolidine-2,4-dione | F2 | 3-(4-Methyl-2,5-dioxo-imidazolidin-4-yl)propionic acid + Int 081 | 429 | 429-431-433 |
| 49 | 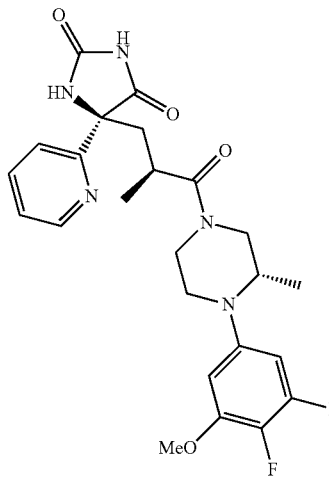  Trans | 5-[3-[(3S)-4-(3,4-difluoro-5-methoxy-phenyl)-3-methyl-piperazin-1-yl]-2-methyl-3-oxo-propyl]-5-(2-pyridyl)imidazolidine-2,4-dione | F2 | Int 030 + Int 047 | 488 | 488 |
| 50 | 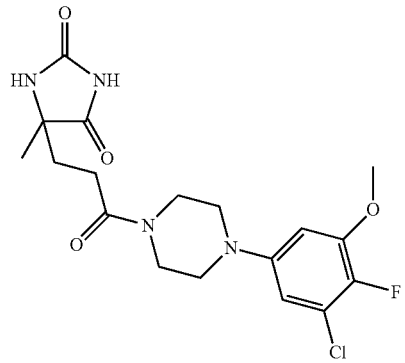 [SMILES: COc1cc(N2CCN(C(=O)CCC3(C)NC(=O)NC3=O)CC2)cc(Cl)c1F] | 5-[3-[4-(3-chloro-4-fluoro-5-methoxy-phenyl)piperazin-1-yl]-3-oxo-propyl]-5-methyl-imidazolidine-2,4-dione | F2 | 3-(4-Methyl-2,5-dioxo-imidazolidin-4-yl)propionic acid + Int 082 | 413 | 413-415 |

| | | | | | | |
|---|---|---|---|---|---|---|
| 51 | 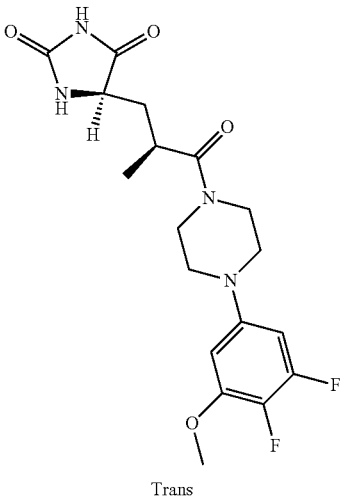 [SMILES: COc1cc(N2CCN(C(=O)[C@@H](C)C[C@H]3NC(=O)NC3=O)CC2)cc(F)c1F] Trans | 5-[3-[4-(3,4-difluoro-5-methoxy-phenyl)piperazin-1-yl]-2-methyl-3-oxo-propyl]imidazolidine-2,4-dione | F2 | Int 023 + Int 045 | 396 | 397 |
| 52 | 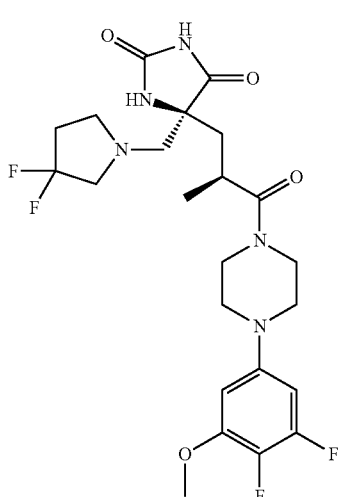 | 5-[3-[4-(3,4-difluoro-5-methoxy-phenyl)piperazin-1-yl]-2-methyl-3-oxo-propyl]-5-[(3,3-difluoro-pyrrolidin-1-yl)methyl]imidazolidine-2,4-dione | F2 | Int 019 + Int 045 | 516 | 516 |
| 53 | 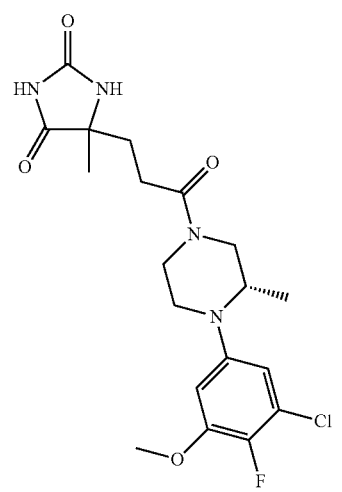 [SMILES: COc1cc(N2CCN(C(=O)CCC3(C)NC(=O)NC3=O)C[C@@H]2C)cc(Cl)c1F] | 5-[3-[(3S)-4-(3-chloro-4-fluoro-5-methoxy-phenyl)-3-methyl-piperazin-1-yl]-3-oxo-propyl]-5-methyl-imidazolidine-2,4-dione | F2 | 3-(4-Methyl-2,5-dioxo-imidazolidin-4-yl)propionic acid + Int 052 | 427 | 427-429 |

TABLE III-continued

| # | Structure | Name | | | MW calc | MW obs |
|---|---|---|---|---|---|---|
| 54 | 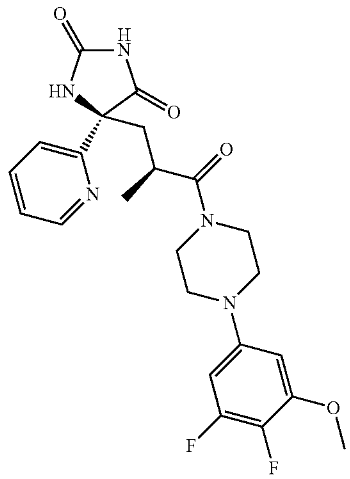 [SMILES: COc1cc(N2CCN(C(=O)[C@@H](C)C[C@@]3(c4ccccn4)NC(=O)NC3=O)CC2)cc(F)c1F] | (5S)-5-[(2S)-3-[4-(3,4-difluoro-5-methoxy-phenyl)piperazin-1-yl]-2-methyl-3-oxo-propyl]-5-(2-pyridyl)imidazolidine-2,4-dione | F2 | Int 030 + Int 045 | 473 | 474 |
| 55 | 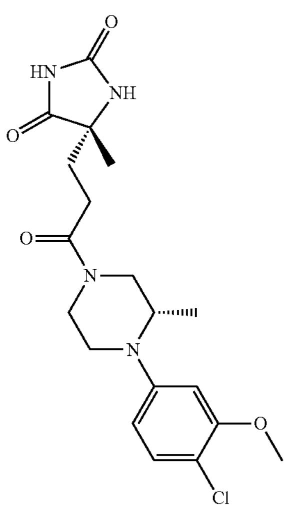 [SMILES: COc1cc(N2CCN(C(=O)CC[C@@]3(C)NC(=O)NC3=O)C[C@@H]2C)ccc1Cl] | (5R)-5-[3-[(3S)-4-(4-chloro-3-methoxy-phenyl)-3-methyl-piperazin-1-yl]-3-oxo-propyl]-5-methyl-imidazolidine-2,4-dione | F2 | Int 043 + Int 045 | 409 | 409 |
| 56 | 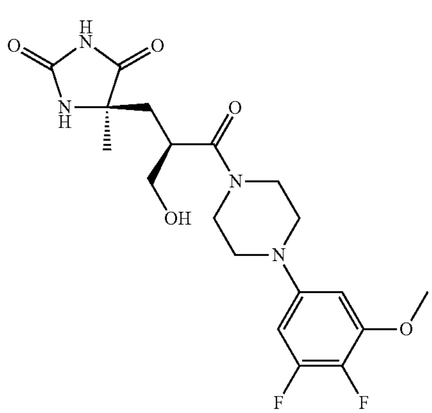 [SMILES: COc1cc(N2CCN(C(=O)[C@@H](CO)C[C@@]3(C)NC(=O)NC3=O)CC2)cc(F)c1F] | (5R)-5-[(2R)-3-[4-(3,4-difluoro-5-methoxy-phenyl)piperazin-1-yl]-2-(hydroxymethyl)-3-oxo-propyl]-5-methyl-imidazolidine-2,4-dione | G1 | Int 005 | 426 | 427 |

TABLE III-continued
| 57 | 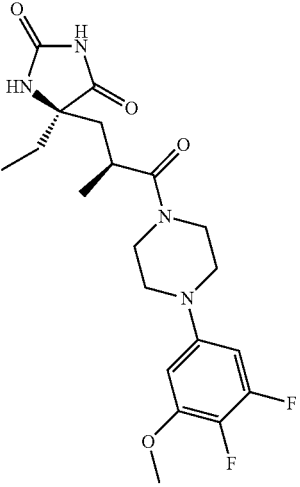 [SMILES: CC[C@]1(C[C@H](C)C(=O)N2CCN(c3cc(F)c(F)c(OC)c3)CC2)NC(=O)NC1=O] | (5R)-5-[(2S)-3-[4-(3,4-difluoro-5-methoxy-phenyl)piperazin-1-yl]-2-methyl-3-oxo-propyl]-5-ethyl-imidazolidine-2,4-dione | F2 | Int 040 + Int 058 | 424 | 425 |
| --- | --- | --- | --- | --- | --- | --- |
| 58 | 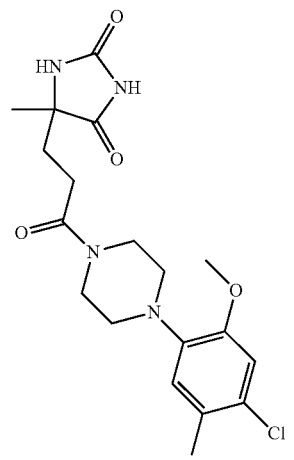 [SMILES: COc1cc(Cl)c(C)cc1N1CCN(C(=O)CCC2(C)NC(=O)NC2=O)CC1] | 5-[3-[4-(4-chloro-2-methoxy-5-methyl-phenyl)piperazin-1-yl]-3-oxo-propyl]-5-methyl-imidazolidine-2,4-dione | F2 | 3-(4-Methyl-2,5-dioxo-imidazolidin-4-yl)propionic acid + Int 083 | 409 | 409-411 |
| 59 | 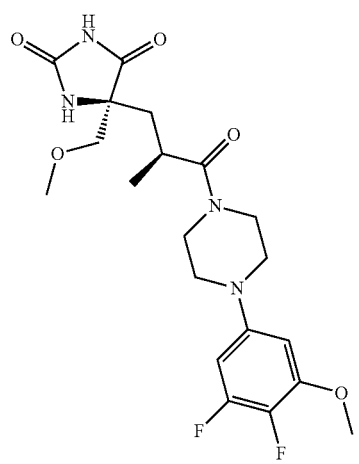 [SMILES: COC[C@]1(C[C@H](C)C(=O)N2CCN(c3cc(F)c(F)c(OC)c3)CC2)NC(=O)NC1=O] | (5S)-5-[(2S)-3-[4-(3,4-difluoro-5-methoxy-phenyl)piperazin-1-yl]-2-methyl-3-oxo-propyl]-5-(methoxymethyl)imidazolidine-2,4-dione | F2 | Int 027 + Int 045 | 440 | 441 |

TABLE III-continued
| | | | | | | |
|---|---|---|---|---|---|---|
| 60 | 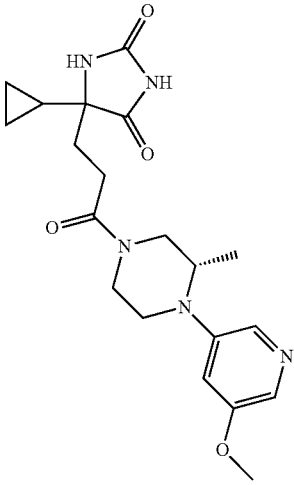 [SMILES: COc1cncc(N2CCN(C(=O)CCC3(C4CC4)NC(=O)NC3=O)C[C@@H]2C)c1] | 5-cyclopropyl-5-[3-[(3S)-4-(5-methoxy-3-pyridyl)-3-methyl-piperazin-1-yl]-3-oxo-propyl]imidazolidine-2,4-dione | F2 | Int 033 + Int 049 | 401 | 402 |
| 61 | 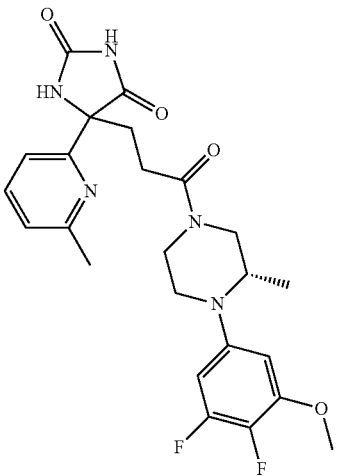 [SMILES: COc1cc(N2CCN(C(=O)CCC3(c4cccc(C)n4)NC(=O)NC3=O)C[C@@H]2C)cc(F)c1F] | 5-[3-[(3S)-4-(3,4-difluoro-5-methoxy-phenyl)-3-methyl-piperazin-1-yl]-3-oxo-propyl]-5-(6-methyl-2-pyridyl)imidazolidine-2,4-dione | F1 | Int 037 + Int 047 | 488 | 488 |
| 62 | 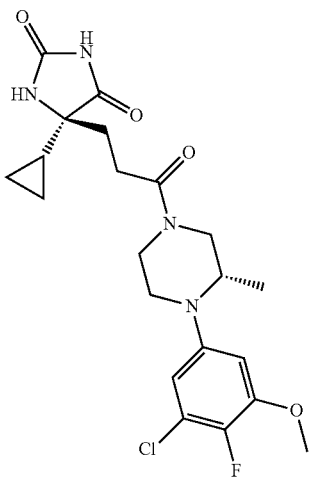 [SMILES: COc1cc(N2CCN(C(=O)CC[C@@]3(C4CC4)NC(=O)NC3=O)C[C@@H]2C)cc(Cl)c1F] | (5S)-5-[3-[(3S)-4-(3-chloro-4-fluoro-5-methoxy-phenyl)-3-methyl-piperazin-1-yl]-3-oxo-propyl]-5-cyclopropyl-imidazolidine-2,4-dione | F2 | Int 034 + Int 052 | 453 | 453-455 |

TABLE III-continued
| | | | | | | | |
|---|---|---|---|---|---|---|---|
| 63 | 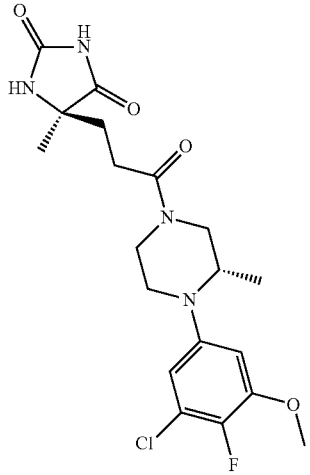 [SMILES: COc1cc(N2CCN(C(=O)CC[C@@]3(C)NC(=O)NC3=O)C[C@@H]2C)cc(Cl)c1F] | | (5R)-5-[3-[(3S)-4-(3-chloro-4-fluoro-5-methoxy-phenyl)-3-methyl-piperazin-1-yl]-3-oxo-propyl]-5-methyl-imidazolidine-2,4-dione | F2 | Int 043 + Int 052 | 427 | 427-429 |
| 64 | 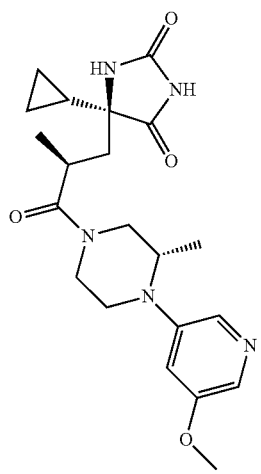 Trans | | 5-cyclopropyl-5-[3-[(3S)-4-(5-methoxy-3-pyridyl)-3-methyl-piperazin-1-yl]-2-methyl-3-oxo-propyl]imidazolidine-2,4-dione | F2 | Int 035 + Int 049 | 415 | 416 |
| 65 | 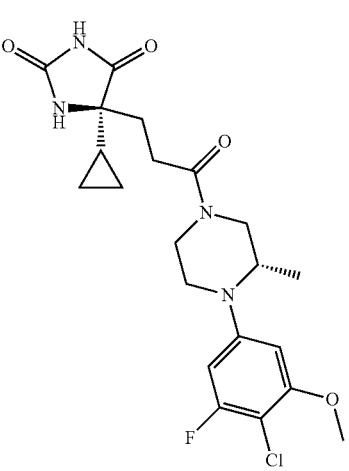 [SMILES: COc1cc(N2CCN(C(=O)CC[C@@]3(C4CC4)NC(=O)NC3=O)C[C@@H]2C)cc(F)c1Cl] | | (5S)-5-[3-[(3S)-4-(4-chloro-3-fluoro-5-methoxy-phenyl)-3-methyl-piperazin-1-yl]-3-oxo-propyl]-5-cyclopropyl-imidazolidine-2,4-dione | F2 | Int 034 + Int 046 | 453 | 453-455 |

TABLE III-continued
| | | | | | | |
|---|---|---|---|---|---|---|
| 66 | 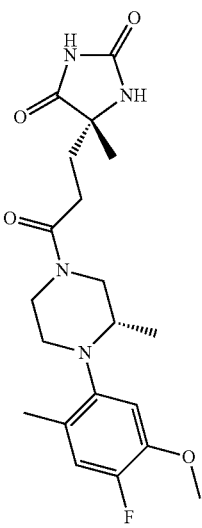 [SMILES: COc1cc(N2CCN(C(=O)CC[C@@]3(C)NC(=O)NC3=O)C[C@@H]2C)c(C)cc1F] | (5R)-5-[3-[(3S)-4-(4-fluoro-5-methoxy-2-methyl-phenyl)-3-methyl-piperazin-1-yl]-3-oxo-propyl]-5-methyl-imidazolidine-2,4-dione | F2 | Int 043 + Int 085 | 406 | 407 |
| 67 | 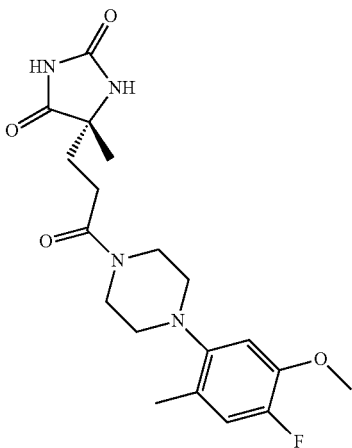 [SMILES: COc1cc(N2CCN(C(=O)CC[C@@]3(C)NC(=O)NC3=O)CC2)c(C)cc1F] | (5R)-5-[3-[4-(4-fluoro-5-methoxy-2-methyl-phenyl)piperazin-1-yl]-3-oxo-propyl]-5-methyl-imidazolidine-2,4-dione | F2 | Int 043 + Int 086 | 392 | 393 |
| 68 | 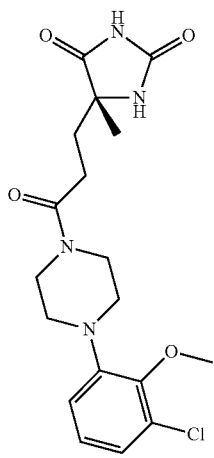 [SMILES: COc1c(Cl)cccc1N1CCN(C(=O)CC[C@@]2(C)NC(=O)NC2=O)CC1] | (5R)-5-[3-[4-(3-chloro-2-methoxy-phenyl)piperazin-1-yl]-3-oxo-propyl]-5-methyl-imidazolidine-2,4-dione | F2 | Int 043 + Int 087 | 395 | ES-: 393-395 |

TABLE III-continued

| | | | | | | |
|---|---|---|---|---|---|---|
| 69 | | (5R)-5-[3-[(3S)-4-(3-chloro-2-methoxy-phenyl)-3-methyl-piperazin-1-yl]-3-oxo-propyl]-5-methyl-imidazolidine-2,4-dione | F2 | Int 043 + Int 088 | 409 | 409-411 |
| 70 | | (5R)-5-[3-[4-(3-ethylphenyl)piperazin-1-yl]-3-oxo-propyl]-5-methyl-imidazolidine-2,4-dione | F2 | Int 043 + Int 090 | 358 | 359 |
| 71 | | (5R)-5-[3-[4-(4-chloro-3-ethyl-phenyl)piperazin-1-yl]-3-oxo-propyl]-5-methyl-imidazolidine-2,4-dione | F2 | Int 043 + Int 091 | 393 | 393-395 |
| 72 | | (5R)-5-[3-[4-(3,5-diethylphenyl)piperazin-1-yl]-3-oxo-propyl]-5-methyl-imidazolidine-2,4-dione | F2 | Int 043 + Int 092 | 387 | 387 |

TABLE III-continued

| 73 | | (5R)-5-[3-[4-(4-chloro-2-methoxy-phenyl)piperazin-1-yl]-3-oxo-propyl]-5-methyl-imidazolidine-2,4-dione | F2 | Int 043 + Int 093 | 395 | 395-397 |
|---|---|---|---|---|---|---|
| 74 | | (5R)-5-[3-[4-(4-fluoro-3,5-dimethoxy-phenyl)piperazin-1-yl]-3-oxo-propyl]-5-methyl-imidazolidine-2,4-dione | F2 | Int 043 + Int 094 | 408 | 409 |
| 75 | | (5R)-5-[3-[(3S)-4-(4-chloro-3-ethyl-phenyl)-3-methyl-piperazin-1-yl]-3-oxo-propyl]-5-methyl-imidazolidine-2,4-dione | F2 | Int 043 + Int 062 | 407 | 407-409 |
| 76 | | (5R)-5-[3-[(3S)-4-(4-chloro-2-methoxy-phenyl)-3-methyl-piperazin-1-yl]-3-oxo-propyl]-5-methyl-imidazolidine-2,4-dione | F2 | Int 043 + Int 095 | 409 | 409-411 |

TABLE III-continued
| | | | | | | |
|---|---|---|---|---|---|---|
| 77 | 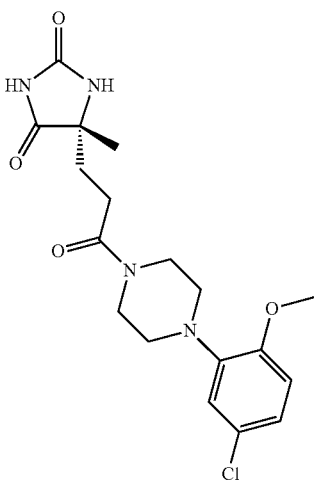 [SMILES: COc1ccc(Cl)cc1N1CCN(C(=O)CC[C@@]2(C)NC(=O)NC2=O)CC1] | (5R)-5-[3-[4-(5-chloro-2-methoxy-phenyl)piperazin-1-yl]-3-oxo-propyl]-5-methyl-imidazolidine-2,4-dione | F2 | Int 043 + Int 096 | 395 | 395-397 |
| 78 | 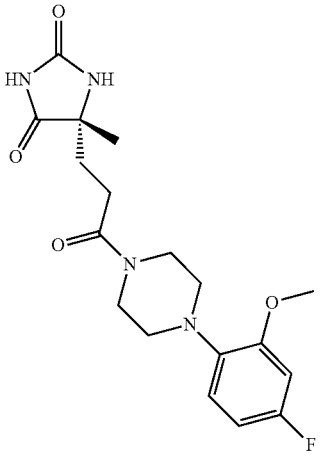 [SMILES: COc1cc(F)ccc1N1CCN(C(=O)CC[C@@]2(C)NC(=O)NC2=O)CC1] | (5R)-5-[3-[4-(4-fluoro-2-methoxy-phenyl)piperazin-1-yl]-3-oxo-propyl]-5-methyl-imidazolidine-2,4-dione | F2 | Int 043 + Int 097 | 378 | — |
| 79 | 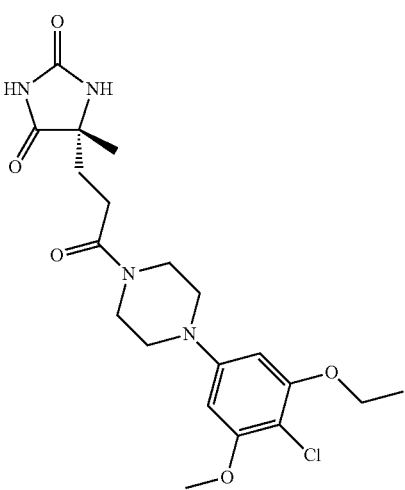 [SMILES: CCOc1cc(N2CCN(C(=O)CC[C@@]3(C)NC(=O)NC3=O)CC2)cc(OC)c1Cl] | (5R)-5-[3-[4-(4-chloro-3-ethoxy-5-methoxy-phenyl)piperazin-1-yl]-3-oxo-propyl]-5-methyl-imidazolidine-2,4-dione | F2 | Int 043 + Int 098 | 439 | 439-441 |

TABLE III-continued

| # | Structure | Name | Method | Intermediates | MW | m/z |
|---|---|---|---|---|---|---|
| 80 | 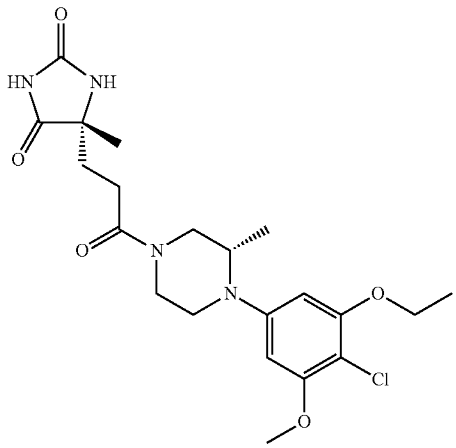 [SMILES: CCOc1cc(N2CCN(C(=O)CC[C@@]3(C)NC(=O)NC3=O)C[C@@H]2C)cc(OC)c1Cl] | (5R)-5-[3-[(3S)-4-(4-chloro-3-ethoxy-5-methoxy-phenyl)-3-methyl-piperazin-1-yl]-3-oxo-propyl]-5-methyl-imidazolidine-2,4-dione | F2 | Int 043 + Int 100 | 453 | 453-455 |
| 81 | 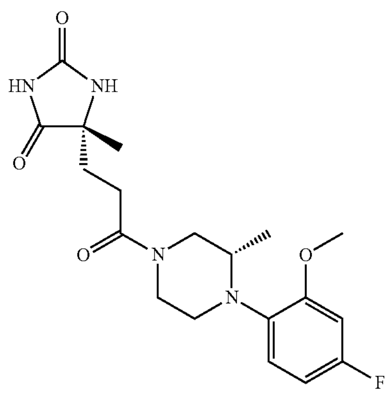 [SMILES: COc1cc(F)ccc1N1CCN(C(=O)CC[C@@]2(C)NC(=O)NC2=O)C[C@@H]1C] | (5R)-5-[3-[(3S)-4-(4-fluoro-2-methoxy-phenyl)-3-methyl-piperazin-1-yl]-3-oxo-propyl]-5-methyl-imidazolidine-2,4-dione | F2 | Int 043 + Int 101 | 392 | 393 |
| 82 | 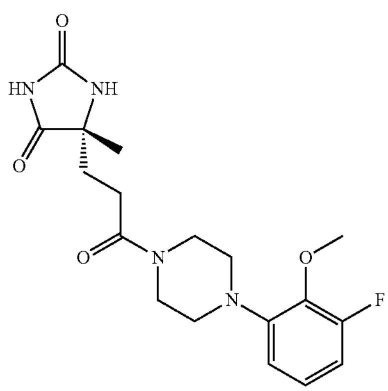 [SMILES: COc1c(F)cccc1N1CCN(C(=O)CC[C@@]2(C)NC(=O)NC2=O)CC1] | (5R)-5-[3-[4-(3-fluoro-2-methoxy-phenyl)piperazin-1-yl]-3-oxo-propyl]-5-methyl-imidazolidine-2,4-dione | F2 | Int 043 + Int 424 | 378 | 379 |
| 83 | 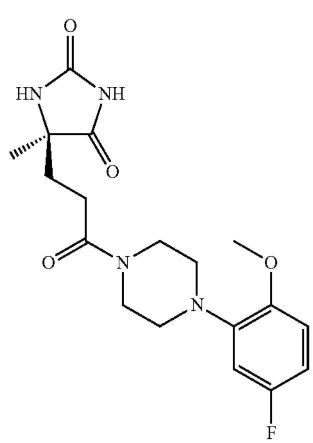 [SMILES: COc1ccc(F)cc1N1CCN(C(=O)CC[C@@]2(C)NC(=O)NC2=O)CC1] | (5R)-5-[3-[4-(5-fluoro-2-methoxy-phenyl)piperazin-1-yl]-3-oxo-propyl]-5-methyl-imidazolidine-2,4-dione | F2 | Int 043 + Int 103 | 378 | 379 |

TABLE III-continued

| | | | | | | |
|---|---|---|---|---|---|---|
| 84 | *(structure)* | (5R)-5-[3-[(3S)-4-(3-fluoro-2-methoxy-phenyl)-3-methyl-piperazin-1-yl]-3-oxo-propyl]-5-methyl-imidazolidine-2,4-dione | F2 | Int 043 + Int 104 | 392 | 393 |
| 85 | *(structure)* | (5R)-5-[3-[(3S)-4-(4-chloro-3-isopropyl-phenyl)-3-methyl-piperazin-1-yl]-3-oxo-propyl]-5-methyl-imidazolidine-2,4-dione | F2 | Int 043 + Int 105 | 421 | 421-423 |
| 86 | *(structure)* | (5R)-5-[3-[(3S)-4-[4-chloro-3-(trifluoromethoxy)phenyl]-3-methyl-piperazin-1-yl]-3-oxo-propyl]-5-methyl-imidazolidine-2,4-dione | F2 | Int 043 + Int 064 | 463 | 463-465 |

TABLE III-continued

| | | | | | | |
|---|---|---|---|---|---|---|
| 87 | | (5R)-5-[3-[4-(4-chloro-3-isopropyl-phenyl)piperazin-1-yl]-3-oxo-propyl]-5-methyl-imidazolidine-2,4-dione | F2 | Int 043 + Int 106 | 407 | 407-409 |
| 88 | | (5R)-5-[3-[4-[4-chloro-3-(trifluoromethoxy)phenyl]piperazin-1-yl]-3-oxo-propyl]-5-methyl-imidazolidine-2,4-dione | F2 | Int 043 + Int 107 | 449 | 449-451 |
| 89 | | (5R)-5-[3-[(3S)-4-(4-fluoro-3,5-dimethoxy-phenyl)-3-methyl-piperazin-1-yl]-3-oxo-propyl]-5-methyl-imidazolidine-2,4-dione | F2 | Int 043 + Int 108 | 422 | 423 |

TABLE III-continued
| | | | | | | |
|---|---|---|---|---|---|---|
| 90 | 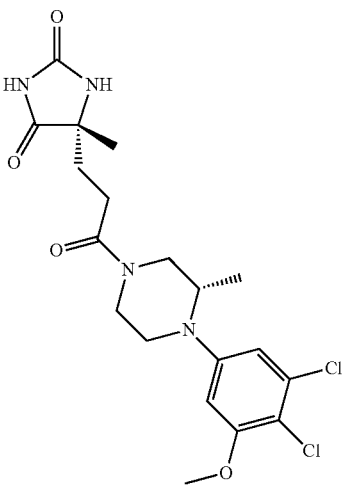 [SMILES: COc1cc(N2CCN(C(=O)CC[C@@]3(C)NC(=O)NC3=O)C[C@@H]2C)cc(Cl)c1Cl] | (5R)-5-[3-[(3S)-4-(3,4-dichloro-5-methoxy-phenyl)-3-methyl-piperazin-1-yl]-3-oxo-propyl]-5-methyl-imidazolidine-2,4-dione | F2 | Int 043 + Int 110 | 443 | 443-445 |
| 91 | 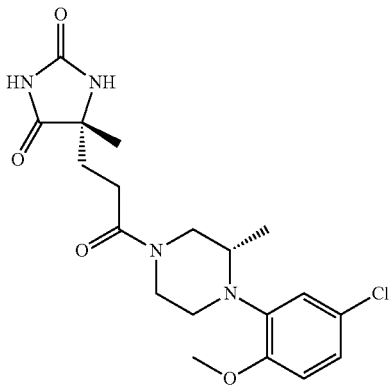 [SMILES: COc1ccc(Cl)cc1N1CCN(C(=O)CC[C@@]2(C)NC(=O)NC2=O)C[C@@H]1C] | (5R)-5-[3-[(3S)-4-(5-chloro-2-methoxy-phenyl)-3-methyl-piperazin-1-yl]-3-oxo-propyl]-5-methyl-imidazolidine-2,4-dione | F2 | Int 043 + Int 111 | 409 | 409-411 |
| 92 | 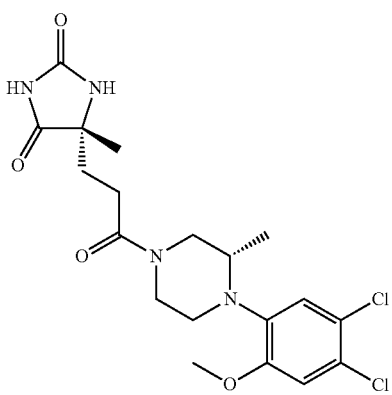 [SMILES: COc1cc(Cl)c(Cl)cc1N1CCN(C(=O)CC[C@@]2(C)NC(=O)NC2=O)C[C@@H]1C] | (5R)-5-[3-[(3S)-4-(4,5-dichloro-2-methoxy-phenyl)-3-methyl-piperazin-1-yl]-3-oxo-propyl]-5-methyl-imidazolidine-2,4-dione | F2 | Int 043 + Int 112 | 443 | 443-445 |

TABLE III-continued
| | | | | | | |
|---|---|---|---|---|---|---|
| 93 | 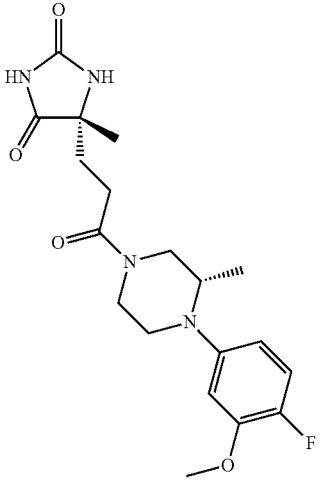 [SMILES: COc1cc(N2CCN(C(=O)CC[C@@]3(C)NC(=O)NC3=O)C[C@@H]2C)ccc1F] | (5R)-5-[3-[(3S)-4-(4-fluoro-3-methoxy-phenyl)-3-methyl-piperazin-1-yl]-3-oxo-propyl]-5-methyl-imidazolidine-2,4-dione | F2 | Int 043 + Int 113 | 392 | 393 |
| 94 | 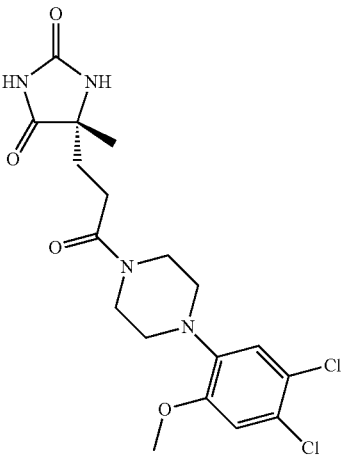 [SMILES: COc1cc(Cl)c(Cl)cc1N1CCN(C(=O)CC[C@@]2(C)NC(=O)NC2=O)CC1] | (5R)-5-[3-[4-(4,5-dichloro-2-methoxy-phenyl)piperazin-1-yl]-3-oxo-propyl]-5-methyl-imidazolidine-2,4-dione | F2 | Int 043 + Int 114 | 429 | 429-431 |
| 95 | 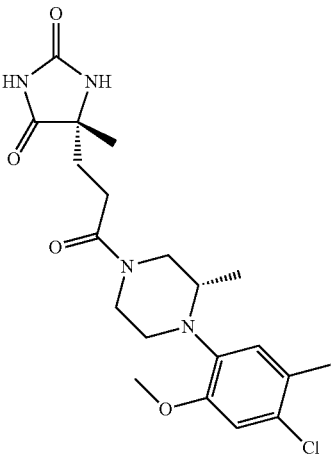 [SMILES: COc1cc(Cl)c(C)cc1N1CCN(C(=O)CC[C@@]2(C)NC(=O)NC2=O)C[C@@H]1C] | (5R)-5-[3-[(3S)-4-(4-chloro-2-methoxy-5-methyl-phenyl)-3-methyl-piperazin-1-yl]-3-oxo-propyl]-5-methyl-imidazolidine-2,4-dione | F2 | Int 043 + Int 115 | 423 | 423-425 |

TABLE III-continued

| | | | | | | |
|---|---|---|---|---|---|---|
| 96 | | (5R)-5-[3-[(3S)-4-(3-chloro-5-methoxy-phenyl)-3-methyl-piperazin-1-yl]-3-oxo-propyl]-5-methyl-imidazolidine-2,4-dione | F2 | Int 043 + Int 116 | 409 | 409-411 |
| 97 | | (5R)-5-[3-[4-(4-chloro-2,5-dimethoxy-phenyl)piperazin-1-yl]-3-oxo-propyl]-5-methyl-imidazolidine-2,4-dione | F2 | Int 043 + Int 051 | 425 | 425-427 |
| 98 | | 2-[4-[3-[(3S)-4-(4-chloro-3-ethyl-phenyl)-3-methyl-piperazin-1-yl]-3-oxo-propyl]-2,5-dioxo-imidazolidin-4-yl]acetic acid | see above | Int 009 | 451 | 451-453 |

TABLE III-continued
| | | | | | | |
|---|---|---|---|---|---|---|
| 99 | 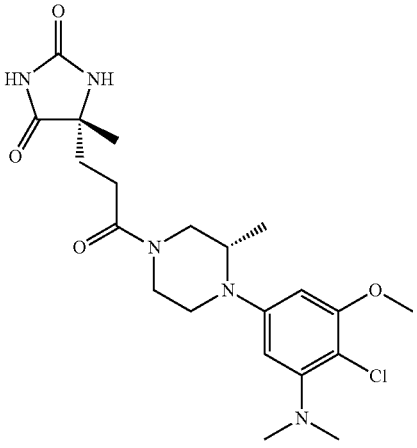 [SMILES: COc1cc(N2CCN(C(=O)CC[C@@]3(C)NC(=O)NC3=O)C[C@@H]2C)cc(N(C)C)c1Cl] | (5R)-5-[3-[(3S)-4-[4-chloro-3-(dimethylamino)-5-methoxy-phenyl]-3-methyl-piperazin-1-yl]-3-oxo-propyl]-5-methyl-imidazolidine-2,4-dione | F2 | Int 043 + Int 063 | 452 | 452-454 |
| 100 | 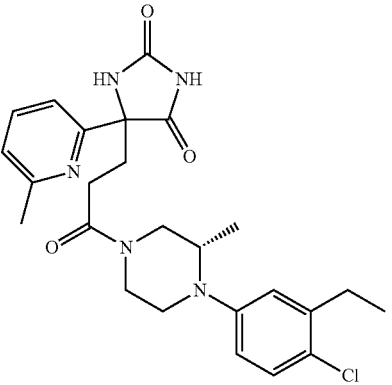 [SMILES: CCc1cc(N2CCN(C(=O)CCC3(c4cccc(C)n4)NC(=O)NC3=O)C[C@@H]2C)ccc1Cl] | 5-[3-[(3S)-4-(4-chloro-3-ethyl-phenyl)-3-methyl-piperazin-1-yl]-3-oxo-propyl]-5-(6-methyl-2-pyridyl)imidazolidine-2,4-dione | F2 | Int 037 + Int 062 | 484 | 484-486 |
| 101 | 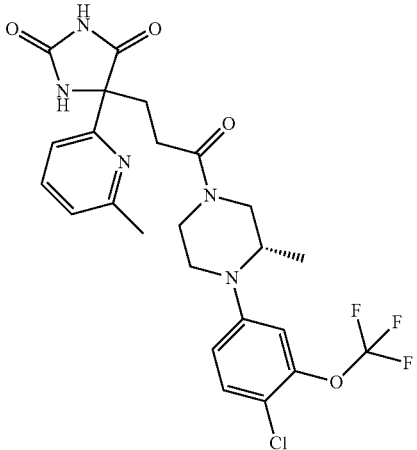 [SMILES: Cc1cccc(C2(CCC(=O)N3CCN(c4ccc(Cl)c(OC(F)(F)F)c4)[C@@H](C)C3)NC(=O)NC2=O)n1] | 5-[3-[(3S)-4-[4-chloro-3-(trifluoromethoxy)phenyl]-3-methyl-piperazin-1-yl]-3-oxo-propyl]-5-(6-methyl-2-pyridyl)imidazolidine-2,4-dione | F2 | Int 037 + Int 064 | 540 | 540-542 |

TABLE III-continued
| 102 | 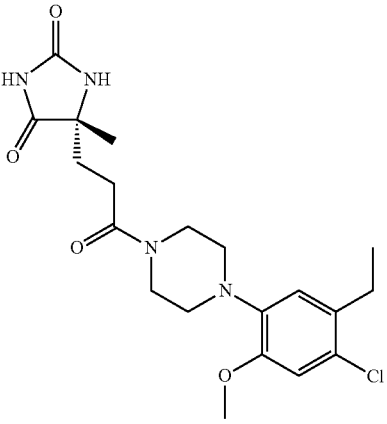 [SMILES: CCc1cc(N2CCN(C(=O)CC[C@@]3(C)NC(=O)NC3=O)CC2)c(OC)cc1Cl] | (5R)-5-[3-[4-(4-chloro-5-ethyl-2-methoxy-phenyl)piperazin-1-yl]-3-oxo-propyl]-5-methyl-imidazolidine-2,4-dione | F2 | Int 043 + Int 065 | 423 | 423-425 |
|---|---|---|---|---|---|---|
| 103 | 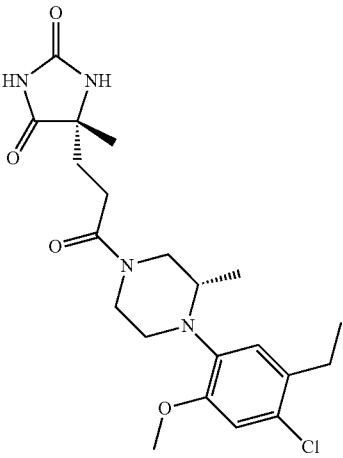 [SMILES: CCc1cc(N2CCN(C(=O)CC[C@@]3(C)NC(=O)NC3=O)C[C@@H]2C)c(OC)cc1Cl] | (5R)-5-[3-[(3S)-4-(4-chloro-5-ethyl-2-methoxy-phenyl)-3-methyl-piperazin-1-yl]-3-oxo-propyl]-5-methyl-imidazolidine-2,4-dione | F2 | Int 043 + Int 066 | 437 | 437-439 |
| 104 | 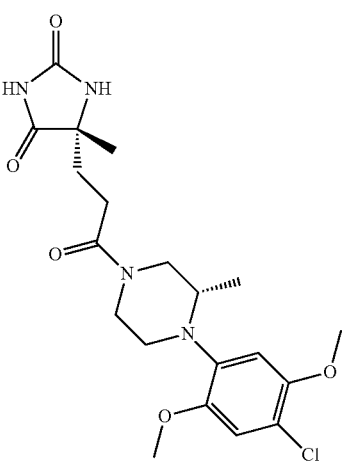 [SMILES: COc1cc(N2CCN(C(=O)CC[C@@]3(C)NC(=O)NC3=O)C[C@@H]2C)c(OC)cc1Cl] | (5R)-5-[3-[(3S)-4-(4-chloro-2,5-dimethoxy-phenyl)-3-methyl-piperazin-1-yl]-3-oxo-propyl]-5-methyl-imidazolidine-2,4-dione | F2 | Int 043 + Int 067 | 439 | 439-441 |

TABLE III-continued
| | | | | | | |
|---|---|---|---|---|---|---|
| 105 | 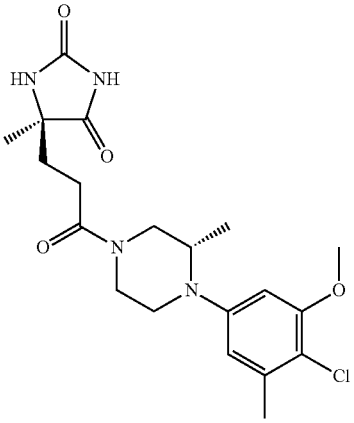 | (5R)-5-[3-[(3S)-4-(4-chloro-3-methoxy-5-methyl-phenyl)-3-methyl-piperazin-1-yl]-3-oxo-propyl]-5-methyl-imidazolidine-2,4-dione | F2 | Int 043 + Int 068 | 423 | 423-425 |
| 106 | 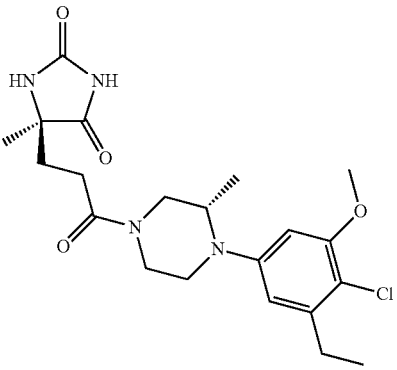 [SMILES: CCc1cc(N2CCN(C(=O)CC[C@@]3(C)NC(=O)NC3=O)C[C@@H]2C)cc(OC)c1Cl] | (5R)-5-[3-[(3S)-4-(4-chloro-3-ethyl-5-methoxy-phenyl)-3-methyl-piperazin-1-yl]-3-oxo-propyl]-5-methyl-imidazolidine-2,4-dione | F2 | Int 043 + Int 076 | 437 | 437-439 |
| 107 | 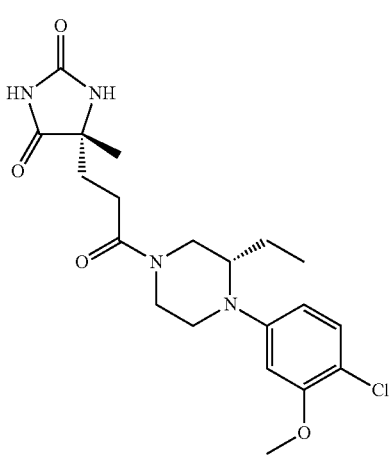 [SMILES: CC[C@H]1CN(C(=O)CC[C@@]2(C)NC(=O)NC2=O)CCN1c1ccc(Cl)c(OC)c1] | (5R)-5-[3-[(3S)-4-(4-chloro-3-methoxy-phenyl)-3-ethyl-piperazin-1-yl]-3-oxo-propyl]-5-methyl-imidazolidine-2,4-dione | F2 | Int 043 + Int 069 | 423 | 423-425 |

TABLE III-continued
| 108 | 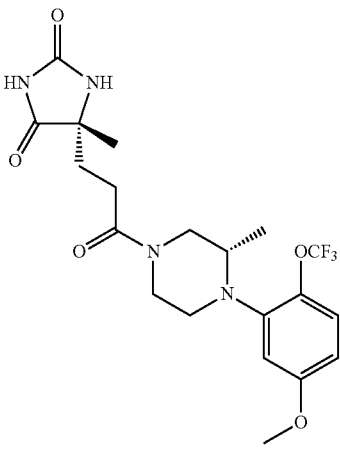 [SMILES: COc1ccc(OC(F)(F)F)c(N2CCN(C(=O)CC[C@@]3(C)NC(=O)NC3=O)C[C@@H]2C)c1] | (5R)-5-[3-[(3S)-4-[5-methoxy-2-(trifluoromethoxy)phenyl]-3-methyl-piperazin-1-yl]-3-oxo-propyl]-5-methyl-imidazolidine-2,4-dione | F2 | Int 043 + Int 070 | 458 | 459 |
| --- | --- | --- | --- | --- | --- | --- |
| 109 | 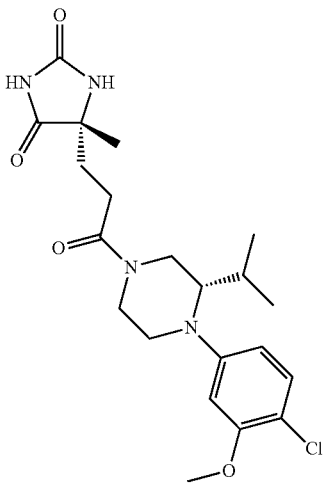 [SMILES: COc1cc(N2CCN(C(=O)CC[C@@]3(C)NC(=O)NC3=O)C[C@@H]2C(C)C)ccc1Cl] | (5R)-5-[3-[(3S)-4-(4-chloro-3-methoxy-phenyl)-3-isopropyl-piperazin-1-yl]-3-oxo-propyl]-5-methyl-imidazolidine-2,4-dione | F2 | Int 043 + Int 071 | 437 | 437-439 |
| 110 | 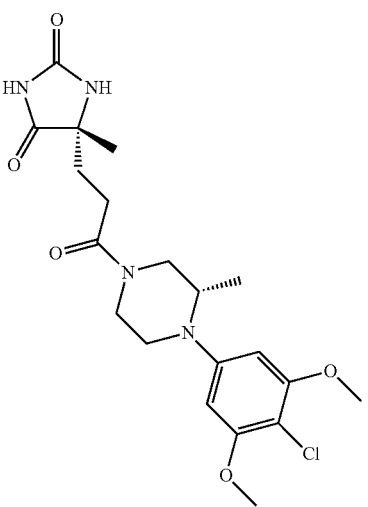 [SMILES: COc1cc(N2CCN(C(=O)CC[C@@]3(C)NC(=O)NC3=O)C[C@@H]2C)cc(OC)c1Cl] | (5R)-5-[3-[(3S)-4-(4-chloro-3,5-dimethoxy-phenyl)-3-methyl-piperazin-1-yl]-3-oxo-propyl]-5-methyl-imidazolidine-2,4-dione | F2 | Int 043 + Int 079 | 439 | 439-441 |

TABLE III-continued

| # | Structure | Name | Method | Intermediates | MW | Found |
|---|---|---|---|---|---|---|
| 111 | 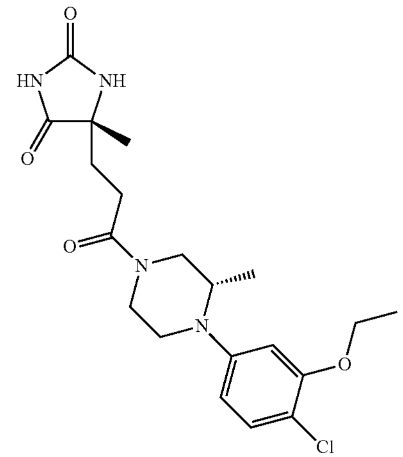 [SMILES: CCOc1cc(N2CCN(C(=O)CC[C@@]3(C)NC(=O)NC3=O)C[C@@H]2C)ccc1Cl] | (5R)-5-[3-[(3S)-4-(4-chloro-3-ethoxy-phenyl)-3-methyl-piperazin-1-yl]-3-oxo-propyl]-5-methyl-imidazolidine-2,4-dione | F2 | Int 043 + Int 072 | 423 | 423 |
| 112 | 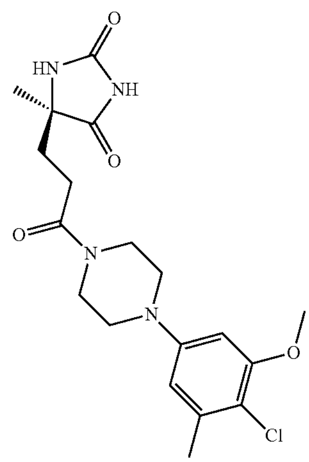 | (5R)-5-[3-[4-(4-chloro-3-methoxy-5-methyl-phenyl)piperazin-1-yl]-3-oxo-propyl]-5-methyl-imidazolidine-2,4-dione | F2 | Int 043 + Int 073 | 409 | 409 |
| 113 | 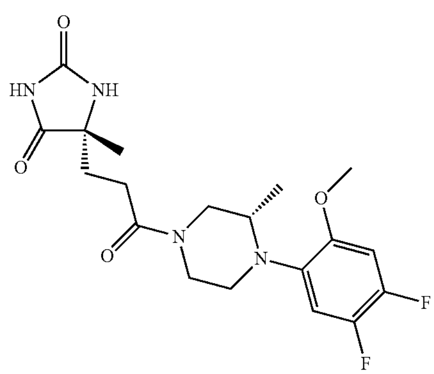 [SMILES: COc1cc(F)c(F)cc1N1CCN(C(=O)CC[C@@]2(C)NC(=O)NC2=O)C[C@@H]1C] | (5R)-5-[3-[(3S)-4-(4,5-difluoro-2-methoxy-phenyl)-3-methyl-piperazin-1-yl]-3-oxo-propyl]-5-methyl-imidazolidine-2,4-dione | F2 | Int 043 + Int 074 | 410 | 411 |
| 114 | 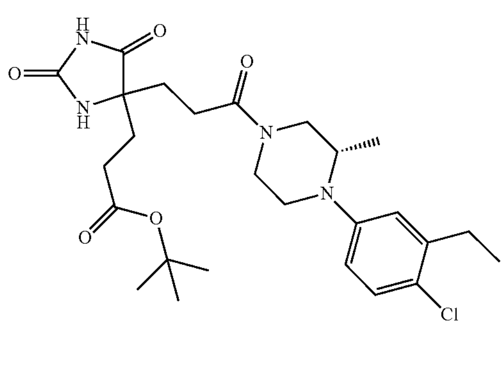 [SMILES: CCc1cc(N2CCN(C(=O)CCC3(CCC(=O)OC(C)(C)C)NC(=O)NC3=O)C[C@@H]2C)ccc1Cl] | tert-butyl 3-[4-[3-[(3S)-4-(4-chloro-3-ethyl-phenyl)-3-methyl-piperazin-1-yl]-3-oxo-propyl]-2,5-dioxo-imidazolidin-4-yl]propanoate | D | Int 002 | 521 | 521-523 |

TABLE III-continued

| | | | | | | |
|---|---|---|---|---|---|---|
| 115 | | (5R)-5-[3-[4-(4-chloro-3-ethyl-5-methoxy-phenyl)piperazin-1-yl]-3-oxo-propyl]-5-methyl-imidazolidine-2,4-dione | F2 | Int 043 + Int 075 | 423 | 423 |
| 116 | | 3-[4-[3-[(3S)-4-(4-chloro-3-ethyl-phenyl)-3-methyl-piperazin-1-yl]-3-oxo-propyl]-2,5-dioxo-imidazolidin-4-yl]propanoic acid | see above | Cpd 114 | 465 | 465-467 |
| 117 | | 5-[3-[(3S)-4-(4-chloro-3-ethyl-5-methoxy-phenyl)-3-methyl-piperazin-1-yl]-2-methyl-3-oxo-propyl]-5-(methoxymethyl)imidazolidine-2,4-dione | F2 | Int 027 + Int 076 | 481 | 481 |

Trans

TABLE III-continued

| # | Structure | Name | | Method | Ints | MW | MS |
|---|---|---|---|---|---|---|---|
| 118 | 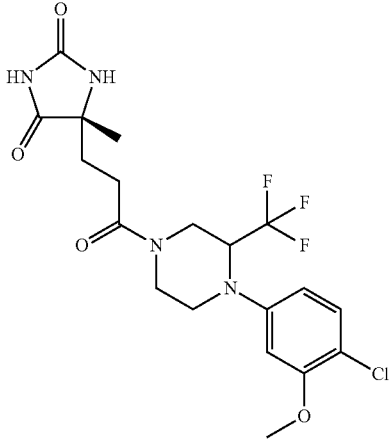 [SMILES: COc1cc(N2CCN(C(=O)CC[C@@]3(C)NC(=O)NC3=O)CC2C(F)(F)F)ccc1Cl] | (5R)-5-[3-[4-(4-chloro-3-methoxy-phenyl)-3-(trifluoromethyl)piperazin-1-yl]-3-oxo-propyl]-5-methyl-imidazolidine-2,4-dione | | F2 | Int 043 + Int 077 | 463 | 463 |
| 119 | 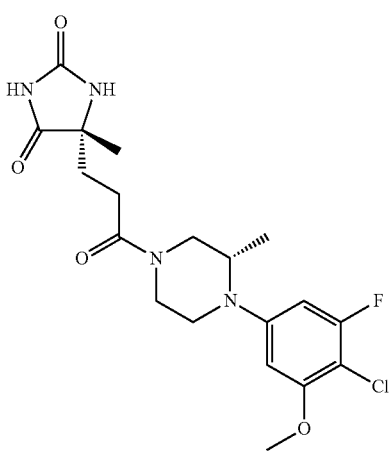 [SMILES: COc1cc(N2CCN(C(=O)CC[C@@]3(C)NC(=O)NC3=O)C[C@@H]2C)cc(F)c1Cl] | (5R)-5-[3-[(3S)-4-(4-chloro-3-fluoro-5-methoxy-phenyl)-3-methyl-piperazin-1-yl]-3-oxo-propyl]-5-methyl-imidazolidine-2,4-dione | | F2 | Int 043 + Int 046 | 427 | 427 |
| 120 | 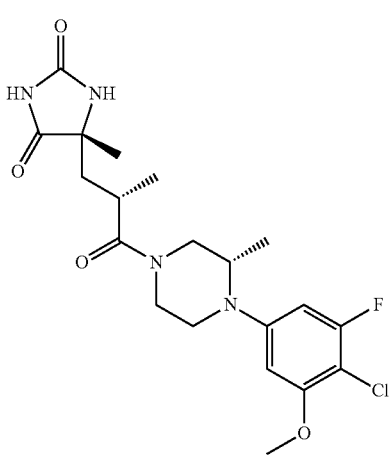<br>Trans | 5-[3-[(3S)-4-(4-chloro-3-fluoro-5-methoxy-phenyl)-3-methyl-piperazin-1-yl]-2-methyl-3-oxo-propyl]-5-methyl-imidazolidine-2,4-dione | | F2 | Int 036 + Int 046 | 441 | 441 |

TABLE III-continued
| | | | | | | |
|---|---|---|---|---|---|---|
| 121 | 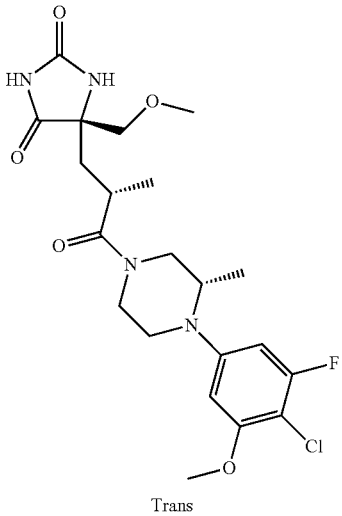 [SMILES: COC[C@]1(C[C@H](C)C(=O)N2CCN(c3cc(F)c(Cl)c(OC)c3)[C@@H](C)C2)NC(=O)NC1=O] Trans | 5-[3-[(3S)-4-(4-chloro-3-fluoro-5-methoxy-phenyl)-3-methyl-piperazin-1-yl]-2-methyl-3-oxo-propyl]-5-(methoxymethyl)imidazolidine-2,4-dione | F2 | Int 027 + Int 046 | 471 | 471 |
| 122 | 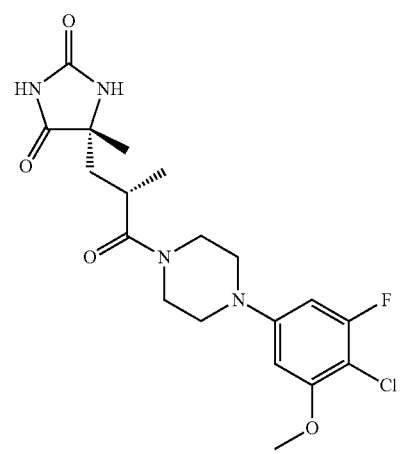 [SMILES: COc1cc(N2CCN(C(=O)[C@@H](C)C[C@@]3(C)NC(=O)NC3=O)CC2)cc(F)c1Cl] | (5R)-5-[(2S)-3-[4-(4-chloro-3-fluoro-5-methoxy-phenyl)piperazin-1-yl]-2-methyl-3-oxo-propyl]-5-methyl-imidazolidine-2,4-dione | F2 | Int 036 + Int 078 | 427 | 427 |
| 123 | 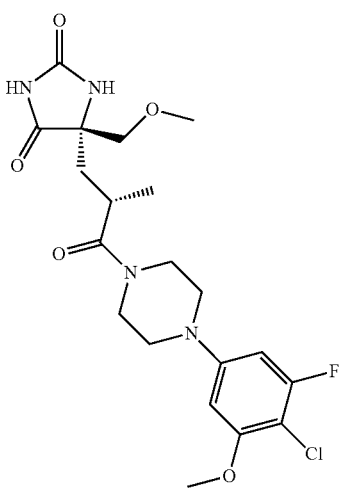 [SMILES: COC[C@]1(C[C@H](C)C(=O)N2CCN(c3cc(F)c(Cl)c(OC)c3)CC2)NC(=O)NC1=O] | (5S)-5-[(2S)-3-[4-(4-chloro-3-fluoro-5-methoxy-phenyl)piperazin-1-yl]-2-methyl-3-oxo-propyl]-5-(methoxymethyl)imidazolidine-2,4-dione | F2 | Int 027 + Int 078 | 457 | 457 |

TABLE III-continued

| 124 | 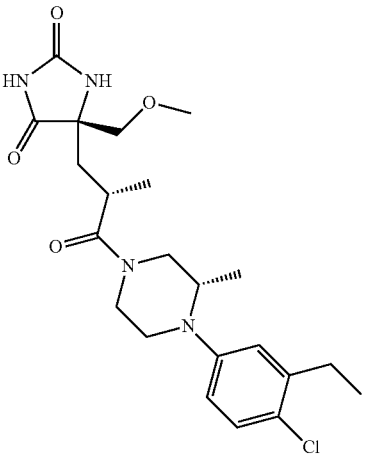 Trans | 5-[3-[(3S)-4-(4-chloro-3-ethyl-phenyl)-3-methyl-piperazin-1-yl]-2-methyl-3-oxo-propyl]-5-(methoxymethyl)imidazolidine-2,4-dione | F2 | Int 027 + Int 062 | 451 | 451 |
|---|---|---|---|---|---|---|
| 125 | 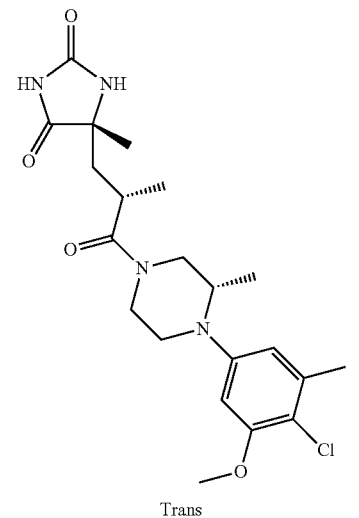 [SMILES: COc1cc(N2CCN(C(=O)[C@@H](C)C[C@@]3(C)NC(=O)NC3=O)C[C@@H]2C)cc(C)c1Cl] Trans | 5-[3-[(3S)-4-(4-chloro-3-methoxy-5-methyl-phenyl)-3-methyl-piperazin-1-yl]-2-methyl-3-oxo-propyl]-5-methyl-imidazolidine-2,4-dione | F2 | Int 036 + Int 068 | 437 | 437 |
| 126 | 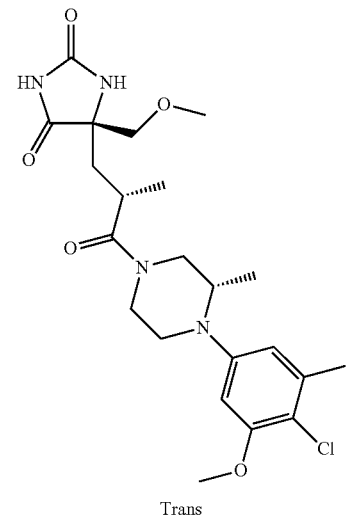 [SMILES: COC[C@]1(C[C@H](C)C(=O)N2CCN(c3cc(C)c(Cl)c(OC)c3)[C@@H](C)C2)NC(=O)NC1=O] Trans | 5-[3-[(3S)-4-(4-chloro-3-methoxy-5-methyl-phenyl)-3-methyl-piperazin-1-yl]-2-methyl-3-oxo-propyl]-5-(methoxymethyl)imidazolidine-2,4-dione | F2 | Int 027 + Int 068 | 467 | 467 |

TABLE III-continued

| | | | | | | |
|---|---|---|---|---|---|---|
| 127 | | (5R)-5-[3-[(3R)-4-(3,4-difluoro-5-methoxy-phenyl)-3-methyl-piperazin-1-yl]-3-oxo-propyl]imidazolidine-2,4-dione | F2 | Int.136 + Int. 135 | 396 | 397 |
| 128 | | (5R)-5-[3-[4-(3,4-difluoro-5-methoxy-phenyl)piperazin-1-yl]-3-oxo-propyl]imidazolidine-2,4-dione | F2 | Int.136 + Int. 045 | 382 | 383 |
| 129 | | (5R)-5-[3-[(3S)-4-(3,4-difluoro-5-methoxy-phenyl)-3-methyl-piperazin-1-yl]-3-oxo-propyl]imidazolidine-2,4-dione | F2 | Int.136 + Int. 047 | 396 | 397 |

TABLE III-continued

| | | | | | | |
|---|---|---|---|---|---|---|
| 130 | | 5-cyclopropyl-5-[3-[4-(3-fluoro-5-methoxy-phenyl)piperazin-1-yl]-2-methyl-3-oxo-propyl]imidazolidine-2,4-dione | D | Int.007 | 418 | 419 |
| 131 | | 5-[3-[4-(3-fluoro-5-methoxy-phenyl)piperazin-1-yl]-2-methyl-3-oxo-propyl]-5-methyl-imidazolidine-2,4-dione | D | Int.008 | 392 | 393 |
| 132 | | (5R)-5-[3-[(3S)-4-(3,5-dimethoxy-phenyl)-3-methyl-piperazin-1-yl]-3-oxo-propyl]imidazolidine-2,4-dione | F2 | Int.136 + Int. 080 | 390 | 391 |
| 133 | | (5R)-5-[3-[(3S)-4-(4-chloro-3-methoxy-phenyl)-3-methyl-piperazin-1-yl]-3-oxo-propyl]imidazolidine-2,4-dione | F2 | Int.136 + Int. 050 | 394 | 395 397 |

TABLE III-continued

| | | | | | | |
|---|---|---|---|---|---|---|
| 134 | 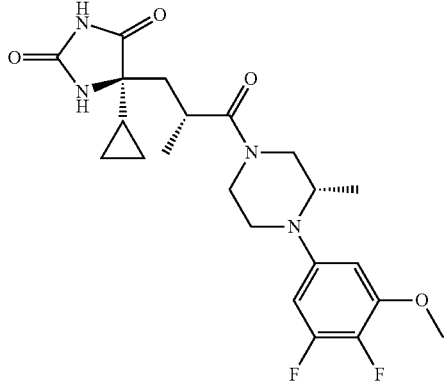 Trans | 5-cyclopropyl-5-[3-[(3S)-4-(3,4-difluoro-5-methoxy-phenyl)-3-methyl-piperazin-1-yl]-2-methyl-3-oxo-propyl] imidazolidine-2,4-dione | D | Int.004 | 450 | 451 |
| 135 | 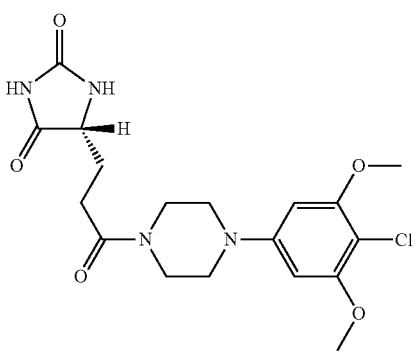 [SMILES: COc1cc(N2CCN(C(=O)CC[C@H]3NC(=O)NC3=O)CC2)cc(OC)c1Cl] | (5R)-5-[3-[4-(4-chloro-3,5-dimethoxy-phenyl) piperazin-1-yl]-3-oxo-propyl] imidazolidine-2,4-dione | F2 | Int.136 + Int. 084 | 410 | 411 413 |
| 136 | 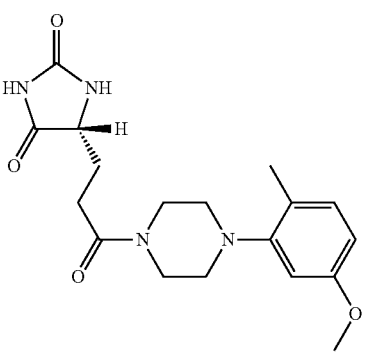 [SMILES: COc1ccc(C)c(N2CCN(C(=O)CC[C@H]3NC(=O)NC3=O)CC2)c1] | (5R)-5-[3-[4-(5-methoxy-2-methyl-phenyl) piperazin-1-yl]-3-oxo-propyl] imidazolidine-2,4-dione | F2 | Int.136 + Int. 089 | 360 | 361 |
| 137 | 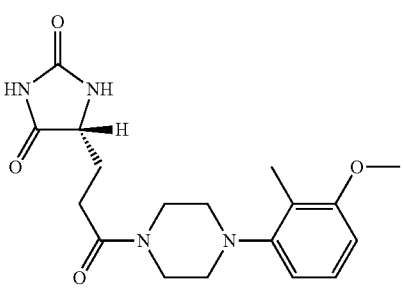 [SMILES: COc1cccc(N2CCN(C(=O)CC[C@H]3NC(=O)NC3=O)CC2)c1C] | (5R)-5-[3-[4-(3-methoxy-2-methyl-phenyl) piperazin-1-yl]-3-oxo-propyl] imidazolidine-2,4-dione | F2 | Int.136 + Int. 099 | 360 | 361 |

TABLE III-continued

| | | | | | | |
|---|---|---|---|---|---|---|
| 138 | | (5R)-5-[3-[4-(4-chloro-5-methoxy-2-methyl-phenyl)piperazin-1-yl]-3-oxo-propyl]imidazolidine-2,4-dione | F2 | Int.136 + Int. 109 | 394 | 395 397 |
| 139 | | (5R)-5-[3-[(3S)-4-(4-chloro-3,5-dimethoxy-phenyl)-3-methyl-piperazin-1-yl]-3-oxo-propyl]imidazolidine-2,4-dione | F2 | Int.136 + Int. 079 | 424 | 425 427 |
| 140 | | (5R)-5-[3-[(3S)-4-(5-methoxy-2-methyl-phenyl)-3-methyl-piperazin-1-yl]-3-oxo-propyl]imidazolidine-2,4-dione | F2 | Int.136 + Int. 044 | 374 | 375 |
| 141 | | (5R)-5-[3-[(3S)-4-(3-methoxy-2-methyl-phenyl)-3-methyl-piperazin-1-yl]-3-oxo-propyl]imidazolidine-2,4-dione | F2 | Int.136 + Int. 137 | 374 | 375 |

TABLE III-continued
| 142 | 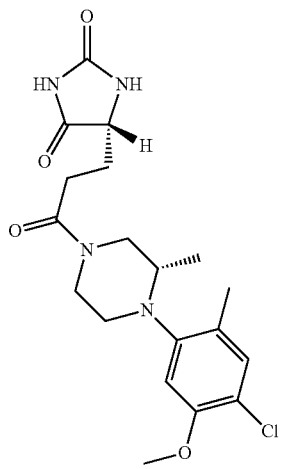 [SMILES: COc1cc(N2CCN(C(=O)CC[C@H]3NC(=O)NC3=O)C[C@@H]2C)c(C)cc1Cl] | (5R)-5-[3-[(3S)-4-(4-chloro-5-methoxy-2-methyl-phenyl)-3-methyl-piperazin-1-yl]-3-oxo-propyl]imidazolidine-2,4-dione | F2 | Int.136 + Int. 061 | 408 | 409 411 |
|---|---|---|---|---|---|---|
| 143 | 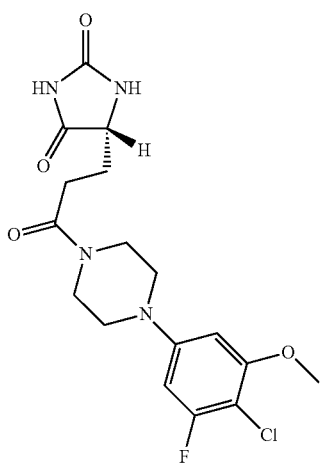 [SMILES: COc1cc(N2CCN(C(=O)CC[C@H]3NC(=O)NC3=O)CC2)cc(F)c1Cl] | (5R)-5-[3-[4-(4-chloro-3-fluoro-5-methoxy-phenyl)piperazin-1-yl]-3-oxo-propyl]imidazolidine-2,4-dione | F2 | Int.136 + Int. 078 | 398 | 399 401 |
| 144 | 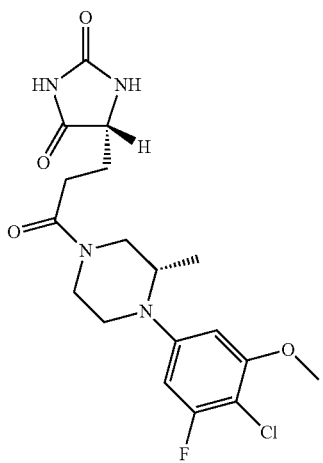 [SMILES: COc1cc(N2CCN(C(=O)CC[C@H]3NC(=O)NC3=O)C[C@@H]2C)cc(F)c1Cl] | (5R)-5-[3-[(3S)-4-(4-chloro-3-fluoro-5-methoxy-phenyl)-3-methyl-piperazin-1-yl]-3-oxo-propyl]imidazolidine-2,4-dione | F2 | Int.136 + Int. 046 | 412 | 413 415 |

TABLE III-continued
| 145 | 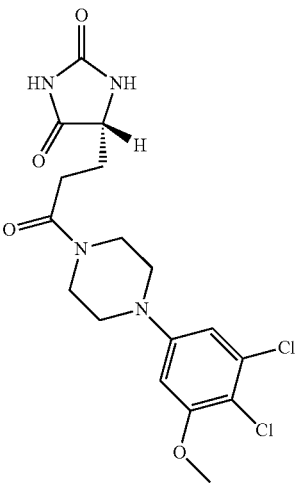 [SMILES: COc1cc(N2CCN(C(=O)CC[C@H]3NC(=O)NC3=O)CC2)cc(Cl)c1Cl] | (5R)-5-[3-[4-(3,4-dichloro-5-methoxy-phenyl)piperazin-1-yl]-3-oxo-propyl]imidazolidine-2,4-dione | F2 | Int.136 + Int. 081 | 414 | 415 417 419 |
| --- | --- | --- | --- | --- | --- | --- |
| 146 | 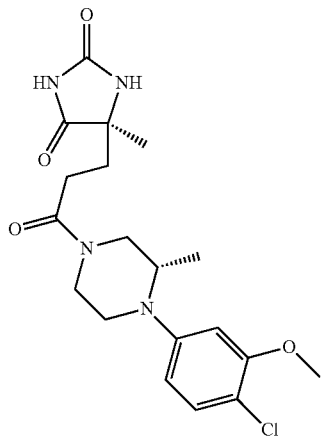 [SMILES: COc1cc(N2CCN(C(=O)CC[C@]3(C)NC(=O)NC3=O)C[C@@H]2C)ccc1Cl] | (5S)-5-[3-[(3S)-4-(4-chloro-3-methoxy-phenyl)-3-methyl-piperazin-1-yl]-3-oxo-propyl]-5-methyl-imidazolidine-2,4-dione | F2 | Int.138 + Int. 050 | 408 | 409 411 |
| 147 | 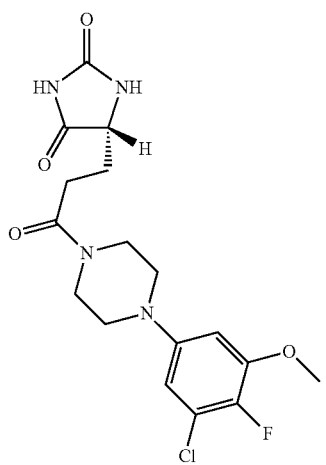 [SMILES: COc1cc(N2CCN(C(=O)CC[C@H]3NC(=O)NC3=O)CC2)cc(Cl)c1F] | (5R)-5-[3-[4-(3-chloro-4-fluoro-5-methoxy-phenyl)piperazin-1-yl]-3-oxo-propyl]imidazolidine-2,4-dione | F2 | Int.136 + Int. 082 | 398 | 399 401 |

TABLE III-continued
| 148 | 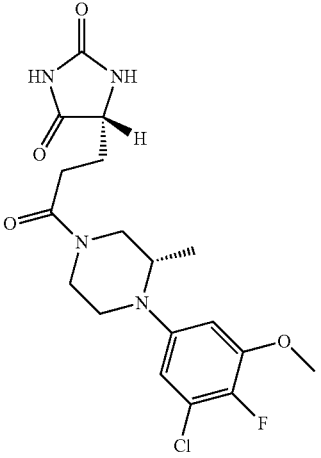 [SMILES: COc1cc(N2CCN(C(=O)CC[C@H]3NC(=O)NC3=O)C[C@@H]2C)cc(Cl)c1F] | (5R)-5-[3-[(3S)-4-(3-chloro-4-fluoro-5-methoxy-phenyl)-3-methyl-piperazin-1-yl]-3-oxo-propyl]imidazolidine-2,4-dione | F2 | Int.136 + Int. 052 | 412 | 413 415 |
| --- | --- | --- | --- | --- | --- | --- |
| 149 | 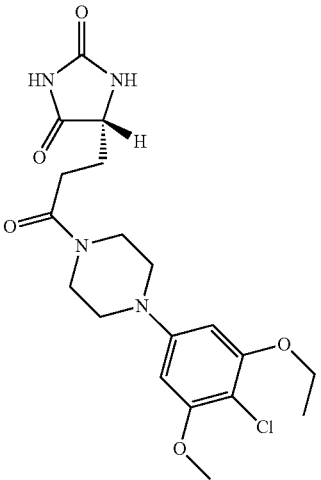 [SMILES: CCOc1cc(N2CCN(C(=O)CC[C@H]3NC(=O)NC3=O)CC2)cc(OC)c1Cl] | (5R)-5-[3-[4-(4-chloro-3-ethoxy-5-methoxy-phenyl)piperazin-1-yl]-3-oxo-propyl]imidazolidine-2,4-dione | F2 | Int.136 + Int. 098 | 424 | 425 427 |
| 150 | 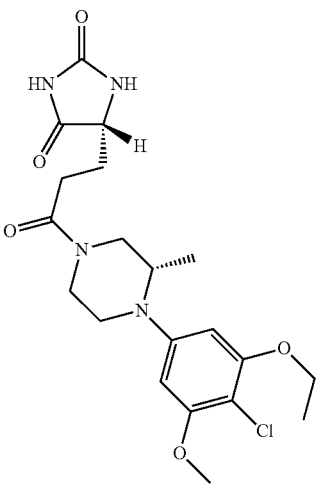 [SMILES: CCOc1cc(N2CCN(C(=O)CC[C@H]3NC(=O)NC3=O)C[C@@H]2C)cc(OC)c1Cl] | (5R)-5-[3-[(3S)-4-(4-chloro-3-ethoxy-5-methoxy-phenyl)-3-methyl-piperazin-1-yl]-3-oxo-propyl]imidazolidine-2,4-dione | F2 | Int.136 + Int. 100 | 63 | 439 441 |

TABLE III-continued

| 151 | [structure] | (5R)-5-[3-[4-(4-fluoro-3,5-dimethoxy-phenyl)piperazin-1-yl]-3-oxo-propyl]imidazolidine-2,4-dione | F2 | Int.136 + Int. 94 | 394 | 395 |

TABLE IV

NMR of illustrative compounds of the invention

| Cpd | NMR |
|---|---|
| 56 | $^1$H NMR (400 MHz, DMSO-d$_6$) δ ppm 10.62 (1H, br. s), 7.76 (1H, m), 6.56-6.46 (2H, m), 4.89-4.80 (1H, m), 3.86 (3H, s), 3.66-3.54 (4H, m), 3.42-3.34 (1H, m), 3.30-3.23 (1H, m), 3.20-3.06 (4H, m), 2.86-2.75 (1H, m), 2.07 (1H, dd), 1.65 (1H, d), 1.18 (3H, s) |
| 68 | $^1$H NMR (500 MHz, DMSO-d$_6$) δ ppm 10.63 (1H, s), 7.92 (1 H, s), 7.09 (1H, dd), 7.05 (1H, t), 6.92 (1H, dd), 3.80 (3H, s), 3.64-3.59 (2H, m), 3.59-3.53 (2H, m), 3.07-3.01 (2H, m), 3.00-2.93 (2H, m), 2.38 (1H, dt), 2.21 (1H, dt), 1.82 (2H, t), 1.27 (3H, s) |
| 78 | $^1$H NMR (400 MHz, DMSO-d$_6$) d ppm 10.6 (1H, s), 7.91 (1H, s), 6.94-6.81 (2H, m), 6.67 (1H, td), 3.79 (3H, s), 3.60-3.40 (4H, m), 3.00-2.75 (4H, m), 2.41-2.30 (1H, m), 2.23-2.11 (1H, m), 1.87-1.74 (2H, m), 1.26 (3H, s) |
| 98 | $^1$H NMR (400 MHz, DMSO-d$_6$) δ ppm 13.0-12.0 (1H, b), 10.61 (1H, s), 7.90-7.84 (1H, m), 7.30-7.15 (1H, m), 7.97-6.66 (2H, m), 4.28-3.92 (2H, m), 3.85-3.72 (1H, m), 3.70-3.20 (2H, m), 3.20-2.80 (2H, m), 2.82-2.72 (1H, m), 2.69-2.52 (3H, m), 2.48-2.13 (2H, m), 1.93-1.73 (2H, m), 1.15 (3H, t), 0.97-0.78 (3H, m) |
| 105 | $^1$H NMR (400 MHz, DMSO-d$_6$) δ ppm 10.63 (1H, s), 7.94 (1 H, m), 6.49-6.44 (2H, m), 4.28-3.99 (2H, m), 3.80 (3H, s), 3.83-3.75 (0.5H, m), 3.63-3.57 (0.5H, m), 3.49-3.42 (0.5H, m), 3.35-3.22 (1.5H, m), 3.08-2.84 (2H, m), 2.48-2.29 (1H, m), 2.25 (3H, s), 2.26-2.13 (1H, m), 1.91-1.75 (2H, m), 1.29-1.24 (3H, m), 0.94-0.81 (3H, m) |
| 116 | $^1$H NMR (400 MHz, DMSO-d$_6$) δ ppm 12.4-12.1 (1H, b), 10.74 (1H, s), 7.93-7.87 (1H, s), 7.19 (1H, d), 6.88-6.81 (1H, m), 6.78-6.70 (1H, m), 4.26-4.05 (1H, m), 4.04-3.94 (1H, m), 3.83-3.21 (3H, m), 3.09-2.83 (2H, m), 2.63 (2H, q), 2.48-2.13 (3H, m), 2.13-2.02 (1H, m), 1.93-1.77 (4H, m), 1.15 (3H, t), 0.93-0.81 (3H, m) |
| 119 | $^1$H NMR (400 MHz, CD$_3$OD) δ ppm 6.46-6.36 (2H, m), 4.41-4.33 (0.5H, m), 4.30-4.21 (0.5H, m), 4.10-3.98 (1H, m), 3.96-3.88 (0.5H, m), 3.87 (3H, s), 3.78-3.69 (0.5H, m), 3.61-3.53 (0.5H, m), 3.43-3.32 (1.5, m), 3.23-3.10 (1H, m), 3.09-3.02 (1H, m), 2.60-2.24 (2H, m), 2.10-1.97 (2H, m), 1.42 (3H, d), 1.04 (1.5H, d), 0.98 (1.5H, d) |

Biological Examples

Example 2. In Vitro Assays 2.1. hADAMTS-1

The basis for the assay is the cleavage of the substrate 5(6)-Fluorescein-NH-AELQGRPISIAK-5(6)-TAMRA (SEQ ID NO: 1) by human ADAMTS1

For the dose response (10 point), 4 μL of a dilution series of compound (2 mM highest concentration, ⅕ dilution in DMSO further diluted 1 in 10 in water corresponding to a final highest concentration of 20 μM), is transferred to 384 well Fluotrac 200 plate (Greiner, cat #781076) and incubated at room temperature for 30 min with a 26 μL buffer solution (50 mM MOPS pH7; 50 mM NaCl; 5 mM CaCl$_2$; 0.05% CHAPS; 5 μM ZnCl$_2$) containing hADAMTS1 (0.38 ng/μL, R&D SYSTEMS INC., Cat #2197-AD)) (it will be appreciated by the skilled person that the potency read out is independent of the enzyme concentration).

The reaction is initiated by adding to the assay plate 5(6)-Fluorescein-NH-AELQGRPISIAK-5(6)-TAMRA (SEQ ID NO: 1) (10 μL, 7 μM, Anaspec) in the same buffer.

Finally, the fluorescence is read on the Envision (Perkin Elmer) after an incubation of 120 min at 37° C. (Excitation 485 nm, Emission 535).

2.2. hADAMTS-4

2.2.1. Protocol 1

The basis for the assay is the cleavage of the substrate TBIS-1 (5-FAM-TEGEARGSVILLK (5TAMRA)K-NH$_2$) (SEQ ID NO: 2) by human ADAMTS4.

For the dose response (10 point), 4 μL of a dilution series of compound (2 mM highest concentration, ⅕ dilution in DMSO further diluted 1 in 10 in water corresponding to a final highest concentration of 20 µM), is transferred to 384 well Fluotrac 200 plate (Greiner, cat #781076) and incubated at room temperature for 30 min with a 26 µL buffer solution (50 mM Hepes pH7.5, 100 mM NaCl, 5 mM $CaCl_2$, 0.1% CHAPS, 5% glycerol) containing hADAMTS4 (0.325 ng/µL) (it will be appreciated by the skilled person that the potency read out is independent of the enzyme concentration).

The reaction is initiated by adding to the assay plate TBIS-1 (10 µL, 4.5 µM, Anaspec) in the same buffer.

Finally, the fluorescence is read on the Envision (Perkin Elmer) after an incubation of 60 min at room temperature (Excitation 485 nm, emission 535).

The $IC_{50}$ measured for illustrative compounds of the invention is reported in the table below.

TABLE V

ADAMTS4 potency of illustrative compounds of the invention

| Cpd # | $IC_{50}$ (nM) |
|---|---|
| 1 | * |
| 2 | *** |

**** 0.001-25 nM
*** >25-50 nM
** >50-100 nM
* >100 nM 2.2.2. Protocol 2

The basis for the assay is the cleavage of the substrate TBIS-1 (5 FAM-TEGEARGSVILLK (5TAMRA)K-$NH_2$) (SEQ ID NO: 2) by human ADAMTS4.

For the dose response (10 point), 4 µL of a dilution series of compound (2 mM highest concentration, ⅓ dilution in DMSO further diluted 1 in 10 in water corresponding to a final highest concentration of 20 µM), is transferred to 384 well Fluotrac 200 plate (Greiner, cat #781076) and incubated at room temperature for 30 min with a 26 µL buffer solution (50 mM Hepes pH 7.5, 100 mM NaCl, 5 mM $CaCl_2$, 0.1% CHAPS) containing hADAMTS4 (0.38 ng/µL) (it will be appreciated by the skilled person that the potency read out is independent of the enzyme concentration).

The reaction is initiated by adding to the assay plate TBIS-1 (10 µL, 4.5 µM, Anaspec) in the same buffer.

Finally, the fluorescence is read on the Envision (Perkin Elmer) after an incubation of 180 min at 37° C. (Excitation 485 nm, emission 535).

The $IC_{50}$ measured for illustrative compounds of the invention is reported in the table below.

TABLE VI

ADAMTS4 potency of illustrative compounds of the invention

| Cpd # | $IC_{50}$ (nM) |
|---|---|
| 3 | * |
| 8 | ** |
| 10 | * |
| 11 | * |
| 14 | * |
| 15 | ** |
| 17 | * |
| 18 | * |
| 19 | * |
| 20 | * |
| 21 | ** |
| 22 | * |
| 23 | ** |
| 24 | * |
| 25 | * |
| 26 | **** |
| 27 | *** |
| 28 | * |
| 29 | *** |
| 30 | * |
| 31 | * |
| 34 | * |
| 36 | * |
| 37 | *** |
| 38 | * |
| 39 | * |
| 40 | *** |
| 41 | * |
| 42 | *** |
| 43 | *** |
| 46 | *** |
| 47 | *** |
| 48 | * |
| 49 | ** |
| 50 | * |
| 51 | * |
| 52 | * |
| 53 | * |
| 54 | *** |
| 55 | * |
| 56 | *** |
| 57 | ** |
| 58 | * |
| 59 | *** |
| 60 | * |
| 61 | * |
| 62 | ** |
| 63 | * |
| 64 | * |
| 65 | ** |
| 71 | * |
| 74 | * |
| 75 | * |
| 79 | * |
| 80 | * |
| 85 | * |
| 86 | * |
| 89 | * |
| 90 | *** |
| 93 | * |
| 96 | * |
| 99 | * |
| 105 | ** |
| 106 | * |
| 107 | * |
| 109 | * |
| 112 | ** |
| 114 | * |
| 115 | * |
| 116 | * |
| 117 | * |
| 118 | * |
| 119 | * |
| 120 | ** |
| 121 | ** |
| 122 | ** |
| 123 | ** |
| 124 | * |
| 125 | ** |
| 128 | * |
| 129 | * |
| 132 | * |
| 133 | * |
| 135 | * |
| 138 | * |
| 139 | * |
| 142 | * |
| 143 | * |
| 144 | * |

TABLE VI-continued

ADAMTS4 potency of illustrative compounds of the invention

| Cpd # | IC$_{50}$ (nM) |
|---|---|
| 145 | * |
| 146 | * |
| 147 | * |
| 148 | * |
| 150 | * |

**** 0.001-25 nM
*** >25-50 nM
** >50-100 nM
* >100 nM

2.3. Rat ADAMTS-5

The basis for the assay is the cleavage of the substrate TBIS-1 (5 FAM-TEGEARGSVILLK (5TAMRA)K-NH$_2$) (SEQ ID NO: 2) by rnADAMTS-5 (1-564-6H).

For the dose response (10 point), 4 μL of a dilution series of compound (2 mM highest concentration, ⅕ dilution in DMSO further diluted 1 in 10 in water, corresponding to a final highest concentration of 20 μM), is transferred to 384 well Fluotrac 200 plate (Greiner, cat #781076) and incubated at room temperature for 30 min with a 26 μL buffer solution (50 mM TRIS pH7.5, 100 mM NaCl, 5 mM CaCl$_2$, 0.1% CHAPS) containing rnADAMTS-5 (0.5 ng/μL) (it will be appreciated by the skilled person that the potency read out is independent of the enzyme concentration).

The reaction is initiated by adding to the assay plate TBIS-1 (10 μL, 4.5 μM, Anaspec) in the same buffer.

Finally, the fluorescence is read on the Envision (Perkin Elmer) after an incubation of 120 min at 37° C. (Excitation 485 nm, emission 535).

The IC$_{50}$ measured for illustrative compounds of the invention is reported in the table below.

TABLE VII

Rat ADAMTS-5 potency of illustrative compounds of the invention

| Cpd # | IC$_{50}$ (nM) |
|---|---|
| 2 | * |
| 6 | * |
| 8 | * |
| 9 | * |
| 10 | * |
| 11 | * |
| 12 | * |
| 13 | * |
| 14 | * |
| 15 | ** |
| 17 | * |
| 18 | * |
| 21 | **** |
| 23 | ** |
| 24 | ** |
| 25 | * |
| 26 | **** |
| 27 | *** |
| 28 | ** |
| 29 | *** |
| 30 | * |
| 31 | * |
| 34 | * |
| 36 | * |
| 37 | **** |
| 38 | ** |
| 39 | ** |
| 40 | * |
| 41 | **** |
| 42 | **** |
| 43 | **** |
| 52 | ** |
| 53 | * |
| 54 | **** |
| 56 | *** |
| 59 | **** |
| 85 | * |
| 86 | * |
| 129 | * |
| 130 | * |
| 131 | * |
| 132 | * |
| 133 | * |
| 135 | * |
| 138 | * |
| 139 | ** |
| 142 | * |
| 144 | ** |

**** 0.001-25 nM
*** >25-50 nM
** >50-100 nM
* >100 nM

2.4. hADAMTS-5

2.4.1. Protocol 1

The basis for the assay is the cleavage of the substrate TBIS-1 (5 FAM-TEGEARGSVILLK (5TAMRA)K-NH$_2$) (SEQ ID NO: 2) by human ADAMTS-5.

For the dose response (10 point), 4 μL of a dilution series of compound (2 mM highest concentration, ⅕ dilution in DMSO further diluted 1 in 10 in water, corresponding to a final highest concentration of 20 μM), is transferred to 384 well Fluotrac 200 plate (Greiner, cat #781076) and incubated at room temperature for 30 min with a 26 μL buffer solution (50 mM Hepes pH7.5, 100 mM NaCl, 5 mM CaCl$_2$, 0.1% CHAPS, 5% glycerol) containing hADAMTS-5 (0.5 ng/μL) (it will be appreciated by the skilled person that the potency read out is independent of the enzyme concentration).

The reaction is initiated by adding to the assay plate TBIS-1 (10 μL, 4.5 μM, Anaspec) in the same buffer.

Finally, the fluorescence is read on the Envision (Perkin Elmer) after an incubation of 60 min at Room Temperature (Excitation 485 nm, emission 530).

2.4.2. Protocol 2

The basis for the assay is the cleavage of the substrate TBIS-1 (5 FAM-TEGEARGSVILLK (5TAMRA)K-NH$_2$) (SEQ ID NO: 2) by human ADAMTS-5.

For the dose response (10 point), 4 μL of a dilution series of compound (2 mM highest concentration, ⅕ dilution in DMSO further diluted 1 in 10 in water, corresponding to a final highest concentration of 20 μM), is transferred to 384 well Fluotrac 200 plate (Greiner, cat #781076) and incubated at room temperature for 30 min with a 26 μL buffer solution (50 mM Hepes pH7.5, 100 mM NaCl, 5 mM CaCl$_2$, 0.1% CHAPS 1) containing hADAMTS-5 (1 ng/μL, affinity purified, followed by overnight digestion of 6His tag by thrombin and dialysis) (it will be appreciated by the skilled person that the potency read out is independent of the enzyme concentration).

The reaction is initiated by adding to the assay plate TBIS-1 (10 μL, 4.5 μM, Anaspec) in the same buffer.

Finally, the fluorescence is read on the Envision (Perkin Elmer) after an incubation of 45 min at 37° C. (Excitation 485 nm, emission 530).

The IC$_{50}$ measured for illustrative compounds of the invention is reported in the table below.

hADAMTS-5 potency of illustrative compounds of the invention

The IC$_{50}$ measured for illustrative compounds of the invention is reported in the table below.

TABLE VIII

ADAMTS5 potency of illustrative compounds of the invention

| Cpd # | IC$_{50}$ (nM) |
|---|---|
| 1 | * |
| 2 | * |
| 3 | * |
| 4 | * |
| 5 | * |
| 6 | * |
| 7 | * |
| 8 | * |
| 9 | * |
| 10 | * |
| 11 | * |
| 12 | * |
| 13 | * |
| 14 | * |
| 15 | ** |
| 16 | * |
| 17 | * |
| 18 | ** |

**** 0.001-25 nM
*** >25-50 nM
** >50-100 nM
* >100 nM 2.4.3. Protocol 3

The basis for the assay is the cleavage of the substrate TBIS-1 (5 FAM-TEGEARGSVILLK (5TAMRA)K-NH$_2$) (SEQ ID NO: 2) by human ADAMTS-5.

For the dose response (10 point), 4 µL of a dilution series of compound (2 mM highest concentration, ⅓ dilution in DMSO further diluted 1 in 10 in water, corresponding to a final highest concentration of 20 µM), is transferred to 384 well Fluotrac 200 plate (Greiner, cat #781076) and incubated at room temperature for 30 min with a 26 µL buffer solution (50 mM Hepes pH 7.5, 100 mM NaCl, 5 mM CaCl$_2$, 0.1% CHAPS) containing hADAMTS-5 (0.63 ng/µL) (it will be appreciated by the skilled person that the potency read out is independent of the enzyme concentration).

The reaction is initiated by adding to the assay plate TBIS-1 (10 µL, 4.5 µM, Anaspec) in the same buffer.

Finally, the fluorescence is read on the Envision (Perkin Elmer) after an incubation of 90 min at 37° C. (Excitation 485 nm, emission 530).

The IC$_{50}$ measured for illustrative compounds of the invention is reported in the table below.

TABLE IX hADAMTS-5 potency of illustrative compounds of the invention

| Cpd # | IC$_{50}$ (nM) |
|---|---|
| 4 | * |
| 7 | * |
| 9 | * |
| 10 | * |
| 14 | * |
| 15 | ** |
| 17 | * |
| 18 | ** |

TABLE IX-continued hADAMTS-5 potency of illustrative compounds of the invention

| Cpd # | IC$_{50}$ (nM) |
|---|---|
| 19 | * |
| 20 | * |
| 21 | **** |
| 22 | * |
| 23 | ** |
| 24 | *** |
| 25 | * |
| 26 | **** |
| 27 | *** |
| 28 | * |
| 29 | *** |
| 30 | * |
| 31 | * |
| 32 | * |
| 33 | * |
| 34 | * |
| 35 | * |
| 36 | * |
| 37 | **** |
| 38 | * |
| 39 | ** |
| 40 | ** |
| 41 | *** |
| 42 | **** |
| 43 | **** |
| 44 | ** |
| 45 | * |
| 46 | *** |
| 47 | *** |
| 48 | ** |
| 49 | *** |
| 50 | * |
| 51 | * |
| 52 | ** |
| 53 | ** |
| 54 | **** |
| 55 | ** |
| 56 | *** |
| 57 | *** |
| 58 | * |
| 59 | **** |
| 60 | * |
| 61 | *** |
| 62 | **** |
| 63 | *** |
| 64 | ** |
| 65 | **** |
| 66 | * |
| 69 | * |
| 70 | * |
| 71 | * |
| 73 | * |
| 74 | * |
| 75 | ** |
| 76 | * |
| 78 | * |
| 79 | * |
| 80 | * |
| 85 | * |
| 86 | * |
| 89 | * |
| 90 | **** |
| 91 | * |
| 93 | * |
| 94 | * |
| 95 | * |
| 96 | * |
| 98 | * |
| 99 | * |
| 105 | * |
| 106 | * |
| 107 | * |
| 109 | * |
| 110 | * |
| 111 | * |
| 112 | * |

TABLE IX-continued hADAMTS-5 potency of illustrative compounds of the invention

| Cpd # | IC$_{50}$ (nM) |
|---|---|
| 113 | * |
| 114 | * |
| 115 | * |
| 116 | * |
| 117 | ** |
| 118 | * |
| 119 | **** |
| 120 | **** |
| 121 | *** |
| 122 | **** |
| 123 | **** |
| 124 | *** |
| 125 | *** |
| 126 | *** |
| 127 | * |
| 128 | * |
| 129 | * |
| 130 | * |
| 131 | * |
| 132 | * |
| 133 | * |
| 134 | * |
| 135 | * |
| 136 | * |
| 137 | * |
| 138 | * |
| 139 | * |
| 140 | * |
| 142 | * |
| 143 | * |
| 144 | ** |
| 145 | ** |
| 146 | * |
| 147 | * |
| 148 | *** |
| 149 | * |
| 150 | * |
| 151 | * |

**** 0.001-25 nM
*** >25-50 nM
** >50-100 nM
* >100 nM 2.5. hADAMTS-6
2.5.1. Preparation of hADAM-TS6 Protein
2.5.1.1. ADAMTS-6 Protein Expression.

The coding sequence from amino acid 1 to 843 of the human ADAMTS6 protein (UniProtKB/Swiss-Prot Q9UKP5, SEQ ID NO: 4) is cloned into the pYD7 vector (vectors and the expression system are described in (Durocher et al., 2002; Loignon et al., 2008; Shi et al., 2005)) (CNRC-NRC) in C-terminal fusion with a sequence containing Tev-GGGGGS-Thr-6his (SEQ ID NO: 5) (pYD7-HsADAM-TS6(1-843)-Tev-GGGGGS-Thr-6his construct). Durocher's 293-6E cells (CNRC-NRC) are grown in suspension at 37° C. in a humidified incubator containing 5% CO$_2$ at 37° C. in F17 culture medium (Invitrogen #A1383501) supplemented with 10 mL/L of 10% Pluronic F68 solution (0.1% final) (Invitrogen #24040032), 20 mL/L of 200 mM L-Glutamine solution (4 mM final) (Lonza #BE17-605E) and 25 μg/mL G418 (PAA laboratories #P11-012).

Transfection is performed according to the protocol given by CNRC-NRC for the 293-6E cells using PEI (Polysciences #23966-2). Cells are diluted to 3.105 cells/mL three days before transfection. On the day of transfection, the cell density is adjusted to 17.105 cells/mL. A DNA/PEI mix is prepared according to CNRC-NRC recommendations with a ratio of DNA/PEI of 1 for 2, meaning, 300 μg of pYD7-HsADAM-TS6(1-843)-Tev-GGGGGS-Thr-6his construct and 600 μg PEI for 300 mL of final transfection volume. The day after transfection, Heparin (Sigma #H3149) and TN1 (Tekniscience Inc. #19553) is added to get 0.1 g/L and 0.5% final concentrations respectively.

The conditioned medium is harvested 168 h post-transfection by centrifugation for 20 min at 5000×g at 4° C. The expression level of secreted HsADAM-TS6 is estimated at 1 mg/L in the conditioned medium (CM) by Western blotting analysis using anti His tag primary antibody. Conditioned medium is either used from fresh or frozen production at −20° C. for later use.

2.5.1.2. Purification of HsADAM-TS6 Protein

10× buffer A (500 mM Tris pH 8, 4 M NaCl, 10 mM CaCl$_2$, 10 μM ZnCl$_2$, 0.5% CHAPS, 200 mM imidazole) is slowly added to the conditioned medium under magnetic stirring, giving Buffered Conditioned Medium (BCM). This sample is clarified by centrifugation at 15,000×g for 60 min at 4° C. in a Beckman 16.250 rotor, providing the starting sample.

Affinity purification is performed using AKTA protein purification system (GE Healthcare) in 4° C. cabinet. 400 mL of the start sample is loaded onto each HisTrap™ HP 5 mL column (GE Healthcare #17-5248-02) at a flow rate of 5 mL/min. The resin is then washed with equilibration buffer B (50 mM Tris (pH 8), 0.5 M NaCl, 1 mM CaCl$_2$, 1 μM ZnCl$_2$, 20 mM imidazole, 0.05% CHAPS) until the absorbance at 280 nm returns to zero. The elution is then performed with 70 mM imidazole (elution of contaminant proteins) and subsequently 300 mM imidazole (elution of the target protein). The fractions containing the non-mature (1-843) ADAMTS6 protein are pooled and subjected to 2 dialyses against 100 volumes of dialysis buffer C (50 mM Tris pH 8+100 mM NaCl+1 mM CaCl$_2$+1 μM ZnCl$_2$+0.1% Polyoxyethyleneglycol Dodecyl Ether [Brij 35]) using 50 kDa cut off membrane (SpectraPor #132 542). This allows to decrease the NaCl concentration for efficient furin cleavage.

2.5.1.3. Maturation of HsADAM-TS6 Protein

In vitro maturation of human ADAMTS6 protein is performed using furin (R&D #1503-SE) (3 ng furin/μg of target protein), in buffer D (25 mM Tris pH 9+100 mM NaCl+1 mM CaCl$_2$+1 μM ZnCl$_2$+0.5% Brij 35). Incubation is conducted overnight at room temperature.

The furin cleaved sample is subsequently dialyzed for 1 hour against 100 volumes of dialysis buffer C. Finally, 10% glycerol is added to the final batch which is subsequently ultracentrifuged for 30 minutes at 35,000 rpm using a Beckman SW41Ti rotor and stored at −80° C.

Following this procedure the final yield reached an average of 0.05 to 0.1 mg matured human ADAMTS6 (SEQ ID NO: 6)/L of culture medium.

2.5.2. hADAMTS-6 Assay

The IC$_{50}$ value for test compounds can be determined in a fluorescent based protease assay.

The basis for the assay is the cleavage of the substrate 520 MMP FRET substrate XII by human ADAMTS6.

The substrate contains sequence Arg-Pro-Lys-Pro-Tyr-Ala-Nva-Trp-Met-Lys (SEQ ID NO: 7) with attached a fluorescent probe and a quencher. Without ADAMTS6, the emission of the probe is quenched. If the substrate is cleaved by ADAMTS6, the emission of the probe is not quenched anymore. Inhibition of ADAMTS6 activity, will result in a decrease of the signal.

To perform the assay, 4 μL of a dilution series of compound in water, starting from 20 μM highest concentration, ⅕ dilution, is added to the wells. 2 ng ADAMTS6 enzyme is diluted in 25 mM Tris pH8.0, 0.05% CHAPS, 2.5 mM CaCl$_2$ in a total volume of 26 μL (final concentration 0.73 nM). The reaction is started by addition of 10 μL of 1 μM 520 MMP FRET Substrate XII (final concentration, diluted in same buffer as described above) and the mixture is incubated at 37° C. for 2 h. The negative control (0% inhibition) is 1% DMSO and the positive control (100% inhibition) is 10 μM Prinomastat in 1% DMSO. After this incubation, cleavage of the substrate is measured using the Envision (Perkin Elmer, exc485/em530).

The IC$_{50}$ measured for illustrative compounds of the invention is reported in the table below.

TABLE X hADAMTS-6 potency of illustrative compounds of the invention

| Cpd # | IC$_{50}$ (nM) |
|---|---|
| 1 | * |
| 2 | * |
| 3 | * |
| 4 | * |
| 5 | * |
| 6 | * |
| 7 | * |
| 8 | * |
| 9 | ** |
| 10 | *** |
| 11 | * |
| 12 | * |
| 13 | *** |
| 14 | *** |
| 15 | * |
| 16 | * |
| 17 | * |
| 18 | **** |
| 19 | ** |
| 20 | **** |
| 21 | **** |
| 22 | **** |
| 23 | *** |
| 24 | **** |
| 25 | *** |
| 26 | **** |
| 27 | **** |
| 28 | *** |
| 29 | **** |
| 30 | **** |
| 31 | **** |
| 32 | * |
| 33 | * |
| 34 | *** |
| 35 | * |
| 36 | *** |
| 37 | **** |
| 38 | **** |
| 39 | **** |
| 40 | **** |
| 41 | **** |
| 42 | **** |
| 43 | **** |
| 44 | **** |
| 45 | * |
| 46 | **** |
| 47 | **** |
| 48 | **** |
| 49 | **** |
| 50 | **** |
| 51 | **** |
| 52 | **** |
| 53 | **** |
| 54 | **** |
| 55 | **** |
| 56 | **** |
| 57 | **** |
| 58 | *** |
| 59 | **** |
| 60 | * |
| 61 | **** |
| 62 | **** |
| 63 | **** |
| 64 | ** |
| 65 | **** |
| 66 | ** |
| 67 | ** |
| 68 | * |
| 69 | * |
| 70 | * |
| 71 | *** |
| 72 | * |
| 73 | * |
| 74 | **** |
| 75 | **** |
| 76 | * |
| 77 | * |
| 78 | * |
| 79 | **** |
| 80 | **** |
| 81 | * |
| 82 | * |
| 83 | * |
| 84 | * |
| 85 | **** |
| 86 | **** |
| 87 | ** |
| 88 | *** |
| 89 | **** |
| 90 | **** |
| 91 | * |
| 92 | **** |
| 93 | **** |
| 94 | **** |
| 95 | **** |
| 96 | **** |
| 97 | *** |
| 98 | **** |
| 99 | **** |
| 100 | **** |
| 101 | **** |
| 102 | * |
| 103 | * |
| 104 | **** |
| 105 | **** |
| 106 | **** |
| 107 | * |
| 108 | * |
| 109 | * |
| 110 | **** |
| 111 | **** |
| 112 | **** |
| 113 | * |
| 114 | **** |
| 115 | **** |
| 116 | **** |
| 117 | **** |
| 118 | **** |
| 119 | **** |
| 120 | **** |
| 121 | **** |
| 122 | **** |
| 123 | **** |
| 124 | **** |
| 125 | **** |
| 126 | **** |
| 127 | * |
| 128 | ** |
| 129 | **** |
| 130 | * |
| 131 | * |
| 132 | *** |
| 133 | **** |
| 134 | ** |
| 135 | **** |
| 136 | * |

TABLE X-continued hADAMTS-6 potency of illustrative compounds of the invention

| Cpd # | IC$_{50}$ (nM) |
|---|---|
| 137 | * |
| 138 | * |
| 139 | **** |
| 140 | * |
| 142 | ** |
| 143 | **** |
| 144 | **** |
| 145 | **** |
| 146 | * |
| 147 | **** |
| 148 | **** |
| 149 | ** |
| 150 | **** |
| 151 | *** |

**** 0.001-25 nM
*** >25-50 nM
** >50-100 nM
* >100 nM

2.6. hTACE

The basis for the assay is the cleavage of the substrate 5FAM-LAQAVRSSSRK-5TAMRA (SEQ ID NO: 3) (Anaspec, custom 34891) by human TACE (R&D SYSTEMS INC., Cat #930-ADB).

For the dose response (10 point), 4 µL of a dilution series of compound (2 mM highest concentration, ⅓ dilution in DMSO further diluted 1 in 10 in water, corresponding to a final highest concentration of 20 µM), is transferred to 384 well Fluotrac 200 plate (Greiner, cat #781076) and incubated at room temperature for 30 min with a 26 µL buffer solution (25 mM Tris pH8.0, 2.5 µM ZnCl$_2$, 0.01% CHAPS) containing TACE (0.05 ng/µL) (it will be appreciated by the skilled person that the potency read out is independent of the enzyme concentration).

The reaction is initiated by adding to the assay plate 5FAM-LAQAVRSSSRK-5TAMRA (5 µL, 5 µM, Anaspec) in the same buffer.

Finally, the fluorescence is read on the Envision (Perkin Elmer) after an incubation of 75 min at room temperature (Excitation 485 nm, Emission 530).

The IC$_{50}$ measured for illustrative compounds of the invention is reported in the table below.

TABLE XI hTACE potency of illustrative compounds of the invention

| Cpd # | IC$_{50}$ (nM) |
|---|---|
| 1 | * |
| 2 | * |
| 3 | * |
| 6 | * |
| 8 | * |
| 9 | * |
| 10 | * |
| 11 | * |
| 12 | * |
| 13 | * |
| 14 | * |
| 15 | * |
| 17 | * |
| 18 | * |
| 19 | * |
| 20 | * |
| 21 | * |
| 22 | * |
| 23 | * |
| 24 | * |
| 25 | * |
| 26 | * |
| 27 | * |
| 28 | * |
| 29 | * |
| 30 | * |
| 31 | * |
| 34 | * |
| 36 | * |
| 37 | * |
| 38 | * |
| 39 | * |
| 40 | * |
| 41 | * |
| 42 | * |
| 43 | * |
| 46 | * |
| 47 | * |
| 48 | * |
| 49 | * |
| 50 | * |
| 51 | * |
| 52 | * |
| 53 | * |
| 54 | * |
| 55 | * |
| 56 | * |
| 57 | * |
| 58 | * |
| 59 | * |
| 60 | * |
| 61 | * |
| 62 | * |
| 63 | * |
| 64 | * |
| 65 | * |
| 66 | * |
| 69 | * |
| 70 | * |
| 71 | * |
| 73 | * |
| 74 | * |
| 75 | * |
| 76 | * |
| 78 | * |
| 79 | * |
| 80 | * |
| 85 | * |
| 86 | * |
| 89 | * |
| 90 | * |
| 91 | * |
| 93 | * |
| 94 | * |
| 95 | * |
| 96 | * |
| 99 | * |
| 105 | * |
| 106 | * |
| 107 | * |
| 109 | * |
| 112 | * |
| 114 | * |
| 115 | * |
| 116 | * |
| 117 | * |
| 118 | * |
| 119 | * |
| 120 | * |
| 121 | * |
| 122 | * |
| 123 | * |
| 124 | * |
| 125 | * |
| 128 | * |
| 129 | * |

TABLE XI-continued hTACE potency of illustrative compounds of the invention

| Cpd # | IC$_{50}$ (nM) |
|---|---|
| 132 | * |
| 133 | * |
| 135 | * |
| 138 | * |
| 139 | * |
| 142 | * |
| 143 | * |
| 144 | * |
| 145 | * |
| 146 | * |
| 147 | * |
| 148 | * |
| 149 | * |
| 150 | * |
| 151 | * |

**** 0.001-25 nM
*** >25-50 nM
** >50-100 nM
* >100 nM 2.7. hMMP1

Inhibition of the proteases human MMP1 was determined at REACTION BIOLOGY (Reaction Biology Corp. 1 Great Valley Parkway, Suite 2 Malvern, Pa. 19355, USA) in fluorescent based biochemical assays. The protease activities were monitored as a time-course measurement of the increase in fluorescence signal from fluorescently-labeled peptide substrates, and initial linear portion of slope (signal/min) was analyzed.

To determine the IC$_{50}$, a compound is tested starting from 100 nM (highest dilution) with a ⅓ dilution.

2.8. hMMP2

2.8.1. Protocol 1

The basis for the assay is the cleavage of the substrate 520 MMP fret substrate XV (Anaspec, Catalog #: AS-60582-01) by human MMP2 (R&D SYSTEMS INC. Systems Inc., Cat #902-MP).

For the dose response (10 point), 4 µL of a dilution series of compound (2 mM highest concentration, ⅕ dilution in DMSO further diluted 1 in 10 in water, corresponding to a final highest concentration of 20 µM), is transferred to 384 well Fluotrac 200 plate (Greiner, cat #781076) and incubated at room temperature for 30 min with a 26 µL buffer solution (50 mM Tris pH 7.5, 10 mM, CaCl$_2$, 150 mM NaCl, 0.05% Brij35) containing preactivated MMP2 (0.0125 ng/µL) (it will be appreciated by the skilled person that the potency read out is independent of the enzyme concentration). Human MMP2 is preactivated by incubated the enzyme in the same buffer complemented with 1 mM freshly prepared p-Aminophenylmercuric acetate (AMPA) for 1 h at 37° C.

The reaction is initiated by adding to the assay plate 520 MMP fret substrate XV (10 µL, 4 µM, Anaspec) in the same buffer.

Finally, the fluorescence is read on the Envision (Perkin Elmer) after an incubation of 30 min at room temperature (Excitation 485 nm, Emission 530).

2.8.2. Protocol 2

The basis for the assay is the cleavage of the substrate 390 MMP FRET substrate I (Anaspec, Catalog n #: AS-27076) by human MMP2 (R&D SYSTEMS INC., Cat #902-MP).

For the dose response (10 point), 4 µL of a dilution series of compound (2 mM highest concentration, ⅕ dilution in DMSO further diluted 1 in 10 in water, corresponding to a final highest concentration of 20 µM), is transferred to 384 well Fluotrac 200 plate (Greiner, cat #781076) and incubated at room temperature for 30 min with a 26 µL buffer solution (45 mM Tris pH 7.5, 9 mM CaCl$_2$, 135 mM NaCl, 0.045% Brij35) containing MMP2 (0.03 ng/µL) (it will be appreciated by the skilled person that the potency read out is independent of the enzyme concentration).

The reaction is initiated by adding to the assay plate 390 MMP FRET substrate I (10 µL, 2.5 µM, Anaspec) in the same buffer.

Finally, the fluorescence is read on the Envision (Perkin Elmer) after an incubation of 30 min at room temperature (Excitation 485 nm, Emission 530).

2.9. hMMP8

Inhibition of the human MMP8 protease is determined at REACTION BIOLOGY (Reaction Biology Corp. 1 Great Valley Parkway, Suite 2 Malvern, Pa. 19355, USA; cat #MMP8) in fluorescence based biochemical assays. The protease activity is monitored as a time-course measurement of the increase in fluorescence signal from fluorescently-labeled peptide substrates, and the slope (signal/min) of the initial linear portion is measured.

The basis for the assay is the cleavage of the substrate 520 MMP FRET Substrate XIV (Anaspec, cat #AS-60581) by human MMP8 (Enzo®, cat #SE-255) in a buffer solution (50 mM HEPES pH 7.5, 10 mM CaCl$_2$, 0.01% Brij-35, 0.1 mg/mL BSA).

A 100% DMSO dilution series of test compound (10 final concentrations starting from 30 µM highest concentration, with ⅓ serial dilutions) is added to MMP8 in buffer solution and incubated at room temperature for 5-15 min (it will be appreciated by the skilled person that the potency read out is independent of the enzyme concentration). The reaction is then initiated by adding 520 MMP FRET Substrate XIV (5 µM final concentration) in the same buffer.

Fluorescence is read at 5 min intervals for 2 h with an Envision (Perkin Elmer) at room temperature (Excitation 485 nm, Emission 520 nm). The slope of the initial linear portion of the fluorescence signal curve is then calculated by using Excel. Percent protease activity is calculated relative to a no inhibitor DMSO control defined as 100% activity. IC$_{50}$ curve fits are performed using Prism software.

2.10. hMMP12

Inhibition of the human MMP12 protease is determined at REACTION BIOLOGY (Reaction Biology Corp. 1 Great Valley Parkway, Suite 2 Malvern, Pa. 19355, USA; cat #MMP12) in fluorescence based biochemical assays. The protease activity is monitored as a time-course measurement of the increase in fluorescence signal from fluorescently-labeled peptide substrates, and the slope (signal/min) of the initial linear portion is measured.

The basis for the assay is the cleavage of the substrate 520 MMP FRET Substrate XIV (Anaspec, cat #AS 60581) by human MMP12 (Enzo®, cat #SE-138) in a buffer solution (50 mM HEPES pH 7.5, 10 mM CaCl$_2$, 0.01% Brij-35, 0.1 mg/mL BSA).

A 100% DMSO dilution series of test compound (10 final concentrations starting from 30 µM highest concentration, with ⅓ serial dilutions) is added to MMP12 in buffer solution and incubated at room temperature for 5-15 min (it will be appreciated by the skilled person that the potency read out is independent of the enzyme concentration). The reaction is then initiated by adding 520 MMP FRET Substrate XIV (5 µM final concentration) in the same buffer.

Fluorescence is read at 5 min intervals for 2 h with an Envision (Perkin Elmer) at room temperature (Excitation 485 nm, Emission 520 nm). The slope of the initial linear portion of the fluorescence signal curve is then calculated by using Excel. Percent protease activity is calculated relative to a no inhibitor DMSO control defined as 100% activity. $IC_{50}$ curve fits are performed using Prism software.

2.11. hMMP13

2.11.1. Protocol 1

The basis for the assay is the cleavage of the substrate 390 MMP FRET Substrate I (Anaspec Cat #AS-27076) by human MMP13 (Chemicon, Cat #CC068).

For the dose response (10 point), 4 μL of a dilution series of compound (20 μM highest concentration, ⅕ dilution in water), is transferred to 384 well Fluotrac 200 plate (Greiner, cat #781076) and incubated at room temperature for 30 min with a 26 μL buffer solution (50 mM Tris pH7.5, 150 mM NaCl, 10 mM $CaCl_2$, 0.05% CHAPS, 5 M $ZnCl_2$) containing MMP13 (0.01 ng/μL) (it will be appreciated by the skilled person that the potency read out is independent of the enzyme concentration). Human MMP13 is preactivated by incubated the enzyme in the same buffer complemented with 1 mM freshly prepared p-Aminophenylmercuric acetate (AMPA) for 1 h at 37° C.

The reaction is initiated by adding to the assay plate 390 MMP FRET Substrate I (10 μL, 2.5 μM) in the same buffer.

Finally, the fluorescence is read on the Envision (Perkin Elmer) after an incubation of 45 min at room temperature (Excitation 485 nm, Emission 530).

The $IC_{50}$ measured for illustrative compounds of the invention is reported in the table below.

TABLE XII

| hMMP-13 potency of illustrative compounds of the invention | |
| --- | --- |
| Cpd # | $IC_{50}$ (nM) |
| 3 | * |
| 6 | * |
| 8 | * |
| 9 | * |
| 10 | * |
| 11 | * |
| 12 | * |
| 13 | * |
| 14 | * |
| 15 | * |
| 17 | * |
| 18 | * |
| 19 | * |
| 20 | * |
| 21 | * |
| 22 | * |
| 23 | * |
| 24 | * |
| 25 | * |
| 26 | * |
| 27 | * |
| 28 | * |
| 29 | * |
| 30 | * |
| 31 | * |
| 34 | * |
| 36 | * |
| 37 | * |
| 38 | * |
| 39 | * |
| 40 | * |
| 41 | * |
| 42 | * |
| 43 | * |
| 46 | * |
| 47 | * |
| 48 | * |
| 50 | * |
| 53 | * |
| 128 | * |
| 129 | * |

TABLE XII-continued

| hMMP-13 potency of illustrative compounds of the invention | |
| --- | --- |
| Cpd # | $IC_{50}$ (nM) |
| 132 | * |
| 133 | * |
| 135 | * |
| 138 | * |
| 139 | * |
| 142 | * |
| 143 | * |
| 144 | * |
| 145 | * |

**** 0.001-25 nM
*** >25-50 nM
** >50-100 nM
* >100 nM 2.11.2. Protocol 2

The basis for the assay is the cleavage of the substrate 390 MMP FRET Substrate I (Anaspec Cat #AS-27076) by human MMP13 (Enzo Life Sciences, Cat #BML-SE493).

For the dose response (10 point), 4 μL of a dilution series of compound (20 μM highest concentration, ⅕ dilution in water), is transferred to 384 well Fluotrac 200 plate (Greiner, cat #781076) and incubated at room temperature for 30 min with a 26 μL buffer solution (50 mM Tris pH7.5, 150 mM NaCl, 10 mM $CaCl_2$, 0.05% CHAPS, 5 μM $ZnCl_2$) containing MMP13 (0.01 ng/μL) (it will be appreciated by the skilled person that the potency read out is independent of the enzyme concentration). Human MMP13 is preactivated by incubated the enzyme in the same buffer complemented with 1 mM freshly prepared p-Aminophenylmercuric acetate (AMPA) for 1 h at 37° C.

The reaction is initiated by adding to the assay plate 390 MMP FRET Substrate I (10 μL, 2.5 μM) in the same buffer.

Finally, the fluorescence is read on the Envision (Perkin Elmer) after an incubation of 45 min at room temperature (Excitation 485 nm, Emission 530).

The $IC_{50}$ measured for illustrative compounds of the invention is reported in the table below.

TABLE XIII

| hMMP-13 potency of illustrative compounds of the invention | |
| --- | --- |
| Cpd # | $IC_{50}$ (nM) |
| 18 | * |
| 51 | * |
| 52 | * |
| 53 | * |
| 54 | * |
| 55 | * |
| 56 | * |
| 57 | * |
| 58 | * |
| 59 | * |
| 61 | * |
| 62 | * |
| 63 | * |
| 64 | * |
| 65 | * |
| 71 | * |
| 74 | * |
| 75 | * |
| 79 | * |
| 80 | * |
| 85 | * |
| 86 | * |
| 89 | * |
| 90 | * |
| 93 | * |

TABLE XIII-continued hMMP-13 potency of illustrative compounds of the invention

| Cpd # | IC$_{50}$ (nM) |
|---|---|
| 96 | * |
| 99 | * |
| 105 | * |
| 106 | * |
| 107 | * |
| 109 | * |
| 112 | * |
| 114 | * |
| 115 | * |
| 116 | * |
| 117 | * |
| 118 | * |
| 119 | * |
| 120 | * |
| 121 | * |
| 122 | * |
| 123 | * |
| 124 | * |
| 125 | * |
| 146 | * |
| 147 | * |
| 148 | * |
| 150 | * |

**** 0.001-25 nM
*** >25-50 nM
** >50-100 nM
* >100 nM 2.11.3. Protocol 3

The basis for the assay is the cleavage of the substrate 520 MMP-fret substrate XV (Anaspec, Catalog #: AS-60582-01) by human MMP13 (Chemicon, Cat #CC068).

For the dose response (10 point), 4 µL of a dilution series of compound (2 mM highest concentration, ⅕ dilution in DMSO further diluted 1 in 10 in water, corresponding to a final highest concentration of 20 µM), is transferred to 384 well Fluotrac 200 plate (Greiner, cat #781076) and incubated at room temperature for 30 min with a 26 µL buffer solution (50 mM Tris pH7.5, 150 mM NaCl, 10 mM CaCl$_2$, 0.05% CHAPS, 5 µM ZnCl$_2$) containing MMP13 (6.25 10$^{-6}$ µg/µL) (it will be appreciated by the skilled person that the potency read out is independent of the enzyme concentration).

The reaction is initiated by adding to the assay plate 520 MMP-fret substrate XV (10 µL, 4 µM) in the same buffer.

Finally, the fluorescence is read on the Envision (Perkin Elmer) after an incubation of 60 min at room temperature (Excitation 485 nm, Emission 530).

2.12. hMMP14

The basis for the assay is the cleavage of the substrate 390 MMP FRET Substrate I (Anaspec Cat #AS-27076) by human MMP14 (Biomol, Cat #SE-259).

For the dose response (10 point), 4 µL of a dilution series of compound 2 mM highest concentration, ⅕ dilution in DMSO further diluted 1 in 10 in water, corresponding to a final highest concentration of 20 µM), is transferred to 384 well Fluotrac 200 plate (Greiner, cat #781076) and incubated at room temperature for 30 min with a 26 µL buffer solution (50 mM MOPS pH7, 5 mM CaCl$_2$, 1 µM ZnCl$_2$, 0.1% Brij-35) containing MMP14 (0.05 ng/µL) (it will be appreciated by the skilled person that the potency read out is independent of the enzyme concentration).

The reaction is initiated by adding to the assay plate 390 MMP FRET Substrate I (10 µL, 2.5 µM) in the same buffer.

Finally, the fluorescence is read on the Envision (Perkin Elmer) after an incubation of 60 min at room temperature (Excitation 485 nm, Emission 530).

The IC$_{50}$ measured for illustrative compounds of the invention is reported in the table below.

TABLE XIV hMMP-14 potency of illustrative compounds of the invention

| Cpd # | IC$_{50}$ (nM) |
|---|---|
| 18 | * |
| 24 | * |
| 37 | * |
| 41 | * |
| 42 | * |
| 43 | * |
| 47 | * |
| 48 | * |
| 51 | * |
| 52 | * |
| 53 | * |
| 54 | * |
| 55 | * |
| 56 | * |
| 57 | * |
| 59 | * |
| 61 | * |
| 62 | * |
| 63 | * |
| 64 | * |
| 65 | * |
| 71 | * |
| 74 | * |
| 75 | * |
| 79 | * |
| 80 | * |
| 85 | * |
| 86 | * |
| 89 | * |
| 90 | * |
| 93 | * |
| 96 | * |
| 99 | * |
| 105 | * |
| 106 | * |
| 107 | * |
| 109 | * |
| 112 | * |
| 114 | * |
| 115 | * |
| 116 | * |
| 117 | * |
| 118 | * |
| 119 | * |
| 120 | * |
| 121 | * |
| 122 | * |
| 123 | * |
| 124 | * |
| 125 | * |
| 145 | * |
| 146 | * |
| 147 | * |
| 148 | * |
| 150 | * |

**** 0.001-25 nM
*** >25-50 nM
** >50-100 nM
* >100 nM

Example 3. Cellular Assays 3.1. Mouse Explant Assay

In this assay, quantitation of glycosaminoglycans (GAGs) in the form of aggrecan fragments released from cartilage in culture is used to determine the efficacy of a test compound in preventing cartilage catabolism.

The protocol of mouse cartilage explants is described by Stanton (Stanton et al., 2011). After euthanasia, the femoral head cartilage from the right and left leg of a 3-days-old C57B16 male mouse (Janvier, 7-10 g), were placed in a 48-wells culture plate. Cell culture medium (400 µL) containing human IL1α (1 ng/mL) and test compound (3 M) were added to the femoral head cartilage.

After 3 days of incubation, the supernatant is harvested and stored at −20° C. until analysis and the cartilages are digested with a papaïn solution at 60° C. for 24 h. Using the standard curve performed with a dose range of chondroitin sulfate, the concentration of GAG is determined in the supernatant and on the lysate using dimethylmethylene blue solution (reading at a wavelength of 590 nm).

The percentage of GAG release is calculated as follows:

$$GAG\ \% = \frac{[GAG]_{supernatant}}{[GAG]_{supernatant} + [GAG]_{lysate}}$$

The test compound effect is expressed as percent of inhibition (PIN) using the following formula:

$$PIN = \frac{mean\ \%\ [GAG]_{vehicle+IL1\alpha} - mean\ \%\ [GAG]_{compound+IL1\alpha}}{mean\ \%\ [GAG]_{vehicle+IL1\alpha} - mean\ \%\ [GAG]_{compound}} * 100$$

3.2. Human Explant Assay

In this assay, compounds are tested in human articular cartilage explants in order to evaluate their activity on aggrecan degradation induced by IL1β. AGNx1 is the epitope for aggrecanase-mediated aggrecan degradation; on the other hand, AGNx2 is the epitope for MMP-mediated aggrecan degradation. Therefore quantification of AGNx1 and AGNx2 may be used to evaluate the activity of a test compound.

These studies were conducted in Nordic Bioscience (Herlev Hovedgade 207, DK-2730 Herlev, Denmark).

Human articular cartilage explants are collected from 3 nearby hospitals under an existing ethical committee application.

Full-depth cartilage explants from OA cartilage from different patients are cultured for 21 days in culture medium (DMEM/F12 with 0.5% FCS, 1% PS) containing various (positive control, untreated, and test compound at 0.1, 1 and 10 µM).

The explants from each patient are cultured in a separate 96-well culture plate with 200 µL/well PBS, and the 6 replicates of each treatment are distributed in a diagonal pattern on the plate. At each experimental time point (5, 12 and 19 days), supernatants are harvested from the explants cultures, and new treatment-mediums are added. The supernatants are stored at −20° C. for later biomarker analysis. The human IL13 (Sigma-Aldrich SRP3083) is used at a concentration of 10 ng/mL.

3.3. Results

The AGNx1 and AGNx2 concentrations were determined against a standard curve. Mean and SEM were graphed using the excel software. One-way ANOVA plus Dunnett's multiple comparisons post-hoc test are used for the statistical analysis (Prism 3.03 software).

Example 4. In Vivo Assays 4.1. In Vivo Menisectomized (MNX) Rat Model 4.1.1. In Vivo Efficacy in the Rat MNX Model In vivo efficacy was studied in a female Lewis meniscectomised rat (MNX) model. The MNX rat model is a well-validated disease model of osteoarthritis (Bendele, 2001; Janusz et al., 2002; Pritzker et al., 2006).

4.1.2. Experimental Procedures 4.1.2.1. Surgery and Dosing

Osteoarthritis is induced by meniscectomy at day 0 (DO) in the right leg of each rat by a transection of the medial collateral ligament and 4 mm of ligament are removed. Internal part of the meniscus is transected vertically into two flaps which are pushed to the front and the back of the synovial cavity. Sham animals undergo only anaesthesia, skin and muscle incision then suture. On day 1, rats are randomly assigned to a treatment group (n=20 per group) according to their body weight, in order to have a homogenous distribution. From C2 to D21, rats are dosed per os (po) once daily (qd) or twice a day (bid) with compounds formulated in methylcellulose (MC) 0.5% or in HPβCD 10% pH3.0.

4.1.2.2. Steady-State PK Determination (ssPK)

After at least 7 days of treatment, blood is sampled at 4 time points post administration: 0, 1, 3 and 6 h (and assuming 24 h is equal to the pre-dose sample), in order to determine steady-state plasma exposure.

4.1.2.3. Histology

At sacrifice, the right tibia of each rat is collected and processed for histological analysis. After 48 h of fixation in 4% formaldehyde, tibias are decalcified in Osteosoft for 7 days, and cut into 2 half parts prior to embedding face to face in paraffin. Five series of sections are cut at 200 µm intervals, covering about 1.5 mm of the middle part of the bone. One series of slides is stained with Safranin O and light green for morphological evaluation and OARSI scoring. The other series of slides are mounted with DAPI for chondrocyte density measurement.

The extent of cartilage injury reflecting osteoarthritis in the tibial plateau is evaluated and scored using the OARSI method based on the grading and the staging of cartilage lesion (Pritzker et al, 2006). The OARSI scoring is assessed in a blinded manner by two different readers. For each tibia, one score is attributed as the median of the OARSI score of the 5 sections.

For statistical analysis, medians of groups are compared with a stratified Kruskal-Wallis test followed by Dunnett multiple comparison post hoc test.

Significance levels: ns: not statistically significant; *p<0.05; p<0.01; *p<0.001 versus MNX-vehicle. Statistical analyses are done on all groups of the studies.

Final Remarks

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

REFERENCES

Abbaszade, I., Liu, R.-Q., Yang, F., Rosenfeld, S. A., Ross, O. H., Link, J. R., Ellis, D. M., Tortorella, M. D., Pratta, M. A., Hollis, J. M., Wynn, R., Duke, J. L., George, H. J., Hillman, M. C., Murphy, K., Wiswall, B. H., Copeland, R. A., Decicco, C. P., Bruckner, R., Nagase, H., Itoh, Y., Newton, R. C., Magolda, R. L., Trzaskos, J. M., Hollis, G. F., Arner, E. C., Burn, T. C., 1999. Cloning and Characterization of ADAMTS11, an Aggrecanase from the ADAMTS Family. J. Biol. Chem. 274, 23443-23450.

Bendele, A., 2001. Animal models of rheumatoid arthritis. J. Musculoskelet. Neuronal Interact. 1, 377-385.

Botter, S. M., Glasson, S. S., Hopkins, B., Clockaerts, S., Weinans, H., van Leeuwen, J. P. T. M., van Osch, G. J. V. M., 2009. ADAMTS5-/- mice have less subchondral bone changes after induction of osteoarthritis through surgical instability: implications for a link between cartilage and subchondral bone changes. Osteoarthritis Cartilage 17, 636-645. doi:10.1016/j.joca.2008.09.018

Bundgaard, H., 1985. Design of prodrugs. Elsevier.

Chiusaroli, R., Visintin, M., Caselli, G., Rovati, L. C., 2013. Anti-Adamts-5 Antibody, Derivatives and Uses Thereof. WO2013153189 (A1).

Chockalingam, P. S., Sun, W., Rivera-Bermudez, M. A., Zeng, W., Dufield, D. R., Larsson, S., Lohmander, L. S., Flannery, C. R., Glasson, S. S., Georgiadis, K. E., Morris, E. A., 2011. Elevated aggrecanase activity in a rat model of joint injury is attenuated by an aggrecanase specific inhibitor. Osteoarthritis Cartilage 19, 315-323. doi: 10.1016/j.joca.2010.12.004

Clegg, D. O., Reda, D. J., Harris, C. L., Klein, M. A., O'Dell, J. R., Hooper, M. M., Bradley, J. D., Bingham, C. O., Weisman, M. H., Jackson, C. G., Lane, N. E., Cush, J. J., Moreland, L. W., Schumacher, H. R., Oddis, C. V., Wolfe, F., Molitor, J. A., Yocum, D. E., Schnitzer, T. J., Furst, D. E., Sawitzke, A. D., Shi, H., Brandt, K. D., Moskowitz, R. W., Williams, H. J., 2006. Glucosamine, Chondroitin Sulfate, and the Two in Combination for Painful Knee Osteoarthritis. N. Engl. J. Med. 354, 795-808. doi: 10.1056/NEJMoa052771

Dufour, A., Overall, C. M., 2013. Missing the target: matrix metalloproteinase antitargets in inflammation and cancer. Trends Pharmacol. Sci. 34, 233-242. doi:10.1016/j.tips.2013.02.004

Durocher, Y., Perret, S., Kamen, A., 2002. High-level and high-throughput recombinant protein production by transient transfection of suspension-growing human 293-EBNA1 cells. Nucleic Acids Res. 30, e9.

Georgiadis, D., Yiotakis, A., 2008. Specific targeting of metzincin family members with small-molecule inhibitors: Progress toward a multifarious challenge. Bioorg. Med. Chem. 16, 8781-8794. doi:10.1016/j.bmc.2008.08.058

Glasson, S. S., Askew, R., Sheppard, B., Carito, B., Blanchet, T., Ma, H.-L., Flannery, C. R., Peluso, D., Kanki, K., Yang, Z., Majumdar, M. K., Morris, E. A., 2005. Deletion of active ADAMTS5 prevents cartilage degradation in a murine model of osteoarthritis. Nature 434, 644-648. doi:10.1038/nature03369

Janusz, M. J., Bendele, A. M., Brown, K. K., Taiwo, Y. O., Hsieh, L., Heitmeyer, S. A., 2002. Induction of osteoarthritis in the rat by surgical tear of the meniscus: Inhibition of joint damage by a matrix metalloproteinase inhibitor. Osteoarthritis Cartilage 10, 785-791. doi:10.1053/joca.2002.0823

Jorgenson, E., Makki, N., Shen, L., Chen, D. C., Tian, C., Eckalbar, W. L., Hinds, D., Ahituv, N., Avins, A., 2015. A genome-wide association study identifies four novel susceptibility loci underlying inguinal hernia. Nat. Commun. 6. doi: 10.1038/ncomms 10130

Kato, I., Higashimoto, M., Tamura, O., Ishibashi, H., 2003. Total Synthesis of Mappicine Ketone (Nothapodytine B) by Means of Sulfur-Directed 5-exo-Selective Aryl Radical Cyclization onto Enamides. J. Org. Chem. 68, 7983-7989. doi:10.1021/jo030177m Larsson, S., Lohmander, L. S., Struglics, A., 2014. An ARGS-aggrecan assay for analysis in blood and synovial fluid. Osteoarthritis Cartilage 22, 242-249. doi:10.1016/j.joca.2013.12.010

Little, C. B., Meeker, C. T., Golub, S. B., Lawlor, K. E., Farmer, P. J., Smith, S. M., Fosang, A. J., 2007. Blocking aggrecanase cleavage in the aggrecan interglobular domain abrogates cartilage erosion and promotes cartilage repair. J. Clin. Invest. 117, 1627-1636. doi:10.1172/JCI30765

Loignon, M., Perret, S., Kelly, J., Boulais, D., Cass, B., Bisson, L., Afkhamizarreh, F., Durocher, Y., 2008. Stable high volumetric production of glycosylated human recombinant IFNalpha2b in HEK293 cells. BMC Biotechnol. 8, 65. doi:10.1186/1472-6750-8-65

Malfait, A. M., Ritchie, J., Gil, A. S., Austin, J.-S., Hartke, J., Qin, W., Tortorella, M. D., Mogil, J. S., 2010. ADAMTS-5 deficient mice do not develop mechanical allodynia associated with osteoarthritis following medial meniscal destabilization. Osteoarthritis Cartilage 18, 572-580. doi:10.1016/j.joca.2009.11.013

Mobasheri, A., 2013. The Future of Osteoarthritis Therapeutics: Targeted Pharmacological Therapy. Curr. Rheumatol. Rep. 15. doi:10.1007/s11926-013-0364-9

Pond, M. J., Nuki, G., 1973. Experimentally-induced osteoarthritis in the dog. Ann. Rheum. Dis. 32, 387-388.

Pritzker, K. P. H., Gay, S., Jimenez, S. A., Ostergaard, K., Pelletier, J.-P., Revell, P. A., Salter, D., van den Berg, W. B., 2006. Osteoarthritis cartilage histopathology: grading and staging. Osteoarthritis Cartilage 14, 13-29. doi: 10.1016/j.joca.2005.07.014

Shi, C., Shin, Y.-O., Hanson, J., Cass, B., Loewen, M. C., Durocher, Y., 2005. Purification and Characterization of a Recombinant G-Protein-Coupled Receptor, *Saccharomyces cerevisiae* Ste2p, Transiently Expressed in HEK293 EBNA1 Cells. Biochemistry (Mosc.) 44, 15705-15714. doi:10.1021/bi051292p Shin, Y.-J., Jeon, Y. J., Jung, N., Park, J.-W., Park, H.-Y., Jung, S.-C., 2015. Substrate-specific gene expression profiles in different kidney cell types are associated with Fabry disease. Mol. Med. Rep. 12, 5049-5057. doi:10.3892/mmr.2015.4010

Shiomi, T., Lemaitre, V., D'Armiento, J., Okada, Y., 2010. Matrix metalloproteinases, a disintegrin and metalloproteinases, and a disintegrin and metalloproteinases with thrombospondin motifs in non-neoplastic diseases. Pathol. Int. 60, 477-496. doi:10.1111/j.1440-1827.2010.02547.x Stanton, H., Golub, S. B., Rogerson, F. M., Last, K., Little, C. B., Fosang, A. J., 2011. Investigating ADAMTS-mediated aggrecanolysis in mouse cartilage. Nat. Protoc. 6, 388-404. doi:10.1038/nprot.2010.179

Stanton, H., Rogerson, F. M., East, C. J., Golub, S. B., Lawlor, K. E., Meeker, C. T., Little, C. B., Last, K., Farmer, P. J., Campbell, I. K., Fourie, A. M., Fosang, A. J., 2005. ADAMTS5 is the major aggrecanase in mouse cartilage in vivo and in vitro. Nature 434, 648-652. doi:10.1038/nature03417

Tortorella, M. D., Malfait, A. M., 2008. Will the real aggrecanase(s) step up: evaluating the criteria that define aggrecanase activity in osteoarthritis. Curr. Pharm. Biotechnol. 9, 16-23.

Wieland, H. A., Michaelis, M., Kirschbaum, B. J., Rudolphi, K. A., 2005. Osteoarthritis—an untreatable disease? Nat. Rev. Drug Discov. 4, 331-344. doi:10.1038/nrd1693

The invention claimed is:
1. A compound according to Formula I:

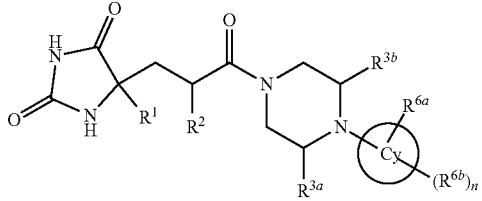

Wherein
R¹ is:
H,
$C_{1-4}$ alkyl optionally substituted with one or more independently selected $R^4$ groups,
$C_{3-7}$ monocyclic cycloalkyl optionally substituted with one or more independently selected $R^4$ groups,
4-7 membered monocyclic heterocycloalkyl comprising 1 to 2 heteroatoms independently selected from N, O, and S, optionally substituted with one or more independently selected $C_{1-4}$ alkyl, —C(=O)$C_{1-4}$ alkyl, or —C(=O)O$C_{1-4}$ alkyl,
phenyl optionally substituted with one or more independently selected $R^5$ groups,
phenyl fused to a 5-6 membered monocyclic heterocycloalkyl comprising 1, 2 or 3 heteroatoms independently selected from N, O, and S, which heterocycloalkyl is optionally substituted with one or more =O,
5-6 membered monocyclic heteroaryl comprising 1 or 2 heteroatoms independently selected from N, O, and S, optionally substituted with one or more independently selected $R^5$ groups;
R² is independently selected from:
H,
OH,
$C_{1-4}$ alkoxy, and
$C_{1-4}$ alkyl optionally substituted with one
OH,
—CN,
$C_{1-4}$ alkoxy optionally substituted with one phenyl, and
5-6 membered monocyclic heteroaryl comprising 1 or 2 heteroatoms independently selected from N, O, and S, optionally substituted with one or more independently selected $C_{1-4}$ alkyl;
each $R^{3a}$, and $R^{3b}$ is independently selected from H, and $C_{1-4}$ alkyl optionally substituted with one or more halo;
Cy is
6-10 membered monocyclic or fused bicyclic aryl,
5-10 membered monocyclic or fused bicyclic heteroaryl comprising 1, 2 or 3 heteroatoms independently selected from N, O, and S;
$R^4$ is
halo,
OH,
—CN,
$C_{1-4}$ alkyl,
$C_{1-4}$ alkoxy optionally substituted with one $C_{1-4}$ alkoxy, or phenyl,
$C_{1-4}$ thioalkoxy,
4-7-membered monocyclic heterocycloalkyl comprising one or more heteroatoms independently selected from N, S, and O, optionally substituted with one or more halo, or —C(=O)O$C_{1-4}$ alkyl,
phenyl,
—S(=O)₂$C_{1-4}$alkyl
—C(=O)O$R^{7a}$
—C(=O)N$R^{7b}R^{7c}$
—NHC(=O)O$R^{7d}$
—NHC(=O)$R^{7e}$
—N$R^{8a}R^{8b}$;
each $R^5$ is
halo,
OH,
—CN,
$C_{1-4}$ alkyl optionally substituted with one or more independently selected halo, —N$R^{9a}R^{9b}$, or —C(=O)N$R^{9c}R^{9d}$,
$C_{1-4}$ alkoxy optionally substituted with —N$R^{9e}R^{9f}$, or —S(=O)₂$C_{1-4}$ alkyl;
each $R^{6a}$ is
$C_{1-4}$ alkoxy optionally substituted with one or more halo,
the subscript n is 0, 1, 2 or 3
each $R^{6b}$ is independently selected from
halo,
—CN,
—NO₂,
—$C_{1-4}$alkyl,
—$C_{1-4}$alkoxy
5-10 membered monocyclic or fused bicyclic heteroaryl comprising 1, 2 or 3 heteroatoms independently selected from N, O, and S, optionally substituted with one or more independently selected halo, $C_{1-4}$ alkyl, or $C_{1-4}$ alkoxy, and
—N$R^{9g}R^{9h}$;
each $R^{7a}$, $R^{7b}$, $R^{7c}$, $R^{7d}$, or $R^{7e}$, is H, or $C_{1-4}$ alkyl optionally substituted with OH or $C_{1-4}$ alkoxy;
each $R^{8a}$, or $R^{8b}$ is independently selected from H, and $C_{1-4}$ alkyl optionally substituted with OH, $C_{1-4}$ alkoxy, or phenyl;
each $R^{9a}$, $R^{9b}$, $R^{9c}$, $R^{9d}$, $R^{9e}$, $R^{9f}$, $R^{9g}$, $R^{9h}$ is independently selected from H, and $C_{1-4}$ alkyl;
or a pharmaceutically acceptable salt, or a solvate, or a pharmaceutically acceptable salt of a solvate thereof;
provided that when R¹, R², $R^{3a}$ and $R^{3b}$ are H, Cy is phenyl and $R^{6a}$ is —OCH₃, then the subscript n is not 0, and the compound is not (5R)-5-[3-[(3S)-4-(4-chloro-3-methoxy-5-methyl-phenyl)-3-methyl-piperazin-1-yl]-3-oxo-propyl]-5-methyl-imidazolidine-2,4-dione.

2. A compound of pharmaceutically acceptable salt thereof according to claim 1, wherein R¹ is H, $C_{1-4}$ alkyl substituted with one $C_{1-4}$ alkoxy, or $C_{3-7}$ monocyclic cycloalkyl.

3. A compound of pharmaceutically acceptable salt thereof according to claim 1, wherein R² is H, or $C_{1-4}$ alkyl.

4. A compound of pharmaceutically acceptable salt thereof according to claim 1, wherein $R^{3a}$ is H.

5. A compound of pharmaceutically acceptable salt thereof according to claim 1, wherein $R^{3b}$ is $C_{1-4}$ alkyl.

6. A compound of pharmaceutically acceptable salt thereof according to claim 1, wherein the compound is according to Formula Va, Vb, Vc, or Vd:

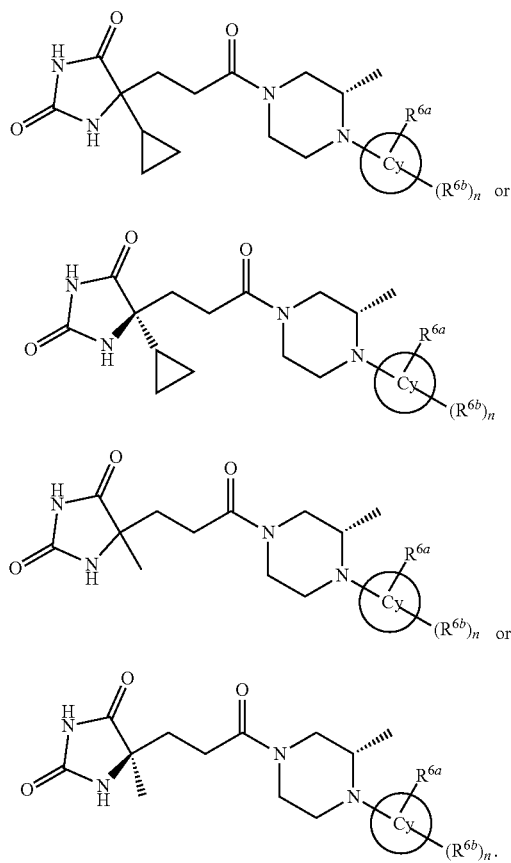

7. A compound of pharmaceutically acceptable salt thereof according to claim 1, wherein Cy is phenyl.

8. A compound of pharmaceutically acceptable salt thereof according to claim 1, wherein $R^{6a}$ is —OCH$_3$ or —OCH$_2$CH$_3$, each of which is optionally substituted with one or more F.

9. A compound of pharmaceutically acceptable salt thereof according to claim 1, wherein the subscript n is 0.

10. A compound of pharmaceutically acceptable salt thereof according to claim 1, wherein the subscript n is 1 or 2.

11. A compound of pharmaceutically acceptable salt thereof according to claim 10, wherein $R^{6b}$ is halo, $C_{1-4}$ alkyl, or $C_{1-4}$ alkoxy.

12. A compound or pharmaceutically acceptable salt thereof according to claim 1, wherein the compound is:
- 5-[3-[4-(3-methoxyphenyl)piperazin-1-yl]-3-oxo-propyl]-5-methyl-imidazolidine-2,4-dione,
- 5-cyclopropyl-5-[3-[4-(3-methoxyphenyl)piperazin-1-yl]-3-oxo-propyl]imidazolidine-2,4-dione,
- 5-methyl-5-[3-oxo-3-[4-[4-(trifluoromethoxy)phenyl]piperazin-1-yl]propyl]imidazolidine-2,4-dione,
- 5-methyl-5-[3-oxo-3-[4-[2-(trifluoromethoxy)phenyl]piperazin-1-yl]propyl]imidazolidine-2,4-dione,
- 5-[3-[4-(4-methoxyphenyl)piperazin-1-yl]-3-oxo-propyl]-5-methyl-imidazolidine-2,4-dione,
- 5-[3-[4-(3-methoxyphenyl)piperazin-1-yl]-3-oxo-propyl]-5-(3-pyridyl)imidazolidine-2,4-dione,
- 5-[3-[4-(2-methoxyphenyl)piperazin-1-yl]-3-oxo-propyl]-5-methyl-imidazolidine-2,4-dione,
- 5-[3-[4-(3-methoxyphenyl)piperazin-1-yl]-3-oxo-propyl]-5-(2-pyridyl)imidazolidine-2,4-dione,
- 5-[3-[4-(4-fluoro-3-methoxy-phenyl)piperazin-1-yl]-3-oxo-propyl]-5-methyl-imidazolidine-2,4-dione,
- 5-[3-[4-(4-chloro-3-methoxy-phenyl)piperazin-1-yl]-3-oxo-propyl]-5-methyl-imidazolidine-2,4-dione,
- 5-[3-[4-(3,5-dimethoxyphenyl)piperazin-1-yl]-3-oxo-propyl]-5-methyl-imidazolidine-2,4-dione,
- 5-[3-[4-(3-fluoro-5-methoxy-phenyl)piperazin-1-yl]-3-oxo-propyl]-5-methyl-imidazolidine-2,4-dione,
- 5-[3-[4-(3-chloro-5-methoxy-phenyl)piperazin-1-yl]-3-oxo-propyl]-5-methyl-imidazolidine-2,4-dione,
- 5-[3-[4-(3,4-difluoro-5-methoxy-phenyl)piperazin-1-yl]-3-oxo-propyl]-5-methyl-imidazolidine-2,4-dione,
- 5-cyclopropyl-5-[3-[4-(3-fluoro-5-methoxy-phenyl)piperazin-1-yl]-3-oxo-propyl]imidazolidine-2,4-dione,
- 5-[3-[4-(3-ethoxyphenyl)piperazin-1-yl]-3-oxo-propyl]-5-methyl-imidazolidine-2,4-dione,
- 5-cyclopropyl-5-[3-[4-(4-fluoro-3-methoxy-phenyl)piperazin-1-yl]-3-oxo-propyl]imidazolidine-2,4-dione,
- 5-cyclopropyl-5-[3-[4-(3,4-difluoro-5-methoxy-phenyl)piperazin-1-yl]-3-oxo-propyl]imidazolidine-2,4-dione,
- (R)-5-[3-[4-(3-fluoro-5-methoxy-phenyl)piperazin-1-yl]-3-oxo-propyl]-5-methyl-imidazolidine-2,4-dione,
- (R)-5-[3-[4-(3,4-difluoro-5-methoxy-phenyl)piperazin-1-yl]-3-oxo-propyl]-5-methyl-imidazolidine-2,4-dione,
- 5-cyclopropyl-5-[3-[(3S)-4-(3,4-difluoro-5-methoxy-phenyl)-3-methyl-piperazin-1-yl]-3-oxo-propyl]imidazolidine-2,4-dione,
- 5-[3-[(3S)-4-(3,4-difluoro-5-methoxy-phenyl)-3-methyl-piperazin-1-yl]-3-oxo-propyl]-5-methyl-imidazolidine-2,4-dione,
- 5-[3-[4-(3-fluoro-5-methoxy-phenyl)piperazin-1-yl]-3-oxo-propyl]-5-(3-pyridyl)imidazolidine-2,4-dione,
- 5-[3-[(3S)-4-(4-chloro-3-methoxy-phenyl)-3-methyl-piperazin-1-yl]-3-oxo-propyl]-5-methyl-imidazolidine-2,4-dione,
- 5-[3-[(3S)-4-(3,5-dimethoxyphenyl)-3-methyl-piperazin-1-yl]-3-oxo-propyl]-5-methyl-imidazolidine-2,4-dione,
- (5S)-5-cyclopropyl-5-[(2S)-3-[4-(3-fluoro-5-methoxy-phenyl)piperazin-1-yl]-2-methyl-3-oxo-propyl]imidazolidine-2,4-dione,
- (5R)-5-[(2S)-3-[4-(3-fluoro-5-methoxy-phenyl)piperazin-1-yl]-2-methyl-3-oxo-propyl]-5-methyl-imidazolidine-2,4-dione,
- 5-[3-[4-(3,4-difluoro-5-methoxy-phenyl)piperazin-1-yl]-3-oxo-propyl]-5-(3-pyridyl)imidazolidine-2,4-dione,
- 5-cyclopropyl-5-[(2S)-3-[(3S)-4-(3,4-difluoro-5-methoxy-phenyl)-3-methyl-piperazin-1-yl]-2-methyl-3-oxo-propyl]imidazolidine-2,4-dione,
- 5-[3-[(3S)-4-(4-chloro-3,5-dimethoxy-phenyl)-3-methyl-piperazin-1-yl]-3-oxo-propyl]-5-methyl-imidazolidine-2,4-dione,
- 5-[3-[4-(4-chloro-3,5-dimethoxy-phenyl)piperazin-1-yl]-3-oxo-propyl]-5-methyl-imidazolidine-2,4-dione,
- 5-[3-[4-(5-methoxy-2-methyl-phenyl)piperazin-1-yl]-3-oxo-propyl]-5-methyl-imidazolidine-2,4-dione,
- 5-[3-[4-(3-methoxy-2-methyl-phenyl)piperazin-1-yl]-3-oxo-propyl]-5-methyl-imidazolidine-2,4-dione,
- 5-[3-[4-(4-chloro-5-methoxy-2-methyl-phenyl)piperazin-1-yl]-3-oxo-propyl]-5-methyl-imidazolidine-2,4-dione,
- 5-[3-[(3S)-4-(5-methoxy-2-methyl-phenyl)-3-methyl-piperazin-1-yl]-3-oxo-propyl]-5-methyl-imidazolidine-2,4-dione, 5-[3-[(3S)-4-(4-chloro-5-methoxy-2-methyl-phenyl)-3-methyl-piperazin-1-yl]-3-oxo-propyl]-5-methyl-imidazolidine-2,4-dione, (5S)-5-cyclopropyl-5-[3-[(3S)-4-(3,4-difluoro-5-methoxy-phenyl)-3-methyl-piperazin-1-yl]-3-oxo-propyl]imidazolidine-2,4-dione, 5-[3-[4-(4-chloro-3-fluoro-5-methoxy-phenyl)piperazin-1-yl]-3-oxo-propyl]-5-methyl-imidazolidine-2,4-dione, 5-[3-[(3S)-4-(4-chloro-3-fluoro-5-methoxy-phenyl)-3-methyl-piperazin-1-yl]-3-oxo-propyl]-5-methyl-imidazolidine-2,4-dione, 5-[3-[4-(4-chloro-3,5-dimethoxy-phenyl)piperazin-1-yl]-2-methyl-3-oxo-propyl]-5-methyl-imidazolidine-2,4-dione, 5-[3-[4-(4-chloro-3-methoxy-phenyl)-3-methyl-piperazin-1-yl]-2-methyl-3-oxo-propyl]-5-methyl-imidazolidine-2,4-dione, 5-[3-[(3S)-4-(3,4-difluoro-5-methoxy-phenyl)-3-methyl-piperazin-1-yl]-2-methyl-3-oxo-propyl]-5-methyl-imidazolidine-2,4-dione, 5-[3-[4-(3,4-difluoro-5-methoxy-phenyl)piperazin-1-yl]-2-methyl-3-oxo-propyl]-5-methyl-imidazolidine-2,4-dione, 5-[3-[(3S)-4-(4-chloro-3,5-dimethoxy-phenyl)-3-methyl-piperazin-1-yl]-2-methyl-3-oxo-propyl]-5-methyl-imidazolidine-2,4-dione, 5-[3-[(3S)-4-(4-chloro-5-methoxy-2-methyl-phenyl)-3-methyl-piperazin-1-yl]-2-methyl-3-oxo-propyl]-5-methyl-imidazolidine-2,4-dione, 5-[3-[(3S)-4-(3,4-difluoro-5-methoxy-phenyl)-3-methyl-piperazin-1-yl]-2-methyl-3-oxo-propyl]-5-(methoxymethyl)imidazolidine-2,4-dione, 5-[3-[(3S)-4-(4-chloro-3-methoxy-phenyl)-3-methyl-piperazin-1-yl]-2-methyl-3-oxo-propyl]-5-(methoxymethyl)imidazolidine-2,4-dione, 5-[3-[4-(3,4-dichloro-5-methoxy-phenyl)piperazin-1-yl]-3-oxo-propyl]-5-methyl-imidazolidine-2,4-dione, 5-[3-[(3S)-4-(3,4-difluoro-5-methoxy-phenyl)-3-methyl-piperazin-1-yl]-2-methyl-3-oxo-propyl]-5-(2-pyridyl)imidazolidine-2,4-dione, 5-[3-[4-(3-chloro-4-fluoro-5-methoxy-phenyl)piperazin-1-yl]-3-oxo-propyl]-5-methyl-imidazolidine-2,4-dione, 5-[3-[4-(3,4-difluoro-5-methoxy-phenyl)piperazin-1-yl]-2-methyl-3-oxo-propyl]imidazolidine-2,4-dione, 5-[3-[4-(3,4-difluoro-5-methoxy-phenyl)piperazin-1-yl]-2-methyl-3-oxo-propyl]-5-[(3,3-difluoropyrrolidin-1-yl)methyl]imidazolidine-2,4-dione, 5-[3-[(3S)-4-(3-chloro-4-fluoro-5-methoxy-phenyl)-3-methyl-piperazin-1-yl]-3-oxo-propyl]-5-methyl-imidazolidine-2,4-dione, (5S)-5-[(2S)-3-[4-(3,4-difluoro-5-methoxy-phenyl)piperazin-1-yl]-2-methyl-3-oxo-propyl]-5-(2-pyridyl)imidazolidine-2,4-dione, (5R)-5-[3-[(3S)-4-(4-chloro-3-methoxy-phenyl)-3-methyl-piperazin-1-yl]-3-oxo-propyl]-5-methyl-imidazolidine-2,4-dione, (5R)-5-[(2R)-3-[4-(3,4-difluoro-5-methoxy-phenyl)piperazin-1-yl]-2-(hydroxymethyl)-3-oxo-propyl]-5-methyl-imidazolidine-2,4-dione, (5R)-5-[(2S)-3-[4-(3,4-difluoro-5-methoxy-phenyl)piperazin-1-yl]-2-methyl-3-oxo-propyl]-5-ethyl-imidazolidine-2,4-dione, 5-[3-[4-(4-chloro-2-methoxy-5-methyl-phenyl)piperazin-1-yl]-3-oxo-propyl]-5-methyl-imidazolidine-2,4-dione, (5S)-5-[(2S)-3-[4-(3,4-difluoro-5-methoxy-phenyl)piperazin-1-yl]-2-methyl-3-oxo-propyl]-5-(methoxymethyl)imidazolidine-2,4-dione, 5-cyclopropyl-5-[3-[(3S)-4-(5-methoxy-3-pyridyl)-3-methyl-piperazin-1-yl]-3-oxo-propyl]imidazolidine-2,4-dione, 5-[3-[(3S)-4-(3,4-difluoro-5-methoxy-phenyl)-3-methyl-piperazin-1-yl]-3-oxo-propyl]-5-(6-methyl-2-pyridyl)imidazolidine-2,4-dione, (5S)-5-[3-[(3S)-4-(3-chloro-4-fluoro-5-methoxy-phenyl)-3-methyl-piperazin-1-yl]-3-oxo-propyl]-5-cyclopropyl-imidazolidine-2,4-dione, (5R)-5-[3-[(3S)-4-(3-chloro-4-fluoro-5-methoxy-phenyl)-3-methyl-piperazin-1-yl]-3-oxo-propyl]-5-methyl-imidazolidine-2,4-dione, 5-cyclopropyl-5-[3-[(3S)-4-(5-methoxy-3-pyridyl)-3-methyl-piperazin-1-yl]-2-methyl-3-oxo-propyl]imidazolidine-2,4-dione, (5S)-5-[3-[(3S)-4-(4-chloro-3-fluoro-5-methoxy-phenyl)-3-methyl-piperazin-1-yl]-3-oxo-propyl]-5-cyclopropyl-imidazolidine-2,4-dione, (5R)-5-[3-[(3S)-4-(4-fluoro-5-methoxy-2-methyl-phenyl)-3-methyl-piperazin-1-yl]-3-oxo-propyl]-5-methyl-imidazolidine-2,4-dione, (5R)-5-[3-[4-(4-fluoro-5-methoxy-2-methyl-phenyl)piperazin-1-yl]-3-oxo-propyl]-5-methyl-imidazolidine-2,4-dione, (5R)-5-[3-[4-(3-chloro-2-methoxy-phenyl)piperazin-1-yl]-3-oxo-propyl]-5-methyl-imidazolidine-2,4-dione, (5R)-5-[3-[(3S)-4-(3-chloro-2-methoxy-phenyl)-3-methyl-piperazin-1-yl]-3-oxo-propyl]-5-methyl-imidazolidine-2,4-dione, (5R)-5-[3-[4-(4-chloro-2-methoxy-phenyl)piperazin-1-yl]-3-oxo-propyl]-5-methyl-imidazolidine-2,4-dione, (5R)-5-[3-[4-(4-fluoro-3,5-dimethoxy-phenyl)piperazin-1-yl]-3-oxo-propyl]-5-methyl-imidazolidine-2,4-dione, (5R)-5-[3-[(3S)-4-(4-chloro-2-methoxy-phenyl)-3-methyl-piperazin-1-yl]-3-oxo-propyl]-5-methyl-imidazolidine-2,4-dione, (5R)-5-[3-[4-(5-chloro-2-methoxy-phenyl)piperazin-1-yl]-3-oxo-propyl]-5-methyl-imidazolidine-2,4-dione, (5R)-5-[3-[4-(4-fluoro-2-methoxy-phenyl)piperazin-1-yl]-3-oxo-propyl]-5-methyl-imidazolidine-2,4-dione, (5R)-5-[3-[4-(4-chloro-3-ethoxy-5-methoxy-phenyl)piperazin-1-yl]-3-oxo-propyl]-5-methyl-imidazolidine-2,4-dione, (5R)-5-[3-[(3S)-4-(4-chloro-3-ethoxy-5-methoxy-phenyl)-3-methyl-piperazin-1-yl]-3-oxo-propyl]-5-methyl-imidazolidine-2,4-dione, (5R)-5-[3-[(3S)-4-(4-fluoro-2-methoxy-phenyl)-3-methyl-piperazin-1-yl]-3-oxo-propyl]-5-methyl-imidazolidine-2,4-dione, (5R)-5-[3-[4-(3-fluoro-2-methoxy-phenyl)piperazin-1-yl]-3-oxo-propyl]-5-methyl-imidazolidine-2,4-dione, (5R)-5-[3-[4-(5-fluoro-2-methoxy-phenyl)piperazin-1-yl]-3-oxo-propyl]-5-methyl-imidazolidine-2,4-dione, (5R)-5-[3-[(3S)-4-(3-fluoro-2-methoxy-phenyl)-3-methyl-piperazin-1-yl]-3-oxo-propyl]-5-methyl-imidazolidine-2,4-dione, (5R)-5-[3-[(3S)-4-[4-chloro-3-(trifluoromethoxy)phenyl]-3-methyl-piperazin-1-yl]-3-oxo-propyl]-5-methyl-imidazolidine-2,4-dione, (5R)-5-[3-[4-[4-chloro-3-(trifluoromethoxy)phenyl]piperazin-1-yl]-3-oxo-propyl]-5-methyl-imidazolidine-2,4-dione, (5R)-5-[3-[(3S)-4-(4-fluoro-3,5-dimethoxy-phenyl)-3-methyl-piperazin-1-yl]-3-oxo-propyl]-5-methyl-imidazolidine-2,4-dione,
(5R)-5-[3-[(3S)-4-(3,4-dichloro-5-methoxy-phenyl)-3-methyl-piperazin-1-yl]-3-oxo-propyl]-5-methyl-imidazolidine-2,4-dione,
(5R)-5-[3-[(3S)-4-(5-chloro-2-methoxy-phenyl)-3-methyl-piperazin-1-yl]-3-oxo-propyl]-5-methyl-imidazolidine-2,4-dione,
(5R)-5-[3-[(3S)-4-(4,5-dichloro-2-methoxy-phenyl)-3-methyl-piperazin-1-yl]-3-oxo-propyl]-5-methyl-imidazolidine-2,4-dione,
(5R)-5-[3-[(3S)-4-(4-fluoro-3-methoxy-phenyl)-3-methyl-piperazin-1-yl]-3-oxo-propyl]-5-methyl-imidazolidine-2,4-dione,
(5R)-5-[3-[4-(4,5-dichloro-2-methoxy-phenyl)piperazin-1-yl]-3-oxo-propyl]-5-methyl-imidazolidine-2,4-dione,
(5R)-5-[3-[(3S)-4-(4-chloro-2-methoxy-5-methyl-phenyl)-3-methyl-piperazin-1-yl]-3-oxo-propyl]-5-methyl-imidazolidine-2,4-dione,
(5R)-5-[3-[(3S)-4-(3-chloro-5-methoxy-phenyl)-3-methyl-piperazin-1-yl]-3-oxo-propyl]-5-methyl-imidazolidine-2,4-dione,
(5R)-5-[3-[4-(4-chloro-2,5-dimethoxy-phenyl)piperazin-1-yl]-3-oxo-propyl]-5-methyl-imidazolidine-2,4-dione,
(5R)-5-[3-[(3S)-4-[4-chloro-3-(dimethylamino)-5-methoxy-phenyl]-3-methyl-piperazin-1-yl]-3-oxo-propyl]-5-methyl-imidazolidine-2,4-dione,
5-[3-[(3S)-4-[4-chloro-3-(trifluoromethoxy)phenyl]-3-methyl-piperazin-1-yl]-3-oxo-propyl]-5-(6-methyl-2-pyridyl)imidazolidine-2,4-dione,
(5R)-5-[3-[4-(4-chloro-5-ethyl-2-methoxy-phenyl)piperazin-1-yl]-3-oxo-propyl]-5-methyl-imidazolidine-2,4-dione,
(5R)-5-[3-[(3S)-4-(4-chloro-5-ethyl-2-methoxy-phenyl)-3-methyl-piperazin-1-yl]-3-oxo-propyl]-5-methyl-imidazolidine-2,4-dione,
(5R)-5-[3-[(3S)-4-(4-chloro-2,5-dimethoxy-phenyl)-3-methyl-piperazin-1-yl]-3-oxo-propyl]-5-methyl-imidazolidine-2,4-dione,
(5R)-5-[3-[(3S)-4-(4-chloro-3-methoxy-5-methyl-phenyl)-3-methyl-piperazin-1-yl]-3-oxo-propyl]-5-methyl-imidazolidine-2,4-dione,
(5R)-5-[3-[(3S)-4-(4-chloro-3-ethyl-5-methoxy-phenyl)-3-methyl-piperazin-1-yl]-3-oxo-propyl]-5-methyl-imidazolidine-2,4-dione,
(5R)-5-[3-[(3S)-4-(4-chloro-3-methoxy-phenyl)-3-ethyl-piperazin-1-yl]-3-oxo-propyl]-5-methyl-imidazolidine-2,4-dione,
(5R)-5-[3-[(3S)-4-[5-methoxy-2-(trifluoromethoxy)phenyl]-3-methyl-piperazin-1-yl]-3-oxo-propyl]-5-methyl-imidazolidine-2,4-dione,
(5R)-5-[3-[(3S)-4-(4-chloro-3-methoxy-phenyl)-3-isopropyl-piperazin-1-yl]-3-oxo-propyl]-5-methyl-imidazolidine-2,4-dione,
(5R)-5-[3-[(3S)-4-(4-chloro-3,5-dimethoxy-phenyl)-3-methyl-piperazin-1-yl]-3-oxo-propyl]-5-methyl-imidazolidine-2,4-dione,
(5R)-5-[3-[(3S)-4-(4-chloro-3-ethoxy-phenyl)-3-methyl-piperazin-1-yl]-3-oxo-propyl]-5-methyl-imidazolidine-2,4-dione,
(5R)-5-[3-[4-(4-chloro-3-methoxy-5-methyl-phenyl)piperazin-1-yl]-3-oxo-propyl]-5-methyl-imidazolidine-2,4-dione,
(5R)-5-[3-[(3S)-4-(4,5-difluoro-2-methoxy-phenyl)-3-methyl-piperazin-1-yl]-3-oxo-propyl]-5-methyl-imidazolidine-2,4-dione,
(5R)-5-[3-[4-(4-chloro-3-ethyl-5-methoxy-phenyl)piperazin-1-yl]-3-oxo-propyl]-5-methyl-imidazolidine-2,4-dione,
5-[3-[(3S)-4-(4-chloro-3-ethyl-5-methoxy-phenyl)-3-methyl-piperazin-1-yl]-2-methyl-3-oxo-propyl]-5-(methoxymethyl)imidazolidine-2,4-dione,
(5R)-5-[3-[4-(4-chloro-3-methoxy-phenyl)-3-(trifluoromethyl)piperazin-1-yl]-3-oxo-propyl]-5-methyl-imidazolidine-2,4-dione,
(5R)-5-[3-[(3S)-4-(4-chloro-3-fluoro-5-methoxy-phenyl)-3-methyl-piperazin-1-yl]-3-oxo-propyl]-5-methyl-imidazolidine-2,4-dione,
5-[3-[(3S)-4-(4-chloro-3-fluoro-5-methoxy-phenyl)-3-methyl-piperazin-1-yl]-2-methyl-3-oxo-propyl]-5-methyl-imidazolidine-2,4-dione,
5-[3-[(3S)-4-(4-chloro-3-fluoro-5-methoxy-phenyl)-3-methyl-piperazin-1-yl]-2-methyl-3-oxo-propyl]-5-(methoxymethyl)imidazolidine-2,4-dione,
(5R)-5-[(2S)-3-[4-(4-chloro-3-fluoro-5-methoxy-phenyl)piperazin-1-yl]-2-methyl-3-oxo-propyl]-5-methyl-imidazolidine-2,4-dione,
(5S)-5-[(2S)-3-[4-(4-chloro-3-fluoro-5-methoxy-phenyl)piperazin-1-yl]-2-methyl-3-oxo-propyl]-5-(methoxymethyl)imidazolidine-2,4-dione,
5-[3-[(3S)-4-(4-chloro-3-methoxy-5-methyl-phenyl)-3-methyl-piperazin-1-yl]-2-methyl-3-oxo-propyl]-5-methyl-imidazolidine-2,4-dione,
5-[3-[(3S)-4-(4-chloro-3-methoxy-5-methyl-phenyl)-3-methyl-piperazin-1-yl]-2-methyl-3-oxo-propyl]-5-(methoxymethyl)imidazolidine-2,4-dione,
(5R)-5-[3-[(3R)-4-(3,4-difluoro-5-methoxy-phenyl)-3-methyl-piperazin-1-yl]-3-oxo-propyl]imidazolidine-2,4-dione,
(5R)-5-[3-[4-(3,4-difluoro-5-methoxy-phenyl)piperazin-1-yl]-3-oxo-propyl]imidazolidine-2,4-dione,
(5R)-5-[3-[(3S)-4-(3,4-difluoro-5-methoxy-phenyl)-3-methyl-piperazin-1-yl]-3-oxo-propyl]imidazolidine-2,4-dione,
5-cyclopropyl-5-[3-[4-(3-fluoro-5-methoxy-phenyl)piperazin-1-yl]-2-methyl-3-oxo-propyl]imidazolidine-2,4-dione,
5-[3-[4-(3-fluoro-5-methoxy-phenyl)piperazin-1-yl]-2-methyl-3-oxo-propyl]-5-methyl-imidazolidine-2,4-dione,
(5R)-5-[3-[(3S)-4-(3,5-dimethoxyphenyl)-3-methyl-piperazin-1-yl]-3-oxo-propyl]imidazolidine-2,4-dione,
(5R)-5-[3-[(3S)-4-(4-chloro-3-methoxy-phenyl)-3-methyl-piperazin-1-yl]-3-oxo-propyl]imidazolidine-2,4-dione,
5-cyclopropyl-5-[3-[(3S)-4-(3,4-difluoro-5-methoxy-phenyl)-3-methyl-piperazin-1-yl]-2-methyl-3-oxo-propyl]imidazolidine-2,4-dione,
(5R)-5-[3-[4-(4-chloro-3,5-dimethoxy-phenyl)piperazin-1-yl]-3-oxo-propyl]imidazolidine-2,4-dione,
(5R)-5-[3-[4-(5-methoxy-2-methyl-phenyl)piperazin-1-yl]-3-oxo-propyl]imidazolidine-2,4-dione,
(5R)-5-[3-[4-(3-methoxy-2-methyl-phenyl)piperazin-1-yl]-3-oxo-propyl]imidazolidine-2,4-dione,
(5R)-5-[3-[4-(4-chloro-5-methoxy-2-methyl-phenyl)piperazin-1-yl]-3-oxo-propyl]imidazolidine-2,4-dione,
(5R)-5-[3-[(3S)-4-(4-chloro-3,5-dimethoxy-phenyl)-3-methyl-piperazin-1-yl]-3-oxo-propyl]imidazolidine-2,4-dione, (5R)-5-[3-[(3S)-4-(5-methoxy-2-methyl-phenyl)-3-methyl-piperazin-1-yl]-3-oxo-propyl]imidazolidine-2,4-dione,
(5R)-5-[3-[(3S)-4-(3-methoxy-2-methyl-phenyl)-3-methyl-piperazin-1-yl]-3-oxo-propyl]imidazolidine-2,4-dione,
(5R)-5-[3-[(3S)-4-(4-chloro-5-methoxy-2-methyl-phenyl)-3-methyl-piperazin-1-yl]-3-oxo-propyl]imidazolidine-2,4-dione,
(5R)-5-[3-[4-(4-chloro-3-fluoro-5-methoxy-phenyl)piperazin-1-yl]-3-oxo-propyl]imidazolidine-2,4-dione,
(5R)-5-[3-[(3S)-4-(4-chloro-3-fluoro-5-methoxy-phenyl)-3-methyl-piperazin-1-yl]-3-oxo-propyl]imidazolidine-2,4-dione,
(5R)-5-[3-[4-(3,4-dichloro-5-methoxy-phenyl)piperazin-1-yl]-3-oxo-propyl]imidazolidine-2,4-dione,
(5S)-5-[3-[(3S)-4-(4-chloro-3-methoxy-phenyl)-3-methyl-piperazin-1-yl]-3-oxo-propyl]-5-methyl-imidazolidine-2,4-dione,
(5R)-5-[3-[4-(3-chloro-4-fluoro-5-methoxy-phenyl)piperazin-1-yl]-3-oxo-propyl]imidazolidine-2,4-dione,
(5R)-5-[3-[(3S)-4-(3-chloro-4-fluoro-5-methoxy-phenyl)-3-methyl-piperazin-1-yl]-3-oxo-propyl]imidazolidine-2,4-dione,
(5R)-5-[3-[4-(4-chloro-3-ethoxy-5-methoxy-phenyl)piperazin-1-yl]-3-oxo-propyl]imidazolidine-2,4-dione,
(5R)-5-[3-[(3S)-4-(4-chloro-3-ethoxy-5-methoxy-phenyl)-3-methyl-piperazin-1-yl]-3-oxo-propyl]imidazolidine-2,4-dione, or
(5R)-5-[3-[4-(4-fluoro-3,5-dimethoxy-phenyl)piperazin-1-yl]-3-oxo-propyl]imidazolidine-2,4-dione.

13. A pharmaceutical composition comprising a compound or pharmaceutically acceptable salt thereof according to claim 1, and a pharmaceutically acceptable carrier.

14. A method of treating inflammatory diseases, and/or diseases involving degradation of cartilage and/or disruption of cartilage homeostasis in a human comprising administering an effective amount of the compound or pharmaceutically acceptable salt thereof according to claim 1, to said human.

15. A method of treating inflammatory diseases, and/or diseases involving degradation of cartilage and/or disruption of cartilage homeostasis in a human comprising administering an effective amount of the pharmaceutical composition according to claim 13, to said human.

16. A pharmaceutical composition comprising a compound or pharmaceutically acceptable salt thereof according to claim 2, and a pharmaceutically acceptable carrier.

17. A pharmaceutical composition comprising a compound or pharmaceutically acceptable salt thereof according to claim 3, and a pharmaceutically acceptable carrier.

18. A pharmaceutical composition comprising a compound or pharmaceutically acceptable salt thereof according to claim 4, and a pharmaceutically acceptable carrier.

19. A pharmaceutical composition comprising a compound or pharmaceutically acceptable salt thereof according to claim 5, and a pharmaceutically acceptable carrier.

20. A pharmaceutical composition comprising a compound or pharmaceutically acceptable salt thereof according to claim 6, and a pharmaceutically acceptable carrier.

21. A pharmaceutical composition comprising a compound or pharmaceutically acceptable salt thereof according to claim 7, and a pharmaceutically acceptable carrier.

22. A pharmaceutical composition comprising a compound or pharmaceutically acceptable salt thereof according to claim 8, and a pharmaceutically acceptable carrier.

23. A pharmaceutical composition comprising a compound or pharmaceutically acceptable salt thereof according to claim 9, and a pharmaceutically acceptable carrier.

24. A pharmaceutical composition comprising a compound or pharmaceutically acceptable salt thereof according to claim 10, and a pharmaceutically acceptable carrier.

25. A pharmaceutical composition comprising a compound or pharmaceutically acceptable salt thereof according to claim 11, and a pharmaceutically acceptable carrier.

26. A pharmaceutical composition comprising a compound or pharmaceutically acceptable salt thereof according to claim 12, and a pharmaceutically acceptable carrier.

27. A method of treating inflammatory diseases, and/or diseases involving degradation of cartilage and/or disruption of cartilage homeostasis in a human comprising administering an effective amount of the pharmaceutical composition according to claim 16, to said human.

28. A method of treating inflammatory diseases, and/or diseases involving degradation of cartilage and/or disruption of cartilage homeostasis in a human comprising administering an effective amount of the pharmaceutical composition according to claim 17, to said human.

29. A method of treating inflammatory diseases, and/or diseases involving degradation of cartilage and/or disruption of cartilage homeostasis in a human comprising administering an effective amount of the pharmaceutical composition according to claim 18, to said human.

30. A method of treating inflammatory diseases, and/or diseases involving degradation of cartilage and/or disruption of cartilage homeostasis in a human comprising administering an effective amount of the pharmaceutical composition according to claim 19, to said human.

31. A method of treating inflammatory diseases, and/or diseases involving degradation of cartilage and/or disruption of cartilage homeostasis in a human comprising administering an effective amount of the pharmaceutical composition according to claim 20, to said human.

32. A method of treating inflammatory diseases, and/or diseases involving degradation of cartilage and/or disruption of cartilage homeostasis in a human comprising administering an effective amount of the pharmaceutical composition according to claim 21, to said human.

33. A method of treating inflammatory diseases, and/or diseases involving degradation of cartilage and/or disruption of cartilage homeostasis in a human comprising administering an effective amount of the pharmaceutical composition according to claim 22, to said human.

34. A method of treating inflammatory diseases, and/or diseases involving degradation of cartilage and/or disruption of cartilage homeostasis in a human comprising administering an effective amount of the pharmaceutical composition according to claim 23, to said human.

35. A method of treating inflammatory diseases, and/or diseases involving degradation of cartilage and/or disruption of cartilage homeostasis in a human comprising administering an effective amount of the pharmaceutical composition according to claim 24, to said human.

36. A method of treating inflammatory diseases, and/or diseases involving degradation of cartilage and/or disruption of cartilage homeostasis in a human comprising administering an effective amount of the pharmaceutical composition according to claim 25, to said human.

37. A method of treating inflammatory diseases, and/or diseases involving degradation of cartilage and/or disruption of cartilage homeostasis in a human comprising administering an effective amount of the pharmaceutical composition according to claim 26, to said human.

* * * * *

SEQUENCE LISTING

```
<160> NUMBER OF SEQ ID NOS: 7

<210> SEQ ID NO 1
<211> LENGTH: 12
<212> TYPE: PRT
<213> ORGANISM: Artificial Sequence
<220> FEATURE:
<223> OTHER INFORMATION: polypeptide
<220> FEATURE:
<221> NAME/KEY: MOD_RES
<222> LOCATION: (1)..(1)
<223> OTHER INFORMATION: 5(6)-Fluorescein-NH AMIDATION
<220> FEATURE:
<221> NAME/KEY: MOD_RES
<222> LOCATION: (12)..(12)
<223> OTHER INFORMATION: 5(6)-TAMRA AMIDATION

<400> SEQUENCE: 1

Ala Glu Leu Gln Gly Arg Pro Ile Ser Ile Ala Lys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: polypeptide
<220> FEATURE:
<221> NAME/KEY: MOD_RES
<222> LOCATION: (1)..(1)
<223> OTHER INFORMATION: 5FAM
<220> FEATURE:
<221> NAME/KEY: MOD_RES
<222> LOCATION: (13)..(13)
<223> OTHER INFORMATION: (5TAMRA)

<400> SEQUENCE: 2

Thr Glu Gly Glu Ala Arg Gly Ser Val Ile Leu Leu Lys Lys
1               5                   10

<210> SEQ ID NO 3
<211> LENGTH: 11
<212> TYPE: PRT
<213> ORGANISM: Artificial Sequence
<220> FEATURE:
<223> OTHER INFORMATION: polypeptide
<220> FEATURE:
<221> NAME/KEY: MOD_RES
<222> LOCATION: (1)..(1)
<223> OTHER INFORMATION: 5 FAM AMIDATION
<220> FEATURE:
<221> NAME/KEY: MOD_RES
<222> LOCATION: (11)..(11)
<223> OTHER INFORMATION: 5 TAMRA AMIDATION
```

<400> SEQUENCE: 3

Leu Ala Gln Ala Val Arg Ser Ser Ser Arg Lys
1               5                   10

<210> SEQ ID NO 4
<211> LENGTH: 1117
<212> TYPE: PRT
<213> ORGANISM: Homo sapiens

<400> SEQUENCE: 4

Met Glu Ile Leu Trp Lys Thr Leu Thr Trp Ile Leu Ser Leu Ile Met
1               5                   10                  15

Ala Ser Ser Glu Phe His Ser Asp His Arg Leu Ser Tyr Ser Ser Gln
            20                  25                  30

Glu Glu Phe Leu Thr Tyr Leu Glu His Tyr Gln Leu Thr Ile Pro Ile
        35                  40                  45

Arg Val Asp Gln Asn Gly Ala Phe Leu Ser Phe Thr Val Lys Asn Asp
    50                  55                  60

Lys His Ser Arg Arg Arg Ser Met Asp Pro Ile Asp Pro Gln Gln
65                  70                  75                  80

Ala Val Ser Lys Leu Phe Phe Lys Leu Ser Ala Tyr Gly Lys His Phe
                85                  90                  95

His Leu Asn Leu Thr Leu Asn Thr Asp Phe Val Ser Lys His Phe Thr
            100                 105                 110

Val Glu Tyr Trp Gly Lys Asp Gly Pro Gln Trp Lys His Asp Phe Leu
        115                 120                 125

Asp Asn Cys His Tyr Thr Gly Tyr Leu Gln Asp Arg Ser Thr Thr
    130                 135                 140

Lys Val Ala Leu Ser Asn Cys Val Gly Leu His Gly Val Ile Ala Thr
145                 150                 155                 160

Glu Asp Glu Glu Tyr Phe Ile Glu Pro Leu Lys Asn Thr Thr Glu Asp
                165                 170                 175

Ser Lys His Phe Ser Tyr Glu Asn Gly His Pro His Val Ile Tyr Lys
            180                 185                 190

Lys Ser Ala Leu Gln Gln Arg His Leu Tyr Asp His Ser His Cys Gly
        195                 200                 205

Val Ser Asp Phe Thr Arg Ser Gly Lys Pro Trp Trp Leu Asn Asp Thr
    210                 215                 220

Ser Thr Val Ser Tyr Ser Leu Pro Ile Asn Asn Thr His Ile His His
225                 230                 235                 240

Arg Gln Lys Arg Ser Val Ser Ile Glu Arg Phe Val Glu Thr Leu Val
                245                 250                 255

Val Ala Asp Lys Met Met Val Gly Tyr His Gly Arg Lys Asp Ile Glu
            260                 265                 270

His Tyr Ile Leu Ser Val Met Asn Ile Val Ala Lys Leu Tyr Arg Asp
        275                 280                 285

Ser Ser Leu Gly Asn Val Val Asn Ile Val Ala Arg Leu Ile Val
    290                 295                 300

Leu Thr Glu Asp Gln Pro Asn Leu Glu Ile Asn His His Ala Asp Lys
305                 310                 315                 320

Ser Leu Asp Ser Phe Cys Lys Trp Gln Lys Ser Ile Leu Ser His Gln
                325                 330                 335

Ser Asp Gly Asn Thr Ile Pro Glu Asn Gly Ile Ala His His Asp Asn
            340                 345                 350

```
Ala Val Leu Ile Thr Arg Tyr Asp Ile Cys Thr Tyr Lys Asn Lys Pro
        355                 360                 365

Cys Gly Thr Leu Gly Leu Ala Ser Val Ala Gly Met Cys Glu Pro Glu
    370                 375                 380

Arg Ser Cys Ser Ile Asn Glu Asp Ile Gly Leu Gly Ser Ala Phe Thr
385                 390                 395                 400

Ile Ala His Glu Ile Gly His Asn Phe Gly Met Asn His Asp Gly Ile
                405                 410                 415

Gly Asn Ser Cys Gly Thr Lys Gly His Glu Ala Ala Lys Leu Met Ala
                420                 425                 430

Ala His Ile Thr Ala Asn Thr Asn Pro Phe Ser Trp Ser Ala Cys Ser
            435                 440                 445

Arg Asp Tyr Ile Thr Ser Phe Leu Asp Ser Gly Arg Gly Thr Cys Leu
    450                 455                 460

Asp Asn Glu Pro Pro Lys Arg Asp Phe Leu Tyr Pro Ala Val Ala Pro
465                 470                 475                 480

Gly Gln Val Tyr Asp Ala Asp Glu Gln Cys Arg Phe Gln Tyr Gly Ala
                485                 490                 495

Thr Ser Arg Gln Cys Lys Tyr Gly Glu Val Cys Arg Glu Leu Trp Cys
                500                 505                 510

Leu Ser Lys Ser Asn Arg Cys Val Thr Asn Ser Ile Pro Ala Ala Glu
    515                 520                 525

Gly Thr Leu Cys Gln Thr Gly Asn Ile Glu Lys Gly Trp Cys Tyr Gln
    530                 535                 540

Gly Asp Cys Val Pro Phe Gly Thr Trp Pro Gln Ser Ile Asp Gly Gly
545                 550                 555                 560

Trp Gly Pro Trp Ser Leu Trp Gly Glu Cys Ser Arg Thr Cys Gly Gly
                565                 570                 575

Gly Val Ser Ser Ser Leu Arg His Cys Asp Ser Pro Ala Pro Ser Gly
                580                 585                 590

Gly Gly Lys Tyr Cys Leu Gly Glu Arg Lys Arg Tyr Arg Ser Cys Asn
            595                 600                 605

Thr Asp Pro Cys Pro Leu Gly Ser Arg Asp Phe Arg Glu Lys Gln Cys
    610                 615                 620

Ala Asp Phe Asp Asn Met Pro Phe Arg Gly Lys Tyr Tyr Asn Trp Lys
625                 630                 635                 640

Pro Tyr Thr Gly Gly Gly Val Lys Pro Cys Ala Leu Asn Cys Leu Ala
                645                 650                 655

Glu Gly Tyr Asn Phe Tyr Thr Glu Arg Ala Pro Ala Val Ile Asp Gly
                660                 665                 670

Thr Gln Cys Asn Ala Asp Ser Leu Asp Ile Cys Ile Asn Gly Glu Cys
            675                 680                 685

Lys His Val Gly Cys Asp Asn Ile Leu Gly Ser Asp Ala Arg Glu Asp
    690                 695                 700

Arg Cys Arg Val Cys Gly Gly Asp Gly Ser Thr Cys Asp Ala Ile Glu
705                 710                 715                 720

Gly Phe Phe Asn Asp Ser Leu Pro Arg Gly Gly Tyr Met Glu Val Val
                725                 730                 735

Gln Ile Pro Arg Gly Ser Val His Ile Glu Val Arg Glu Val Ala Met
            740                 745                 750

Ser Lys Asn Tyr Ile Ala Leu Lys Ser Glu Gly Asp Asp Tyr Tyr Ile
    755                 760                 765

Asn Gly Ala Trp Thr Ile Asp Trp Pro Arg Lys Phe Asp Val Ala Gly
```

```
            770               775               780
Thr Ala Phe His Tyr Lys Arg Pro Thr Asp Glu Pro Glu Ser Leu Glu
785               790               795               800

Ala Leu Gly Pro Thr Ser Glu Asn Leu Ile Val Met Val Leu Leu Gln
            805               810               815

Glu Gln Asn Leu Gly Ile Arg Tyr Lys Phe Asn Val Pro Ile Thr Arg
            820               825               830

Thr Gly Ser Gly Asp Asn Glu Val Gly Phe Thr Trp Asn His Gln Pro
            835               840               845

Trp Ser Glu Cys Ser Ala Thr Cys Ala Gly Val Gln Arg Gln Glu
            850               855               860

Val Val Cys Lys Arg Leu Asp Asp Asn Ser Ile Val Gln Asn Asn Tyr
865               870               875               880

Cys Asp Pro Asp Ser Lys Pro Pro Glu Asn Gln Arg Ala Cys Asn Thr
            885               890               895

Glu Pro Cys Pro Pro Glu Trp Phe Ile Gly Asp Trp Leu Glu Cys Ser
            900               905               910

Lys Thr Cys Asp Gly Gly Met Arg Thr Arg Ala Val Leu Cys Ile Arg
            915               920               925

Lys Ile Gly Pro Ser Glu Glu Glu Thr Leu Asp Tyr Ser Gly Cys Leu
            930               935               940

Thr His Arg Pro Val Glu Lys Glu Pro Cys Asn Asn Gln Ser Cys Pro
945               950               955               960

Pro Gln Trp Val Ala Leu Asp Trp Ser Glu Cys Thr Pro Lys Cys Gly
            965               970               975

Pro Gly Phe Lys His Arg Ile Val Leu Cys Lys Ser Ser Asp Leu Ser
            980               985               990

Lys Thr Phe Pro Ala Ala Gln Cys Pro Glu Glu Ser Lys Pro Pro Val
            995               1000              1005

Arg Ile Arg Cys Ser Leu Gly Arg Cys Pro Pro Arg Trp Val
    1010              1015              1020

Thr Gly Asp Trp Gly Gln Cys Ser Ala Gln Cys Gly Leu Gly Gln
    1025              1030              1035

Gln Met Arg Thr Val Gln Cys Leu Ser Tyr Thr Gly Gln Ala Ser
    1040              1045              1050

Ser Asp Cys Leu Glu Thr Val Arg Pro Pro Ser Met Gln Gln Cys
    1055              1060              1065

Glu Ser Lys Cys Asp Ser Pro Ile Ser Asn Thr Glu Glu Cys
    1070              1075              1080

Lys Asp Val Asn Lys Val Ala Tyr Cys Pro Leu Val Leu Lys Phe
    1085              1090              1095

Lys Phe Cys Ser Arg Ala Tyr Phe Arg Gln Met Cys Cys Lys Thr
    1100              1105              1110

Cys Gln Gly His
    1115

<210> SEQ ID NO 5
<211> LENGTH: 24
<212> TYPE: PRT
<213> ORGANISM: Artificial Sequence
<220> FEATURE:
<223> OTHER INFORMATION: Histidine tag sequence

<400> SEQUENCE: 5

Glu Asn Leu Tyr Phe Gln Gly Gly Gly Gly Gly Ser Leu Val Pro Arg
```

```
                1               5                    10                       15
Gly Ser His His His His His
                20
```

<210> SEQ ID NO 6
<211> LENGTH: 623
<212> TYPE: PRT
<213> ORGANISM: Artificial Sequence
<220> FEATURE:
<223> OTHER INFORMATION: Mature ADAMTS6 sequence with His tag

<400> SEQUENCE: 6

```
Ser Val Ser Ile Glu Arg Phe Val Glu Thr Leu Val Val Ala Asp Lys
1               5                   10                  15

Met Met Val Gly Tyr His Gly Arg Lys Asp Ile Glu His Tyr Ile Leu
                20                  25                  30

Ser Val Met Asn Ile Val Ala Lys Leu Tyr Arg Asp Ser Ser Leu Gly
            35                  40                  45

Asn Val Val Asn Ile Ile Val Ala Arg Leu Ile Val Leu Thr Glu Asp
        50                  55                  60

Gln Pro Asn Leu Glu Ile Asn His His Ala Asp Lys Ser Leu Asp Ser
65                  70                  75                  80

Phe Cys Lys Trp Gln Lys Ser Ile Leu Ser His Gln Ser Asp Gly Asn
                85                  90                  95

Thr Ile Pro Glu Asn Gly Ile Ala His His Asp Asn Ala Val Leu Ile
            100                 105                 110

Thr Arg Tyr Asp Ile Cys Thr Tyr Lys Asn Lys Pro Cys Gly Thr Leu
        115                 120                 125

Gly Leu Ala Ser Val Ala Gly Met Cys Glu Pro Glu Arg Ser Cys Ser
130                 135                 140

Ile Asn Glu Asp Ile Gly Leu Gly Ser Ala Phe Thr Ile Ala His Glu
145                 150                 155                 160

Ile Gly His Asn Phe Gly Met Asn His Asp Gly Ile Gly Asn Ser Cys
                165                 170                 175

Gly Thr Lys Gly His Glu Ala Ala Lys Leu Met Ala Ala His Ile Thr
            180                 185                 190

Ala Asn Thr Asn Pro Phe Ser Trp Ser Ala Cys Ser Arg Asp Tyr Ile
        195                 200                 205

Thr Ser Phe Leu Asp Ser Gly Arg Gly Thr Cys Leu Asp Asn Glu Pro
        210                 215                 220

Pro Lys Arg Asp Phe Leu Tyr Pro Ala Val Ala Pro Gly Gln Val Tyr
225                 230                 235                 240

Asp Ala Asp Glu Gln Cys Arg Phe Gln Tyr Gly Ala Thr Ser Arg Gln
                245                 250                 255

Cys Lys Tyr Gly Glu Val Cys Arg Glu Leu Trp Cys Leu Ser Lys Ser
            260                 265                 270

Asn Arg Cys Val Thr Asn Ser Ile Pro Ala Ala Glu Gly Thr Leu Cys
        275                 280                 285

Gln Thr Gly Asn Ile Glu Lys Gly Trp Cys Tyr Gln Gly Asp Cys Val
    290                 295                 300

Pro Phe Gly Thr Trp Pro Gln Ser Ile Asp Gly Gly Trp Gly Pro Trp
305                 310                 315                 320

Ser Leu Trp Gly Glu Cys Ser Arg Thr Cys Gly Gly Gly Val Ser Ser
                325                 330                 335

Ser Leu Arg His Cys Asp Ser Pro Ala Pro Ser Gly Gly Gly Lys Tyr
```

```
                   340                 345                 350

Cys Leu Gly Glu Arg Lys Arg Tyr Arg Ser Cys Asn Thr Asp Pro Cys
                    355                 360                 365

Pro Leu Gly Ser Arg Asp Phe Arg Glu Lys Gln Cys Ala Asp Phe Asp
                370                 375                 380

Asn Met Pro Phe Arg Gly Lys Tyr Tyr Asn Trp Lys Pro Tyr Thr Gly
        385                 390                 395                 400

Gly Gly Val Lys Pro Cys Ala Leu Asn Cys Leu Ala Glu Gly Tyr Asn
                        405                 410                 415

Phe Tyr Thr Glu Arg Ala Pro Ala Val Ile Asp Gly Thr Gln Cys Asn
                    420                 425                 430

Ala Asp Ser Leu Asp Ile Cys Ile Asn Gly Glu Cys Lys His Val Gly
                435                 440                 445

Cys Asp Asn Ile Leu Gly Ser Asp Ala Arg Glu Asp Arg Cys Arg Val
            450                 455                 460

Cys Gly Gly Asp Gly Ser Thr Cys Asp Ala Ile Glu Gly Phe Phe Asn
        465                 470                 475                 480

Asp Ser Leu Pro Arg Gly Gly Tyr Met Glu Val Val Gln Ile Pro Arg
                        485                 490                 495

Gly Ser Val His Ile Glu Val Arg Glu Val Ala Met Ser Lys Asn Tyr
                    500                 505                 510

Ile Ala Leu Lys Ser Glu Gly Asp Asp Tyr Tyr Ile Asn Gly Ala Trp
                515                 520                 525

Thr Ile Asp Trp Pro Arg Lys Phe Asp Val Ala Gly Thr Ala Phe His
            530                 535                 540

Tyr Lys Arg Pro Thr Asp Glu Pro Glu Ser Leu Glu Ala Leu Gly Pro
        545                 550                 555                 560

Thr Ser Glu Asn Leu Ile Val Met Val Leu Leu Gln Glu Gln Asn Leu
                        565                 570                 575

Gly Ile Arg Tyr Lys Phe Asn Val Pro Ile Thr Arg Thr Gly Ser Gly
                    580                 585                 590

Asp Asn Glu Val Gly Phe Thr Glu Asn Leu Tyr Phe Gln Gly Gly Gly
                595                 600                 605

Gly Gly Ser Leu Val Pro Arg Gly Ser His His His His His His
            610                 615                 620

<210> SEQ ID NO 7
<211> LENGTH: 10
<212> TYPE: PRT
<213> ORGANISM: Artificial Sequence
<220> FEATURE:
<223> OTHER INFORMATION: Substrate XII
<220> FEATURE:
<221> NAME/KEY: substrat12_pos7
<222> LOCATION: (7)..(7)
<223> OTHER INFORMATION: Nva

<400> SEQUENCE: 7

Arg Pro Lys Pro Tyr Ala Xaa Trp Met Lys
1               5                   10
```